(12) United States Patent
Bailly et al.

(10) Patent No.: US 7,396,837 B2
(45) Date of Patent: Jul. 8, 2008

(54) ANTITUMORAL ANALOGS OF LAMELLARINS

(75) Inventors: Christian Bailly, Lille (FR); Andrés Francesch, Madrid (ES); Maria Cristina Mateo Urbano, Madrid (ES); José Antonio Jiménez Guerrero, Madrid (ES); Alfredo Pastor Del Castillo, Madrid (ES); Carmen Cuevas Marchante, Madrid (ES)

(73) Assignee: Pharma Mar, S.A.U., Madrid (ES)

( * ) Notice: Subject to any disclaimer, the term of this patent is extended or adjusted under 35 U.S.C. 154(b) by 0 days.

(21) Appl. No.: 10/524,151

(22) PCT Filed: Aug. 13, 2003

(86) PCT No.: PCT/GB03/03541

§ 371 (c)(1),
(2), (4) Date: Aug. 1, 2005

(87) PCT Pub. No.: WO2004/014917

PCT Pub. Date: Feb. 19, 2004

(65) Prior Publication Data

US 2006/0173030 A1 Aug. 3, 2006

(30) Foreign Application Priority Data

Aug. 13, 2002 (GB) .................. 0218816.7

(51) Int. Cl.
*A61K 31/4738* (2006.01)
*C07D 491/12* (2006.01)
(52) U.S. Cl. .................... 514/283; 546/47; 546/51
(58) Field of Classification Search ............. 514/283; 546/47, 51
See application file for complete search history.

(56) References Cited

U.S. PATENT DOCUMENTS 5,852,033 A * 12/1998 Fernandez Puentes et al. ... 514/283
6,469,171 B1 * 10/2002 Banwell et al. .............. 546/49

FOREIGN PATENT DOCUMENTS

| WO | 97/01336 | 1/1997 |
| WO | 98/50365 | 11/1998 |
| WO | 99/67250 | 12/1999 |

OTHER PUBLICATIONS

Andersen et al., "Metabolites of the Marne Prosobranch Mollusc Lamellaria SP", *J. of Amer. Chem. Soc.*, vol. 107, pp. 5492-5495, 1985.
Banwell et al., "Assessment of Double-Barrelled Heck Cyclizations as a Means for Constructions of the 14-phenyl-8, 9-dihydro-6h-[1]benzopyrano[4',3':4,5]pyrrolo[2,1-a]isoquinolin-6-one Core Associated with Certain Members of the Lamellarin Class of Marine Natural Product", *Aust. J. of Chem.*, vol. 52, pp. 755-765, 1998.
Banwell et al., "Convergent Total Synthesis of Lamellarin K", *Chem. Comm.*, vol. 23, pp. 2259-2260, 1997.
Cantrell et al., "A New Staurosporine Analog from the Prosobranch Mollusk Coriocella Nigra", *Natural Prod. Ltrs.*, vol. 14:1, pp. 39-46, 1999.
Carroll et al., "Studies of Australian Ascidians I Six New Lamellarin-Class Alkaloids from a Colonial Ascidian, Didemnum SP", *Aust. J. of Chem.*, vol. 46, pp. 489-501, 1993.
Cironi et al., "Solid-Phase Total Synthesis of the Pentacyclic System Lamellarins U and L", *Organic Ltrs.*, vol. 5:16, pp. 2959-2962, 2003.
Davis et al., "New Lamellarin Alkaloids from the Australian Acidian, Didemnum Chartaceum", *J. of Nat. Prod*, vol. 62, pp. 419-424, 1999.
Diaz et al., "Syntheses of Lamellarins I and K by [3+2] Cycloaddition of a Nitrone to an Alkyne", *Synlett*, vol. 7, pp. 1164-1166, 2001.
Ham et al., "A Novel Cytotoxic Alkaloid of Lamellarin Class From a Marine Ascidian Didemnum sp.", *Bull. Korean Chem. Soc.*, vol. 23:1, pp. 163-166, 2002.
Heim et al., "Biomimetic Synthesis of Lamellarin G Trimethyl Ether", *Angewandte Chemie Int'l Ed.*, vol. 36, pp. 155-156, 1997.
Ishibashi et al., "Synthesis and Structure-Activity Relationship Study of Lamellarin Derivatives", *J. of Nat. Prod.*, vol. 65, pp. 500-504, 2002.
Ishibashi et al., "Total Synthesis of Lamellarin D and H. The first Synthesis of Lamellarin-Class Marine Alkaloids", *Tetrahedron*, vol. 53:17, pp. 5951-5962, 1997.
Iwao et al., "Short and Flexible Route to 3,4-diarylpyrrole Marine Alkaloids: Syntheses of Permethyl Storniamide A, Ningalin B and Lamellarin G Trimethyl Ether", *Tetrahedron Ltrs.*, vol. 44, pp. 4443-4446, 2003.
Lindquist et al., New Alkaloids of the Lamellarian Class from the Marine Ascidian Didemnum Chartaceum, *J. Org. Chem.*, vol. 53:19, pp. 4570-4574, 1988.

(Continued)

*Primary Examiner*—Charanjit S. Aulakh
(74) *Attorney, Agent, or Firm*—King & Spalding, LLP; Kenneth H. Sonnenfeld; Michael A. Willis

(57) ABSTRACT

New lamellarins are provided of the general formula III or a pharmaceutically acceptable salt, derivative, prodrug or stereoisomer thereof

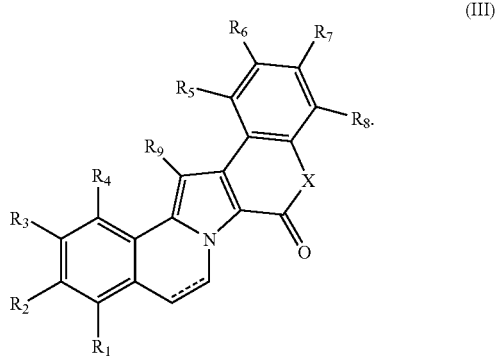

(III)

28 Claims, No Drawings

OTHER PUBLICATIONS

Ploypradith et al., "Further developments in the Synthesis of Lamellarin Alkaloids via Direct Metal-Halogen Exchange", *Tetrahedron Ltrs.*, vol. 44, pp. 1363-1366, 2003.

Quesada et al., "Polyaromatic Alkaloids From Marine Invertebrates as Cytotoxic Comounds and Inhibitors of Multidrug Resistance caused by P-Glycoprotein" *British J. of Cancer*, vol. 74, pp. 677-682, 1996.

Reddy et al., "Lamellarin Alpha 20-Sulfate, an inhibitor of HIV-Integrase Active Against HIV-1 Virus in Cell Culture", *J. of Med. Chem.*, vol. 42, pp. 1901-1907, 1999.

Reddy et al., "New Lamellarin Alkaloids from an Unidentified Ascidian from the Arabian Sea", *Tetrahedron*, vol. 53:19, pp. 3457-3466, 1997.

Ridley et al., "Total Synthesis and Evaluation of Lamellarin Alpha 20-Sulfate Analogues", *Bioorganic & Medicinal Chem.*, vol. 10, pp. 3285-3290, 2002.

Ruchirawat et al., "An Efficient Synthesis of Lamellarin Alkaloids;Synthesis of Lamellarin G Trimethyl Ether", *Tetrahedron Letters*, vol. 42, pp. 1205-1208, 2001.

Urban et al., "Lamellarins O and P: New Aromatic Metabolites from the Australian Marine Sponge Dendrilla Cactos", *Aust. J. Chem.*, vol. 14:10, pp. 1919-1924, 1994.

Urban et al., "Lamellarin-S: A New Aromatic Metabolite From an Australian Tunicate, Didemnum SP", *Aust. J. Chem.*, vol. 49, pp. 711-713, 1996.

\* cited by examiner

ANTITUMORAL ANALOGS OF LAMELLARINS

FIELD OF THE INVENTION

The present invention relates to antitumoral compounds, and in particular to new antitumoral analogs of lamellarins, pharmaceutical compositions containing them and their use in the treatment of cancer.

BACKGROUND OF THE INVENTION

The lamellarins are polyaromatics alkaloids originally isolated from marine sources and comprising a fused polyaromatic framework. The family of lamellarins are constituted by two basic structures:

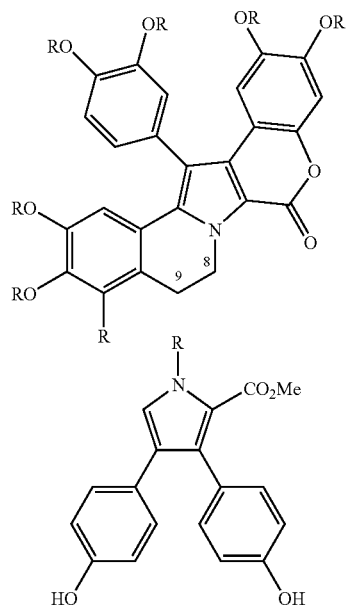

Both structures have a pyrrolic ring substituted with aryl units. The hexacyclic structure 1 is a 14-phenyl-6H-[1]benzopiran[4',3',4,5]pyrrolo[2,1-a]isoquinolin-6-one. Depending of the substituents and the presence of a double bond between C8-C9 the members of this family are designed with different letters.

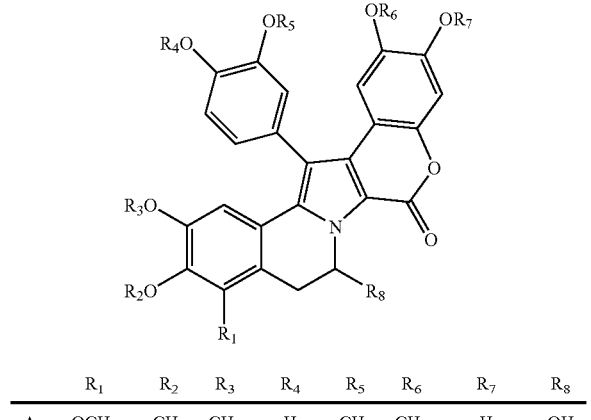

| | $R_1$ | $R_2$ | $R_3$ | $R_4$ | $R_5$ | $R_6$ | $R_7$ | $R_8$ |
|---|---|---|---|---|---|---|---|---|
| A | $OCH_3$ | $CH_3$ | $CH_3$ | H | $CH_3$ | $CH_3$ | H | OH |
| C | $OCH_3$ | $CH_3$ | $CH_3$ | H | $CH_3$ | $CH_3$ | H | H |
| E | OH | $CH_3$ | $CH_3$ | $CH_3$ | H | $CH_3$ | H | H |
| F | OH | $CH_3$ | $CH_3$ | $CH_3$ | $CH_3$ | $CH_3$ | H | H |

-continued

| | $R_1$ | $R_2$ | $R_3$ | $R_4$ | $R_5$ | $R_6$ | $R_7$ | $R_8$ |
|---|---|---|---|---|---|---|---|---|
| G | H | H | $CH_3$ | $CH_3$ | H | H | $CH_3$ | H |
| I | $OCH_3$ | $CH_3$ | $CH_3$ | $CH_3$ | $CH_3$ | $CH_3$ | H | H |
| J | H | H | $CH_3$ | $CH_3$ | $CH_3$ | $CH_3$ | H | H |
| K | OH | $CH_3$ | $CH_3$ | H | $CH_3$ | $CH_3$ | H | H |
| L | H | H | $CH_3$ | $CH_3$ | H | $CH_3$ | H | H |
| S | H | H | $CH_3$ | H | H | H | H | H |
| T | $OCH_3$ | $CH_3$ | $CH_3$ | $CH_3$ | H | $CH_3$ | H | H |
| U | H | $CH_3$ | $CH_3$ | $CH_3$ | H | $CH_3$ | H | H |
| V | $OCH_3$ | $CH_3$ | $CH_3$ | $CH_3$ | H | $CH_3$ | H | OH |
| Y | H | $CH_3$ | H | $CH_3$ | H | $CH_3$ | $SO_3Na$ | H |
| Z | H | H | $CH_3$ | H | H | H | $CH_3$ | H |
| β | H | H | H | $CH_3$ | H | H | H | H |

| | $R_1$ | $R_2$ | $R_3$ | $R_4$ | $R_5$ | $R_6$ | $R_7$ |
|---|---|---|---|---|---|---|---|
| B | $OCH_3$ | $CH_3$ | $CH_3$ | H | $CH_3$ | $CH_3$ | H |
| D | H | H | $CH_3$ | H | $CH_3$ | $CH_3$ | H |
| H | H | H | H | H | H | H | H |
| M | OH | $CH_3$ | $CH_3$ | H | $CH_3$ | $CH_3$ | H |
| N | H | H | $CH_3$ | $CH_3$ | H | $CH_3$ | H |
| W | $OCH_3$ | $CH_3$ | $CH_3$ | $CH_3$ | H | $CH_3$ | H |
| X | OH | $CH_3$ | $CH_3$ | $CH_3$ | H | $CH_3$ | H |
| α | H | $CH_3$ | $CH_3$ | $CH_3$ | H | $CH_3$ | $SO_3Na$ |

R. J. Anderson et al, *J. Am. Chem. Soc.* 1985, 107, 5492, describes the isolation and characterization of four polyaromatic metabolites, the lamellarins A-D, obtained from a marine prosobranch mollusc *Lamellana* sp. The structure of lamellarin A was determined by an X-Ray crystallographic study and the structures of lamellarins B-D were assigned by interpretation of spectral data.

N. Lindquist et al, *J. Org. Chem.* 1988, 53, 4570, describes the isolation and characterization of four new lamellarins: E-H from the marine ascidian *Didemnum chartaceum* obtained from the Indian Ocean. The structure of lamellarin E was determined by an X-Ray crystallographic study.

A. R. Carroll et al, *Aust. J. Chem.* 1993, 46, 489, isolated six new lamellarins: I, J, K, L, M and the triacetate of the lamellarin N, and four known of this type: A, B, C, and the triacetate of lamellarin D, isolated from a marine ascidian *Didemnum* sp.

S. Urban et al, *Aust. J. Chem.* 1994, 47, 1919 and *Aust. J. Chem.* 1995, 48, 1491, described the isolation and characterization of four new lamellarins, O, P, Q, R, with the substructure type 2 from the marine sponge *Dendnilla cactos*. Later S. Urban et al, *Aust. J. Chem.* 1996, 49, 711, described the structure of lamellarin S from the ascidian *Didemnum* sp.

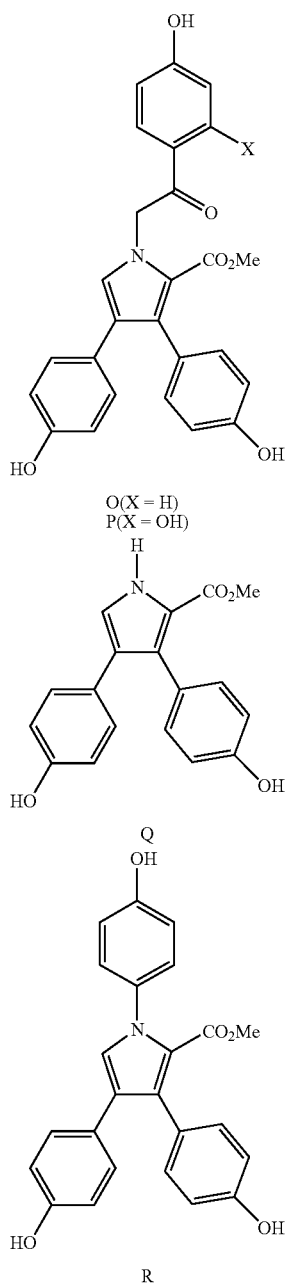

O (X = H)
P (X = OH)

Q

R

M. V. R. Reddy et al, *Tetrahedron* 1997, 53, 3457, isolated five new lamellarins: T, U, V, W, and X, and the first example of sulfated lamellarin, Y, isolated from the marine ascidian *Didemnum* sp obtained from the Arabian sea.

R. A. Davis et al, *J. Nat. Prod.* 1999, 62, 419, described one new lamellarin, Z, and various examples of sulphated lamellarins isolated from the marine ascidian *Didemnum chartaceum*.

M. V. R. Reddy et al, *J. Med. Chem.* 1999, 42, 1901, isolated a new lamellarin, α, isolated from the marine ascidian *Didemnum* sp.

Finally, J. Ham et al, *Bull. Korean Chem. Soc.* 2002, 23, 163, described the isolation and characterization of the lamellarin β obtained from a marine ascidian *Didemnum* sp.

Lamellarins C and D have been shown to cause inhibition of cell division in a fertilised sea urchin assay, whereas lamellarins I, K, and L all exhibit comparable cytoxicity against P388 and A549 cell lines in culture. Recently, lamellarin N has been shown to exhibit activity in lung cancer cell lines by acting as a Type IV microtubule poison.

Furthermore, J. L. Fernández-Puentes et al, PCT Int. Appl WO 97/01336, describe that these compounds have also cytotoxic activity on multidrug resistant cells as well as efficacy as non-toxic modulators of the multidrug resistant phenotype and, therefore, afford an attractive potential source of chemotherapeutic agents.

The limited availability of natural material has resulted in the search for alternative synthetic methods being sought for the natural compounds and related analogs. M. G. Banwell et al, Int. Patent Appl. WO 98/50365 and Int. Patent Appl. WO 99/67250 described the synthesis of lamellarin K via 1,3-dipolar cycloaddition between an alkyne and an N-ylide of isoquinolin.

Lamellarin G trimethyl ether was also synthetised by S. Ruchirawat et al, *Tetrahedron Lett.* 2001, 42, 1250. The synthesis involved the formation of the core pyrrolo[2,1-a]isoquinoline, followed by the formation of the lactone ring.

Lamellarins I and K (1) were obtained by L. Castedo et al, *Synlett* 2001, 7, 1164, by a new approach based on the 1,3-dipolar cycloaddition of a nitrone to an alkyne. The key cycloaddition yield an isoxazoline which rearranged to afford the central pyrrole ring.

F. Albericio et al, *Org. Lett* 2003, 5, 2959, has described a total solid-phase synthesis of Lamellarins U and L.

Ishibashi F. et al., *J. Nat. Prod.,* 2002, 65, 500-504 describe the synthesis and structure activity relationship for some lamellarin derivatives.

The discovery of the main target for an anticancer agent is an essential element to better understand its mechanism of action and to guide the development of clinically useful analogs. To illustrate this, one can refer to camptothecin (CPT) discovered in the early 1960s but successfully developed only a quarter of a century later when its main, and perhaps unique, molecular target was identified: topoisomerase I. The observation in 1985 that CPT stabilizes DNA-topoisomerase I complexes provided the starting point for the rational development of safe CPT analogs which culminated in the mid 1990s with the approval of topotecan and irinotecan for the treatment of ovarian and colon cancers.

The search for non-CPT topoisomerase I poisons has been very active for the past ten years but only a limited number of potent topoisomerase I poisons has been discovered.

SUMMARY OF THE INVENTION

We have found that the lamellarins represent a new and promising series of topoisomerase I inhibitors. The correlation between the capacity of the drugs to stimulate topoisomerase I-mediated DNA cleavage and their cytotoxic potential makes them useful as antitumor agents.

The present invention is directed to compounds of the general formula III:

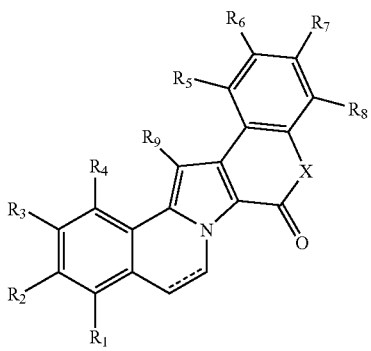

wherein X is selected from the group consisting of N, O and S; wherein $R_1$, $R_2$, $R_3$, $R_4$, $R_5$, $R_6$, $R_7$, $R_8$ and $R_9$ are each independently selected from the group consisting of H, OH, OR', SH, SR', SOR', $SO_2R'$, NHR', $N(R')_2$, N=R', NHCOR', $N(COR')_2$, $NHSO_2R'$, $NO_2$, $PO(R')_2$, $PO_2R'$, C(=O)H, C(=O)R', $CO_2H$, $CO_2R'$, $OPO(R')_2$, $OPO_2R'$, OC(=O)H, OC(=O)R', N=C(R')_2$, substituted or unsubstituted $C_1$-$C_{12}$ alkyl, substituted or unsubstituted $C_1$-$C_{12}$ haloalkyl, substituted or unsubstituted $C_2$-$C_{12}$ alkenyl, substituted or unsubstituted $C_2$-$C_{12}$ alkynyl, substituted or unsubstituted aryl, substituted or unsubstituted aralkyl and substituted or unsubstituted heteroaromatic; wherein each of the R' groups is independently selected from the group consisting of H, OH, $NO_2$, $NH_2$, SH, CN, halogen, =O, C(=O)H, C(=O)CH$_3$, $CO_2H$, C(=O)R', substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, substituted or unsubstituted $C_1$-$C_{18}$ alkoxyl, substituted or unsubstituted $C_1$-$C_{18}$ aminoalkyl, substituted or unsubstituted $C_1$-$C_{18}$ aminoacid, substituted or unsubstituted $C_1$-$C_{18}$ thioalkyl, substituted or unsubstituted $C_1$-$C_{18}$ alkylsulfinyl, substituted or unsubstituted $C_1$-$C_{18}$ alkylsulfonyl; wherein the pairs of groups $R_1$ and $R_2$, $R_2$ and $R_3$, $R_3$ and $R_4$, $R_3$ and $R_9$, $R_4$ and $R_9$, $R_9$ and $R_5$, $R_9$ and $R_6$, or $R_6$ and $R_7$, $R_7$ and $R_5$ may be joined into a carbocyclic or heterocyclic ring system; and the dotted line represents a single or double bond; or a pharmaceutically acceptable salt, derivative, prodrug or stereoisomer thereof.

We exclude compounds that are known lamellarins, especially known lamellarins described in the literature acknowledged in the present introduction, and more especially lamellarins A-N and S-Z or lamellarins α or β, as well as lamellarin D, K, L, M or N triacetate, lamellarin G trimethyl ether and compounds in WO 9850365. In this respect, we explicitly incorporate by specific reference each of the prior art documents mentioned in the present introduction, particularly for any disclsoure of a known compound which needs to be excluded from the present claims.

PREFERRED EMBODIMENTS

Preferred compounds of this invention are those of formula IV:

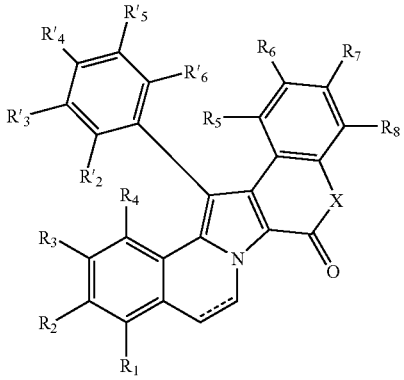

wherein $R_1$-$R_8$ are as defined above and $R'_2$-$R'_6$ and the dotted line have the same definitions as for $R_1$-$R_8$. In this respect, appropriate pairs of $R'_2$-$R'_6$ may be joined into a carbocyclic or heterocyclic ring system.

In formula III or IV X is preferably O or NH, most preferably O.

Preferred compounds are those that have a double bond between C-8 and C-9 (dotted line), they have shown higher antitumoral activity.

In a preferred aspect of the invention each of $R_1$-$R_8$ is independently selected from H, OR', OC(=O)R'.

$R_3$ is preferably selected from the group consisting of H, OH, alkoxy, most preferably methoxy.

$R_4$, $R_5$, $R_6$ and $R_8$ are preferably each independently selected from the group consisting of H or alkoxy, most preferably they are H. Suitably at least 2, 3 or preferably all 4 of $R_4$, $R_5$, $R_6$ and $R_8$ are the same, and $R_3$ is preferably that group.

$R_1$, $R_2$ and $R_7$ are preferably each independently selected from the group consisting of H, OH, alkoxy, OC(=O)R', $SO_2R'$, $PO(R')_2$, Alkyl, $NO_2$, $NH_2$.

In a most preferred embodiment $R_1$, $R_2$ and $R_7$ are OC(=O)R' wherein R' is a substituted or unsubstituted aminoacid or aminoacids chain, preferably with a cationic group. Suitably at least 2, or preferably all 3 of $R_1$, $R_2$ and $R_7$ are the same.

In formula IV $R'_2$, $R'_3$ and $R'_6$ are preferably each independently selected from the group consisting of H or alkoxy, most preferably H; and $R'_5$ is preferably selected from the group consisting of H or alkoxy, most preferably methoxy.

$R'_4$ is preferably selected from the group consisting of H, OH, alkoxy, OC(=O)R', $SO_2R'$, $PO(R')_2$, Alkyl, $NO_2$, $NH_2$. Most preferably $R'_4$ is C(=O)R' wherein R' is a substituted or unsubstituted aminoacid or aminoacids chain, preferably with a cationic group.

Often $R'_4$, $R_7$ and either $R_1$ or $R_2$ is the same.

Any of the groups with a protectable hydroxy or amino subsituent may be in protected form, using available protecting groups.

Suitable protecting groups for phenols and hydroxy groups include ethers and esters, such as alkyl, alkoxyalkyl, aryloxyalkyl, alkoxyalkoxyalkyl, alkylsilylalkoxyalkyl, alkylthioalkyl, arylthioalkyl, azidoalkyl, cyanoalkyl, chloroalkyl, heterocyclic, arylacyl, haloarylacyl, cycloalkylalkyl, alkenyl, cycloalkyl, alyklarylalkyl, alkoxyarylalkyl, nitroarylalkyl, haloarylalkyl, alkylaminocarbonylarylalkyl, alkylsulfinylarylalkyl, alkylsilyl and other ethers, and arylacyl, aryl alkyl carbonate, aliphatic carbonate, alkylsulfinylarlyalkyl carbonate, alkyl carbonate, aryl haloalkyl carbonate, aryl alkenyl carbonate, aryl carbamate, alkyl phosphinyl, alkylphosphinothioyl, aryl phosphinothioyl, aryl alkyl sulphonate and other esters. Such groups may optionally be substituted with the previously mentioned groups in $R^1$.

Suitable protecting groups for amines include carbamates, amides, and other protecting groups, such as alkyl, arylalkyl, sulpho- or halo-arylalkyl, haloalkyl, alkylsilylalkyl, arylalkyl, cycloalkylalkyl, alkylarylalkyl, heterocyclylalkyl, nitroarylalkyl, acylaminoalkyl, nitroaryldithioarylalkyl, dicycloalkylcarboxamidoalkyl, cycloalkyl, alkenyl, arylalkenyl, nitroarylalkenyl, heterocyclylalkenyl, heterocyclyl, hydroxyheterocyclyl, alkyldithio, alkoxy- or halo- or alkylsulphinyl arylalkyl, hetercyclylacyl, and other carbamates, and alkanoyl, haloalkanoyl, arylalkanoyl, alkenoyl, heterocyclylacyl, aroyl, arylaroyl, haloaroyl, nitroaroyl, and other amides, as well as alkyl, alkenyl, alkylsilylalkoxyalkyl, alkoxyalkyl, cyanoalkyl, heterocyclyl, alkoxyarylalkyl, cycloalkyl, nitroaryl, arylalkyl, alkoxy- or hydroxy-arylalkyl, and many other groups. Such groups may optionally be substituted with the previously mentioned groups in $R^1$.

Examples of such protecting groups are given in the following tables.

| protection for —OH group | abbreviation |
|---|---|
| ethers | |
| methyl | |
| methoxymethyl | MOM |
| benzyloxymethyl | BOM |
| methoxyethoxymethyl | MEM |
| 2-(trimethylsilyl) ethoxymethyl | SEM |
| methylthiomethyl | MTM |
| phenylthiomethyl | PTM |
| azidomethyl | |
| cyanomethyl | |
| 2,2-dichloro-1,1-difluoroethyl | |
| 2-chloroethyl | |
| 2-bromoethyl | |
| tetrahydropyranyl | THP |
| 1-ethoxyethyl | EE |
| phenacyl | |
| 4-bromophenacyl | |
| cyclopropylmethyl | |
| allyl | |
| propargyl | |
| isopropyl | |
| cyclohexyl | |
| t-butyl | |
| benzyl | |
| 2,6-dimethylbenzyl | |
| 4-methoxybenzyl | MPM or PMB |
| o-nitrobenzyl | |
| 2,6-dichlorobenzyl | |
| 3,4-dichlorobenzyl | |
| 4-(dimethylamino)carbonylbenzyl | |
| 4-methylsuflinylbenzyl | Msib |
| 9-anthrylmethyl | |
| 4-picolyl | |
| heptafluoro-p-tolyl | |
| tetrafluoro-4-pyridyl | |
| trimethylsilyl | TMS |
| t-butyldimethylsilyl | TBDMS |
| t-butyldiphenylsilyl | TBDPS |
| triisopropylsilyl | TIPS |
| esters | |
| aryl formate | |
| aryl acetate | |
| aryl levulinate | |
| aryl pivaloate | ArOPv |

| -continued | |
|---|---|
| protection for —OH group | abbreviation |
| aryl benzoate | |
| aryl 9-fluorocarboxylate | |
| aryl methyl carbonate | |
| 1-adamantyl carbonate | |
| t-butyl carbonate | BOC-OAr |
| 4-methylsulfinylbenzyl carbonate | Msz-Oar |
| 2,4-dimethylpent-3-yl carbonate | Doc-Oar |
| aryl 2,2,2-trichloroethyl carbonate | |
| aryl vinyl carbonate | |
| aryl benzyl carbonate | |
| aryl carbamate | |
| dimethylphosphinyl | Dmp-OAr |
| dimethylphosphinothioyl | Mpt-OAr |
| diphenylphosphinothioyl | Dpt-Oar |
| aryl methanesulfonate | |
| aryl toluenesulfonate | |
| aryl 2-formylbenzenesulfonate | |

| protection for the —NH$_2$ group | abbreviation |
|---|---|
| carbamates | |
| methyl | |
| ethyl | |
| 9-fluorenylmethyl | Fmoc |
| 9-(2-sulfo)fluroenylmethyl | |
| 9-(2,7-dibromo)fluorenylmethyl | |
| 17-tetrabenzo[a,c,g,i]fluorenylmethyl | Tbfmoc |
| 2-chloro-3-indenylmethyl | Climoc |
| benz[f]inden-3-ylmethyl | Bimoc |
| 2,7-di-t-butyl[9-(10,10-dioxo-10,10,10-tetrahydrothioxanthyl)]methyl | DBD-Tmoc |
| 2,2,2-trichloroethyl | Troc |
| 2-trimethylsilylethyl | Teoc |
| 2-phenylethyl | hZ |
| 1-(1-adamantyl)-1-methylethyl | Adpoc |
| 2-chlooethyl | |
| 1,1-dimethyl-2-chloroethyl | |
| 1,1-dimethyl-2-bromoethyl | |
| 1,1-dimethyl-2,2-dibromoethyl | DB-t-BOC |
| 1,1-dimethyl-2,2,2-trichloroethyl | TCBOC |
| 1-methyl-1-(4-biphenyl)ethyl | Bpoc |
| 1-(3,5-di-t-butylphenyl)-1-1-methylethyl | t-Burmeoc |
| 2-(2'-and 4'-pyridyl)ethyl | Pyoc |
| 2,2-bis(4'-nitrophenyl)ethyl | Bnpeoc |
| n-(2-pivaloylamino)-1,1-dimethylethyl | |
| 2-[(2-nitrophenyl)dithio]-1-phenylethyl | NpSSPeoc |
| 2-(n,n-dicyclohexylcarboxamido)ethyl | |
| t-butyl | BOC |
| 1-adamantyl | 1-Adoc |
| 2-adamantyl | 2-Adoc |
| vinyl | Voc |
| allyl | Aloc or Alloc |
| 1-isopropylallyl | Ipaoc |
| cinnamyl | Coc |
| 4-nitrocinnamyl | Noc |
| 3-(3'-pyridyl)prop-2-enyl | Paloc |
| 8-quinolyl | |
| n-hydroxypiperidinyl | |
| alkyldithio | |
| benzyl | Cbz or Z |
| p-methoxybenzyl | Moz |
| p-nitrobenzyl | PNZ |
| p-bromobenzyl | |
| p-chlorobenzyl | |
| 2,4-dichlorobenzyl | |
| 4-methylsulfinylbenzyl | Msz |
| 9-anthrylmethyl | |

-continued

| protection for the —NH₂ group | abbreviation |
|---|---|
| diphenylmethyl | |
| phenothiazinyl-(10)-carbonyl | |
| n'-p-toluenesulfonylaminocarbonyl | |
| n'-phenylaminothiocarbonyl | |
| amides | |
| formamide | |
| acetamide | |
| chloroacetamide | |
| trifluoroacetamide | TFA |
| phenylacetamide | |
| 3-phenylpropanamide | |
| pent-4-enamide | |
| picolinamide | |
| 3-pyridylcarboxamide | |
| benzamide | |
| p-phenylbenzamide | |
| n-phthalimide | |
| n-tetrachlorophthalimide | TCP |
| 4-nitro-n-phthalimide | |
| n-dithiasuccinimide | Dts |
| n-2,3-diphenylmaleimide | |
| n-2,5-dimethylpyrrole | |
| n-2,5-bis(triisopropylsiloxyl)pyrrole | BIPSOP |
| n-1,1,4,4-tetramethyldisiliazacyclopentante adduct | STABASE |
| 1,1,3,3-tetramethyl-1,3-disilaisoindoline | BSB |
| special —NH protective groups | |
| n-methylamine | |
| n-t-butylamine | |
| n-allylamine | |
| n-[2-trimethylsilyl)ethoxy]methylamine | SEM |
| n-3-acetoxypropylamine | |
| n-cyanomethylamine | |
| n-(1-isopropyl-4-nitro-2-oxo-3-pyrrolin-3-yl)amine | |
| n-2,4-dimethoxybenzylamine | Dmb |
| 2-azanorbornenes | |
| n-2,4-dinitrophenylamine | |
| n-benzylamine | Bn |
| n-4-methoxybenzylamine | MPM |
| n-2,4-dimethoxybenzylamine | DMPM |
| n-2-hydroxybenzylamine | Hbn |
| n-(diphenylmethyl)amino | DPM |
| n-bis(4-methoxyphenyl)methylamine | |
| n-5-dibenzosuberylamine | DBS |
| n-triphenylmethylamine | Tr |
| n-[(4-methoxyphenyl)diphenylmethyl]amino | MMTr |
| n-9-phenylflurenylamine | Pf |
| n-ferrocenylmethylamine | Fcm |
| n-2-picolylamine n'-oxide | |
| n-1,1-dimethylthiomethyleneamine | |
| n-benzylideneamine | |
| n-p-methoxybenzylideneamine | |
| n-diphenylmethyleneamine | |
| n-(5,5-dimethyl-3-oxo-1-cyclohexenyl)amine | |
| n-nitroamine | |
| n-nitrosoamine | |
| diphenylphosphinamide | Dpp |
| dimethylthiophosphinamide | Mpt |
| diphenylthiophosphinamide | Ppt |
| dibenzyl phosphoramidate | |
| 2-nitrobenzenesulfenamide | Nps |
| n-1-(2,2,2-trifluoro-1,1-diphenyl)ethylsufenamide | TDE |
| 3-nitro-2-pyridinesulfenamide | Npys |
| p-toluenesulfonamide | Ts |
| benzenesulfonamide | |

It is preferred that at least one of $R_1$-$R_8$ and $R'_2$-$R'_6$ is not H, OH, $OCH_3$, $SO_3Na$, most preferably at least two are not H, OH, $OCH_3$, $SO_3Na$. It is also preferred that at least one of these substituents has at least 2, more preferably at 3, yet more preferably at least 4 carbon atoms. In particular, we prefer that $R'_4$ and $R_7$, and possibly also $R_1$, have these minimal numbers of carbon atoms.

Antitumoral activities of these compounds include leukaemias, lung cancer, colon cancer, kidney cancer, prostate cancer, pancreatic cancer, cervix cancer, ovarian cancer, breast cancer, sarcomas and melanomas.

In another aspect the present invention is directed to pharmaceutical compositions useful as antitumor agents that contain as active ingredient a compound or compounds of the invention or a pharmaceutically acceptable salt, derivative, prodrug or stereoisomer thereof and a pharmaceutically acceptable carrier.

The present invention is also directed to the use compounds of the general formula III above or pharmaceutically acceptable salts, derivatives, prodrugs or stereoisomers thereof in the treatment of cancer, or in the preparation of a medicament for the treatment of cancer.

In a further aspect the present invention is also directed to the use of compounds of the general formula III above or pharmaceutically acceptable salts, derivatives, prodrugs or stereoisomers thereof as topoisomerase I inhibitors.

DETAILED DESCRIPTION OF THE INVENTION

Fifteen years of efforts in targeting topoisomerase I for the discovery of anticancer agents have lead to the identification of several families of compounds capable of stabilizing DNA-topoisomerase I covalent complexes. The lead series is with no doubt the camptothecin family with two drugs, topotecan and irinotecan, approved for cancer treatment and several second (e.g. lurtotecan, exatecan) and third (e.g. diflomotecan) generations of camptothecin analogs currently in clinical trials. However, apart from the camptothecins, only a few topoisomerase I poisons have reached phase I clinical trials. Promising results have been reported with glycosyl indolocarbazoles but so far there is still no non-CPT topoisomerase I poisons in advanced clinical trials. The need for new series of topoisomerase I poisons remains pressing.

We have now surprisingly found that the natural lamellarins and their analogs are potent Topoisomerase I inhibitors, and that they exhibit sequence specificity profiles distinct from Camptothecin which is a well know Topoisomerase I inhibitor and chemotherapeutic agent, suggesting that they recognize differently with the topoisomerase I-DNA interface.

Therefore the invention is directed at compounds of formula III as defined above, their use as antitumoral agents and pharmaceutical compositions containing them.

The following gives guidance for the substituents in formulae III and IV:

Preferred R' groups are present in groups of formula R', COR' or OCOR' and include alkyl or alkenyl, that may be substituted at one or more available positions by one or more suitable groups, e.g., halogen such as fluoro, chloro, bromo and iodo, especially ω-chloro or perfluoro; aminoalkyl groups such as groups having one or more N atoms and from 1 to about 12 carbon atoms or from 1 to about 6 carbon atoms, and especially including substituted or unsubstituted aminoacids or aminoacid chains, notably glycine, alanine, arginine, asparagine, asparaginic acid, cystein, glutamine, glutamic acid, histidine, isoleucine, leucine, lysine, methionine, phenylalanine, proline, serine, threonine, tiyptophan, tyrosine or valine, especially protected forms of such amino acids; carbocylic aryl having 6 or more carbons, particularly phenyl; and aralkyl such as benzyl; heterocyclic groups including heteroalicyclic and heteroaromatic groups, especially with 5 to 10 ring atoms of which 1 to 4 are heteroatoms, more preferably heterocyclic groups with 5 or 6 ring atoms and 1 or 2 heteratoms or with 10 ring atoms and 1 to 3 heteroatoms, the heterocyclic groups optionally being substituted with one or more of the subsitituents permitted for R' and especially amino such as dimethylamino or with keto.

Suitable halogen substituents in the compounds of the present invention include F, Cl, Br and I.

Alkyl groups preferably have from 1 to 24 carbon atoms. One more preferred class of alkyl groups has 1 to about 12 carbon atoms, yet more preferably 1 to about 8 carbon atoms, still more preferably 1 to about 6 carbon atoms, and most preferably 1, 2, 3 or 4 carbon atoms. Another more preferred class of alkyl groups has 12 to about 24 carbon atoms, yet more preferably 12 to about 18 carbon atoms, and most preferably 13, 15 or 17 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members.

Preferred alkenyl and alkynyl groups in the compounds of the present invention have one or more unsaturated linkages and from 2 to about 12 carbon atoms, more preferably 2 to about 8 carbon atoms, still more preferably 2 to about 6 carbon atoms, even more preferably 2, 3 or 4 carbon atoms. The terms alkenyl and alkynyl as used herein refer to both cyclic and noncyclic groups, although straight or branched noncyclic groups are generally more preferred.

Alkylidene groups may be branched or unbranched and preferably have from 1 to 12 carbon atoms. One more preferred class of alkylidene groups has from 1 to about 8 carbon atoms, yet more preferably from 1 to about 6 carbon atoms, and most preferably 1, 2, 3 or 4 carbon atoms. Methylidene, ethylidene and propylidene including isopropylidene are particularly preferred alkylidene groups in the compounds of the present invention.

Preferred alkylsulfinyl groups in the compounds of the present invention include those groups having one or more sulfoxide (SO) groups and from 1 to about 12 carbon atoms, more preferably from 1 to about 8 carbon atoms, and still more preferably 1 to about 6 carbon atoms. Alkylsulfinyl groups having 1, 2, 3 or 4 carbon atoms are particularly preferred.

Preferred alkylsulfonyl groups in the compounds of the present invention include those groups having one or more sulfonyl ($SO_2$) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred.

Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties.

Suitable heterocyclic groups include heteroaromatic and heteroalicyclic groups. Suitable heteroaromatic groups in the compounds of the present invention contain one, two or three heteroatoms selected from N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazol. Suitable heteroalicyclic groups in the compounds of the present invention contain one, two or three heteroatoms selected from N, O or S atoms and include, e.g., tetrahydrofuranyl, tetrahydropyranyl, piperidinyl, morpholino and pyrrolindinyl groups.

Suitable carbocyclic aryl groups in the compounds of the present invention include single and multiple ring compounds, including multiple ring compounds that contain separate and/or fused aryl groups. Typical carbocyclic aryl groups contain 1 to 3 separate or fused rings and from 6 to about 18 carbon ring atoms. Specifically preferred carbocyclic aryl groups include phenyl including substituted phenyl such as 2-substituted phenyl, 3-substituted phenyl, 2.3-substituted phenyl, 2.5-substituted phenyl, 2.3.5-substituted and 2.4.5-substituted phenyl, including where one or more of the phenyl substituents is an electron-withdrawing group such as halogen, cyano, nitro, alkanoyl, sulfinyl, sulfonyl and the like; naphthyl including 1-naphthyl and 2-naphthyl; biphenyl; phenanthryl; and anthracyl.

References herein to substituted R' groups in the compounds of the present invention refer to the specified moiety, typically alkyl or alkenyl, that may be substituted at one or more available positions by one or more suitable groups, e.g., halogen such as fluoro, chloro, bromo and iodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having those having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl (e.g., R being a substituted or unsubstituted biphenyl moiety); and aralkyl such as benzyl; heterocyclic groups including heteroalicyclic and heteroaromatic groups, especially with 5 to 10 ring atoms of which 1 to 4 are heteroatoms, more preferably heterocyclic groups with 5 or 6 ring atoms and 1 or 2 heteratoms or with 10 ring atoms and 1 to 3 heteroatoms.

As further guidance, we prefer as substituents for $R_1$-$R_9$ and $R'_2$-$R'_6$:

Amino Acids and Peptides (L)-Val-OH; (L)-N-Boc-Val-OH (D)-Val-OH; (D)-N-Boc-Val-OH (L)-Ala-OH; (L)-N-Boc-Ala-OH; (L)-N-Alloc-Ala-OH; (L)-N-Fmoc-Ala-OH (L)-Phe-OH; (L)-N-Boc-Phe-OH (L)-N-Boc-Lys(Cbz)-OH (L)-Leu-OH; (L)-N-Boc-Leu-OH (L)-Pro-OH; (L)-N-Boc-Pro-OH (L)-Trp-OH; (L)-N-Boc-Trp-OH (L)-Ile-OH; (L)-N-Boc-Ile-OH (L)-Ser(Bn)-OH; (L)-N-Boc-Ser(Bn)-OH (L)-Cys(Fm)-OH; (L)-N-Boc-Cys(Fm)-OH
(L)-N-Boc-β-Leu-OH
(L)-N-Boc-Lys(Boc) Gly-OH
(L)-AlaAla-OH; (L)-N-Boc-AlaAla-OH Esters
Hydrocinnamoyl
Cyclohexylpropyl
Methanosulfonyl (Ms)
Trifluoromethanosulfonyl (Tf)
Octanoyl
Biotin
Acetyl
Coumarin 3-carboxyl
2[(4-fluorophenyl)thio]acetyl
4-fluorenecarboxyl
9H-fluorene-4-carboxyl
2,3,4,5-Tetrafluorobenzoyl
4-Pentynoyl
4-Methyl cinnamoyl
3,5-Dibromobenzoyl
5(2-Phenyleth-1-ynyl)nicotinyl
6-(Boc-amino)caproyl
6-Aminocaproyl
3-(Boc-amino)propyl
3-Aminopropyl Ethers
Methyl
Isopropyl
Benzyl
4-Methoxybenzyl
Methoxymethyl
Methilenedioxy
Tert-butyldiphenylsilyl Nitrogen Compounds
Nitro
Amino
Methylamino
Dimethylamino
Benzophenone imine Phosphates
Diethyl phosphate Halogens
Cl, Br, I Cyanides
CN The term "pharmaceutically acceptable salts, derivatives, prodrugs" refers to any pharmaceutically acceptable salt, ester, solvate, hydrate or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

The compounds of the invention may be in crystalline form either as free compounds or as solvates (e.g. hydrates) and it is intended that both forms are within the scope of the present invention. Methods of solvation are generally known within the art.

Any compound that is a prodrug of a compound of formula III is within the scope and spirit of the invention. The term "prodrug" is used in its broadest sense and encompasses those derivatives that are converted in vivo to the compounds of the invention. Such derivatives would readily occur to those skilled in the art, and include, for example, compounds where a free hydroxy group is converted into an ester derivative.

The compounds of the present invention represented by the above described formula III may include enantiomers depending on their asymmetry or diastereoisomers. The single isomers and mixtures of the isomers fall within the scope of the present invention.

The compound of the present invention can be prepared synthetically from the intermediate compound Va described in the PCT Int. Appl WO 98 50365. Numerous active antitumoral compounds have been prepared from this compound and it is believed that many more compounds can be formed in accordance with the teachings of the present disclosure.

Va

The compounds of formula III can be prepared from simple starting materials based on the following retrosynthesis.

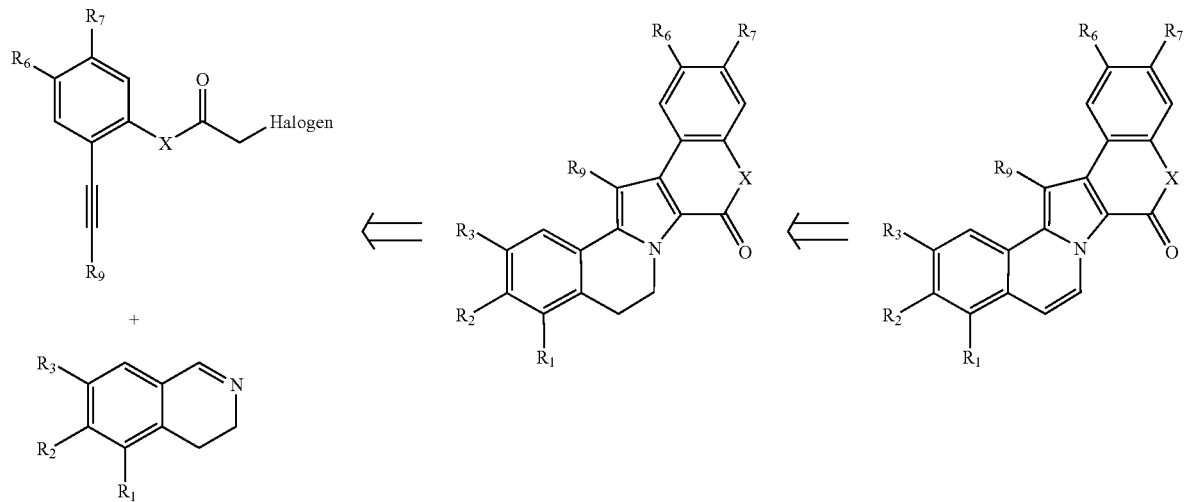

Dependent on the choice of the R substituents of the starting materials or the chemical transformations into different definitions of this R, the methodology can provide access to a wide range of Lamellarins analogs as exemplified herein.

The preparation of compounds of general formula III is illustrated below for $R_9$ as H, Halogen, substituted or unsubstituted aryl or substituted or unsubstituted heteroaromatic.

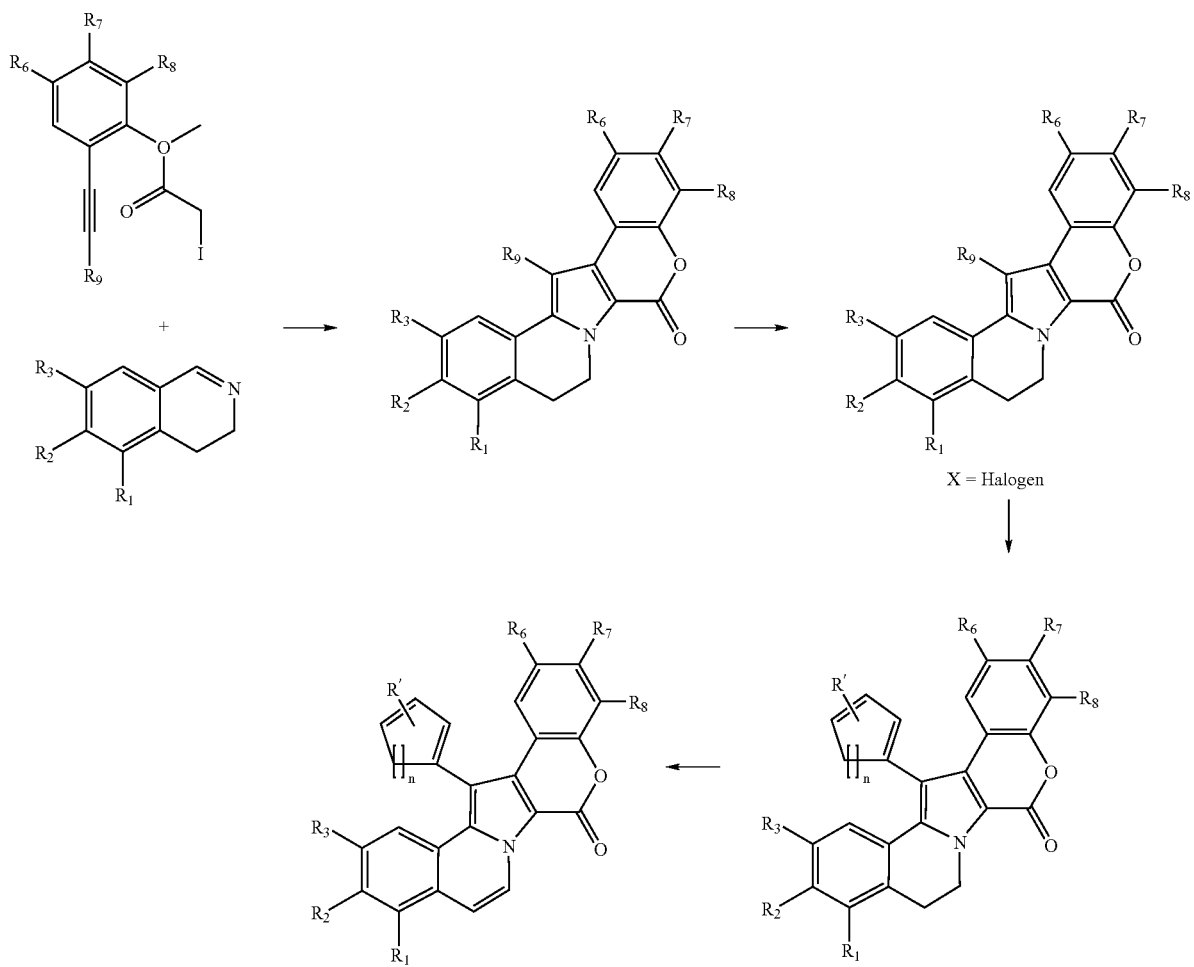

The preparation of compounds of general formula IV is illustrated below:

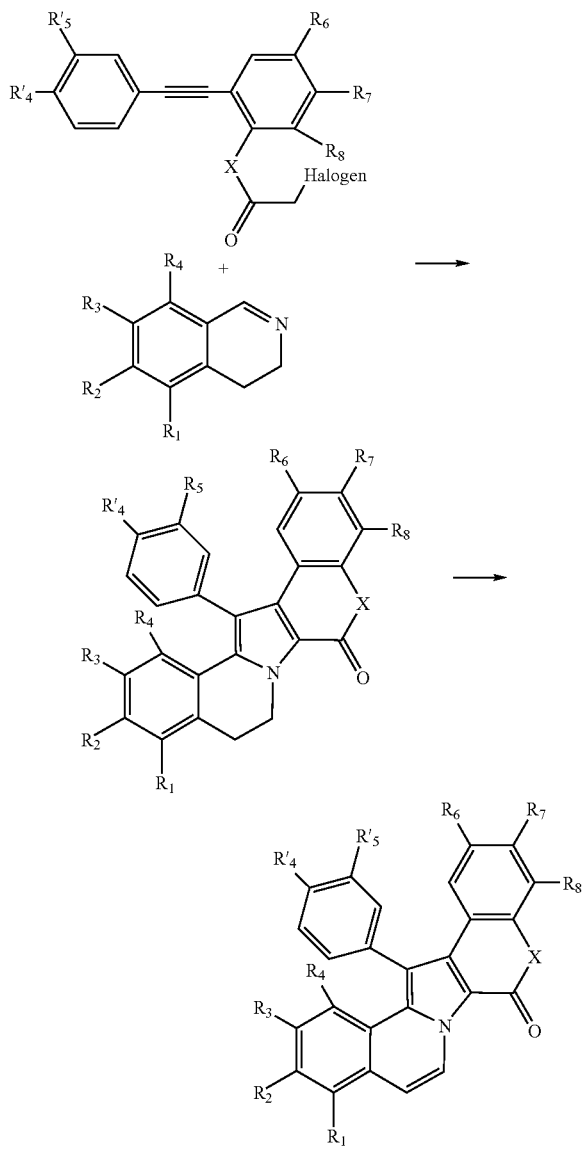

Further details are given in the the experimental procedures and the physicochemical characteristics of the compounds in the examples.

Another especially preferred embodiment of the present invention is pharmaceutical compositions useful as antitumor agents which contain as active ingredient a compound or compounds of the invention, as well as the processes for their preparation.

An important feature of the above described compounds of formula III is their bioactivity and in particular their cytotoxic activity. With this invention we provide novel pharmaceutical compositions of compounds of general formula III that possess cytotoxic activity, and their use as antitumor agents. Thus the present invention further provides pharmaceutical compositions comprising a compound of this invention, a pharmaceutically acceptable salts, derivatives, prodrugs or stereoisomers thereof with a pharmaceutically acceptable carrier.

Examples of pharmaceutical compositions include any solid (tablets, pills, capsules, granules etc.) or liquid (solutions, suspensions or emulsions) with suitable composition for oral, topical or parenteral administration.

Administration of the compounds or compositions of the present invention may be any suitable method, such as intravenous infusion, oral preparation, intraperitoneal and intravenous preparation. We prefer that infusion times of up to 24 hours are used, more preferably 2-12 hours, with 2-6 hours most preferred. Short infusion times which allow treatment to be carried out without an overnight stay in hospital are especially desirable. However, infusion may be 12 to 24 hours or even longer if required. Infusion may be carried out at suitable intervals of say 1 to 4 weeks. Pharmaceutical compositions containing compounds of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of this invention may be used with other drugs to provide a combination therapy. The other drugs may form part of the same composition, or be provided as a separate composition for administration at the same time or a different time.

Antitumoral activities of these compounds include among others leukaemias, lung cancer, colon cancer, kidney cancer, prostate cancer, ovarian cancer, breast cancer, pancreas cancer, cervix cancer, sarcomas and melanomas.

The present invention will be further explained with the following examples. These examples are illustrative of the present invention and should not be interpreted as limitative.

EXAMPLES

Example 1

Synthesis of Compounds 1-240

General Procedure A

A 0.15M suspension of the corresponding Isopropoxylated-Lamellarin (1 eq.) and $AlCl_3$ (1.3 eq. per isopropoxy group) in anhydrous dichloromethane was stirred at room temperature until the reaction was completed (2 to 6 h) under Argon atmosphere. Methanol was added, the solvent was evaporated under reduced pressure and the residue was purified by chromatography on silica gel to provide the corresponding Lamellarin.

General Procedure B

A solution of anhydrous dichloromethane/TFA (3:1) was added to the corresponding Boc-aminoacid-Lamellarin (0.01M) at 0° C. under Argon atmosphere. The reaction mixture was stirred at room temperature for 1 h. The solvent was evaporated under reduced pressure and the mixture was treated with dichloromethane in order to remove the remaining TFA. After final evaporation to dryness, the corresponding Lamellarin was collected by triturating and filtrating in ethyl ether.

General Procedure C

A solution of the corresponding Boc-aminoacid-Lamellarin in a 3.0M solution of HCl in ethyl acetate was stirred at room temperature for 30 min. The resulting suspension was filtered and the solid was washed with ethyl acetate and hexanes to provide the corresponding Lamellarin.

General Procedure D

To a 0.01M suspension of Lamellarin (1 eq.) in anhydrous dichloromethane, the corresponding carboxylic acid (2 eq. per hydroxy group), 1-(3-dimethylaminopropyl)-3-ethylcarbodiimide hydrochloride (2 eq. per hydroxy group) and dimethyl-aminopyridine (0.2 eq. per hydroxy group) were added. The mixture was stirred under argon atmosphere at room temperature for 6 h. The resulting solution was diluted with dichloromethane, washed with water and saturated sodium bicarbonate. The organic layer was dried over anhydrous sodium sulfate and the solvent removed under vacuum. The residue was purified by chromatography on silica gel to provide the corresponding Lamellarin.

General Procedure E

A 0.02M solution of the corresponding Lamellarin (1 eq.) and 2,3-dichloro-5,6-dicyano-1,4-benzoquinone (1.3 eq.) in chloroform was heated at 65° C. until the reaction was completed. The mixture was cooled to room temperature and the solvent evaporated under reduced pressure. The residue was purified by chromatography on silica gel to provide the corresponding Lamellarin.

General Procedure F

To a 0.01M solution of Lamellarin (1 eq.) in dichloromethane, pyridine (1.1 eq. per hydroxy group) and the corresponding acid chloride (1.1 eq. per hydroxy group) were added under argon atmosphere and stirred at room temperature for 3 h. The reaction mixture was washed with saturated solution of sodium bicarbonate, dried over anhydrous sodium sulfate, filtered and the solvent was evaporated under reduced pressure. The residue was purified by chromatography on silica gel to provide the corresponding Lamellarin.

General Procedure G

Iodo-acetic acid 5-isopropoxy-2-(4-isopropoxy-3-methoxy-phenylethynyl)-4-methoxy-phenyl ester (1 eq.) was added in one portion to a 0.1M solution of the corresponding dihydro-isoquinoline or isoquinoline (1.1 eq.) in anhydrous dimethylacetamide under argon atmosphere. The solution was stirred at room temperature for 14 hours, then triethylamine (1.1 eq.) was added and the reaction mixture was heated at 80° C. for 19 hours. The mixture was cooled, Fremy's Salt (1.1 eq) and sodium carbonate saturated solution was added and the suspension was stirred for 1 hour. The mixture was treated with sodium bicarbonate saturated solution and extracted with dichloromethane. The organic layers were dried over anhydrous sodium sulfate and the solvent was evaporated under reduced pressure. The resulted residue was purified by chromatography on silica gel to provide the corresponding Lamellarin.

General Procedure H

Iodo-acetic acid 5-isopropoxy-2-(4-isopropoxy-3-methoxyphenyl-ethynyl)-4-methoxy-phenyl ester (1 eq.) was added in one portion to a 0.1 M solution of the corresponding dihydro-isoquinoline or isoquinoline (1.1 eq.) in dry 1,2-dichloroethane under argon atmosphere. The solution was stirred at room temperature for 14 hours, then diisopropyl-ethylamine (1.1 eq.) was added and the reaction mixture was heated at 85° C. for 32 hours. The resulting mixture was cooled, silica gel (1 g per mmol) was added and the solvent was evaporated under reduced pressure. The resulted residue was subjected to flash chromatography on silica gel (sequential elution with 5:5:1 to 5:5:2 hexane-dichloromethane-ether) to provide the corresponding Lamellarin.

General Procedure I

To a 0.015M suspension of the corresponding Lamellarin (1 eq.) in anhydrous dichloromethane at 0° C., N-phenyltrifluoro-methanesulfonimide (4 eq.), triethylamine (7 eq.) and dimethyl amino-pyridine (0.2 eq.) were added and the mixture was stirred to room temperature for 3 h. The mixture was diluted with dichloromethane, washed with sodium bicarbonate saturated solution, dried over anhydrous sodium sulfate and evaporated to dryness. The residue was purified by chromatography on silica gel to provide the corresponding Lamellarin.

General Procedure J

To a 0.005M solution of Lamellarin (1 eq.) in methanol, palladium/C 10% (1 eq., w/w) was added and the resulting suspension was stirred at room temperature under hydrogen atmosphere. The mixture was filtered on celite and washed with dichloromethane. Evaporation of the solvent gave the corresponding Lamellarin.

General Procedure K

To a 0.01M suspension of Lamellarin (1 eq.) in anhydrous dichloromethane, the corresponding carboxylic acid (2 eq. per hydroxy group), 1,3-dicyclohexylcarbodiimide (2 eq. per hydroxy group) and dimethyl-aminopyridine (0.2 eq. per hydroxy group) were added. The mixture was stirred under argon atmosphere at room temperature for 6 h. The resulting solution was diluted with dichloromethane, washed with water and saturated sodium bicarbonate. The organic layer was dried over anhydrous sodium sulfate and the solvent removed under vacuum. The residue was purified by chromatography on silica gel to provide the corresponding Lamellarin.

General Procedure L

A 0.01M mixture of the corresponding Lamellarin in acetic anhydride/pyridine (1:2) was stirred overnight at room temperature under argon atmosphere. The solvent was evaporated under reduced pressure to provide the acylated-Lamellarin.

General Procedure M

To a 0.03M solution of 189 (1 eq.) in toluene/ethanol (10:1) under argon atmosphere, the corresponding boronic acid (2 eq.), tetrakis-triphenylphosphine palladium(0) (0.05 eq.) and sodium carbonate 2M (6 eq.) were added. The resulting mixture was heated at 90° C. for 16 hours, then water was added and the mixture was extracted with ethyl acetate. The organic layer was washed with sodium hydroxide 1M, water and brine. After drying over sodium sulfate and evaporation of the solvent under reduced pressure, the residue was purified by chromatography on silica gel to provide the corresponding Lamellarin.

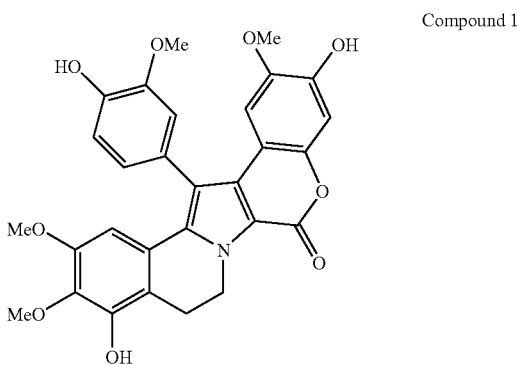

Compound 1

General procedure A (starting from 104) and chromatography on silica gel (CH$_2$Cl$_2$:MeOH, from 20:1 to 15:1) to afford 1 (2.27 g, 95%).

$^1$H NMR (300 MHz, CDCl$_3$) δ 7.13 (d, J=7.8 Hz, 1H), 7.06 (dd, J=7.8, 1.7 Hz, 1H), 6.98 (d, J=1.7 Hz, 1H), 6.93 (s, 1H), 6.59 (s, 1H), 6.38 (s, 1H), 6.02 (s, 1H), 5.85 (s, 1H), 5.82 (s, 1H), 5.00-4.80 (m, 1H), 4.70-4.50 (m, 1H), 3.88 (s, 3H), 3.87 (s, 3H), 3.49 (s, 3H), 3.36 (s, 3H), 3.20-3.00 (m, 2H). $^{13}$C NMR (75 MHz, CDCl$_3$) δ 155.6, 150.3, 147.2, 146.3, 146.1, 145.5, 145.4, 143.3, 135.4, 135.3, 128.1, 127.3, 124.2, 123.2, 115.5, 115.1, 113.8, 113.4, 113.0, 110.1, 103.9, 103.3, 101.8, 61.0, 56.2, 55.6, 55.5, 42.0, 21.4. MS (ESI) m/z: 532 (M+1)$^+$. Rf: 0.30 (CH$_2$Cl$_2$:MeOH, 20:1).

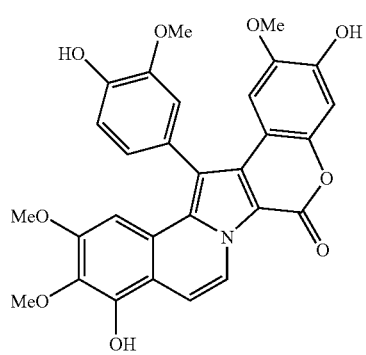

Compound 2

General procedure A (starting from 27) and chromatography on silica gel (CH$_2$Cl$_2$:MeOH, from 20:1 to 10:1) to afford 2 (8 mg, 80%).

$^1$H NMR (300 MHz, CDCl$_3$) δ 9.18 (d, J=7.5 Hz, 1H), 7.40 (d, J=7.5 Hz, 1H), 7.20-7.16 (m, 2H), 7.10 (s, 1H), 6.99 (s, 1H), 6.80 (s, 1H), 6.68 (s, 1H), 6.20 (br s, 1H), 5.80 (br s, 2H), 5.80 (br s, 2H), 3.94 (s, 3H), 3.91 (s, 3H), 3.52 (s, 3H), 3.46 (s, 3H). $^{13}$C NMR (75 MHz, CDCl$_3$) δ 155.5, 151.9, 147.3, 147.0, 146.3, 145.7, 144.5, 143.3, 134.8, 133.7, 129.3, 127.5, 124.7, 122.3, 121.4, 119.7, 115.2, 113.9, 113.8, 111.9, 109.8, 106.9, 104.6, 103.5, 98.3, 61.2, 56.3, 55.6, 55.1. MS (ESI) m/z: 529 (M+1)$^+$. Rf: 0.30 (CH$_2$Cl$_2$:MeOH, 20:1).

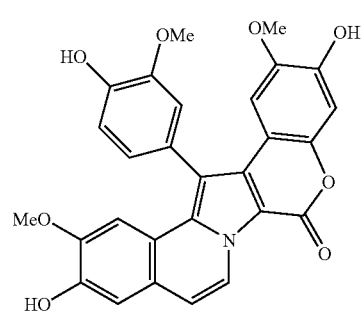

Compound 3

General procedure A (starting from 107) and chromatography on silica gel (EtOAc, 100%) to afford 3 (92 mg, 43%).

$^1$H NMR (300 MHz, DMSO-d$_6$) δ 9.92 (s, 1H), 9.81 (s, 1H), 9.32 (s, 1H), 8.98 (d, J=7.3 Hz, 1H), 7.22-6.98 (m, 6H), 6.85 (s, 1H), 6.70 (s, 1H), 3.75 (s, 3H), 3.36 (s, 6H). $^{13}$C NMR (75 MHz, DMSO-d$_6$) δ 154.3, 148.7, 148.5, 148.3, 147.8, 146.8, 146.3, 144.6, 134.1, 129.2, 128.9, 125.5, 124.7, 123.9, 117.6, 116.4, 115.1, 113.9, 112.3, 111.5, 110.8, 106.4, 105.7, 105.4, 103.7, 56.0, 55.1, 54.5. MS (APCI) m/z: 500 (M+1)$^+$. Rf: 0.60 (EtOAc).

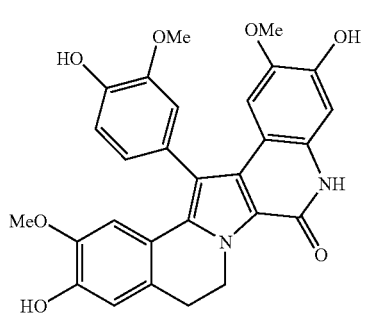

Compound 4

General procedure A (starting from 50) and chromatography on silica gel (CH$_2$Cl$_2$:MeOH, 10:1) to provide 4 (9.1 mg, 76%).

$^1$H NMR (300 MHz, CD$_3$OD) δ 7.07-7.05 (m, 2H), 6.99-6.97 (m, 1H), 6.80 (br s, 2H), 6.75 (s, 1H), 6.71 (s, 1H), 4.75 (m, 1H), 3.82 (s, 3H), 3.43 (s, 3H), 3.36 (s, 3H), 3.02 (br t, 2H). MS (ESI) m/z: 501 (M+1)$^+$. Rf: 0.32 (CH$_2$Cl$_2$:MeOH, 10:1).

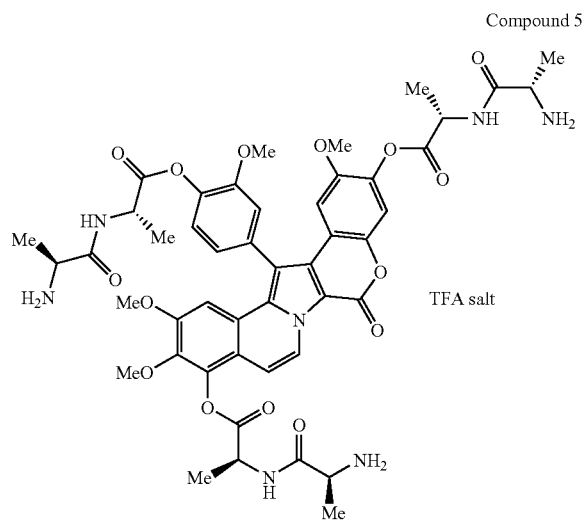

Compound 5

General procedure B (starting from 6) to afford 5 (30 mg, quant.).

$^1$H NMR (300 MHz, CD$_3$OD) δ 9.07 (br s, 1H), 7.60-7.10 (m, 5H), 6.90-6.60 (m, 2H), 4.85-4.60 (m, 3H), 4.10-3.90 (m, 3H), 3.84 (s, 6H), 3.50 (s, 3H), 3.44 (s, 3H), 1.80-1.50 (m, 18H). MS (ESI) m/z: 956 (M+1)$^+$.

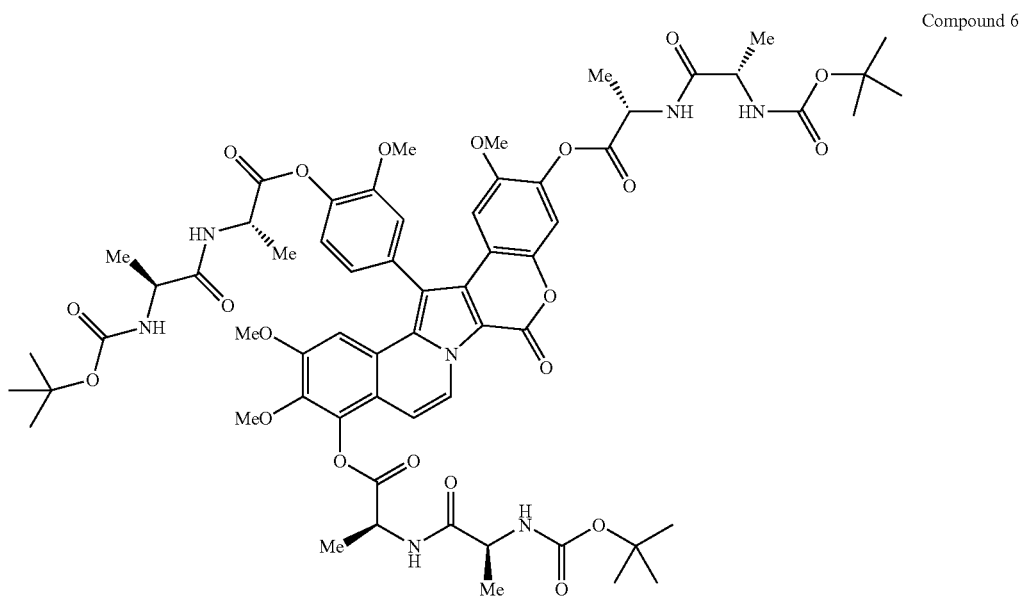

Compound 6

General procedure D (starting from 2 and Boc-Ala-Ala-OH) and chromatography on silica gel (CH$_2$Cl$_2$:MeOH, 20:1) to afford 6 (56 mg, 87%).

$^1$H NMR (300 MHz, CDCl$_3$) δ 9.02 (br s, 1H), 7.40-7.10 (m, 4H), 7.10-6.90 (m, 3H), 6.90-6.60 (m, 3H), 5.30-5.00 (m, 3H), 5.00-4.75 (m, 3H), 4.26 (br s, 3H), 3.85 (s, 6H), 3.47 (s, 3H), 3.43 (s, 3H), 1.80-1.30 (m, 45H). $^{13}$C NMR (75 MHz, CDCl$_3$) δ 173.1, 172.6, 171.3, 171.2, 171.1, 171.0, 170.9, 155.8, 154.8, 153.4, 153.3, 153.2, 152.4, 152.3, 147.6, 146.8, 145.5, 143.9, 141.8, 140.2, 140.0, 139.5, 138.9, 135.2, 134.8, 133.3, 133.2, 128.3, 128.2, 124.1, 123.8, 123.6, 121.1, 118.4, 115.9, 115.7, 115.5, 112.2, 111.9, 111.4, 109.1, 106.8, 106.4, 106.1, 104.5, 103.7, 80.5, 61.1, 56.6, 55.9, 55.8, 53.6, 50.2, 48.6, 48.4, 48.3, 28.5, 18.6, 18.3. MS (ESI) m/z: 1279 (M+23)$^+$. Rf: 0.24 (CH$_2$Cl$_2$:MeOH, 20:1).

General procedure D (starting from 109 and Boc-Ala-Ala-OH) and chromatography on silica gel (CH$_2$Cl$_2$:MeOH, 20:1) to afford 7 (46 mg, 75%).

$^1$H NMR (300 MHz, CDCl$_3$) δ 7.26-6.50 (m, 10H), 5.13-5.11 (m, 3H), 4.87-4.65 (m, 5H), 4.23 (br s, 3H), 3.78 (s, 3H), 3.39 (s, 3H), 3.32 (s, 3H), 3.06 (br t, 2H), 1.63-1.53 (m, 9H), 1.44-1.35 (m, 36H). MS (ESI) m/z: 1250 (M+23)$^+$. Rf: 0.40 (CH$_2$Cl$_2$:MeOH, 20:1).

Compound 7

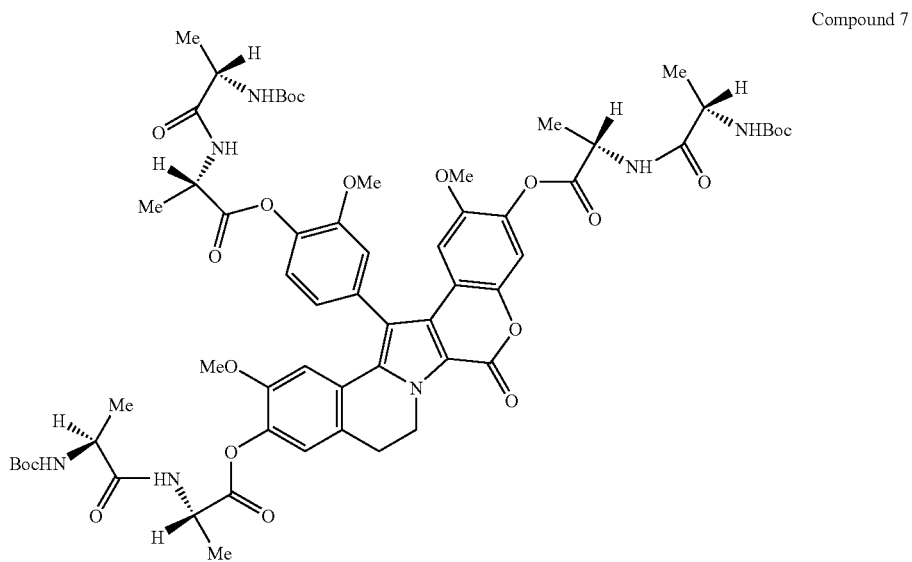

Compound 8

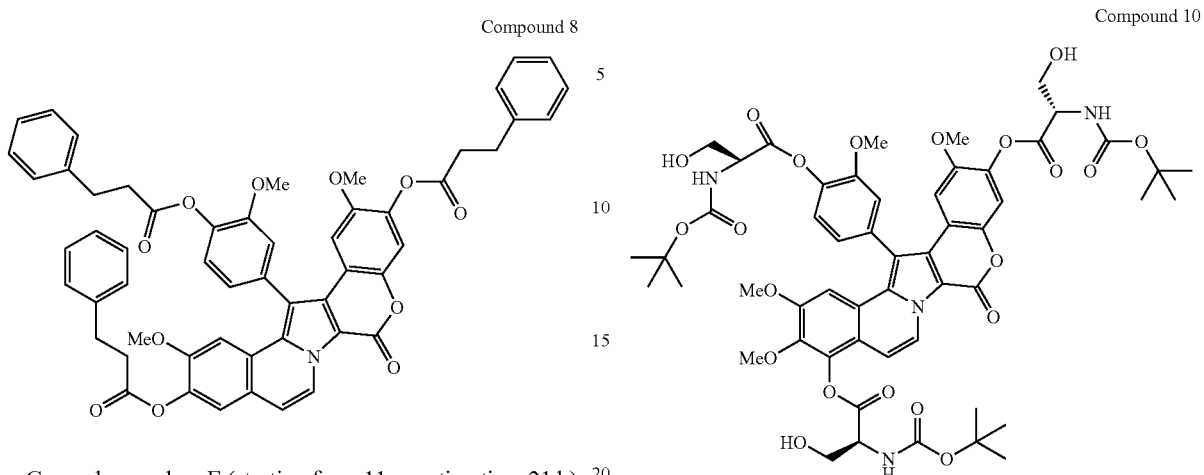

Compound 10

General procedure E (starting from 11, reaction time 21 h) and chromatography on silica gel (CH$_2$Cl$_2$:MeOH, 100:1) to afford 8 (16 mg, 70%).

$^1$H NMR (300 MHz, CDCl$_3$) δ 9.23 (d, J=7.3 Hz, 1H), 7.39-7.20 (m, 20H), 7.08-7.03 (m, 2H), 6.80 (s, 1H), 3.79 (s, 3H), 3.42 (s, 6H), 3.16-3.06 (m, 6H), 3.00-2.90 (m, 6H). $^{13}$C NMR (75 MHz, CDCl$_3$) δ 170.8, 170.7, 170.6, 155.1, 152.4, 151.0, 147.7, 145.4, 140.9, 140.2, 140.1 (2C), 139.7, 134.2, 133.5, 128.5 (6C), 128.4 (2C), 128.4 (4C), 128.2, 126.4, 126.4 (2C), 124.0, 123.8, 123.6, 123.6, 123.1, 120.7, 115.6, 115.0, 112.8, 112.3, 112.1, 109.0, 106.4, 106.1, 56.2, 55.7, 55.6, 35.4 (3C), 30.9, 30.8 (2C). MS (APCI) m/z: 896 (M+1)$^+$. Rf: 0.25 (CH$_2$Cl$_2$:MeOH, 200:1).

General procedure E (starting from 60, reaction time 22 h) and chromatography on silica gel (CH$_2$Cl$_2$:MeOH, 20:1) to afford 10 (17 mg, 61%).

$^1$H NMR (300 MHz, CDCl$_3$) δ 9.05 (br s, 1H), 7.40-7.00 (m, 6H), 6.72 (d, J=12.4 Hz, 1H), 5.70 (br s, 1H), 5.55 (br s, 2H), 4.90-4.60 (m, 3H), 4.32 (br s, 2H), 4.20-3.80 (m, 9H), 3.49 (s, 3H), 3.46 (s, 3H), 3.00-2.50 (m, 3H), 1.51 (s, 18H), 1.47 (s, 9H). $^{13}$C NMR (75 MHz, CDCl$_3$) δ 169.6, 169.2, 155.6, 154.5, 153.0, 151.7, 146.8, 145.5, 141.3, 139.8, 139.2, 138.7, 134.7, 133.0, 127.9, 124.0, 123.4, 120.9, 118.2, 115.8, 115.3, 112.1, 111.8, 108.9, 106.9, 106.2, 104.3, 80.6, 64.0, 63.7, 61.1, 56.5, 56.1, 55.8, 55.6, 28.3. MS (ESI) m/z: 1113 (M+23)$^+$, 1091 (M+1)$^+$. Rf: 0.30 (CH$_2$Cl$_2$:MeOH, 20:1).

Compound 9

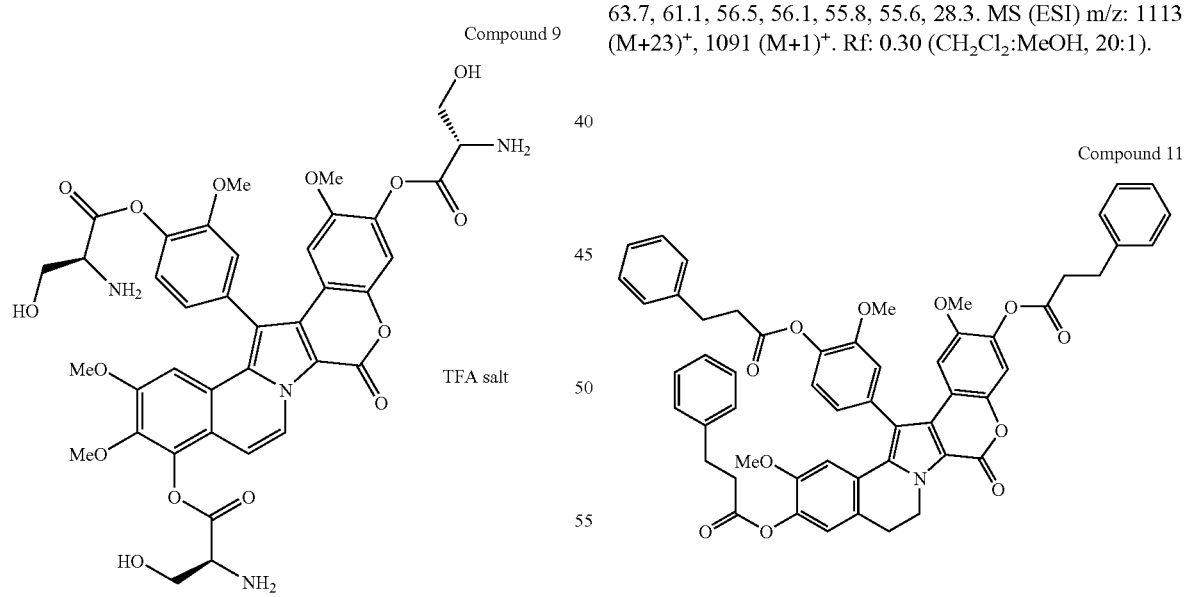

Compound 11

General procedure B (starting from 10) to afford 9 (12 mg, quant.).

$^1$H NMR (300 MHz, CD$_3$OD) δ 9.15 (d, J=7.5 Hz, 1H), 7.60-7.50 (m, 2H), 7.30-7.35 (m, 2H), 7.29 (s, 1H), 7.23 (s, 1H), 6.89 (s, 1H), 4.73 (br t, 1H), 4.54 (br t, 1H), 4.44 (br t, 1H), 4.30-4.10 (m, 6H), 3.89 (s, 6H), 3.54 (s, 3H), 3.47 (s, 3H). MS (ESI) m/z: 791 (M+1)$^+$.

General procedure F (starting from 109 and hydrocinnamoyl chloride) and chromatography on silica gel (CH$_2$Cl$_2$:MeOH, from 200:1 to 100:1) to afford 11 (31 mg, 69%).

$^1$H NMR (300 MHz, CDCl$_3$) δ 7.37-7.21 (m, 15H), 7.13-7.02 (m, 4H), 6.87 (s, 1H), 6.77 (s, 1H), 6.68 (s, 1H), 4.92-4.83 (m, 1H), 4.79-4.70 (m, 1H), 3.76 (s, 3H), 3.39 (s, 3H), 3.32 (s, 3H), 3.13-3.04 (m, 8H), 2.97-2.87 (m, 6H). $^{13}$C NMR (75 MHz, CDCl$_3$) δ 171.0, 170.7, 170.6, 155.1, 152.2, 149.8, 147.7, 144.9, 140.1 (3C), 140.0, 139.4, 138.9, 135.0, 133.9, 128.5 (6C), 128.4 (6C), 127.1, 126.4, 126.4, 126.4, 125.9, 125.6, 123.8, 123.1, 122.6, 116.0, 115.9, 114.9, 114.6, 111.9, 109.7, 105.4, 56.1, 55.7, 55.5, 42.4, 35.5 (3C), 30.9, 30.9, 30.8, 28.0. MS (ESI) m/z: 898 (M+1)$^+$. Rf: 0.25 (CH$_2$Cl$_2$:MeOH, 200:1).

(d, J=7.3 Hz, 1H), 7.08 (s, 1H), 7.05 (d, J=4.0 Hz, 1H), 6.83 (s, 1H), 4.76 (br t, J=6.8 Hz, 1H), 4.61 (m, 1H), 3.95 (s, 3H), 3.86 (s, 3H), 3.46-3.31 (m, 7H). MS (ESI) m/z: 830.1 (M+23)$^+$, 808 (M+1)$^+$.

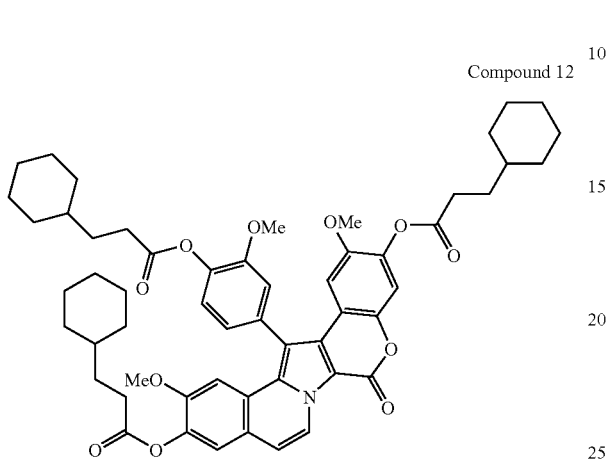

Compound 12

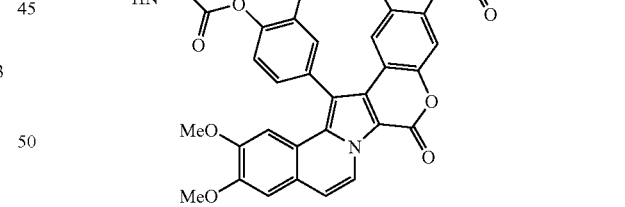

Compound 14

General procedure E (starting from 106, reaction time 17 h) and chromatography on silica gel (CH$_2$Cl$_2$:MeOH, 50:1) to afford 12 (21 mg, quant.).

$^1$H NMR (300 MHz, CDCl$_3$) δ 9.23 (d, J=7.3 Hz, 1H), 7.38 (s, 1H), 7.29-7.13 (m, 5H), 7.06 (d, J=7.5 Hz, 1H), 6.81 (s, 1H), 3.82 (s, 3H), 3.45 (s, 6H), 2.67-2.57 (m, 6H), 1.82 (m, 21H), 1.40-1.13 (m, 12H), 1.04-0.85 (m, 6H). $^{13}$C NMR (75 MHz, CDCl$_3$) δ 172.0, 171.9 (2C), 155.1, 152.5, 151.1, 147.9, 145.5, 141.0, 140.4, 139.9, 134.1, 133.6, 128.3, 124.1, 123.8, 123.6, 123.1, 120.7, 115.6, 115.0, 112.8, 112.3, 112.2, 109.0, 106.4, 106.1, 56.2, 55.8, 55.7, 37.3 (3C), 37.1 (3C), 33.0 (6C), 32.3, 32.3, 32.2, 31.6 (3C), 26.5 (2C), 26.3 (2C), 26.3 (2C). MS (ESI) m/z: 914 (M+1)$^+$. Rf: 0.17 (hexane:EtOAc, 4:1).

General procedure B (starting from 15) to afford 14 (11.6 mg, quant).

$^1$H NMR (300 MHz, CD$_3$OD) δ 9.05 (m, 1H), 7.58-7.47 (m, 2H), 7.38-7.31 (m, 3H), 7.38-7.10 (m, 4H), 6.88 (br d, 1H), 4.36 (m, 1H), 4.25 (m, 2H), 3.92 (s, 3H), 3.88 (s, 3H), 3.47 (s, 6H), 2.50-2.48 (m, 2H), 1.27 (d, J=6.1 Hz, 6H), 1.20 (d, J=6.8 Hz, 6H). MS (ESI) m/z: 712 (M+1)$^+$.

Compound 15

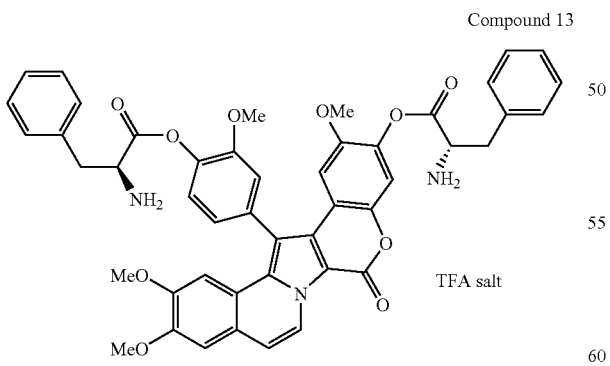

Compound 13

General procedure E (starting from 65, reaction time 20 h) and chromatography on silica gel (CH$_2$Cl$_2$:MeOH, 60:1) to afford 15 (29.0 mg, 90%).

$^1$H NMR (300 MHz, CDCl$_3$) δ 9.20 (d, J=7.6 Hz, 1H), 7.32-7.23 (m, 3H), 7.12-7.05 (m, 4H), 6.80 (d, J=9.2 Hz, 1H), 5.09 (br d, 2H), 4.52 (br s, 2H), 3.98 (s, 3H), 3.80 (s, 3H), 3.50 (s, 3H), 3.43 (s, 3H), 2.43-2.37 (m, 2H), 1.49 (s, 9H), 1.46 (s, 9H), 1.14-0.99 (m, 12H). $^{13}$C NMR (75 MHz, CDCl$_3$) δ 170.4, 155.7 (2C), 154.9, 152.2, 150.3, 149.6, 147.5, 145.5, 139.9, 139.3, 134.8, 134.2, 128.3, 128.2, 124.7, 123.9 (2C), 123.1, 118.9, 116.0, 115.3, 113.0, 112.1, 110.9, 108.4, 107.4,

General procedure B (starting from 58) to afford 13 (10.5 mg, quant).

$^1$H NMR (300 MHz, CD$_3$OD) δ 8.93 (d, J=7.1 Hz, 1H), 7.58 (d, J=7.8 Hz, 1H), 7.47-7.34 (m, 12H), 7.20 (s, 1H), 7.12

106.2, 105.1, 80.0 (2C), 58.6 (2C), 56.0, 55.9, 55.7, 55.6, 31.3, 31.2, 28.3 (9C), 19.2, 19.0, 17.1 (2C). MS (ESI) m/z: 934.2 (M+23)$^+$, 912 (M+1)$^+$. Rf: 0.54 (CH$_2$Cl$_2$:MeOH, 60:1).

General procedure B (starting from 122) to afford 17 (21 mg, quant.).

$^1$H NMR (300 MHz, CD$_3$OD) δ 9.13-9.09 (m, 1H), 7.63-7.52 (m, 3H), 7.44-7.22 (m, 4H), 6.89 (d, J=9.2 Hz, 1H), 4.36 (d, J=4.4 Hz, 1H), 4.32 (d, J=4.0 Hz, 1H), 4.25 (t, J=3.8 Hz, 1H), 3.91 (s, 3H), 3.48 (s, 6H), 2.61-2.44 (m, 3H), 1.29-1.19 (m, 18H). MS (ESI) m/z: 797 (M+1)$^+$.

Compound 16

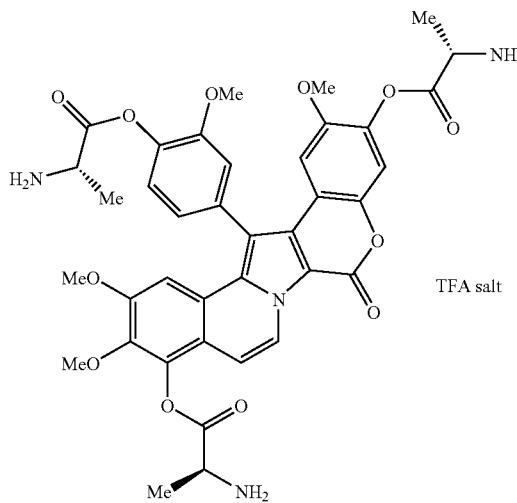

Compound 18

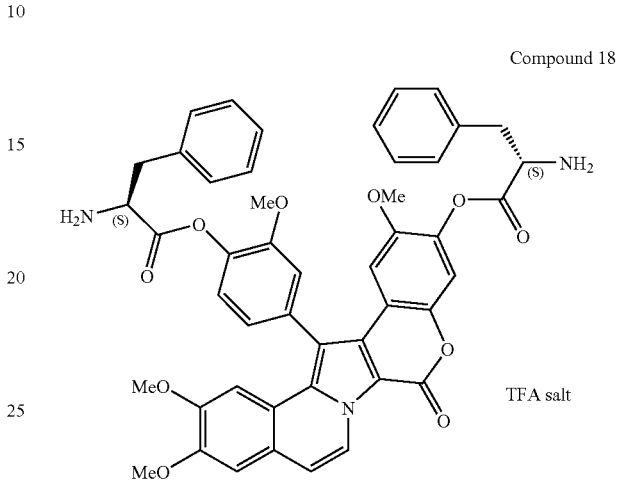

General procedure B (starting from 97) to afford 16 (31 mg, quant.).

$^1$H NMR (300 MHz, CD$_3$OD) δ 9.11 (dd, J=7.5, 2.3 Hz, 1H), 7.60-7.50 (m, 2H), 7.35 (t, J=6.6 Hz, 1H), 7.25-7.20 (m, 3H), 6.86 (d, J=9.5 Hz, 1H), 4.66 (q, J=7.3 Hz, 1H), 4.52 (q, J=7.3 Hz, 1H), 4.38 (q, J=7.1 Hz, 1H), 3.90 (d, J=3.2 Hz, 3H), 3.89 (d, J=1.8 Hz, 3H), 3.53 (d, J=2.7 Hz, 3H), 3.47 (s, 3H), 1.85 (d, J=7.0 Hz, 3H), 1.80 (d, J=7.1 Hz, 3H), 1.69 (dd, J=7.1, 4.0 Hz, 3H). MS (ESI) m/z: 743 (M+1)$^+$.

General procedure B (starting from 84) to afford 18 (21.6 mg, quant.).

$^1$H NMR (300 MHz, CD$_3$OD) δ 7.44-7.37 (m, 11H), 7.23-7.20 (m, 2H), 7.03 (s, 1H), 6.90 (s, 1H), 6.78 (m, 1H), 6.67 (s, 1H), 4.72-4.60 (m, 4H), 3.90 (s, 3H), 3.81 (s, 3H), 3.44 (s, 3H), 3.39-3.30 (m, 4H), 3.11 (br t, 2H). MS (ESI) m/z: 810 (M+1)$^+$.

Compound 17

Compound 19

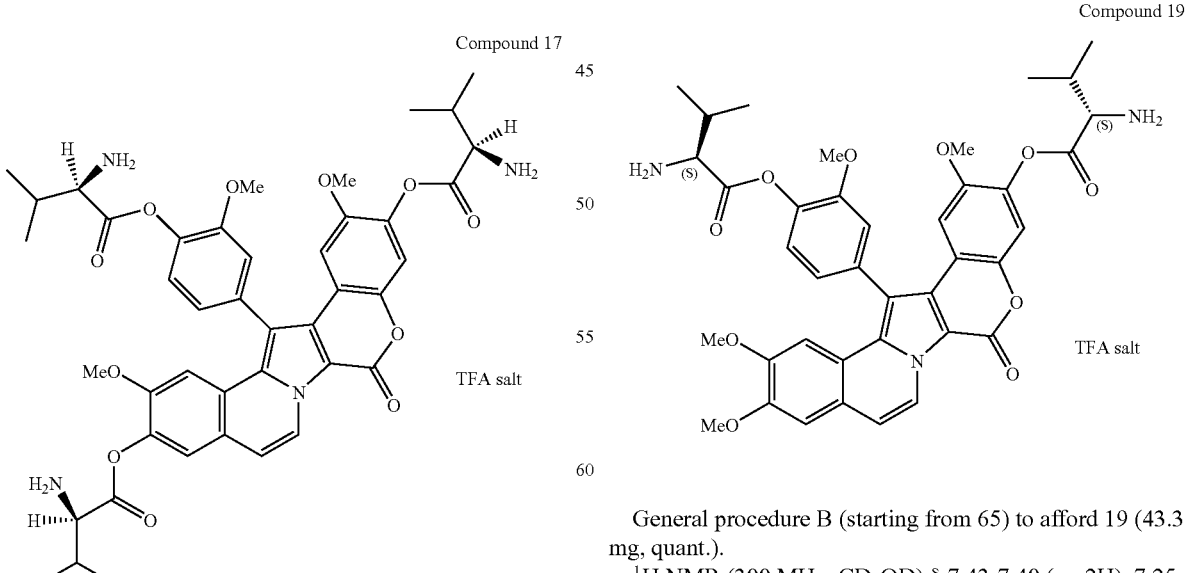

General procedure B (starting from 65) to afford 19 (43.3 mg, quant.).

$^1$H NMR (300 MHz, CD$_3$OD) δ 7.43-7.40 (m, 2H), 7.25-7.17 (m, 3H), 6.94 (br s, 1H), 6.80 (d, J=13.4 Hz, 1H), 6.69 (d, J=9.03 Hz, 1H), 4.90 (m, 2H), 4.32 (m, 1H), 4.22 (m, 2H), 3.86 (s, 3H), 3.45 (s, 3H), 3.36 (s, 3H), 3.13 (br t, 2H), 2.58-2.40 (m, 2H), 1.25 (br d, 6H), 1.17 (br d, 6H). MS (ESI) m/z: 736 (M+23)$^+$, 714 (M+1)$^+$.

Compound 20

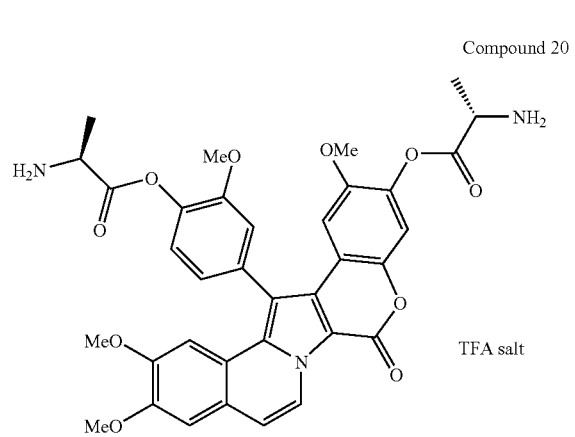

TFA salt

General procedure B (starting from 77) to afford 20 (11.7 mg, quant).

$^1$H NMR (300 MHz, CD$_3$OD) δ 9.03 (d, J=7.3 Hz, 1H), 7.57-7.48 (m, 2H), 7.37-7.32 (m, 1H), 7.26-7.25 (m, 1H), 7.21-7.20 (m, 2H), 7.11 (d, J=6.8 Hz, 1H), 6.87 (d, J=8.3 Hz, 1H), 4.52 (br q, J=6.8 Hz, 1H), 4.42 (br q, J=6.8 Hz, 1H), 3.91 (s, 3H), 3.90 (s, 3H), 3.48 (s, 6H), 1.85 (d, J=7.3 Hz, 1H), 1.71 (d, J=7.1 Hz, 1H). MS (ESI) m/z: 678 (M+23)$^+$, 656 (M+1)$^+$.

Compound 21

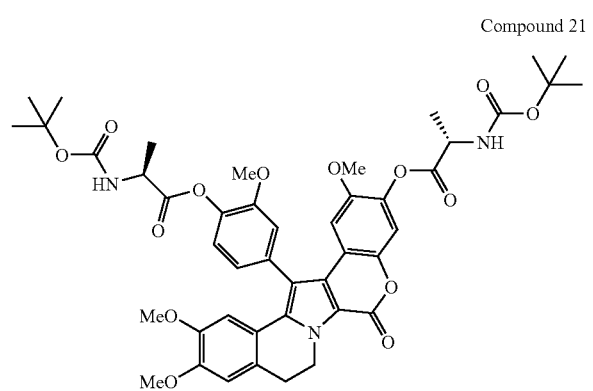

General procedure D (starting from 95 and Boc-Ala-OH) and chromatography on silica gel (CH$_2$Cl$_2$:MeOH, 60:1) to afford 21 (83.2 mg, 100%).

$^1$H NMR (300 MHz, CDCl$_3$) δ 7.23 (br s, 1H), 7.16-7.10 (m, 3H), 6.76 (s, 1H), 6.71-6.56 (m, 2H), 5.10 (m, 1H), 4.92-4.70 (m, 2H), 4.60-4.58 (m, 2H), 3.89 (s, 3H), 3.78 (s, 3H), 3.41 (s, 3H), 3.40 (s, 3H), 3.13 (t, J=7.1 Hz, 2H), 1.63-1.46 (m, 24H). $^{13}$C NMR (75 MHz, CDCl$_3$) δ 171.3, 154.9, 151.9, 149.1, 147.6, 147.3, 144.8, 139.6, 138.4, 135.8, 134.4, 127.0, 126.4, 123.6, 123.3, 119.5, 116.2, 114.8, 114.6, 114.3, 111.6, 110.9, 108.4, 105.4, 79.9 (2C), 56.1, 55.8, 55.7, 55.3, 49.3 (2C), 42.4, 28.4, 28.2 (6C), 18.5 (2C). MS (ESI) m/z: 880 (M+23)$^+$, 857 (M+1)$^+$. Rf: 0.15 (CH$_2$Cl$_2$:MeOH, 60:1).

Compound 22

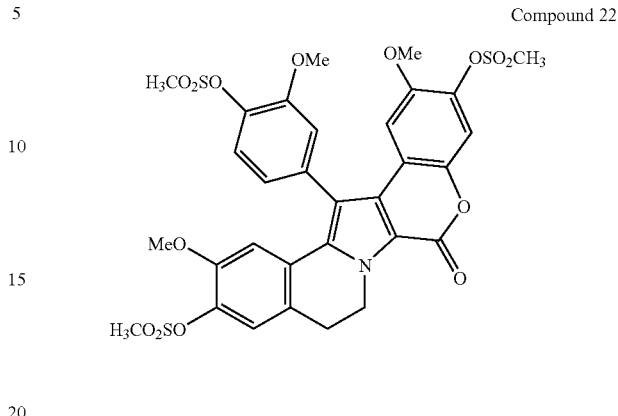

To a suspension of 109 (50 mg, 0.0997 mmol) in anhydrous CH$_2$Cl$_2$ (2 mL) under Argon at 0° C., Et$_3$N (83 μL, 0.5982 mmol) and methanesulfonyl chloride (47 μL, 0.5982 mmol) were added. The resulting mixture was stirred at 23° C. for 6 h, then quenched with H$_2$O and extracted with CH$_2$Cl$_2$ (3×20 mL).

The combined organic layers were washed with saturated aqueous solution of NaHCO$_3$, dried over anhydrous Na$_2$SO$_4$, filtered, and evaporated under vacuum. The resulting residue was purified on silica gel (CH$_2$Cl$_2$:MeOH, 80:1) to afford 22 as a pale yellow solid (47 mg, 64%).

$^1$H NMR (300 MHz, CDCl$_3$) δ 7.52 (d, J=8.1 Hz, 1H), 7.30 (s, 1H), 7.23-7.20 (m, 2H), 7.17 (d, J=1.6 Hz, 1H), 6.75 (s, 1H), 6.65 (s, 1H), 4.99-4.90 (m, 1H), 4.71-4.61 (m, 1H), 3.92 (s, 3H), 3.46 (s, 3H), 3.38 (s, 3H), 3.34 (s, 3H), 3.19 (s, 3H), 3.18 (s, 3H), 3.14 (t, J=6.0 Hz, 2H). $^{13}$C NMR (75 MHz, CDCl$_3$) δ 154.5, 152.8, 150.1, 148.0, 144.6, 138.0, 137.7, 136.9, 135.4, 134.4, 126.5, 126.4, 126.3, 125.6, 124.4, 123.3, 117.0, 115.8, 115.4, 115.2, 113.5, 109.9, 105.6. MS (ESI) m/z: 736 (M+1)$^+$. Rf: 0.33 (CH$_2$Cl$_2$:MeOH, 80:1).

Compound 23

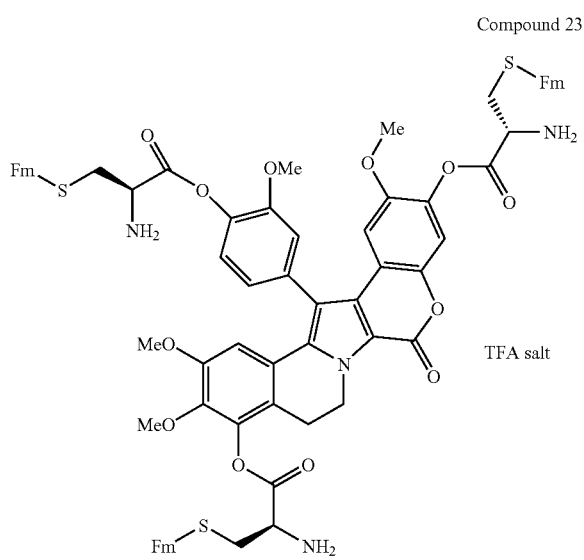

TFA salt

General procedure B (starting from 114) to give 23 (20 mg, quant.).

$^1$H NMR (300 MHz, CD$_3$OD) δ 7.90-7.60 (m, 12H), 7.45-7.20 (m, 16H), 6.80-6.70 (m, 2H), 4.80-4.40 (m, 5H), 4.35-4.20 (m, 3H), 3.74 (d, J=2.9 Hz, 3H), 3.71 (d, J=2.3 Hz, 3H), 3.55-3.30 (m, 12H) 3.35-3.00 (m, 6H), 2.91 (br s, 2H). MS (ESI) m/z: 1375 (M)$^+$.

Compound 24

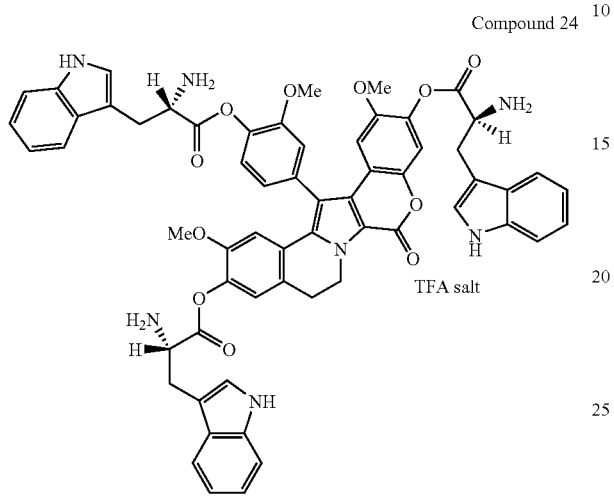

TFA salt

General procedure B (starting from 29) to afford 24 (27 mg, quant.)

$^1$H NMR (300 MHz, CD$_3$OD) δ 7.68 (d, J=8.1 Hz, 1H), 7.62 (s, 1H), 7.60 (s, 1H), 7.44 (s, 1H), 7.42 (s, 3H), 7.34 (s, 1H), 7.30 (s, 1H), 7.29 (s, 1H), 7.21-7.16 (m, 5H), 7.12-7.09 (m, 3H), 6.98 (s, 1H), 6.85 (d, J=2.0 Hz, 1H), 6.77-6.76 (m, 2H), 4.73-4.69 (m, 3H), 4.60 (br t, 2H), 3.87 (s, 3H), 3.77-3.34 (m, 6H), 3.43 (s, 3H), 3.34 (s, 3H). MS (ESI) m/z: 1060 (M+1)$^+$.

Compound 25

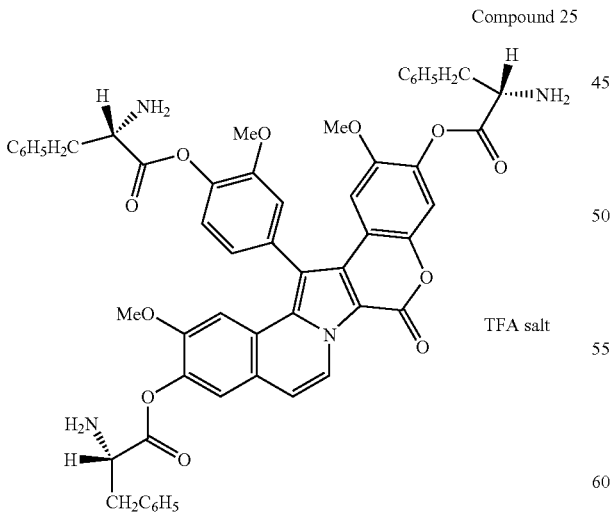

TFA salt

General procedure B (starting from 113) to afford 25 (20 mg, quant.).

$^1$H NMR (300 MHz, CD$_3$OD) δ 9.08 (d, J=7.5 Hz, 1H), 7.60 (d, J=2.2 Hz, 1H), 7.53 (s, 1H), 7.49-7.36 (m, 17H), 7.30 (d, J=3.5 Hz, 1H), 7.20 (d, J=7.5 Hz, 1H), 7.08 (d, J=4.8 Hz, 1H), 6.87 (d, J=4.2 Hz, 1H), 4.76 (t, J=7.0 Hz, 1H), 4.70 (t, J=6.9 Hz, 1H), 4.63 (t, J=6.2 Hz, 1H), 3.95 (s, 3H), 3.47 (s, 6H), 3.61-3.36 (m, 6H). MS (ESI) m/z: 941 (M+1)$^+$.

Compound 26

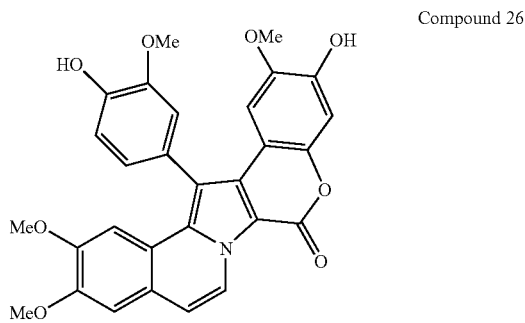

General procedure A (starting from 111) and chromatography on silica gel (CH$_2$Cl$_2$:MeOH, 20:1) to afford 26 (116 mg, 82%).

$^1$H NMR (300 MHz, CDCl$_3$) δ 9.19 (d, J=7.3 Hz, 1H), 7.19-6.98 (m, 7H), 6.71 (s, 1H), 5.86-5.85 (br s, 2H), 3.97 (s, 3H), 3.90 (s, 3H), 3.52 (s, 3H), 3.48 (s, 3H). $^{13}$C NMR (75 MHz, DMSO-d$_6$) δ 154.2, 149.7, 148.7, 148.6, 147.7, 146.8, 146.3, 144.4, 133.5, 128.7, 125.5, 124.2, 124.0, 121.9, 118.2, 116.2, 115.2, 112.2, 110.8, 108.3, 107.7, 106.5, 105.6, 104.8, 103.6, 56.0, 55.4, 55.0, 54.4. MS (ESI) m/z: 536 (M+23)$^+$, 514 (M+1)$^+$. Rf: 0.45 (CH$_2$Cl$_2$:MeOH, 20:1).

Compound 27

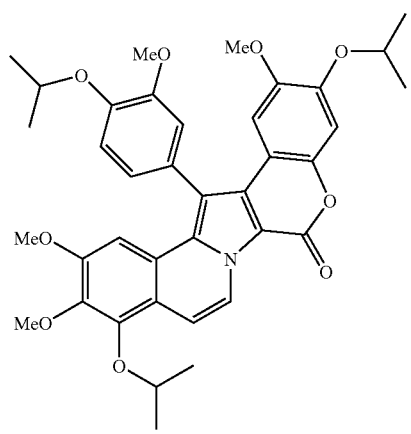

General procedure G (starting from 6,7-dimethoxy-5-isopropoxyisoquinoline) and chromatography on silica gel (hexane:EtOAc, from 3:1 to 2:1) to afford 27 (15 mg, 7%).

$^1$H NMR (300 MHz, CDCl$_3$) δ 9.20 (d, J=7.5 Hz, 1H), 7.43 (d, J=7.6 Hz, 1H), 7.20-7.15 (m, 3H), 7.01 (s, 1H), 6.97 (s, 1H), 6.72 (s, 1H), 4.75-4.50 (m, 3H), 4.65-4.50 (m, 3H), 3.90 (s, 3H), 3.85 (s, 3H), 3.44 (s, 3H), 1.50-1.35 (m, 18H). $^{13}$C NMR (75 MHz, CDCl$_3$) δ 159.3, 155.6, 153.2, 151.4, 147.8, 147.2, 146.6, 146.5, 146.4, 142.5, 133.8, 129.3, 128.7, 123.8, 122.6, 121.3, 120.8, 116.9, 114.9, 111.9, 109.9, 107.7, 105.4, 103.4, 101.4, 76.4, 71.8, 71.4, 60.7, 56.2, 55.4, 55.1, 22.7, 21.9, 21.8. MS (ESI) m/z: 656 (M+1)$^+$. Rf: 0.20 (hexane:EtOAc, 2:1).

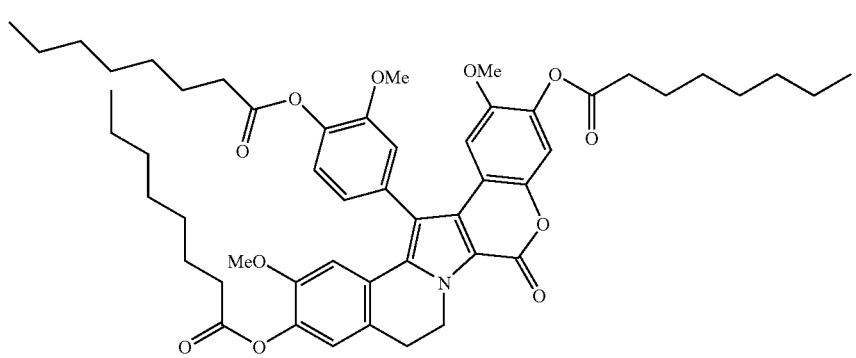

Compound 28

General procedure D (starting from 109 and n-octanoic acid) and chromatography on silica gel (CH$_2$Cl$_2$:MeOH, 100:1) to afford 28 (42 mg, 95%).

$^1$H NMR (300 MHz, CDCl$_3$) δ 7.21-7.07 (m, 4H), 6.94 (s, 1H), 6.79 (s, 1H), 6.70 (s, 1H), 4.93-4.84 (m, 1H), 4.79-4.70 (m, 1H), 3.80 (s, 3H), 3.42 (s, 3H), 3.35 (s, 3H), 3.11 (t, J=6.6 Hz, 2H), 2.63-2.53 (m, 6H), 1.83-1.69 (m, 6H), 1.41-1.30 (m, 24H), 0.93-0.87 (m, 9H). $^{13}$C NMR (75 MHz, CDCl$_3$) δ 171.9, 171.6, 171.5, 155.1, 152.3, 149.9, 147.7, 144.9, 140.1, 139.5, 139.1, 135.1, 133.8, 127.1, 125.9, 125.5, 123.9, 123.1, 122.6, 115.9, 114.9, 114.6, 111.9, 109.7, 105.4, 56.1, 55.7, 55.5, 42.4, 34.0 (3C), 31.7 (3C), 29.0 (2C), 28.9 (4C), 28.0, 25.0 (2C), 24.9, 22.6 (3C), 14.0 (3C). MS (ESI) m/z: 902 (M+23)$^+$, 880 (M+1)$^+$. Rf: 0.31 (CH$_2$Cl$_2$:MeOH, 100:1).

$^1$H NMR (300 MHz, CDCl$_3$) δ 8.35 (s, 1H), 8.28 (s, 2H), 7.68-7.62 (m, 3H), 7.39-7.36 (m, 3H), 7.26-7.07 (m, 12H), 6.90 (s, 1H), 6.72 (s, 1H), 6.65 (br s, 2H), 5.15-5.12 (m, 2H), 5.00-4.59 (m, 6H), 3.75 (s, 3H), 3.52-3.28 (m, 12H), 3.00 (br t, 2H), 1.43 (s, 27H). $^{13}$C NMR (75 MHz, CDCl$_3$) δ 170.7, 170.4, 170.4, 155.3 (2C), 154.9, 152.0, 149.6, 147.5, 144.6, 139.6, 139.0, 138.4, 136.1 (3C), 134.9, 134.0, 127.7 (3C), 126.8, 125.9, 125.5, 123.8, 123.1 (3C), 122.5, 122.0 (3C), 119.5 (3C), 118.6 (3C), 116.0, 115.8, 114.7, 111.7, 111.3 (3C), 109.5 (3C), 105.3, 80.0 (3C), 56.0 (2C), 55.6, 55.4, 54.4 (2C), 42.3, 28.2 (12C), 27.7. MS (ESI) m/z: 1382 (M+23)$^+$. Rf: 0.13 (CH$_2$Cl$_2$:MeOH, 30:1).

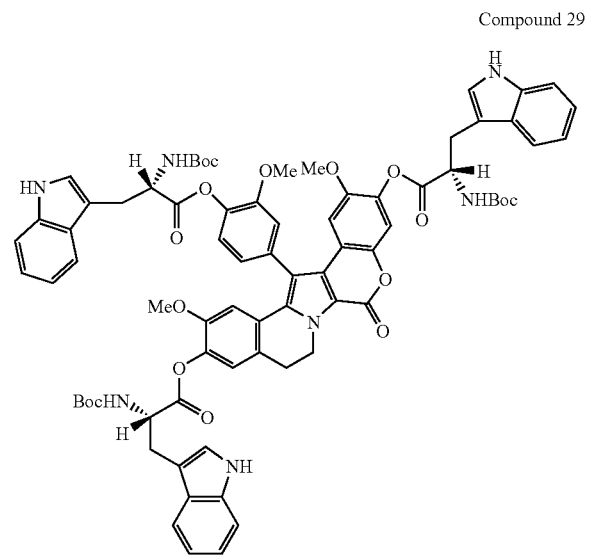

Compound 29

General procedure D (starting from 109 and Boc-L-Trp-OH) and chromatography on silica gel (CH$_2$Cl$_2$:MeOH, from 30:1 to 15:1) to afford 29 (115 mg, 85%).

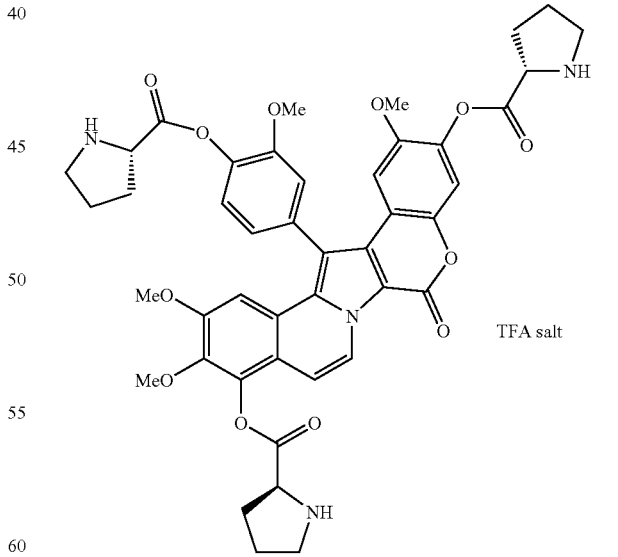

Compound 30

TFA salt

General procedure B (starting from 117) to afford 30 (11 mg, quant.).

$^1$H NMR (300 MHz, CD$_3$OD) δ 9.15 (d, J=7.6 Hz, 1H), 7.65-7.55 (m, 2H), 7.50-7.20 (m, 4H), 6.87 (d, J=12.3 Hz,

1H), 4.90-4.70 (m, 3H), 3.90 (s, 6H), 3.85-3.40 (m, 12H), 2.90-2.00 (m, 12H). MS (ESI) m/z: 821 (M+1)+.

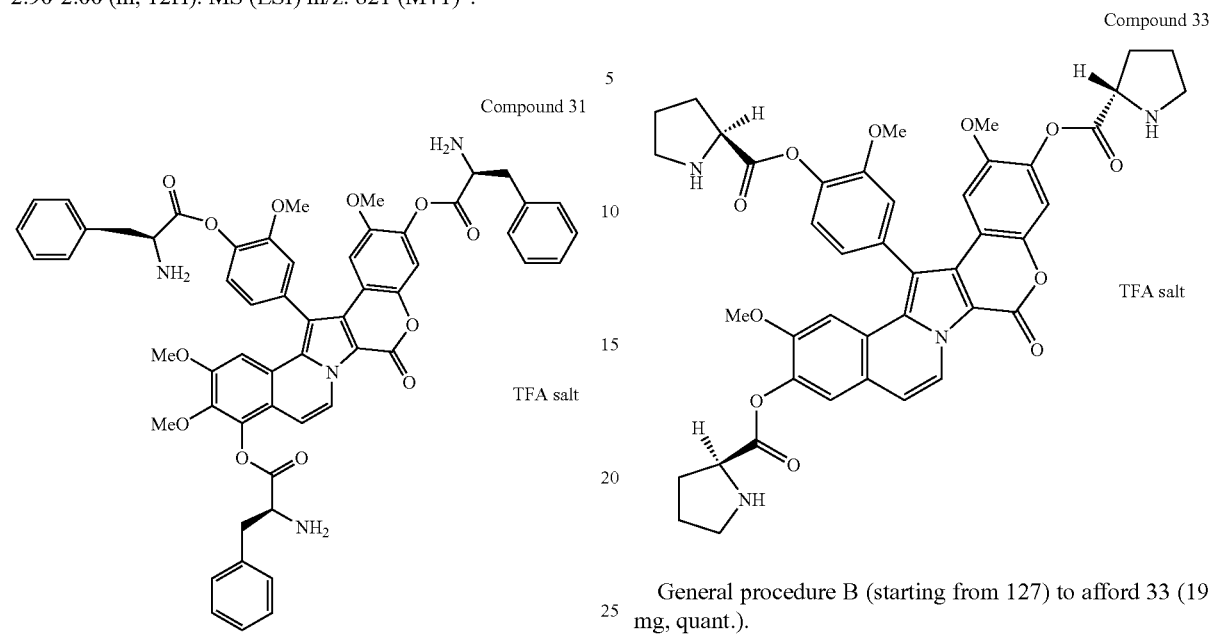

General procedure B (starting from 120) to afford 31 (31 mg, quant.).

$^1$H NMR (300 MHz, CD$_3$OD) δ 9.09 (d, J=7.8 Hz, 1H), 7.80-7.40 (m, 18H), 7.30-7.00 (m, 3H), 6.87 (d, J=5.3 Hz, 1H), 4.80-4.60 (m, 3H), 3.92 (s, 3H), 3.90 (s, 3H), 3.80-3.40 (m, 12H). MS (ESI) m/z: 971 (M)+.

General procedure B (starting from 34) to afford 32 (19 mg, quant.).

$^1$H NMR (300 MHz, CD$_3$OD) δ 7.46-7.44 (m, 2H), 7.29-7.25 (m, 1H), 7.17-7.14 (m, 2H), 6.90-6.78 (m, 2H), 4.76 (br t, 2H), 4.33-4.21 (m, 3H), 3.88 (s, 3H), 3.45 (s, 3H), 3.38 (s, 3H), 3.16 (br t, 2H), 2.59-2.43 (m, 3H), 1.27-1.10 (m, 18H). MS (ESI) m/z: 799 (M+1)+.

General procedure B (starting from 127) to afford 33 (19 mg, quant.).

$^1$H NMR (300 MHz, CD$_3$OD) δ 8.96-8.90 (m, 1H), 7.67-7.52 (m, 3H), 7.40-7.24 (m, 2H), 7.13-7.08 (m, 2H), 6.84-6.80 (m, 1H), 4.86-4.67 (m, 3H), 3.95 (s, 3H), 3.55-3.43 (m, 12H), 2.66-2.35 (m, 6H), 2.27-2.14 (m, 6H). MS (ESI) m/z: 791 (M+1)+.

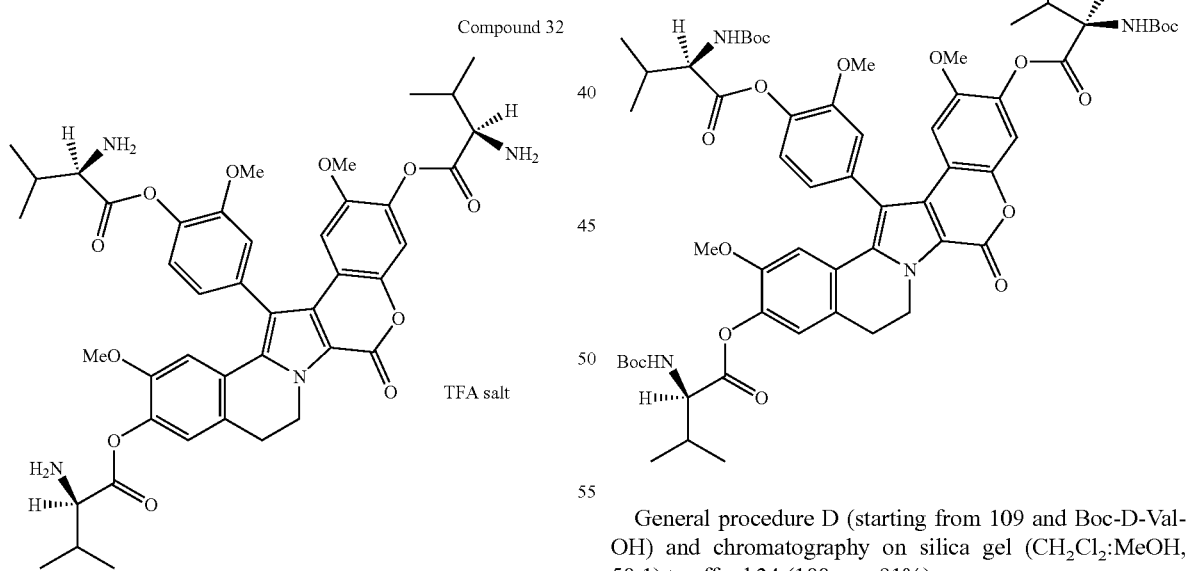

General procedure D (starting from 109 and Boc-D-Val-OH) and chromatography on silica gel (CH$_2$Cl$_2$:MeOH, 50:1) to afford 34 (100 mg, 91%).

$^1$H NMR (300 MHz, CDCl$_3$) δ 7.26-7.08 (m, 4H), 6.97 (s, 1H), 6.77 (d, J=7.1 Hz, 1H), 6.69 (d, J=9.3 Hz, 1H), 5.07-5.05 (m, 3H), 4.96-4.90 (m, 1H), 4.75-4.70 (m, 1H), 4.55-4.47 (m, 3H), 3.78 (s, 3H), 3.40 (s, 3H), 3.33 (s, 3H), 3.21 (br t, 2H), 2.45-2.30 (m, 3H), 1.49 (s, 9H), 1.47 (s, 18H), 1.12-0.99 (m, 18H). $^{13}$C NMR (75 MHz, CDCl$_3$) δ 170.5, 170.3 (2C), 155.6, 154.9, 152.0, 149.7, 147.5, 144.8, 139.6, 139.1, 138.5, 134.9, 134.2, 126.9, 125.9, 125.7, 123.8, 123.1, 122.5, 116.1, 115.8, 114.9, 114.6, 111.8, 109.6, 105.4, 79.9 (3C), 58.5, 55.9, 55.5, 55.5, 55.3, 55.2, 42.3, 31.5, 31.2, 31.1, 28.2 (9C), 27.9, 19.0 (2C), 17.1 (4C). MS (ESI) m/z: 1099 (M+1)⁺. Rf: 0.35 (CH₂Cl₂:MeOH 50:1).

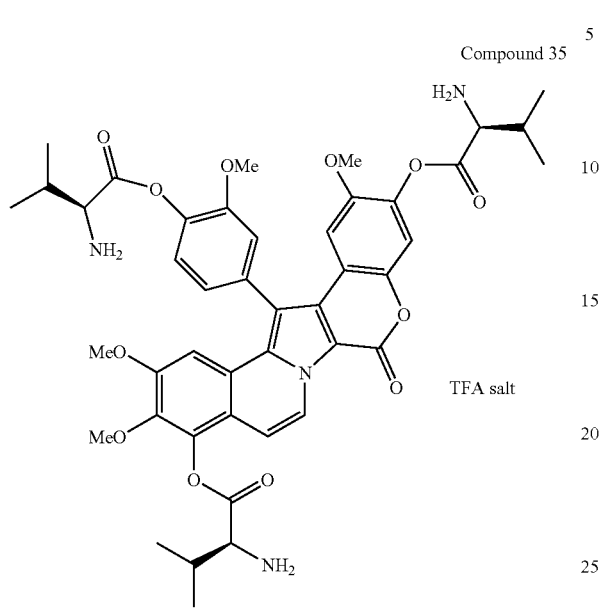

Compound 35 — TFA salt

General procedure B (starting from 129) to afford 35 (13 mg, 98%).

¹H NMR (300 MHz, CD₃OD) δ 9.14 (dd, J=7.5, 3.0 Hz, 1H), 7.60-7.50 (m, 2H), 7.50-7.20 (m, 4H), 6.87 (d, J=11.1 Hz, 1H), 4.60-4.50 (m, 1H), 4.40-4.30 (m, 1H), 4.25-4.20 (m, 1H), 3.89 (s, 3H), 3.88 (s, 3H), 3.52 (s, 3H), 3.47 (s, 3H), 2.80-2.40 (m, 3H), 1.40-1.10 (m, 18H). MS (ESI) m/z: 827 (M+1)⁺.

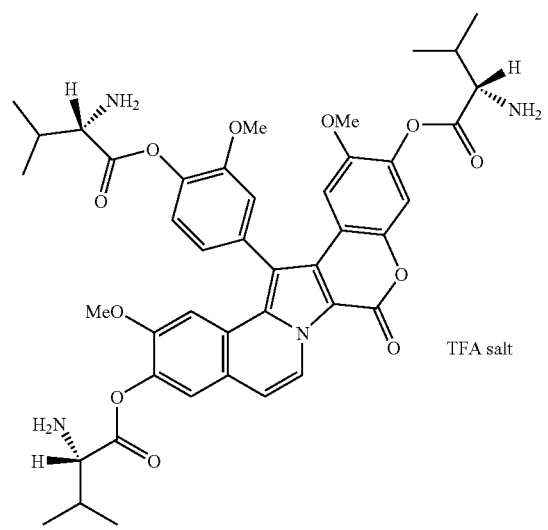

Compound 36 — TFA salt

General procedure B (starting from 38) to afford 36 (21 mg, quant.).

¹H NMR (300 MHz, CD₃OD) δ 9.09-9.04 (m, 1H), 7.62-7.51 (m, 3H), 7.41-7.32 (m, 2H), 7.23-7.18 (m, 2H), 6.88 (d, J=9.0 Hz, 1H), 4.36 (d, J=4.4 Hz, 1H), 4.31 (d, J=4.4 Hz, 1H), 4.24 (t, J=4.4 Hz, 1H), 3.92 (s, 3H), 3.48 (s, 6H), 2.62-2.43 (m, 3H), 1.29-1.19 (m, 18H). MS (APCI) m/z: 797 (M+1)⁺.

Compound 37 — HCl salt

General procedure C (starting from 144) to afford 37 as a white solid (654 mg, 83%).

¹H NMR (300 MHz, CD₃OD) δ 7.46-7.43 (m, 2H), 7.26-7.16 (m, 3H), 6.89-6.78 (m, 2H), 4.80 (br t, 2H), 4.33 (s, 1H), 4.24 (s, 2H), 3.84 (s, 3H), 3.45 (s, 3H), 3.37 (s, 3H), 3.18 (br t, 2H), 2.60-2.40 (m, 3H), 1.27-1.17 (m, 18H). ¹³C NMR (75 MHz, CD₃OD) δ 168.7, 168.3 (2C), 156.2, 153.5, 150.8, 148.8, 146.1, 140.6, 140.0, 139.3, 136.6, 136.4, 128.4, 128.0, 127.5, 125.2, 124.7, 123.7, 117.9, 117.6, 116.5, 116.2, 112.8, 110.9, 106.7, 59.5, 59.4, 56.9, 56.4, 56.2, 56.0, 43.7, 31.3 (3C), 28.8, 18.3 (2C), 18.2 (4C). MS (ESI) m/z: 799 (M+1)⁺.

Compound 38

General procedure E (starting from 144, overnight) and chromatography on silica gel (CH₂Cl₂:MeOH, from 100:1 to 50:1) to afford 38 (43 mg, 88%).

¹H NMR (300 MHz, CDCl₃) δ 9.20 (d, J=7.3 Hz, 1H), 7.40 (s, 1H), 7.30-7.13 (m, 5H), 7.04 (d, J=7.3 Hz, 1H), 6.79 (d, J=7.5 Hz, 1H), 5.10-5.06 (m, 3H), 4.56-4.48 (m, 3H), 3.81 (s, 3H), 3.43 (s, 6H), 2.45-2.32 (m, 3H), 1.49 (s, 9H), 1.47 (s, 18H), 1.14-1.00 (m, 18H). ¹³C NMR (75 MHz, CDCl₃) δ 170.4 (3C), 155.7, 155.0, 152.3, 150.9, 147.6, 145.4, 140.6, 140.0, 139.4, 134.5, 133.5, 130.9, 128.8, 128.2, 128.1, 124.1, 123.8, 123.6, 123.2, 120.8, 115.9, 115.1, 112.8, 112.3, 112.2, 109.1, 106.4, 106.2, 80.0 (3C), 58.5, 56.0, 55.6, 55.6, 55.5, 55.5, 31.3 (2C), 31.2, 28.3 (9C), 19.2, 19.1, 17.2 (2C), 17.1 (2C). MS (ESI) m/z: 1119 (M+23)⁺, 1097 (M+1)⁺. Rf: 0.33 (CH₂Cl₂:MeOH, 100:1).

3.93 (s, 3H), 3.48 (s, 6H), 1.80 (d, J=7.1 Hz, 3H), 1.74 (d, J=7.3 Hz, 3H), 1.71-1.68 (m, 3H). MS (ESI) m/z: 713 (M+1)⁺.

Compound 39

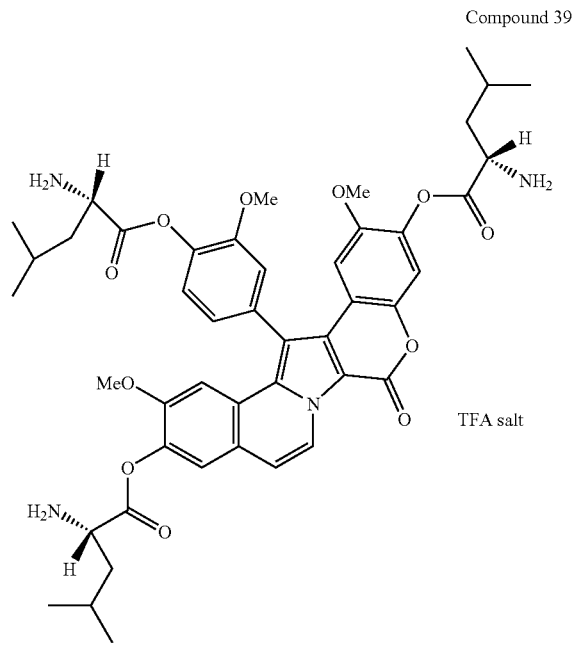

Compound 41

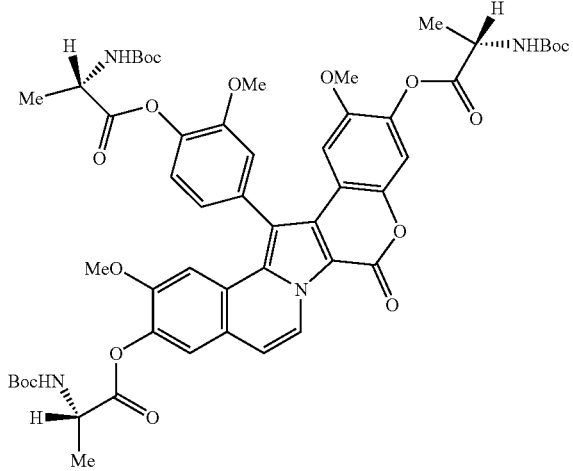

General procedure E (starting from 156, 2 days) and chromatography on silica gel (hexane:EtOAc, 1:1) to afford 41 (58 mg, 92%).

¹H NMR (300 MHz, CDCl₃) δ 9.24 (d, J=7.3 Hz, 1H), 7.44-7.32 (m, 2H), 7.25-7.18 (m, 4H), 7.07 (d, J=7.5 Hz, 1H), 6.79 (d, J=7.5 Hz, 1H), 5.11-5.09 (m, 3H), 4.64-4.60 (m, 3H), 3.81 (s, 3H), 3.44 (s, 6H), 1.63-1.55 (m, 9H), 1.49 (s, 9H), 1.47 (s, 18H). ¹³C NMR (75 MHz, CDCl₃) δ 171.5, 171.3, 171.1, 155.0, 154.8, 152.2, 150.8, 147.6, 145.3, 140.6, 140.0, 139.4, 134.4, 133.3, 128.0, 127.9, 123.9, 123.7, 123.7, 123.7, 123.6, 123.0, 120.6, 115.7, 115.1, 112.7, 112.2, 112.0, 108.9, 106.3, 106.1, 80.0 (3C), 56.2 (2C), 55.8, 55.7, 55.7, 55.5, 28.3 (9C), 18.6 (3C). MS (ESI) m/z: 1035 (M+23)⁺, 1013 (M+1)⁺. Rf: 0.43 (hexane:EtOAc, 50:50).

General procedure B (starting from 146) to afford 39 (19 mg, quant.).

¹H NMR (300 MHz, CD₃OD) δ 9.15-9.12 (m, 1H), 7.64 (d, J=2.7 Hz, 1H), 7.58-7.52 (m, 2H), 7.40-7.29 (m, 2H), 7.26-7.22 (m, 2H), 6.89 (d, J=7.3 Hz, 1H), 4.45-4.31 (m, 3H), 3.90 (s, 3H), 3.48 (s, 3H), 3.48 (s, 3H), 2.11-1.79 (m, 9H), 1.13-1.06 (m, 18H). MS (ESI) m/z: 839 (M+1)⁺.

Compound 40

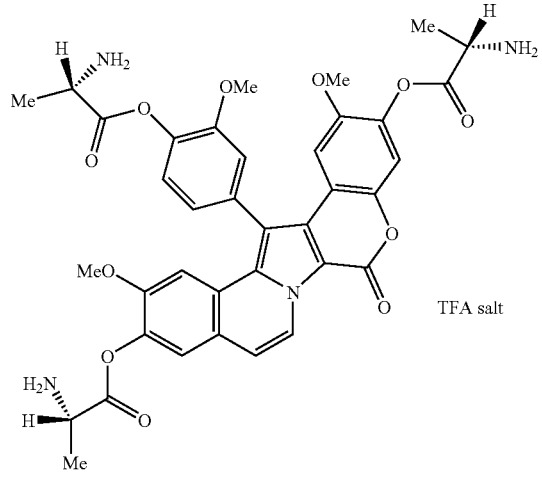

Compound 42

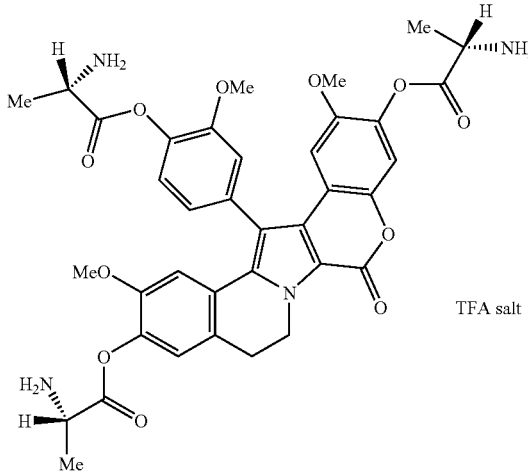

General procedure B (starting from 41) to afford 40 (16 mg, quant.).

¹H NMR (300 MHz, CD₃OD) δ 9.03-8.99 (m, 1H), 7.63-7.60 (m, 2H), 7.52 (dd, J=8.0, 1.6 Hz, 1H), 7.39-7.27 (m, 2H), 7.18-7.15 (m, 2H), 6.85 (d, J=9.2 Hz, 1H), 4.53-4.36 (m, 3H),

General procedure B (starting from 156) to afford 42 (17 mg, quant.)

¹H NMR (300 MHz, CD₃OD) δ 7.46-7.44 (m, 2H), 7.28-7.27 (m, 1H), 7.19 (s, 1H), 7.16 (s, 1H), 6.87 (d, J=8.8 Hz,

1H), 6.78 (d, J=10.0 Hz, 1H), 4.75 (t, J=6.2 Hz, 2H), 4.77-4.37 (m, 3H), 3.87 (s, 3H), 3.45 (s, 3H), 3.38 (s, 3H), 3.16 (t, J=6.2 Hz, 2H), 1.77 (d, J=6.9 Hz, 3H), 1.71-1.67 (m, 6H). MS (ESI) m/z: 715 (M+1)⁺.

Compound 43

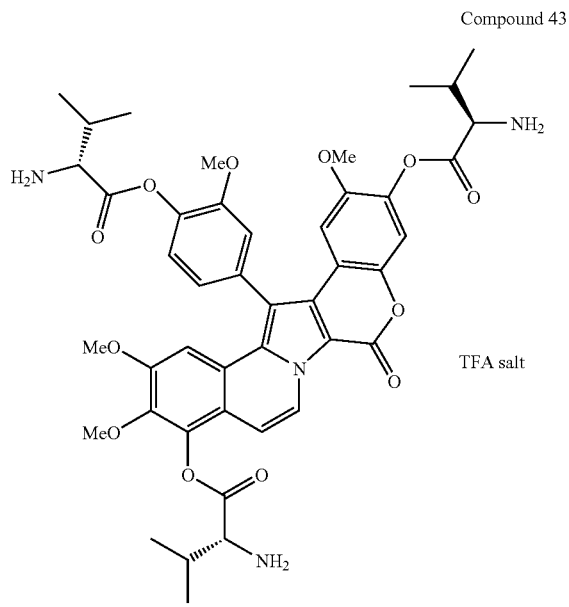

TFA salt

General procedure B (starting from 160) to afford 43 (13.0 mg, quant.)

¹H NMR (300 MHz, CD₃OD) δ 9.18 (d, J=7.6 Hz, 1H), 7.56-7.52 (m, 2H), 7.40-7.22 (m, 4H), 6.90 (d, J=10.7 Hz, 1H), 4.60-4.59 (m, 1H), 4.37-4.35 (m, 1H), 4.26-4.24 (m, 1H), 3.90 (br s, 6H), 3.54 (br s, 3H), 3.47 (s, 3H); 2.62-2.47 (s, 3H), 1.32-1.19 (s, 18H). MS (ESI) m/z: 827 (M+1)⁺.

General procedure B (starting from 158) to afford 44 (12.3 mg, quant.).

¹H NMR (300 MHz, CD₃OD) δ 9.20 (d, J=8.1 Hz, 1H); 7.55-7.47 (m, 2H), 7.27-7.18 (m, 19H), 6.87 (d, J=9.3 Hz, 1H), 5.03 (s, 6H), 4.65 (br t, 1H), 4.49 (br t, 1H), 4.36 (br t, 1H), 3.88 (br s, 3H), 3.85 (br s, 3H), 3.51 (br s, 3H), 3.46 (br s, 3H), 3.22-3.18 (m, 6H), 2.40-2.00 (m, 6H), 1.65-1.50 (m, 12H). MS (ESI) m/z: 1339 (M+23)⁺, 1316 (M+1)⁺.

Compound 45

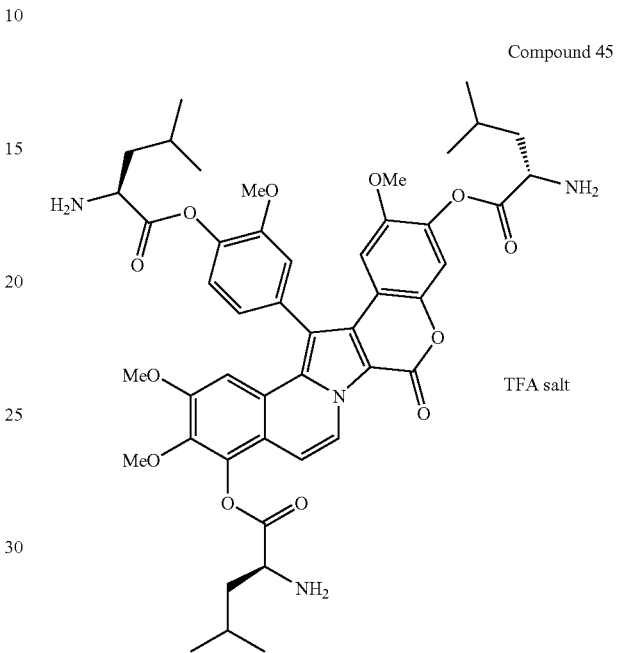

TFA salt

General procedure B (starting from 159) to afford 45 (27.3 mg, quant.).

Compound 44

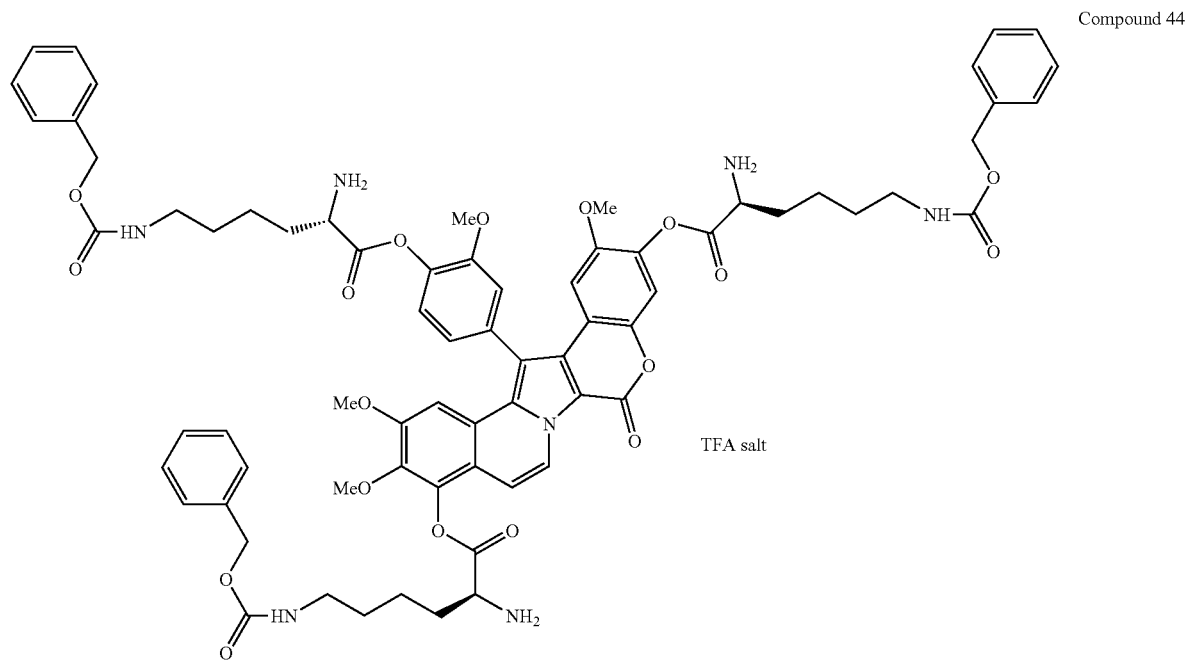

TFA salt

¹H NMR (300 MHz, CD₃OD) δ 9.20 (d, J=7.6 Hz, 1H), 7.56-7.51 (m, 2H), 7.40-7.22 (m, 4H), 6.89 (d, J=8.3 Hz, 1H), 4.64 (t, J=6.0 Hz, 1H), 4.44 (t, J=6.3 Hz, 1H), 4.34 (t, J=7.2 Hz, 1H), 3.89 (br s, 6H), 3.54 (br s, 3H), 3.48 (br s, 3H), 2.19-1.79 (m, 9H), 1.15-1.07 (m, 18H). MS (ESI) m/z: 869 (M+1)⁺.

Compound 46

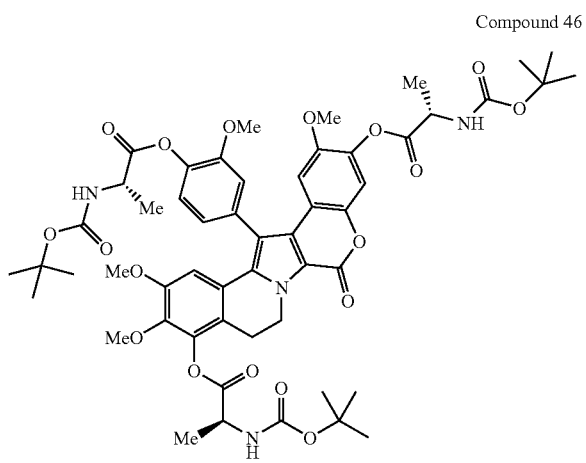

General procedure D (starting from 1 and Boc-Ala-OH) and chromatography on silica gel (hexane:EtOAc, 50:50) to afford 46 (80 mg, 80%).

¹H NMR (300 MHz, CDCl₃) δ 7.28-7.20 (m, 1H), 7.20-7.05 (m, 3H), 6.67 (d, J=3.7 Hz, 1H), 6.65 (d, J=4.0 Hz, 1H), 5.15-5.05 (m, 2H), 4.70-4.50 (m, 3H), 3.80 (s, 3H), 3.78 (s, 3H), 3.40 (s, 3H), 3.38 (s, 3H), 3.01 (br t, 2H), 1.70-1.50 (m, 9H), 1.48 (s, 9H), 1.47 (s, 9H), 1.46 (s, 9H). ¹³C NMR (75 MHz, CDCl₃) δ 171.8, 171.4, 155.0, 152.1, 151.8, 147.5, 144.9, 144.8, 141.3, 141.0, 139.8, 138.7, 134.8, 134.7, 134.3, 127.1, 127.0, 123.7, 123.2, 122.7, 119.7, 119.4, 116.2, 115.7, 114.9, 114.7, 111.8, 107.6, 105.5, 80.2, 80.1 (2C), 60.8, 56.2, 55.7, 55.5, 49.5, 49.3 (2C), 41.9, 28.3 (9C), 22.1, 18.7, 18.6, 18.3. MS (ESI) m/z: 1067 (M+23)⁺, 1045 (M+1)⁺. Rf: 0.70 (hexane:EtOAc, 1:2).

General procedure D (starting from 95 and (+)-biotine) and chromatography on silica gel (CH₂Cl₂:MeOH, 10:1) to afford 47 (5 mg, 10%).

¹H NMR (300 MHz, CDCl₃) δ 7.30-7.10 (m, 4H), 6.80-6.60 (m, 3H), 6.40 (br s, 1H), 6.30 (br s, 1H), 6.20 (br s, 1H), 6.10 (br s, 1H), 4.90-4.70 (m, 2H), 4.60-4.45 (m, 2H), 4.40-4.25 (m, 2H), 3.90 (s, 3H), 3.80 (s, 3H), 3.45 (s, 3H), 3.39 (s, 3H), 3.20-3.10 (m, 4H), 3.00-2.50 (m, 8H), 2.00-1.50 (m, 12H). ¹³C NMR (75 MHz, CDCl₃) δ 171.6, 171.3, 163.8, 155.2, 152.1, 149.1, 147.6, 144.9, 139.8, 139.0, 135.7, 134.2, 127.4, 126.5, 123.8, 123.5, 123.3, 119.7, 116.0, 114.8, 114.4, 111.8, 111.0, 108.5, 105.4, 62.3, 62.2, 61.4, 60.3, 59.9, 56.2, 56.1, 55.9, 55.8, 55.5, 55.3, 55.2, 42.5, 40.6, 40.5, 33.8, 33.1, 29.7, 28.6, 28.2, 28.1, 27.8, 27.4, 25.1, 24.7, 21.0, 14.2. MS (ESI) m/z: 990 (M+23)⁺, 968 (M+1)⁺. Rf: 0.20 (CH₂Cl₂:MeOH, 10:1).

Compound 48

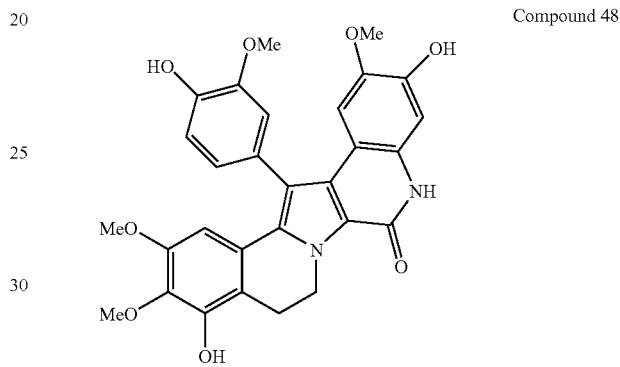

General procedure A (starting from 49) and purification by chromatography on silica gel (CH₂Cl₂:MeOH, 10:1) to afford 48 (9.9 mg, 84%).

¹H NMR (300 MHz, CDCl₃) δ 9.60 (br s, 1H), 7.15-7.07 (m, 2H), 7.00 (br s, 1H), 6.82 (s, 1H), 6.72 (s, 1H), 6.40 (s, 1H), 6.02 (br s, 1H), 5.80 (br s, 2H), 5.16-5.08 (m, 1H), 4.85-4.78 (m, 1H), 3.88 (s, 3H), 3.87 (s, 3H), 3.47 (s, 3H), 3.36 (s, 3H), 3.18-3.10 (m, 2H). MS (ESI) m/z: 531 (M+1)⁺. Rf: 0.25 (CH₂Cl₂:MeOH, 10:1).

Compound 47

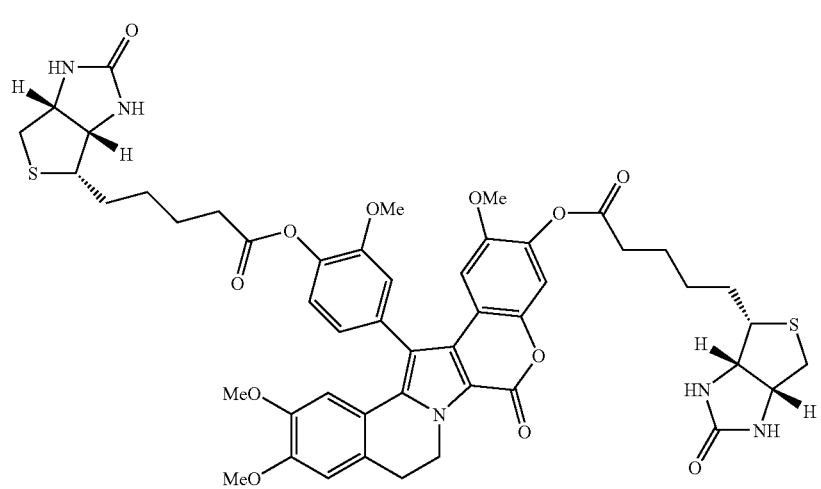

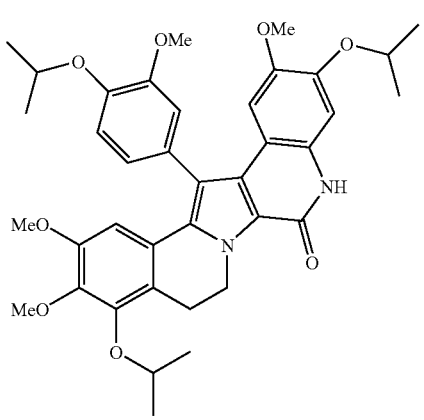

Compound 49

General procedure G (starting from 6,7-dimethoxy-5-isopropoxy-3,4-dihydroisoquinoline and 2-Bromo-N-[5-isopropoxy-2-(4-isopropoxy-3-methoxy-phenylethynyl)-4-methoxy-phenyl]-acetamide) and purification by chromatography on silica gel (EtOAc:hexane, 4:1) to afford 49 (55.7 mg, 21%).

$^1$H NMR (300 MHz, CDCl$_3$) δ 7.10-7.08 (m, 3H), 7.00 (s, 1H), 6.77 (s, 1H), 6.63 (s, 1H), 4.99 (br t, 2H), 4.63-4.53 (m, 3H), 3.83 (s, 6H), 3.41 (s, 3H), 3.35 (s, 3H), 3.16 (br t, 2H), 1.42 (d, J=5.4 Hz, 6H), 1.40 (d, 5.4 Hz, 6H), 1.32 (d, 6.1 Hz, 6H). $^{13}$C NMR (75 MHz, CDCl$_3$) δ 156.7, 151.7, 151.3, 148.5, 146.8, 145.9, 142.0, 133.3, 129.8, 129.7, 127.3, 123.7, 123.6, 121.0, 118.9, 117.0, 115.4, 114.9, 111.2, 105.3, 104.9, 102.6, 75.7, 71.8, 71.6, 60.5, 56.2, 55.3, 55.1, 42.3, 23.0, 22.7 (2C), 22.0 (2C), 21.9 (2C). MS (ESI) m/z: 657 (M+1)$^+$. Rf: 0.34 (EtOAc:hexane, 4:1).

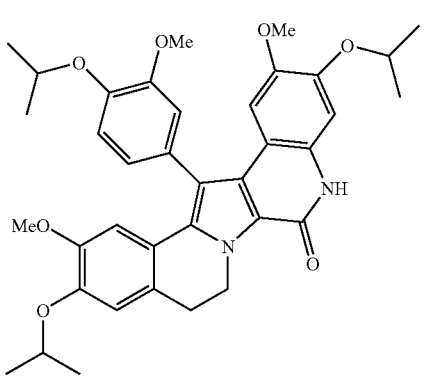

Compound 50

General procedure G (starting from 6-isopropoxy-7-methoxy-3,4-dihydroisoquinoline and 2-Bromo-N-[5-isopropoxy-2-(4-isopropoxy-3-methoxy-phenylethynyl)-4-methoxy-phenyl]-acetamide) and purification by chromatography on silica gel (EtOAc) to provide 50 (51.7 mg, 18%).

$^1$H NMR (300 MHz, CDCl$_3$) δ 7.09-7.08 (m, 3H), 6.95 (br s, 1H), 6.80-6.76 (m, 3H), 5.03-5.00 (m, 2H), 4.62-4.52 (m, 3H), 3.81 (s, 3H), 3.41 (s, 3H), 3.34 (s, 3H), 3.11 (t, J=6.3 Hz, 2H), 1.42-1.34 (m, 18H). $^{13}$C NMR (75 MHz, CDCl$_3$) δ 156.1, 151.1, 148.4, 146.5, 145.8, 134.0, 129.6, 129.3, 127.4, 126.3, 123.5, 120.7, 118.4, 116.9, 114.7, 114.4, 111.1, 109.0, 105.0, 102.3, 71.8, 71.4, 71.3, 55.9, 55.0, 54.9, 42.3, 28.7, 21.7 (6C). MS (ESI) m/z: 627 (M+1)$^+$. Rf: 0.42 (EtOAc).

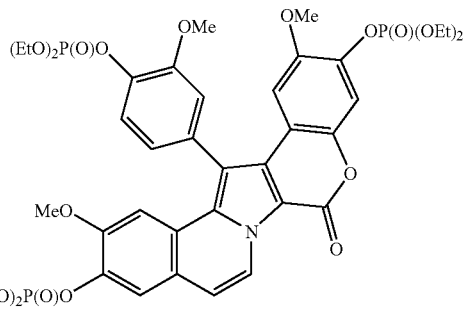

Compound 51

General procedure E (starting from 52) and purification by chromatography on silica gel (CH$_2$Cl$_2$:MeOH, 20:1) to afford 51 (7 mg, 64%).

$^1$H NMR (300 MHz, CDCl$_3$) δ 9.24 (d, J=7.3 Hz, 1H), 7.63 (d, J=1.2 Hz, 1H), 7.53 (dd, J=8.0, 1.7 Hz, 1H), 7.37 (d, J=1.5 Hz, 1H), 7.23-7.15 (m, 3H), 7.08 (d, J=7.3 Hz, 1H), 6.76 (s, 1H), 4.38-4.22 (m, 12H), 3.88 (s, 3H), 3.48 (s, 3H), 3.47 (s, 3H), 1.45 (t, J=7.0 Hz, 6H), 1.38 (t, J=7.0 Hz, 12H). $^{13}$C NMR (75 MHz, CDCl$_3$) δ 155.1, 152.0 (d, J$_{C-P}$=4.5 Hz), 150.6 (d, J$_{C-P}$=5.5 Hz), 147.4 (d, J$_{C-P}$=5.0 Hz), 145.5, 140.9 (d, J$_{C-P}$=7.1 Hz), 140.2 (d, J$_{C-P}$=7.1 Hz), 139.9 (d, J$_{C-P}$=7.1 Hz), 133.5, 133.3, 128.2, 123.9, 123.7, 123.3, 122.8 (d, J$_{C-P}$=3.0 Hz), 122.6, 118.8, 115.4, 114.6, 112.8, 111.9, 110.8, 108.9, 106.5, 106.3, 64.9, 64.8 (2C), 64.7 (2C), 64.6, 56.3, 55.8, 55.6, 16.2, 16.1 (3C), 16.0. MS (ESI) m/z: 908 (M+1)$^+$. Rf: 0.29 (CH$_2$Cl$_2$:MeOH, 20:1).

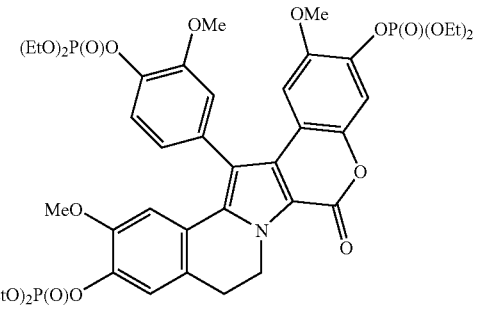

Compound 52

To a suspension of 109 (15 mg, 0.030 mmol) in anhydrous CH$_2$Cl$_2$ under Argon atmosphere, Et$_3$N (17 μL, 0.120 mmol) and diethyl chlorophosphate (18 μL, 0.120 mmol) were added and the mixture was stirred at 23° C. After 4.5 h, two more equivalents of Et$_3$N (9 μL, 0.060 mmol) and diethyl chlorophosphate (9 μL, 0.060 mmol) were added and the mixture stirred at 23° C. overnight. The mixture was concentrated under reduced pressure and the residue purified by chromatography on silica gel (CH$_2$Cl$_2$:MeOH, from 30:1 to 15:1) to give 52 as a white solid (20 mg, 74%).

$^1$H NMR (300 MHz, CDCl$_3$) δ 7.45 (dd, J=8.1, 1.5 Hz, 1H), 7.29 (d, J=1.5 Hz, 1H), 7.18 (s, 1H), 7.10 (dd, J=8.1, 1.6 Hz, 1H), 7.06 (s, 1H), 6.71 (s, 1H), 6.64 (s, 1H), 4.94-4.86 (m, 1H), 4.72-4.63 (m, 1H), 4.34-4.18 (m, 12H), 3.84 (s, 3H), 3.44 (s, 3H), 3.36 (s, 3H), 3.09 (br t, 2H), 1.44-1.31 (m, 18H). $^{13}$C NMR (75 MHz, CDCl$_3$) δ 155.1, 151.7 (d, J$_{C-P}$=4.5 Hz), 149.3 (d, J$_{C-P}$=5.5 Hz), 147.4 (d, J$_{C-P}$=5.0 Hz), 144.9, 139.9 (d, J$_{C-P}$=7.1 Hz), 139.6 (d, J$_{C-P}$=6.5 Hz), 139.1 (d, J$_{C-P}$=7.6 Hz), 135.0, 133.0, 127.0, 126.2, 124.4, 123.2, 122.6, 122.6, 121.1, 115.5, 114.9, 114.8, 110.5, 109.8, 105.6, 64.7, 64.7, 64.7 (3C), 64.6, 56.2, 55.8, 55.5, 42.4, 28.1, 16.2, 16.1 (3C), 16.0, 16.0. MS (ESI) m/z: 910 (M+1)$^+$. Rf: 0.23 (CH$_2$Cl$_2$:MeOH, 30:1).

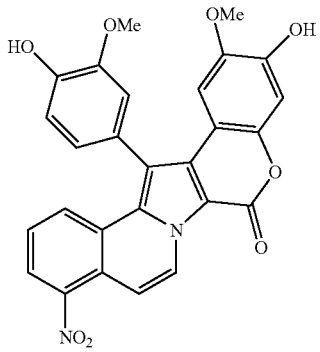

Compound 53

General procedure A (starting from 54) and purification by chromatography on silica gel (CH$_2$Cl$_2$:MeOH, from 20:1 to 10:1) to afford 53 (70 mg, 51%).

$^1$H NMR (300 MHz, DMSO-d$_6$) δ 9.30 (d, J=7.6 Hz, 1H), 8.20 (d, J=7.7 Hz, 1H), 8.08 (d, J=8.0 Hz, 1H), 7.70-7.50 (m, 2H), 7.20-7.10 (m, 2H), 7.00 (d, J=7.8 Hz, 1H), 6.88 (s, 1H), 6.57 (s, 1H), 5.69 (s, 1H), 3.76 (s, 3H), 3.40 (s, 3H). MS (ESI) m/z: 499 (M+1)$^+$. Rf: 0.61 (CH$_2$Cl$_2$:MeOH, 10:1).

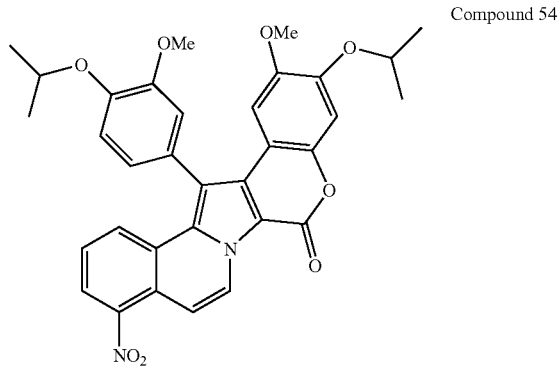

Compound 54

General procedure H (starting from 5-nitroisoquinoline) and purification by chromatography on silica gel (hexane:CH$_2$Cl$_2$:Et$_2$O, from 5:5:1 to 5:5:2) to afford 54 (190 mg, 33%).

$^1$H NMR (300 MHz, CD$_3$OD) δ 9.41 (d, J=7.8 Hz, 1H), 8.12 (dd, J=7.8, 1.1 Hz, 1H), 8.06 (dt, J=8.0, 0.9 Hz, 1H), 7.78 (dd, J=7.8, 0.7 Hz, 1H), 7.36 (t, J=8.2 Hz, 1H), 7.19 (d, J=8.2 Hz, 1H), 7.11 (dd, J=8.2, 1.8 Hz, 1H), 7.05 (d, J=1.8 Hz, 1H), 6.96 (s, 1H), 6.63 (s, 1H), 4.71 (hp, J=6.0 Hz, 1H), 4.58 (hp, J=6.0 Hz, 1H), 3.84 (s, 3H), 3.44 (s, 3H), 1.51 (d, J=6.0 Hz, 3H), 1.44 (d, J=6.0 Hz, 3H), 1.40 (d, J=7.8 Hz, 6H). MS (ESI) m/z: 583 (M+1)$^+$. Rf: 0.50 (hexane:CH$_2$Cl$_2$:Et$_2$O, 5:5:2).

General procedure E (starting from 28, reaction time 15 h) and purification by chromatography on silica gel (CH$_2$Cl$_2$:MeOH, 100:1) to afford 55 (17 mg, quant.).

$^1$H NMR (300 MHz, CDCl$_3$) δ 9.23 (d, J=7.5 Hz, 1H), 7.38 (s, 1H), 7.30-7.13 (m, 5H), 7.05 (d, J=7.3 Hz, 1H), 6.81 (s, 1H), 3.82 (s, 3H), 3.45 (s, 6H), 2.65-2.55 (m, 6H), 1.82-1.73 (m, 6H), 1.42-1.25 (m, 24H), 0.91-0.85 (m, 9H). $^{13}$C NMR (75 MHz, CDCl$_3$) δ 171.7, 171.6, 171.6, 155.1, 152.4, 151.1, 147.8, 145.5, 141.0, 140.4, 139.9, 134.1, 133.6, 128.3, 124.1, 123.8, 123.6, 123.6, 123.1, 120.7, 115.6, 115.0, 112.8, 112.3, 112.2, 109.0, 106.4, 106.1, 56.2, 55.8, 55.6, 34.0 (3C), 31.7 (3C), 29.7, 29.0 (2C), 28.9 (3C), 25.0, 25.0, 24.9, 22.6 (3C), 14.1 (3C). MS (ESI) m/z: 878 (M+1)$^+$. Rf: 0.31 (CH$_2$Cl$_2$:MeOH, 100:1).

Compound 56

A suspension of 86 (0.2248 g, 0.288 mmol), Pd(OAc)$_2$ (3.8 mg, 0.017 mmol), BINAP (16.2 mg, 0.026 mmol), and Cs$_2$CO$_3$ (0.263 g, 0.807 mmol) in anhydrous toluene (5 mL) was stirred at 23° C. under Argon atmosphere for 5 min. Then benzophenone imine (116 mL, 0.692 mmol) was added and the mixture was heated at 110° C. for 3 d. The reaction was cooled to 23° C., CH$_2$Cl$_2$ was added (20 mL), and washed with H$_2$O (20 mL).

The combined organic layers were dried over anhydrous Na$_2$SO$_4$, filtered and evaporated to dryness. The residue was purified by chromatography on silica gel (hexane:EtOAc, 50:50) to give LL-MA-triflate-NPh$_2$ (56.2 mg, 24%) and 56 (0.102 g, 42%) as a yellow solids.

$^1$H NMR (300 MHz, CDCl$_3$) δ 7.76-7.70 (m, 4H), 7.48-7.37 (m, 7H), 7.32-7.20 (m, 7H), 7.14-7.10 (m, 2H), 6.98 (dd,

Compound 55

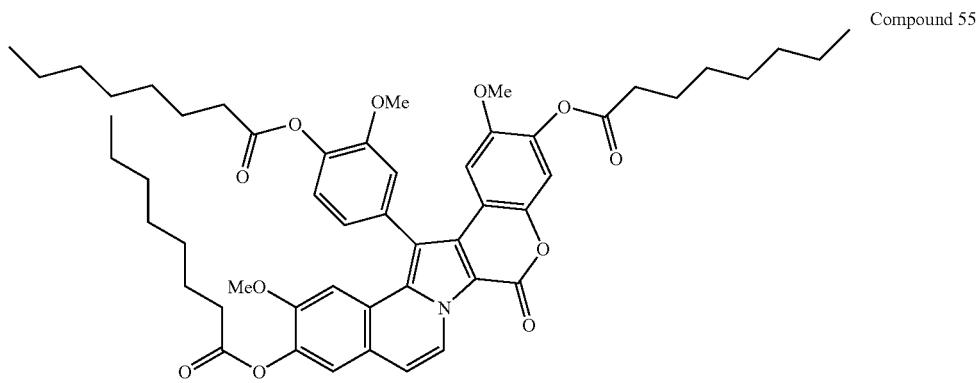

J=7.8, 1.5 Hz, 1H), 6.91 (d, J=1.5 Hz, 1H), 6.77 (d, J=7.8 Hz, 1H), 6.74 (s, 1H), 6.71 (s, 1H), 6.60 (s, 1H), 6.59 (s, 1H), 4.89-4.81 (m, 1H), 4.68-4.59 (m, 1H), 3.90 (s, 3H), 3.68 (s, 3H), 3.35 (s, 3H), 3.27 (s, 3H), 3.05 (m, 2H). $^{13}$C NMR (75 MHz, CDCl$_3$) δ 170.2, 169.2, 155.4, 150.1, 148.8, 147.4, 146.3, 145.4, 140.9, 140.7, 139.3, 138.9, 136.8, 136.3, 135.6, 130.8, 130.7, 130.6, 129.4, 129.3, 128.7, 128.6, 128.5, 128.4, 128.0, 127.7, 127.6, 126.6, 123.3, 120.9, 119.9, 115.1, 114.0, 113.9, 113.4, 110.8, 109.0, 108.9, 104.6, 55.8, 55.6, 55.5, 55.4, 42.2, 28.6. MS (ESI) m/z: 842 (M+1)$^+$. Rf: 0.33 (hexane:EtOAc, 50:50).

3.49 (s, 3H), 3.44 (s, 3H), 3.37-3.23 (m, 4H), 1.45 (s, 9H), 1.42 (s, 9H). $^{13}$C NMR (75 MHz, CDCl$_3$) δ 170.0, 154.9, 152.1, 150.3, 149.5, 147.5, 145.4, 139.8, 139.2, 135.7 (2C), 134.8, 134.2 (2C), 129.5, 128.6, 128.1 (2C), 124.7, 123.8, 123.0, 119.0, 116.0, 115.4, 113.0, 112.0, 110.8, 108.4, 107.4, 106.2, 105.1, 80.1 (2C), 56.1, 55.9, 55.6 (2C), 54.4 (2C), 38.1 (2C), 28.2 (6C). MS (ESI) m/z: 1008 (M+1)$^+$. Rf: 0.60 (CH$_2$Cl$_2$:MeOH, 60:1).

Compound 57

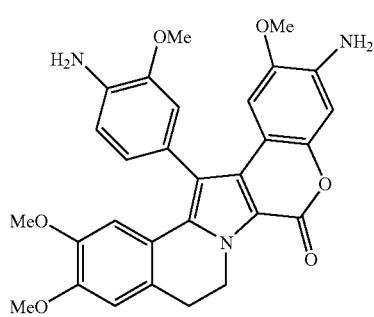

HCl 1.5 N (1.5 mL) was added to a solution of 56 (91.0 mg, 0.108 mmol) in THF (20 mL) at 23° C. The solution turned from yellow to colorless in 10 min. The solvent was evaporated to dryness and H$_2$O was added (20 mL).

The suspension was basified with aqueous ammonia 32% (0.5 mL) and extracted with CH$_2$Cl$_2$ (3×20 mL), dried over anhydrous Na$_2$SO$_4$, filtered, and the solvent was evaporated to give a residue which was purified by chromatography on silica gel (hexane:EtOAc, 1:4) to give 57 as a white solid (55 mg, quant).

$^1$H NMR (300 MHz, CDCl$_3$) δ 6.95-6.85 (m, 3H), 6.78 (s, 1H), 6.72 (s, 1H), 6.69 (s, 1H), 6.64 (s, 1H), 4.84-4.78 (m, 1H), 4.71-4.65 (m, 1H), 3.98 (br s, 4H), 3.86 (s, 3H), 3.79 (s, 3H), 3.45 (s, 3H), 3.38 (s, 3H), 3.08 (br t, J=7.3 Hz, 2H). $^{13}$C NMR (75 MHz, CDCl$_3$) δ 155.8, 148.6, 147.7, 147.2, 146.6, 143.7, 136.4, 135.8, 135.7, 128.9, 126.4, 124.9, 123.7, 120.3, 115.0, 113.1, 112.9, 110.8, 108.7, 108.3, 103.9, 102.1, 55.8, 55.6, 55.1 (2C), 42.2, 29.2, 28.6. MS (ESI) m/z: 514 (M+1)$^+$. Rf: 0.32 (hexane:EtOAc, 1:4).

Compound 58

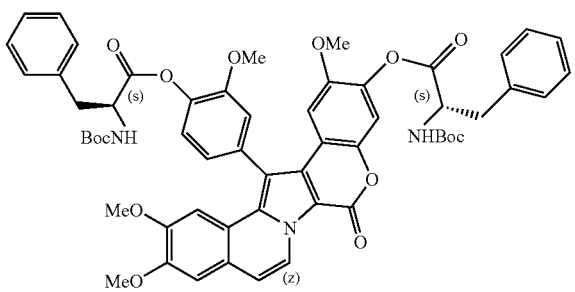

General procedure E (starting from 84, reaction time 20 h) and purification by chromatography on silica gel (CH$_2$Cl$_2$:MeOH, 60:1) to give 58 (30.7 mg, 96%).

$^1$H NMR (300 MHz, CDCl$_3$) δ 9.22 (d, J=7.3 Hz, 1H), 7.39-7.25 (m, 11H), 7.10-7.05 (m, 6H), 6.82 (d, J=7.3 Hz, 1H), 5.03 (m, 2H), 4.91 (m, 2H), 3.99 (s, 3H), 3.84 (s, 3H),

Compound 59

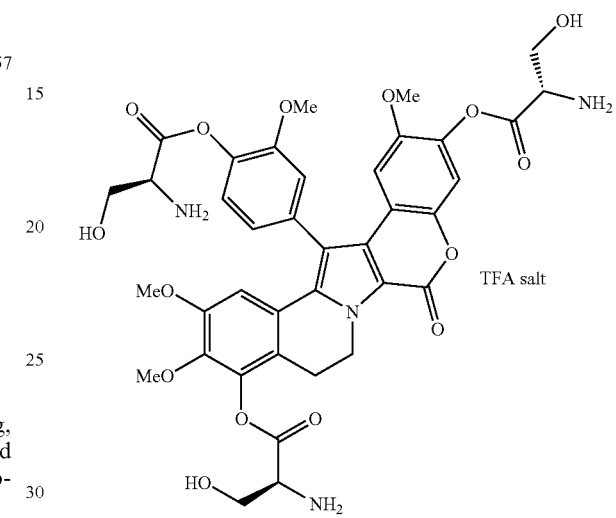

General procedure B (starting from 60) to afford 59 (15 mg, quant.).

$^1$H NMR (300 MHz, CD$_3$OD) δ 7.50-7.35 (m, 2H), 7.30-7.20 (m, 2H), 6.85-6.75 (m, 2H), 4.80-4.65 (m, 2H), 4.60 (br s, 1H), 4.53 (t, J=3.8 Hz, 1H), 4.42 (br t, 1H), 4.30-4.05 (m, 6H), 3.87 (s, 3H), 3.79 (s, 3H), 3.43 (s, 3H), 3.42 (s, 3H), 3.06 (br s, 2H). MS (ESI) m/z: 793 (M+1)$^+$.

Compound 60

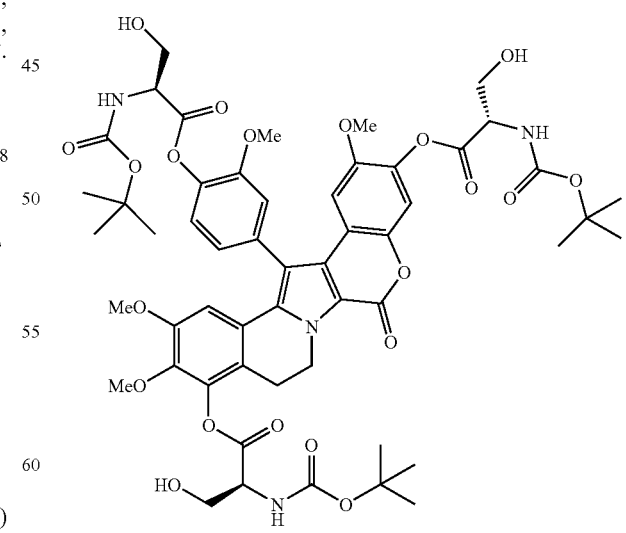

General procedure J (starting from 68, overnight) and purification by chromatography on silica gel (CH$_2$Cl$_2$:MeOH, 10:1) to afford 60 (23 mg, 82%).

$^1$H NMR (300 MHz, CDCl$_3$) δ 7.40-7.00 (m, 4H), 6.75-6.60 (m, 2H), 5.70-5.40 (m, 3H), 4.90-4.50 (m, 4H), 4.40-4.20 (m, 3H), 4.10-3.80 (m, 10H), 3.43 (s, 3H), 3.39 (s, 3H), 3.00 (br s, 2H), 2.80-2.50 (m, 3H), 1.49 (s, 9H), 1.46 (s, 9H), 1.45 (s, 9H). $^{13}$C NMR (75 MHz, CDCl$_3$) δ 169.4, 169.1, 155.6, 154.7, 151.5, 151.4, 147.4, 146.7, 146.4, 145.7, 145.1, 143.5, 141.1, 140.4, 139.6, 139.4, 138.4, 135.0, 134.7, 134.6, 126.9, 126.7, 126.5, 123.9, 123.8, 123.7, 122.9, 119.5, 116.3, 115.6, 114.9, 114.8, 114.3, 113.1, 112.1, 109.7, 107.8, 105.5, 103.5, 80.5, 64.0, 63.7, 61.0, 56.5, 56.3, 56.1, 55.8, 55.6, 55.5, 55.3, 41.9, 28.3, 22.1. MS (ESI) m/z: 1115 (M+23)$^+$, 1093 (M+1)$^+$. Rf: 0.45 (CH$_2$Cl$_2$:MeOH, 10:1).

General procedure D (starting from 109 and coumarin 3-carboxylic acid) and purification by chromatography on silica gel (CH$_2$Cl$_2$:MeOH, from 50:1 to 40:1) to afford 62 (41 mg, 80%).

$^1$H NMR (300 MHz, CDCl$_3$) δ 8.80 (s, 1H), 8.79 (s, 1H), 8.75 (s, 1H), 7.72-7.65 (m, 6H), 7.42-7.34 (m, 7H), 7.26-7.21 (m, 3H), 7.23 (s, 1H), 6.85 (s, 1H), 6.81 (s, 1H), 4.93-4.86 (m, 1H), 4.78-4.69 (m, 1H), 3.84 (s, 3H), 3.50 (s, 3H), 3.44 (s, 3H), 3.15 (br t, 2H). MS (ESI) m/z: 1040 (M+23)$^+$. Rf: 0.24 (CH$_2$Cl$_2$:MeOH, 50:1).

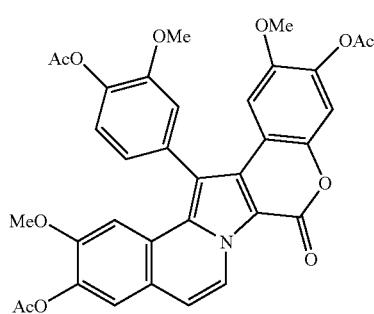

Compound 61

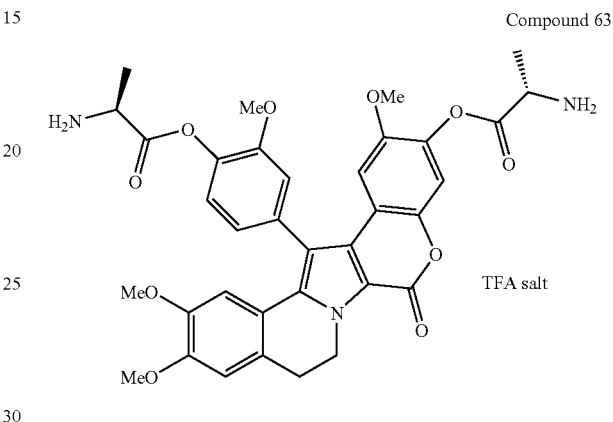

Compound 63

General procedure E (starting from 108, reaction time 24 h) and purification by chromatography on silica gel (CH$_2$Cl$_2$:MeOH, 40:1) to afford 61 (12 mg, 60%).

$^1$H NMR (300 MHz, CDCl$_3$) δ 9.22 (d, J=7.3 Hz, 1H), 7.39 (s, 1H), 7.30 (d, J=7.7 Hz, 1H), 7.25-7.22 (m, 3H), 7.14 (s, 1H), 7.05 (d, J=7.5 Hz, 1H), 6.81 (s, 1H), 3.84 (s, 3H), 3.45 (s, 6H), 2.37 (s, 3H), 2.34 (s, 3H), 2.32 (s, 3H). $^{13}$C NMR (75 MHz, CDCl$_3$) δ 168.9, 168.7, 168.7, 155.0, 152.4, 151.0, 147.8, 145.4, 140.9, 140.3, 139.7, 134.2, 133.5, 128.2, 124.1, 123.8, 123.7, 123.6, 123.1, 120.7, 115.7, 115.0, 112.8, 112.3, 112.2, 109.1, 106.4, 106.1, 56.2, 55.7, 55.6, 20.6 (3C). MS (ESI) m/z: 626 (M+1)$^+$. Rf: 0.40 (CH$_2$Cl$_2$:MeOH, 100:1).

General procedure B (starting from 21) to afford 63 (31.9 mg, quant.).

$^1$H NMR (300 MHz, CD$_3$OD) δ 7.44-7.38 (m, 2H), 7.24-7.20 (m, 2H), 6.94 (br s, 1H), 6.82-6.78 (m, 1H), 6.71-6.68 (m, 1H), 4.72 (m, 1H), 4.49-4.38 (m, 2H), 3.44 (s, 3H), 3.35 (s, 6H), 3.30 (s, 3H), 3.13 (br t, 2H), 1.77 (br d, 3H), 1.70 (br d, 3H). MS (ESI) m/z: 658 (M+1)$^+$.

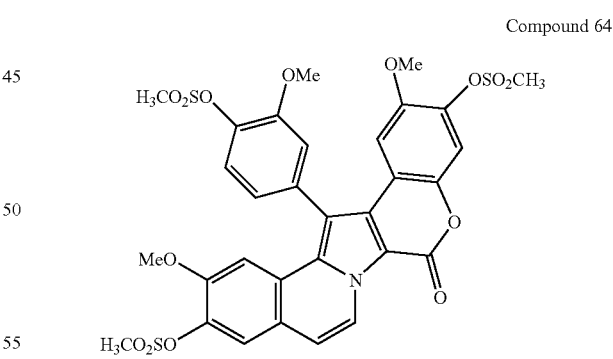

Compound 64

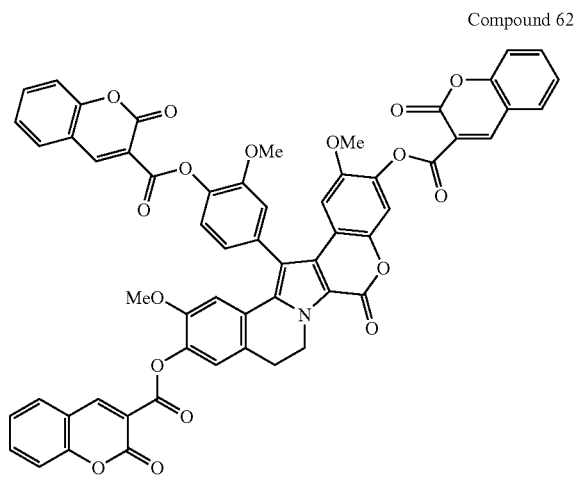

Compound 62

General procedure E (starting from 22, reaction time 77 h) and purification by chromatography on silica gel (CH$_2$Cl$_2$:MeOH, 80:1) to afford 64 (17 mg, 68%).

$^1$H NMR (300 MHz, CDCl$_3$) δ 9.16 (d, J=7.5 Hz, 1H), 7.66 (s, 1H), 7.60 (d, J=8.6 Hz, 1H), 7.33-7.30 (m, 3H), 7.18 (s, 1H), 7.06 (d, J=7.7 Hz, 1H), 6.76 (s, 1H), 3.96 (s, 3H), 3.49 (s, 6H), 3.37 (s, 3H), 3.24 (s, 3H), 3.21 (s, 3H). MS (APCI) m/z: 734 (M+1)$^+$. Rf: 0.33 (CH$_2$Cl$_2$:MeOH, 80:1).

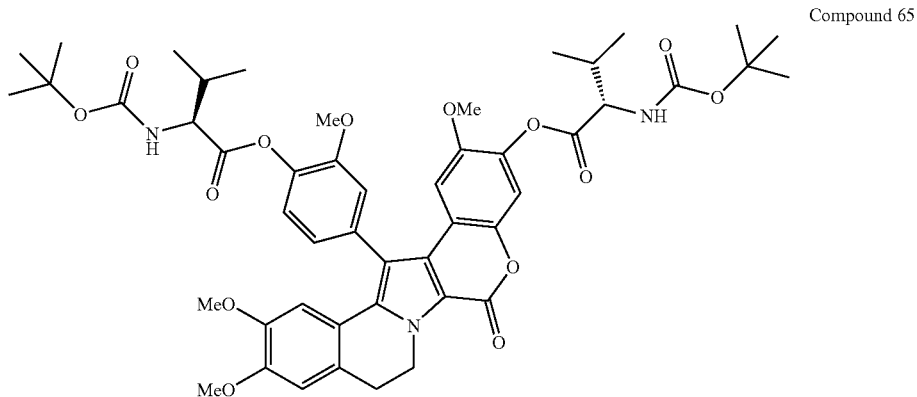

Compound 65

General procedure D (starting from 95 and (L)-N-Boc-valine) and purification by chromatography on silica gel (CH$_2$Cl$_2$:MeOH, 60:1) to afford 65 (83.6 mg, 94%).

$^1$H NMR (300 MHz, CDCl$_3$) δ 7.25-7.09 (m, 4H), 6.76 (br s, 1H), 6.71-6.66 (m, 2H), 5.06 (br d, J=9.3 Hz, 1H), 4.91-4.71 (m, 2H), 4.53-4.50 (m, 2H), 3.89 (s, 3H), 3.77 (s, 3H), 3.40 (s, 6H), 3.13 (t, J=7.3 Hz, 2H), 2.41-2.37 (m, 2H), 1.47 (d, J=6.1 Hz, 18H), 1.12-0.99 (m, 12H). $^{13}$C NMR (75 MHz, CDCl$_3$) δ 170.3, 155.6 (2C), 154.9, 151.9, 149.1, 147.6, 147.4, 144.8, 139.5, 138.4, 135.7, 134.4, 127.1, 127.0, 126.4, 123.7, 123.3, 119.5, 116.2, 114.8, 114.6, 114.4, 111.7, 110.9, 108.5, 105.4, 79.9 (2C), 58.5 (2C), 55.9, 55.8, 55.5, 55.4, 42.4, 31.2, 31.1, 28.5, 28.2 (6C), 19.1, 18.9, 17.1, 17.0. MS (ESI) m/z: 936 (M+23)$^+$, 914 (M+1)$^+$. Rf: 0.22 (CH$_2$Cl$_2$:MeOH, 60:1).

General procedure B (starting from 68) to afford 66 (18 mg, quant.).

$^1$H NMR (300 MHz, CD$_3$OD) δ 7.50-7.20 (m, 17H), 7.16-7.12 (m, 2H), 6.80-6.75 (m, 2H), 4.80-4.60 (m, 11H), 4.35-3.95 (m, 6H), 3.78 (s, 3H), 3.76 (s, 3H), 3.39 (d, J=2.1 Hz, 3H), 3.36 (d, J=2.1 Hz, 3H), 2.91 (br s, 2H). MS (ESI) m/z: 1063 (M)$^+$.

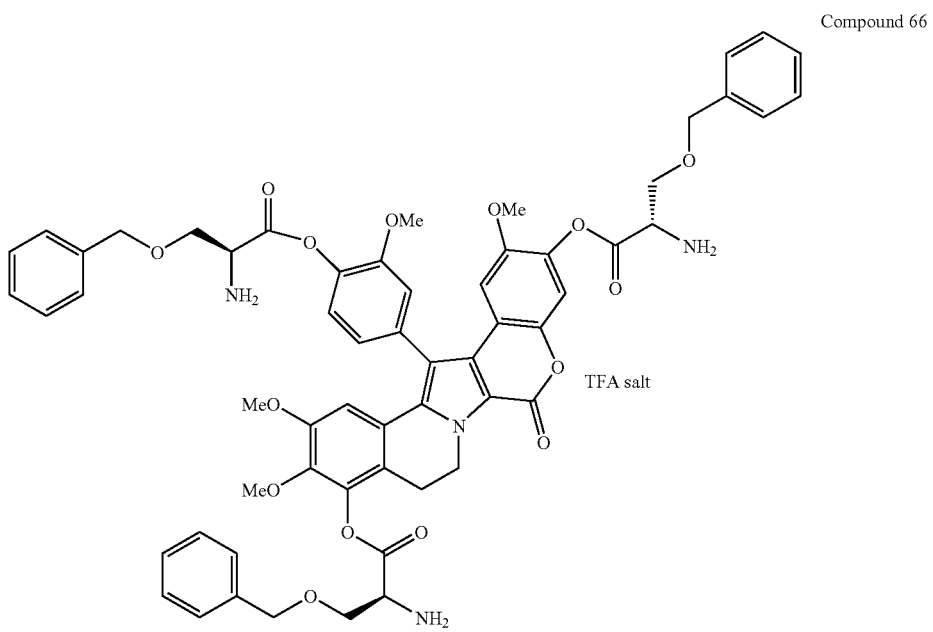

Compound 66

TFA salt

Compound 67

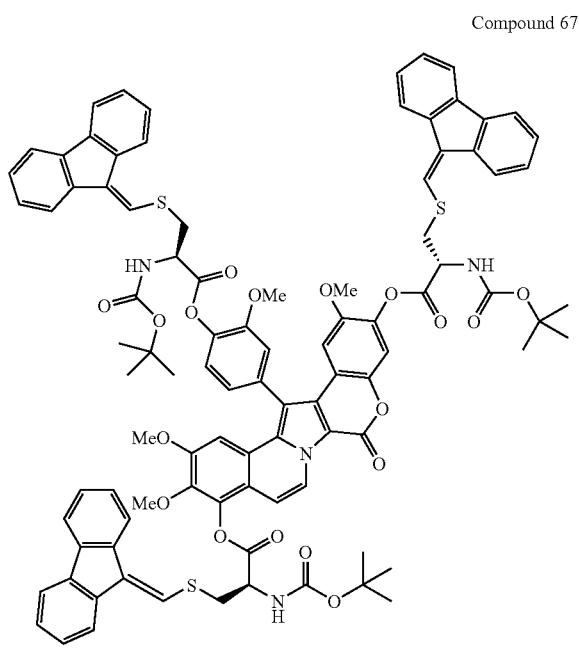

General procedure E (starting from 114, reaction time 70 h) and purification by chromatography on silica gel (hexane:EtOAc, 1:1) to afford 67 (52 mg, 81%).

¹H NMR (300 MHz, CDCl₃) δ 9.06 (d, J=7.5 Hz, 1H), 8.10-8.00 (m, 3H), 7.80-7.65 (m, 6H), 7.60-7.50 (m, 3H), 7.50-7.10 (m, 21H), 6.74 (s, 1H), 5.80-5.50 (m, 3H), 5.20-5.00 (m, 3H), 3.91 (s, 3H), 3.81 (s, 3H), 3.80-3.60 (m, 6H), 3.50-3.40 (m, 6H), 1.49 (s, 18H), 1.45 (s, 9H). ¹³C NMR (75 MHz, CDCl₃) δ 168.8, 168.4, 168.3, 168.2, 155.1, 154.9, 154.6, 153.1, 153.0, 152.0, 147.3, 145.3, 141.5, 140.2, 140.1, 140.0, 139.6, 139.0, 138.5, 138.1, 138.0, 136.7, 134.8, 132.9, 132.7, 132.5, 128.0, 127.9, 127.8, 127.7, 127.5, 127.3, 127.2, 127.1, 127.0, 126.9, 126.8, 126.7, 125.9, 125.3, 125.2, 123.8, 123.6, 123.5, 120.8, 119.9, 119.8, 119.7, 119.4, 119.2, 119.1, 117.9, 116.0, 115.1, 112.0, 111.9, 109.0, 106.6, 106.1, 104.4, 80.9, 80.8, 80.7, 61.0, 56.2, 55.8, 55.7, 55.6, 54.3, 54.1, 38.8, 29.7, 28.3, 28.2, 27.3. MS (ESI) m/z: 1689 (M+23)⁺. Rf: 0.19 (hexane:EtOAc, 2:1).

Compound 68

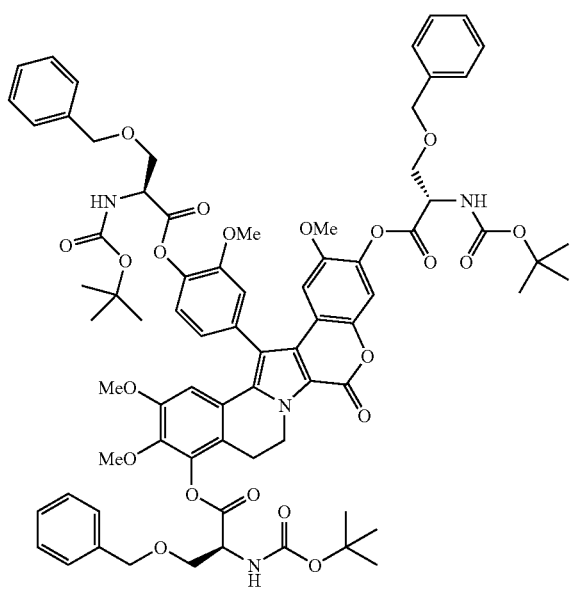

General procedure D (starting from 1 and (L)-N-Boc-Ser(Bzl)) and purification by chromatography on silica gel (hexane:EtOAc, 50:50) to afford 68 (153 mg, quant.).

¹H NMR (300 MHz, CDCl₃) δ 7.40-7.25 (m, 15H), 7.20-7.05 (m, 4H), 6.70-6.65 (m, 2H), 5.60-5.45 (m, 3H), 4.80-4.50 (m, 11H), 4.20-4.00 (m, 3H), 3.90-3.80 (m, 3H), 3.74 (s, 6H), 3.36 (t, J=4.7 Hz, 6H), 2.89 (br s, 2H), 1.48 (s, 18H), 1.46 (s, 9H). ¹³C NMR (75 MHz, CDCl₃) δ 169.0, 168.8, 155.4, 155.3, 154.9, 152.1, 151.8, 147.5, 144.8, 141.3, 141.1, 139.7, 138.6, 137.4, 137.0, 134.7, 134.3, 128.6, 128.5, 128.4, 128.2, 127.8, 127.6, 127.5, 126.9, 123.8, 123.1, 122.8, 119.4, 116.1, 115.6, 114.7, 111.8, 107.6, 105.5, 80.2, 80.1, 80.0, 73.7, 73.4, 70.0, 69.9, 60.8, 60.3, 56.1, 55.7, 55.5, 54.2, 54.1, 54.0, 41.8, 28.2, 22.0. MS (ESI) m/z: 1385 (M+23)⁺. Rf: 0.59 (hexane:EtOAc, 50:50).

Compound 69

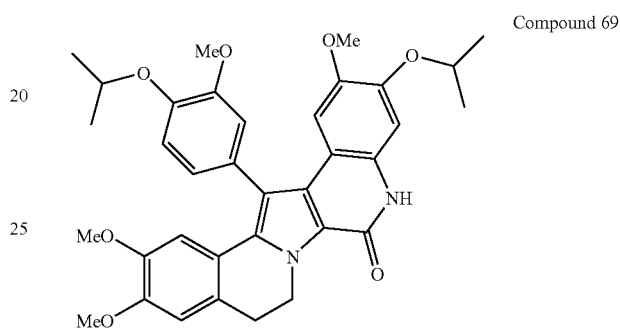

General procedure G (starting from 6,7-dimethoxy-3,4-dihydroisoquinoline and 2-bromo-N-[5-isopropoxy-2-(4-isopropoxy-3-methoxy-phenylethynyl)-4-methoxy-phenyl]-acetamide) and purification by chromatography on silica gel (EtOAc) to afford 69 (4.2 mg, 9%).

¹H NMR (300 MHz, CDCl₃) δ 9.71 (br s, 1H), 7.10 (br s, 2H), 7.07 (s, 1H), 6.81 (s, 1H), 6.78 (s, 1H), 6.76 (m, 2H), 5.03-4.94 (m, 2H), 4.61-4.55 (m, 2H), 3.89 (s, 3H), 3.82 (s, 3H), 3.41 (s, 3H), 3.37 (s, 3H), 3.12 (t, J=6.8 Hz, 2H), 1.40 (d, J=5.9 Hz, 12H). ¹³C NMR (75 MHz, CDCl₃) δ 156.6, 151.2, 148.3, 147.3, 146.6, 145.8, 133.6, 129.7, 127.3, 126.3, 123.5, 120.7, 118.6, 116.9, 114.8, 114.5, 111.1, 110.9, 108.5, 105.1, 102.5, 71.7, 71.4, 56.0, 55.8, 55.1, 55.0, 42.3, 29.0, 21.9 (2C), 20.9 (2C). MS (ESI) m/z: 599 (M+1)⁺. Rf: 0.21 (EtOAc).

Compound 70

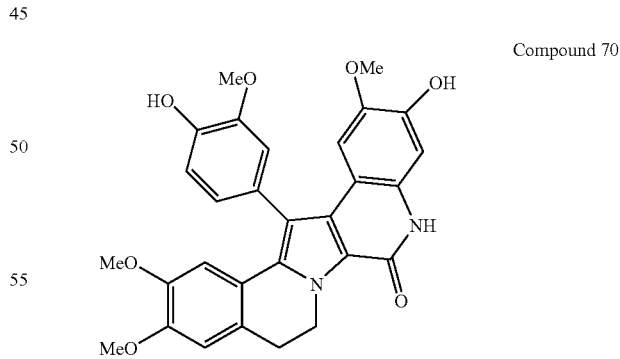

General procedure A (starting from 69) and purification by chromatography on silica gel (EtOAc) to afford 70 (2.4 mg, 94%).

¹H NMR (300 MHz, CDCl₃) δ 9.26 (br s, 1H), 7.12-7.07 (m, 2H), 7.00 (s, 1H), 6.79-6.73 (m, 4H), 5.75 (s, 2H), 5.15-5.11 (m, 1H), 4.81 (m, 1H), 3.89 (s, 3H), 3.86 (s, 3H), 3.49 (s, 3H), 3.39 (s, 3H), 3.13-3.11 (m, 2H). MS (ESI) m/z: 515 (M+1)⁺. Rf: 0.41 (CH₂Cl₂:MeOH, 10:1).

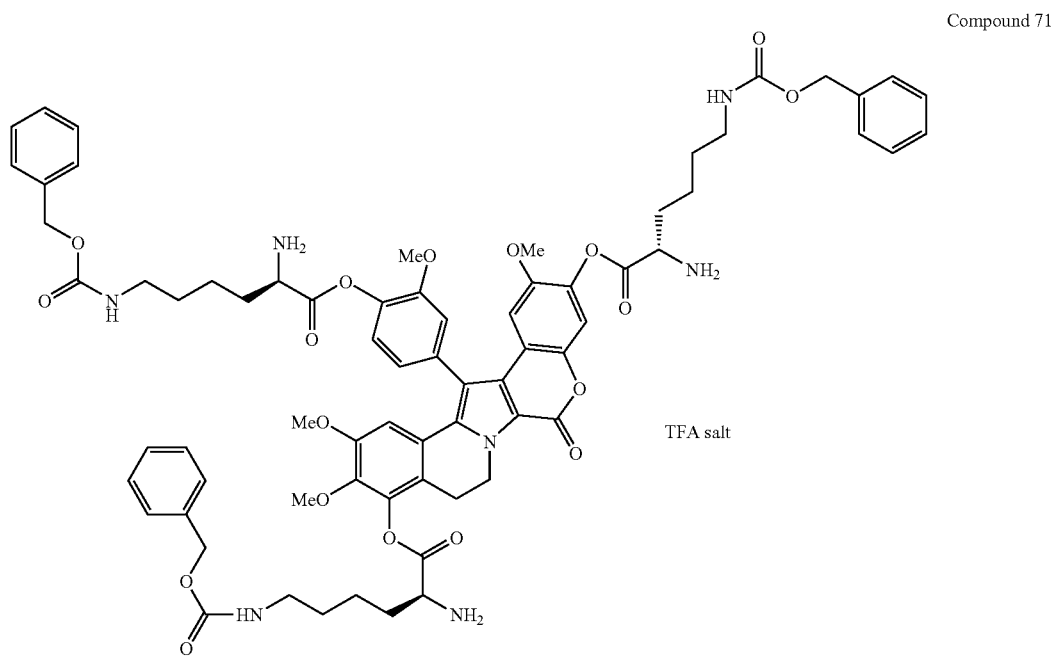

Compound 71

TFA salt

General procedure B (starting from 74) to afford 71 (14.0 mg, quant.)

$^1$H NMR (300 MHz, CD$_3$OD) δ 7.45-7.22 (m, 19H), 6.80-6.74 (m, 2H), 5.08 (m, 1H), 5.03 (s, 6H), 4.78 (m, 1H), 4.51 (br t, 1H), 4.42 (br t, 1H), 4.35 (br t, 1H), 3.79 (s, 6H), 3.42 (s, 3H), 3.41 (s, 3H), 3.21 (br s, 6H), 3.05 (m, 2H), 2.15 (m, 6H), 1.65 (m, 12H). MS (ESI) m/z: 1340 (M+23)$^+$, 1318 (M+1)$^+$.

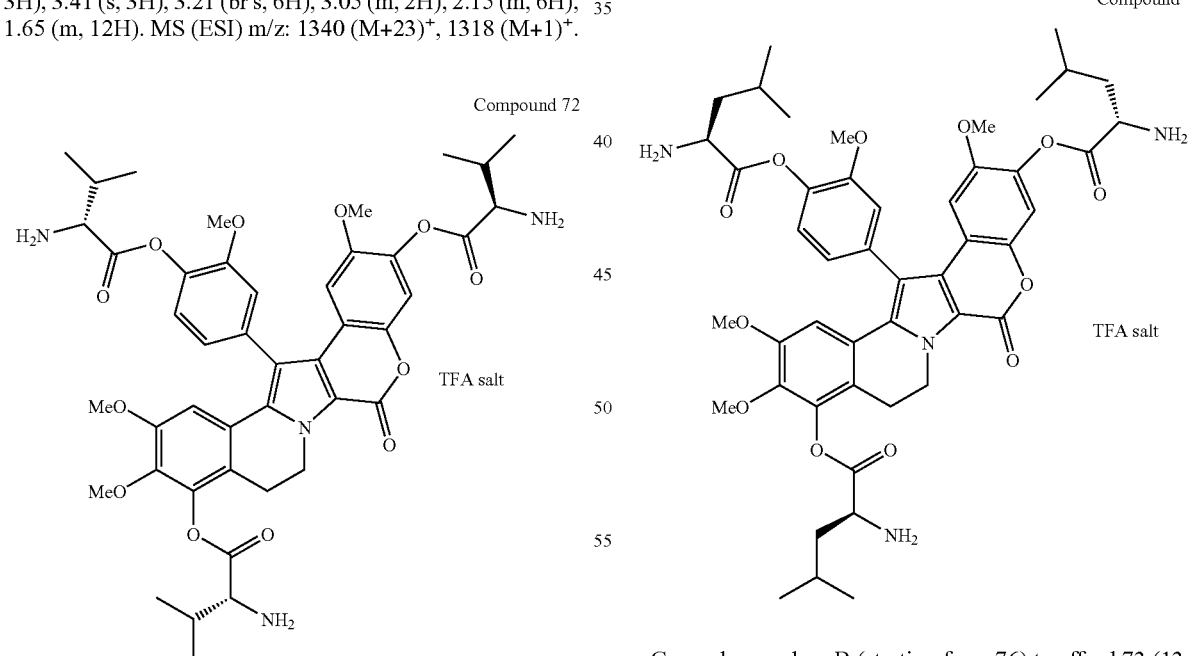

Compound 72

TFA salt

Compound 73

TFA salt

General procedure B (starting from 75) to afford 72 (14.1 mg, quant.)

$^1$H NMR (300 MHz, CD$_3$OD) δ 7.48-7.42 (m, 2H), 7.28-7.20 (m, 2H), 6.83-6.77 (m, 2H), 4.76 (m, 2H), 4.45 (dd, J=4.4, 2.0 Hz, 1H), 4.33 (dd, J=4.4, 2.0 Hz, 1H), 4.23 (dd, J=4.4, 2.0 Hz, 1H), 3.87 (s, 3H), 3.82 (s, 3H), 3.44 (s, 3H), 3.43 (s, 3H), 3.05 (m, 2H), 2.59-2.44 (m, 3H), 1.38-1.20 (m, 18H). MS (ESI) m/z: 829 (M+1)$^+$. Rf: 0.28 (CH$_2$Cl$_2$:MeOH, 10:1).

General procedure B (starting from 76) to afford 73 (13.8 mg, quant.).

$^1$H NMR (300 MHz, CD$_3$OD) δ 7.47-7.41 (m, 2H), 7.31-7.21 (m, 2H), 6.81-6.77 (m, 2H), 4.90-4.76 (m, 2H), 4.48 (t, J=7.3 Hz, 1H), 4.40 (t, J=7.1 Hz, 1H), 4.42 (t, J=6.6 Hz, 1H), 3.86 (s, 3H), 3.80 (s, 3H), 3.44 (s, 3H), 3.42 (s, 3H), 3.17-3.06 (m, 2H), 2.14-1.77 (m, 9H), 1.12-1.00 (m, 18H). MS (ESI) m/z: 871 (M+1)$^+$. Rf: 0.30 (CH$_2$Cl$_2$:MeOH, 10:1).

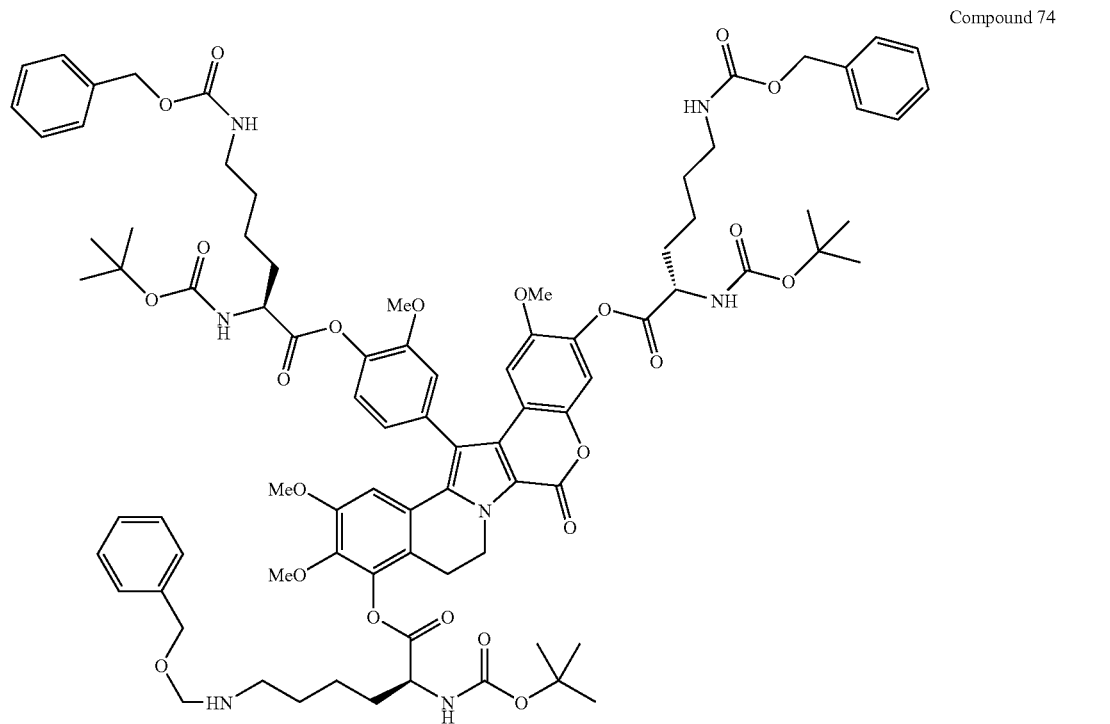
Compound 74
General procedure D (starting from 1 and (L)-N-Boc-Lysine-CBz) and purification by chromatography on silica gel (hexane:EtOAc, 2:3) to afford 74 (114.6 mg, 75%).
$^1$H NMR (300 MHz, CDCl$_3$) δ 7.34-7.31 (m, 15H), 7.15-7.07 (m, 4H), 6.67-6.63 (m, 2H), 5.08 (br s, 6H), 4.92 (m, 3H), 4.55 (m, 2H), 3.77 (s, 6H), 3.39 (s, 3H), 3.37 (s, 3H), 3.26-3.17 (m, 6H), 3.00 (br t, 2H), 2.04-1.76 (m, 6H), 1.58-1.29 (m, 38H). $^{13}$C NMR (75 MHz, CDCl$_3$) δ 171.0, 170.7 (2C), 156.5, 156.4, 155.5, 155.3 (2C), 154.8, 152.0, 151.7, 147.4 (2C), 144.8, 144.7, 141.2 (2C), 140.9 (2C), 139.6, 138.4 (2C), 136.5, 136.4, 134.7, 134.6, 134.2, 128.4, 128.0, 126.9, 126.8, 123.7, 123.2, 122.6, 119.4 (2C), 116.0, 115.6, 114.7 (2C), 111.7, 110.8, 105.4 (2C). MS (ESI) m/z: 1640 (M+23)$^+$. Rf: 0.30 (hexane:EtOAc, 2:3).
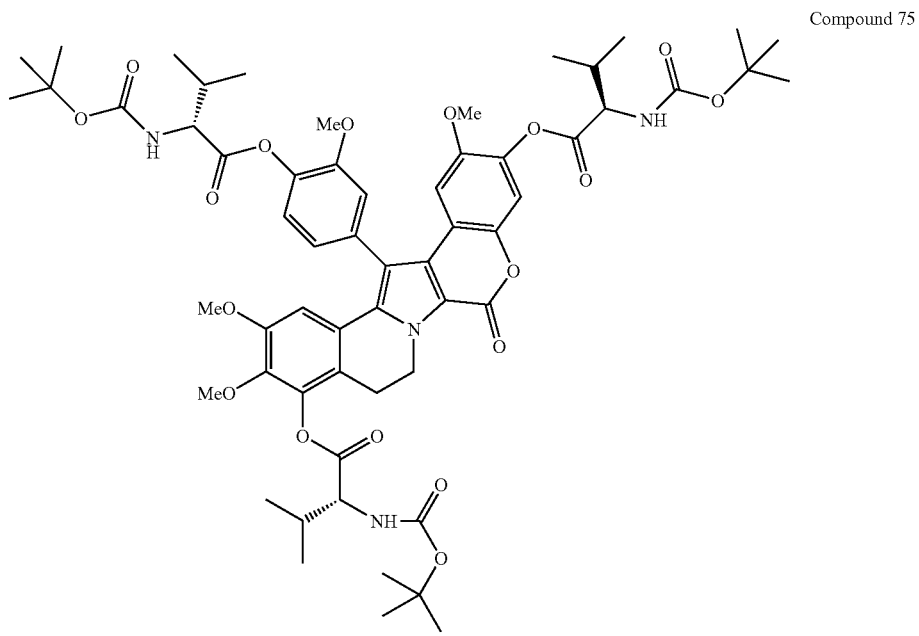
Compound 75

General procedure D (starting from 1 and (D)-N-Boc-Valine) and purification by chromatography on silica gel (hexane:EtOAc, 2:1) to afford 75 (96.5 mg, 91%).

$^1$H NMR (300 MHz, CDCl$_3$) δ 7.23 (s, 1H), 7.17-7.15 (m, 1H), 7.10-7.09 (m, 2H), 6.69-6.40 (m, 2H), 5.05 (br t, J=8.1 Hz, 2H), 4.53-4.51 (m, 3H), 3.78 (s, 6H), 3.40 (s, 3H), 3.38 (s, 3H), 3.01 (br t, 2H), 2.40-2.38 (m, 3H), 1.49 (br s, 27H), 1.15-0.99 (m, 18H). $^{13}$C NMR (75 MHz, CDCl$_3$) δ 170.5, 170.3, 155.7, 155.6 (2C), 154.9, 152.0, 151.8, 147.5, 144.8, 141.2, 141.0, 139.6, 138.5, 134.8, 134.3, 127.0, 126.9, 123.8, 123.2, 122.6, 119.4, 116.1, 115.6, 114.8, 114.7, 111.8, 107.6, 105.4, 80.1, 79.9 (2C), 58.9, 58.5 (2C), 56.0 (2C), 55.5 (2C), 41.8, 31.2, 31.1, 30.8, 28.2 (9C), 22.2, 19.2, 19.1, 18.9, 17.4, 17.1, 17.0. MS (ESI) m/z: 1129 (M+1)$^+$. Rf: 0.23 (hexane:EtOAc, 2:1).

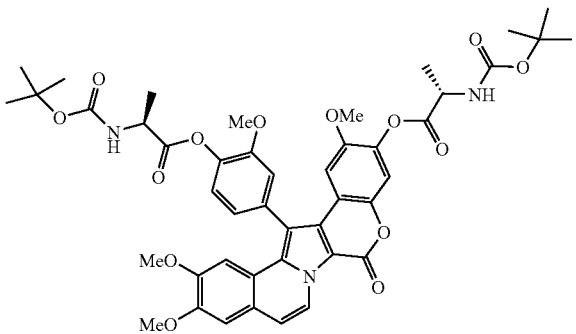

Compound 77

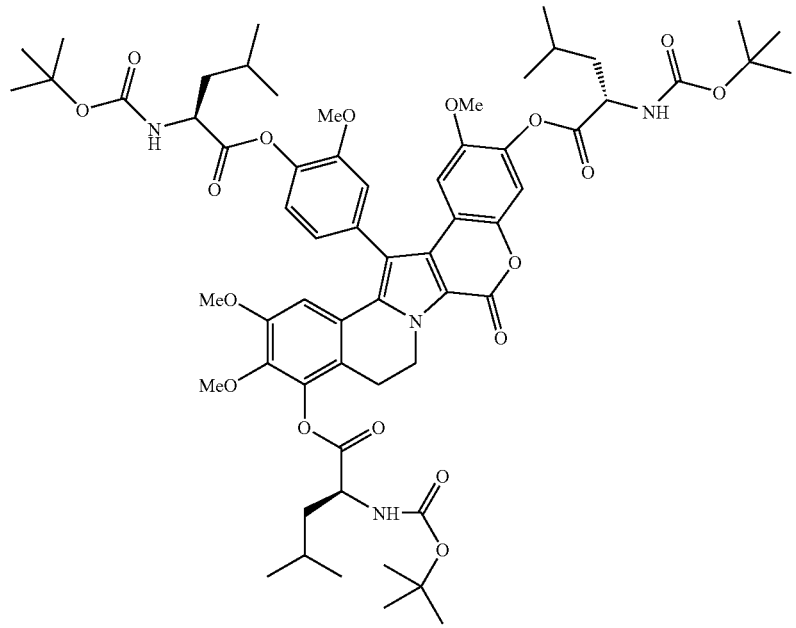

Compound 76

General procedure D (starting from 1 and (L)-N-Boc-Leucine) and purification by chromatography on silica gel (hexane:EtOAc, 2:1) to afford 76 (100.1 mg, 91%).

$^1$H NMR (300 MHz, CDCl$_3$) δ 7.24-7.08 (m, 4H), 6.68-6.64 (m, 2H), 4.92 (m, 2H), 4.57 (m, 3H), 3.79 (s, 3H), 3.77 (s, 3H), 3.40 (s, 3H), 3.39 (s, 3H), 3.02 (br t, 2H), 1.87-1.85 (m, 2H), 1.87-1.85 (m, 3H), 1.70-1.61 (m, 3H), 1.58 (br s, 27H), 1.05-0.98 (m, 18H). $^{13}$C NMR (75 MHz, CDCl$_3$) δ 171.4 (2C), 155.5, 155.4, 155.3, 155.0, 152.1, 151.8, 147.5, 144.8, 141.4, 141.0, 139.8, 138.7, 134.8, 134.2, 127.1, 123.8, 123.2, 122.7, 119.5, 116.1, 115.7, 114.7 (2C), 111.8, 107.6, 105.4 (2C), 80.2, 80.0 (2C), 60.7, 56.1, 55.7, 55.5, 52.3 (3C), 41.9, 41.6, 41.5, 41.2, 29.6, 28.3 (9C), 24.7 (3C), 22.9 (2C), 22.8 (2C), 22.7, 21.8. MS (ESI) m/z: 1193 (M+23)$^+$, 1171 (M+1)$^+$. Rf: 0.29 (hexane:EtOAc, 2:1).

General procedure D (starting from 26 and (L)-N-Boc-Alanine) and purification by chromatography on silica gel (CH$_2$Cl$_2$:MeOH, 60:1) to afford 77 (12.4 mg, 62%).

$^1$H NMR (300 MHz, CDCl$_3$) δ 9.24 (d, J=7.6 Hz, 1H), 7.34-7.08 (m, 7H), 6.74 (d, J=8.1 Hz, 1H), 5.30-5.12 (m, 2H), 4.62-4.60 (m, 2H), 4.00 (s, 3H), 3.80 (s, 3H), 3.51 (s, 3H), 3.44 (s, 3H), 1.64-1.44 (m, 24H). $^{13}$C NMR (75 MHz, CDCl$_3$) δ 171.5, 155.0, 152.2, 150.3, 149.6, 147.5, 145.5, 140.0, 139.4, 134.8, 134.2 (2C), 128.3 (2C), 124.7, 123.8, 123.2. 119.0, 116.0, 115.3, 113.0, 112.0, 110.9, 108.4, 107.5, 106.2, 105.1, 80.1, 56.2, 56.0, 55.8, 55.7, 49.3, 28.3, 18.7. MS (ESI) m/z: 878 (M+23)$^+$, 856 (M+1)$^+$. Rf: 0.13 (CH$_2$Cl$_2$:MeOH, 60:1).

Compound 78

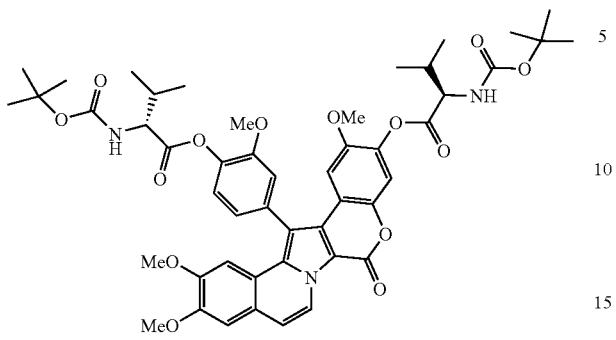

General procedure D (starting from 26 and (D)-N-Boc-Valine) and purification by chromatography on silica gel (CH$_2$Cl$_2$:MeOH, 60:1) to afford 78 (15.4 mg, 86%).

$^1$H NMR (300 MHz, CDCl$_3$) δ 9.23 (d, J=7.3 Hz, 1H), 7.32-7.22 (m, 3H), 7.14-7.07 (m, 4H), 6.68 (d, J=8.8 Hz, 1H), 5.09-5.06 (m, 2H), 4.57-4.52 (m, 2H), 3.99 (s, 3H), 3.80 (s, 3H), 3.51 (s, 3H), 3.43 (s, 3H), 2.46-2.38 (m, 2H), 1.49-1.45 (m, 18H), 1.27-1.00 (m, 12H). $^{13}$C NMR (75 MHz, CDCl$_3$) δ 170.4, 155.7, 155.0, 152.2, 150.3, 149.6, 147.5, 145.5, 139.9, 139.3, 134.9, 130.3, 134.8, 134.2, 128.2, 124.7, 123.7, 123.8, 123.1, 119.0, 116.0, 115.3, 113.0, 112.1, 110.9, 108.4, 107.5, 106.2, 105.1, 80.0 (2C), 58.6, 58.5, 56.0, 55.7, 55.6, 55.5, 31.3, 31.2, 28.3 (6C), 19.2, 19.1, 17.2, 17.1. MS (ESI) m/z: 934 (M+23)$^+$, 912 (M+1)$^+$. Rf: 0.32 (CH$_2$Cl$_2$:MeOH, 60:1).

Compound 79

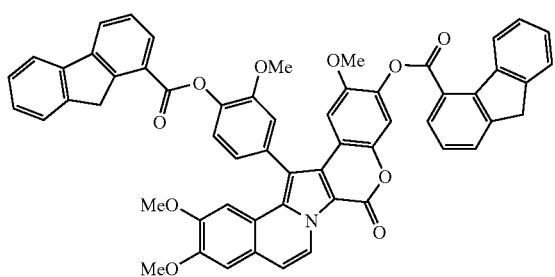

General procedure D (starting from 26 and 9H-fluorene-4-carboxilic acid) and purification by chromatography on silica gel (hexane:EtOAc, from 2:1 to 1:1) to afford 79 (8.6 mg, 41%).

$^1$H NMR (300 MHz, CDCl$_3$) δ 9.31 (d, J=7.3 Hz, 1H), 8.53-8.45 (m, 2H), 8.21 (d, J=7.8 Hz, 1H), 8.20 (d, J=8.0 Hz, 1H), 7.71 (t, J=7.1 Hz, 2H), 7.61-7.53 (m, 3H), 7.47-7.32 (m, 10H), 7.16-7.13 (m, 2H), 7.05 (s, 1H), 4.02 (s, 3H), 3.99 (s, 2H), 3.96 (s, 2H), 3.90 (s, 3H), 3.66 (s, 3H), 3.61 (s, 3H). $^{13}$C NMR (75 MHz, CDCl$_3$) δ 166.0, 165.9, 155.2, 152.6, 150.4, 149.6, 148.0, 145.7, 145.2, 145.1, 144.3, 144.2, 141.6, 141.4, 140.5, 140.0, 139 (2C), 134.8, 134.3, 129.6, 129.4, 129.1 (2C), 128.5, 127.8, 127.7, 126.9, 126.7, 126.1, 126.0, 125.4, 125.1, 125.0, 124.9, 124.8 (2C), 124.6, 124.2, 124.0, 123.2, 119.1, 116.1, 115.4, 113.0, 112.4, 111.2, 108.5, 107.5, 106.4, 105.2, 56.3, 56.0, 55.9, 55.9, 37.0 (2C). MS (ESI) m/z: 898 (M+1)$^+$. Rf: 0.50 (hexane:EtOAc, 50:50).

Compound 80

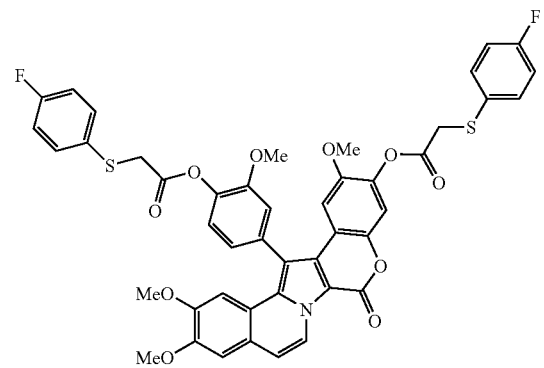

General procedure D (starting from 26 and 2[(4-fluorophenyl)thio]acetic acid) and purification by chromatography on silica gel (hexane:EtOAc, 2:1) to afford 80 (20.4 mg, quant.).

$^1$H NMR (300 MHz, CDCl$_3$) δ 9.23 (d, J=7.3 Hz, 1H), 7.58-7.50 (m, 4H), 7.26-7.20 (m, 4H), 7.11-7.01 (m, 8H), 6.78 (s, 1H), 4.00 (s, 3H), 3.87 (s, 2H), 3.81 (s, 2H), 3.77 (s, 3H), 3.48 (s, 3H), 3.37 (s, 3H). $^{13}$C NMR (75 MHz, CDCl$_3$) δ 167.5, 164.2, 161.0, 154.9, 152.1, 150.3, 149.5, 147.5, 145.4, 139.9, 139.3, 134.9, 134.2, 133.9, 133.8, 133.8, 133.7, 129.3, 128.1, 125.0, 124.7, 123.8, 123.6, 123.1, 118.9, 116.4, 116.1, 115.4, 113.0, 111.9, 110.8, 108.4, 107.5, 106.2, 105.0, 56.2, 56.0, 55.6, 55.5, 37.5, 37.4. MS (ESI) m/z: 872 (M+23)$^+$, 850 (M+1)$^+$. Rf: 0.52 (hexane:EtOAc, 2:1).

Compound 81

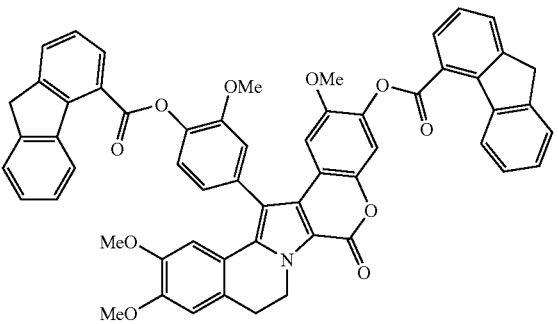

General procedure K (starting from 95 and 9H-fluorene-4-carboxilic acid) and chromatography on silica gel (CH$_2$Cl$_2$:MeOH, 200:1) to afford 81 as a yellow solid (20.0 mg, 95%).

$^1$H NMR (300 MHz, CDCl$_3$) δ 8.53-8.43 (m, 2H), 8.17 (m, 2H), 7.78-7.41 (m, 2H), 7.30-7.10 (m, 12H), 6.94 (s, 1H), 6.83 (s, 1H), 6.80 (s, 1H), 4.96-4.80 (m, 2H), 3.98 (s, 2H), 3.96 (s, 2H), 3.93 (s, 3H), 3.88 (s, 3H), 3.60 (s, 3H), 3.54 (s, 3H), 3.19 (t, J=6.1 Hz, 2H). $^{13}$C NMR (75 MHz, CDCl$_3$) δ 165.9, 155.2, 152.5, 149.2, 147.9, 147.8, 145.2, 145.1, 144.3, 144.1, 141.5, 141.3, 140.3, 139.9, 139.1, 136.0, 134.5, 129.5, 129.3, 129.0, 127.7, 127.6, 127.4, 127.3, 127.2, 126.8, 126.7, 126.6, 126.5, 126.1, 126.0, 125.9, 125.4, 125.2, 125.1, 125.0, 124.7, 124.5, 124.0, 123.5, 121.5, 119.7, 116.3, 115.0, 114.5, 112.1, 111.0, 108.6, 105.7, 56.2, 55.9, 55.9, 55.6, 42.6, 37.0 (2 C), 28.6. MS (ESI) m/z: 922 (M+23)$^+$, 900 (M+1)$^+$. Rf: 0.44 (CH$_2$Cl$_2$:MeOH, 200:1).

Compound 82

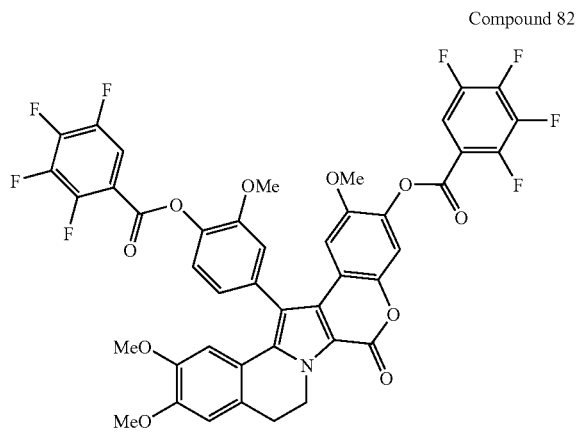

General procedure K (starting from 95 and 2,3,4,5-tetrafluorobenzoic acid) and chromatography on silica gel (CH$_2$Cl$_2$:MeOH, 200:1) to afford 82 as a yellow solid (20.7 mg, quant.).

$^1$H NMR (300 MHz, CDCl$_3$) δ 7.81-7.76 (m, 2H), 7.35 (d, J$_{H-F}$=7.8 Hz, 1H), 7.25-7.20 (m, 3H), 6.79 (br s, 2H), 6.71 (s, 1H), 4.92-4.79 (m, 2H), 3.91 (s, 3H), 3.82 (s, 3H), 3.48 (s, 3H), 3.46 (s, 3H), 3.16 (t, J=7.3 Hz, 2H). $^{13}$C NMR (75 MHz, CDCl$_3$) δ 159.7 (2C), 155.0, 152.0, 150.2 (m), 149.3, 148.2 (m), 147.7, 147.4, 146.7 (m), 145.8 (m), 145.0 (m), 144.9, 143.4 (m), 142.3 (m), 140.0 (m), 139.4, 138.2, 136.0, 135.0, 127.0, 126.6, 123.6, 123.5, 119.5, 116.7, 115.1, 114.7, 114.6, 113.6 (m), 111.8, 111.0, 108.5, 105.6, 56.3, 55.9, 55.8, 55.5, 42.5, 28.6. MS (ESI) m/z: 889 (M+23)$^+$, 867 (M+1)$^+$. Rf: 0.25 (CH$_2$Cl$_2$:MeOH, 200:1).

Compound 83

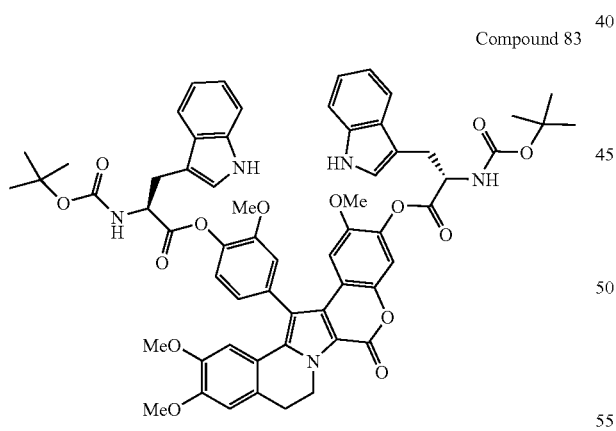

General procedure K (starting from 95 and (L)-N-Boc-Tryptophane) and chromatography on silica gel (CH$_2$Cl$_2$:MeOH, 25:1) to afford 83 as a yellow solid (13.0 mg, 98%).

$^1$H NMR (300 MHz, CDCl$_3$) δ 8.25-8.23 (br d, 2H), 7.68-7.63 (m, 2H), 7.40-7.34 (m, 2H), 7.26-7.05 (m, 7H), 6.93 (s, 1H), 6.77 (s, 1H), 6.67 (br s, 2H), 4.95-4.74 (m, 4H), 3.90 (s, 3H), 3.75 (s, 3H), 3.57-3.50 (m, 4H), 3.82 (s, 3H), 3.36 (s, 3H), 3.13 (br t, J=6.6 Hz, 2H), 1.43 (br d, 18H). MS (ESI) m/z: 1110 (M+23)$^+$. Rf: 0.11 (CH$_2$Cl$_2$:MeOH, 30:1).

Compound 84

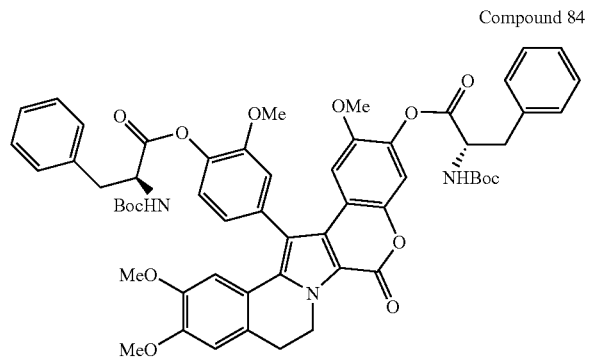

General procedure K (starting from 95 and (L)-N-Boc-Phenylalanine) and chromatography on silica gel (CH$_2$Cl$_2$:MeOH, 60:1) to afford 84 as a yellow solid (13.0 mg, 96%).

$^1$H NMR (300 MHz, CDCl$_3$) δ 7.36-7.20 (m, 9H), 7.17-7.04 (m, 5H), 6.77 (s, 1H), 6.79-6.66 (m, 2H), 5.02-4.74 (m, 4H), 3.90 (s, 3H), 3.80 (s, 3H), 3.40 (s, 3H), 3.39 (s, 3H), 3.34-3.12 (m, 6H), 1.44-138 (m, 18H). $^{13}$C NMR (75 MHz, CDCl$_3$) δ 169.9, 154.9, 151.9, 149.1, 147.6, 147.4, 144.7, 139.4, 138.3, 135.8, 134.4, 129.4, 129.2, 128.5, 127.1, 126.4, 126.3, 123.6, 123.3, 119.5, 116.3, 114.9, 114.6, 114.4, 111.7, 110.9, 108.4, 105.4, 79.9 (2C), 56.0, 55.8, 55.6, 55.4, 54.3 (2C), 42.4, 38.0 (2C), 28.4, 28.2 (6C). MS (ESI) m/z: 1032 (M+23)$^+$. Rf: 0.76 (CH$_2$Cl$_2$:MeOH, 60:1).

Compound 85

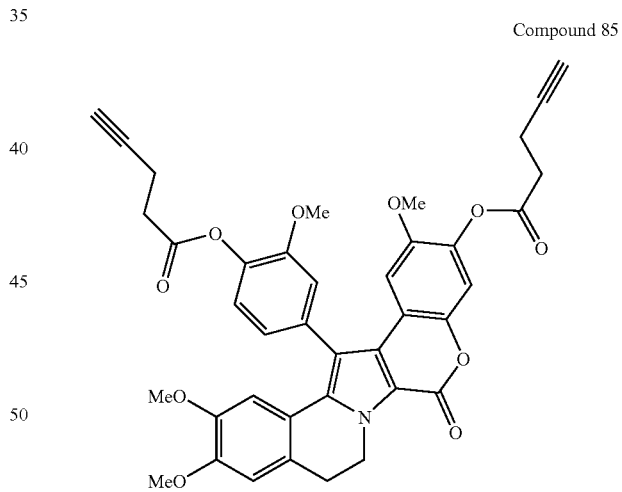

General procedure K (starting from 95 and 4-pentynoic acid) and chromatography on silica gel (CH$_2$Cl$_2$:MeOH, 60:1) to afford 85 as a yellow solid (9.0 mg, 99%).

$^1$H NMR (300 MHz, CDCl$_3$) δ 7.26-7.21 (m, 2H), 7.15-7.10 (m, 2H), 6.76 (s, 1H), 6.71 (s, 1H), 6.68 (s, 1H), 4.89-4.30 (m, 2H), 3.89 (s, 3H), 3.42 (s, 3H), 3.42 (s, 3H), 3.40 (s, 3H), 3.23 (t, J=7.1 Hz, 2H), 2.89-2.80 (m, 4H), 2.69-2.59 (m, 4H), 2.05-2.03 (m, 2H). $^{13}$C NMR (75 MHz, CDCl$_3$) δ 169.7, 169.5, 155.1, 152.1, 149.1, 147.7, 147.6, 144.9, 139.8, 138.7, 135.9, 134.4, 130.9, 128.8, 127.2, 126.4, 123.8, 123.3, 119.6, 116.2, 114.8, 114.5, 111.9, 111.0, 108.5, 105.5, 82.1, 82.0, 69.3 (2C), 56.2, 55.9, 55.7, 55.4, 42.5, 33.1 (2C), 28.6. MS (ESI) m/z: 698 (M+23)$^+$, 676 (M+1)$^+$. Rf: 0.65 (CH$_2$Cl$_2$:MeOH, 60:1).

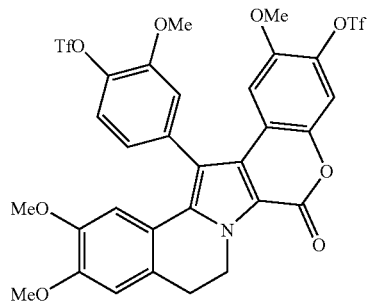

Compound 86

General procedure I (starting from 95) and chromatography on silica gel (CH$_2$Cl$_2$) to give 86 as a yellow solid (13.4 mg, 89%).

$^1$H NMR (300 MHz, CDCl$_3$) δ 7.45 (d, J=8.8 Hz, 1H), 7.27 (s, 1H), 7.24-7.20 (m, 2H), 6.79 (s, 1H), 6.66 (s, 1H), 6.54 (s, 1H), 4.93-4.86 (m, 1H), 4.77-4.70 (m, 1H), 3.92 (s, 3H), 3.90 (s, 3H), 3.47 (s, 3H), 3.36 (s, 3H), 3.15 (br t, 2H). $^{13}$C NMR (75 MHz, CDCl$_3$) δ 154.4, 152.5, 149.6, 147.8 (2C), 144.4, 138.5, 137.0 (3C), 136.2, 129.7, 126.8, 126.1, 123.6, 123.5, 118.6 (q, J$_{C-F}$=136.7 Hz), 118.6 (q, J$_{C-F}$=132.2 Hz), 115.7, 114.9, 114.0, 111.9, 111.2, 108.3, 105.7, 56.6, 56.0, 55.8, 55.2, 42.6, 28.5. MS (ESI) m/z: 780 (M+1)$^+$. Rf: 0.43 (CH$_2$Cl$_2$).

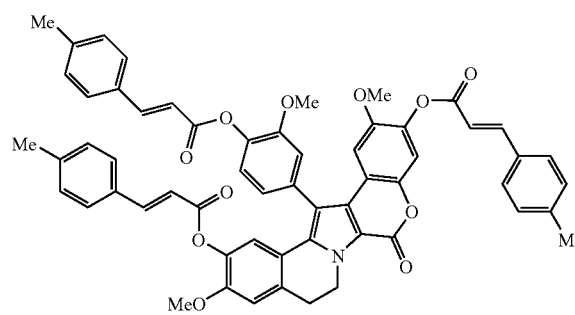

Compound 87

General procedure K (starting from 167 and 4-methylcinnamic acid) and chromatography on silica gel (hexane:EtOAc, 1:1) to afford 87 as a white solid (5.5 mg, 86%).

$^1$H NMR (300 MHz, CDCl$_3$) δ 7.85 (d, J=16.4 Hz, 1H), 7.79 (d, J=16.8 Hz, 1H), 7.75 (d, J=15.8 Hz, 1H), 7.52-7.47 (m, 4H), 7.43-7.40 (m, 2H), 7.28-7.10 (m, 10H), 6.91 (s, 1H), 6.87 (s, 1H), 6.77 (s, 1H), 6.60 (d, J=16.1 Hz, 1H), 6.58 (d, J=16.1 Hz, 1H), 6.57 (d, J=16.1 Hz, 1H), 4.96-4.90 (m, 1H), 4.82-4.78 (m, 1H), 3.87 (s, 3H), 3.81 (s, 3H), 3.50 (s, 3H), 3.21 (t, J=7.1 Hz, 2H), 2.39 (s, 9H). MS (ESI) m/z: 956 (M+23)$^+$, 934 (M+1)$^+$. Rf: 0.45 (hexane:EtOAc, 1:1).

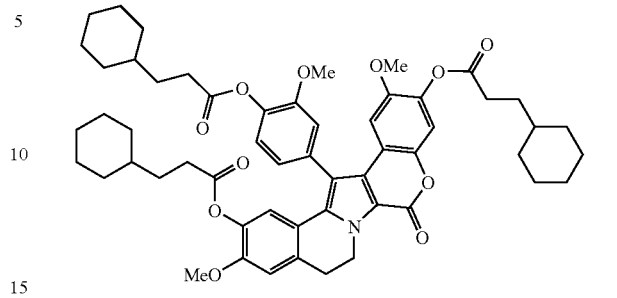

Compound 88

General procedure K (starting from 167 and cyclohexilpropionic acid) and chromatography on silica gel (hexane:EtOAc, 1:1) to afford 88 as a yellow oil (4.5 mg, quant.).

$^1$H NMR (300 MHz, CDCl$_3$) δ 7.19-7.15 (m, 1H), 7.08-7.03 (m, 3H), 6.86 (s, 1H), 6.72-6.69 (m, 2H), 4.93-4.87 (m, 1H), 4.76-4.71 (m, 1H), 3.84 (s, 3H), 3.78 (s, 3H), 3.43 (s, 3H), 3.17 (br t, 2H), 2.64-2.55 (m, 6H), 1.77-1.40 (m, 21H), 1.36-1.02 (m, 12H), 0.98-0.88 (m, 6H). MS (ESI) m/z: 938 (M+23)$^+$, 916 (M+1)$^+$. Rf: 0.63 (hexane:EtOAc, 1:1).

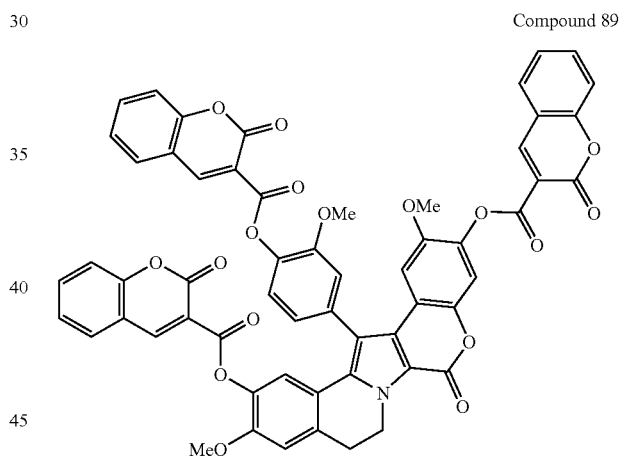

Compound 89

General procedure K (starting from 167 and coumarin-3-carboxylic acid), chromatography on silica gel (CH$_2$Cl$_2$:MeOH, 20:1) and the yellow solid was triturated with MeOH to afford 89 as a bright yellow solid (9.2 mg, 86%).

$^1$H NMR (300 MHz, CDCl$_3$) δ 8.78 (s, 1H), 8.75 (s, 1H), 8.70 (s, 1H), 7.77-7.62 (m, 6H), 7.37-7.33 (m, 6H), 7.24-7.13 (m, 4H), 6.93 (s, 1H), 6.87 (s, 1H), 6.80 (s, 1H), 4.92 (m, 1H), 4.84 (m, 1H), 3.87 (s, 3H), 3.82 (s, 3H), 3.50 (s, 3H), 3.23 (br t, 2H). $^{13}$C NMR (75 MHz, CDCl$_3$) δ 160.8, 160.4 (2C), 156.5 (2C), 155.5, 155.4, 155.1, 152.1, 151.2, 150.3 (2C), 147.7, 144.9, 139.7, 138.6, 138.2, 134.9 (4C), 134.7, 133.9, 133.3, 130.2, 129.8 (2C), 127.1, 125.0, 124.9, 124.1, 123.2, 120.3, 120.1, 117.9, 117.8, 117.1, 116.9 (2C), 116.7, 116.5, 115.5, 114.8; 112.3, 112.1, 105.6, 56.3, 56.2 (2C), 42.2, 29.3. MS (ESI) m/z: 1017 (M)$^+$. Rf: 0.24 (CH$_2$Cl$_2$:MeOH, 40:1).

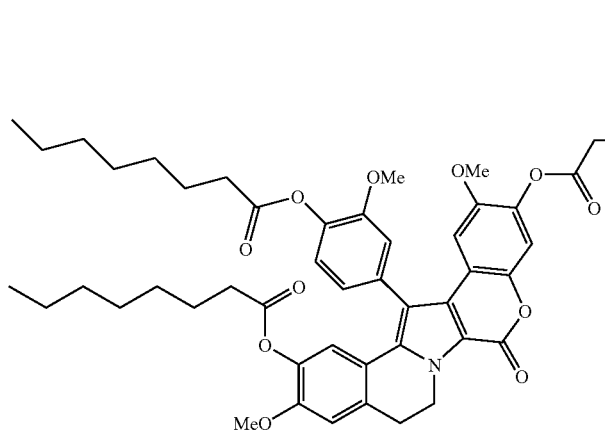

Compound 90

General procedure K (starting from 167 and n-octanoic acid) and chromatography on silica gel (hexane:EtOAc, 2:1) to afford 90 as a yellow oil (7.8 mg, 90%).

$^1$H NMR (300 MHz, CDCl$_3$) δ 7.18-7.15 (m, 1H), 7.08-7.02 (m, 3H), 6.86 (s, 1H), 6.72-6.69 (m, 2H), 4.93-4.89 (m, 1H), 4.76-4.72 (m, 1H), 3.84 (s, 3H), 3.78 (s, 3H), 3.43 (s, 3H), 3.17 (br t, 2H), 2.63-2.47 (m, 6H), 1.78-1.69 (m, 6H), 1.32-1.25 (m, 18H), 0.90-0.88 (m, 15H). $^{13}$C NMR (75 MHz, CDCl$_3$) δ 171.9, 171.7, 171.4, 155.2, 152.2, 151.2, 147.8, 144.9, 142.6, 140.0, 139.0, 138.5, 133.3, 132.7, 127.3, 123.9, 123.1, 123.0, 120.3, 116.0, 115.4, 114.6, 113.3, 112.1, 111.9, 105.5, 56.1, 55.9, 55.8, 42.2, 34.0, 33.9, 33.8, 31.7 (2C), 31.6, 29.2, 29.0, 28.9 (5C), 25.1, 24.9 (2C), 22.6 (3C), 14.1 (3C). MS (ESI) m/z: 902 (M+23)$^+$, 880 (M+1)$^+$. Rf: 0.38 (hexane: EtOAc, 2:1).

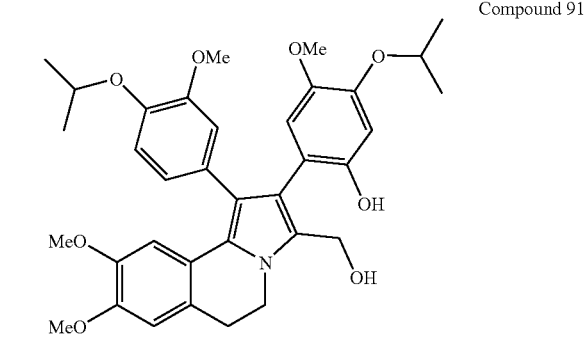

Compound 91

A solution of 162 (6.0 mg, 0.01 mmol) was added to a suspension of NaBH$_4$ (1.0 mg, 0.02 mmol) in anhydrous THF (2 mL) at 0° C. under Argon atmosphere. The reaction mixture was stirred at 23° C. for 3 h, then H$_2$O (5 mL) was slowly added at 0° C. The mixture was extracted with CH$_2$Cl$_2$ (3×10 mL), dried over anhydrous Na$_2$SO$_4$, filtered, and evaporated under reduced pressure to give 91 as a white solid (6.0 mg, quant).

$^1$H NMR (300 MHz, CDCl$_3$) δ 6.84 (s, 1H), 6.80 (br s, 2H), 6.80 (s, 1H), 6.72 (s, 1H), 6.67 (s, 1H), 6.51 (s, 1H), 6.42 (s, 1H), 4.59 (s, 2H), 4.49-4.44 (m, 2H), 4.28-4.00 (m, 2H), 3.88 (s, 3H), 3.58 (s, 3H), 3.54 (s, 3H), 3.40 (s, 3H), 3.07 (m, 2H), 1.36 (d, J=6.1 Hz, 6H), 1.31 (d, J=6.1 Hz, 6H). MS (ESI) m/z: 626 (M+23)$^+$. Rf: 0.10 (CH$_2$Cl$_2$:MeOH, 20:1).

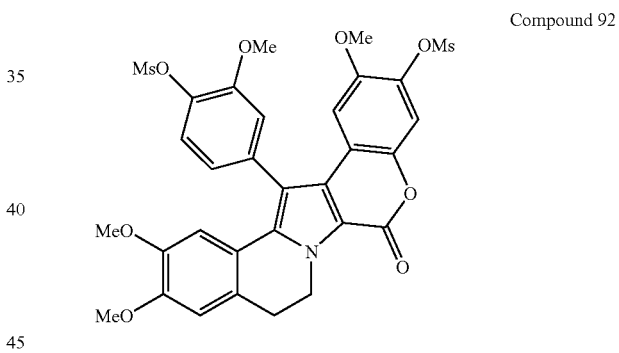

Compound 92

A suspension of 95 (7.0 mg, 0.0135 mmol), methanesulfonyl chloride (6 mL, 0.077 mmol), pyridine (6 mL, 0.077 mmol) and DMAP (1 mg, 0.008 mmol) in anhydrous CH$_2$Cl$_2$ (2 mL) was stirred at 23° C. for 48 h under Argon atmosphere. The solvent was evaporated under reduced pressure and the residue was purified by chromatography on silica gel (CH$_2$Cl$_2$:MeOH, 20:1) to give 92 as a yellow solid (7.5 mg, 83%).

$^1$H NMR (300 MHz, CDCl$_3$) δ 7.50 (d, J=8.1 Hz, 1H), 7.32 (br s, 1H), 7.21 (br d, J=8.1 Hz, 1H), 7.14 (br s, 1H), 6.77 (s, 1H), 6.68 (s, 1H), 6.61 (s, 1H), 4.99-4.94 (m, 1H), 4.70-4.66 (m, 1H), 3.90 (s, 3H), 3.87 (s, 3H), 3.46 (s, 3H), 3.37 (s, 3H), 3.31 (s, 3H), 3.19 (s, 3H), 3.12 (br t, J=6.3 Hz, 2H). $^{13}$C NMR (75 MHz, CDCl$_3$) δ 154.7, 152.6, 149.4, 148.0, 147.7, 144.8, 138.0, 137.0, 135.9 (2C), 126.7, 125.5, 123.7, 119.3, 117.3, 115.5, 113.7, 111.1, 108.4, 105.7, 56.4, 56.0, 55.8, 55.3, 42.5, 39.1, 38.6, 29.7. MS (ESI) m/z: 694 (M+23)$^+$, 672 (M+1)$^+$. Rf: 0.50 (CH$_2$Cl$_2$:MeOH, 20:1).

Compound 93

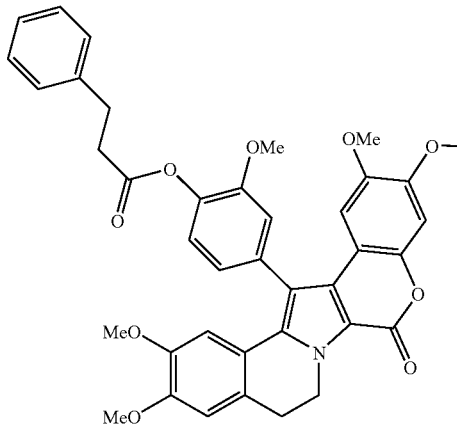

General procedure F (starting from 95 and hydrocinnamoyl chloride) and chromatography on silica gel (hexane:EtOAc, 1:1) to afford 93 as a white solid (4.9 mg, 43%).

$^1$H NMR (300 MHz, CDCl$_3$) δ 7.36-7.22 (m, 9H), 7.15-7.02 (m, 3H), 6.76 (s, 1H), 6.70 (s, 1H), 6.68 (s, 1H), 4.90-4.74 (m, 2H), 3.90 (s, 3H), 3.75 (s, 3H), 3.40 (s, 3H), 3.38 (s, 3H), 3.16-2.89 (m, 10H). MS (ESI) m/z: 802 (M+23)$^+$, 780 (M+1)$^+$. Rf: 0.38 (hexane:EtOAc, 1:1).

Compound 94

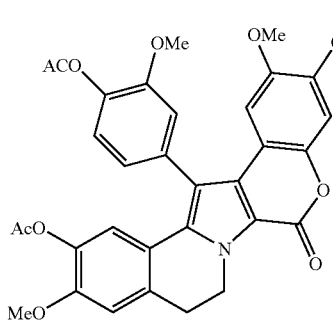

General procedure L (starting from 167 and Ac$_2$O) to afford 94 as a brown solid (11.0 mg, 91%.).

$^1$H NMR (300 MHz, CDCl$_3$) δ 7.20 (d, J=7.8 Hz, 1H), 7.09-7.04 (m, 3H), 6.87 (s, 1H), 6.70 (br s, 2H), 4.92-4.86 (m, 1H), 4.79-4.72 (m, 1H), 3.85 (s, 3H), 3.79 (s, 3H), 3.43 (s, 3H), 3.17 (t, J=6.3 Hz, 2H), 2.35 (s, 3H), 2.23 (s, 3H). $^{13}$C NMR (75 MHz, CDCl$_3$) δ 169.0, 168.8, 168.5, 155.1, 152.1, 151.1, 147.7, 144.8, 139.9, 138.8, 138.4, 134.9, 133.4, 132.9, 127.2, 123.9, 123.1, 120.3, 120.0, 116.1, 115.4, 114.6, 112.1, 111.9, 105.5, 56.1, 56.0, 55.8, 42.1, 29.2, 20.6 (2C), 20.5. MS (ESI) m/z: 650 (M+23)$^+$, 628 (M+1)$^+$. Rf: 0.28 (hexane:EtOAc, 1:1).

Compound 95

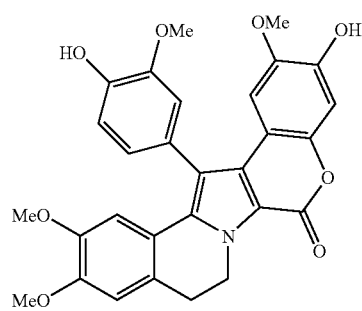

General procedure A (starting from 162) and chromatography on silica gel (CH$_2$Cl$_2$:MeOH, 20:1) to afford 95 as a yellow solid (170 mg, 61%).

$^1$H NMR (300 MHz, CDCl$_3$) δ 7.14-7.07 (m, 2H), 6.07-6.96 (m, 2H), 6.76 (s, 1H), 6.71 (s, 1H), 6.64 (s, 1H), 5.75 (s, 1H), 5.72 (s, 1H), 4.98-4.89 (m, 1H), 4.69-4.59 (m, 1H), 3.89 (s, 3H), 3.87 (s, 3H), 3.50 (s, 3H), 3.38 (s, 3H), 3.15-3.09 (m, 2H). $^{13}$C NMR (75 MHz, DMSO-d$_6$) δ 154.3, 148.8, 148.5, 147.0, 146.9, 146.6, 145.7, 144.5, 135.5, 127.7, 126.8, 125.4, 123.4, 119.4, 116.3, 114.7, 112.5, 111.7, 108.7, 105.0, 103.6, 56.0, 55.5, 55.1, 54.5, 42.0, 27.7. MS (ESI) m/z: 516 (M+1)$^+$. Rf: 0.33 (CH$_2$Cl$_2$:MeOH, 20:1).

Compound 96

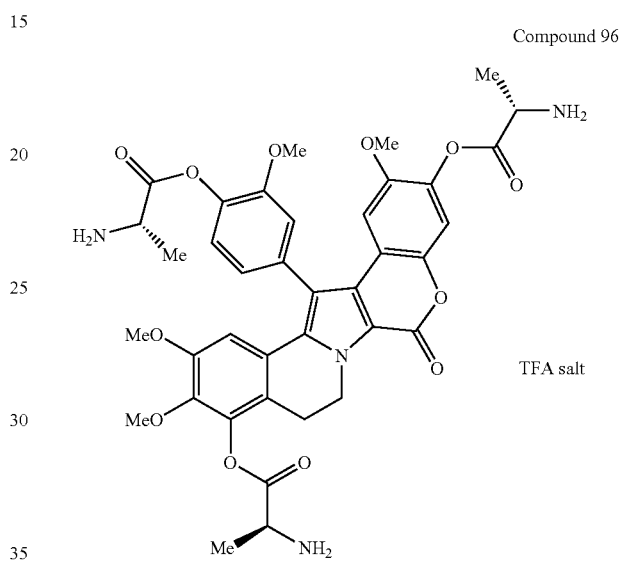

TFA salt

General procedure B (starting from 46) to afford 96.

$^1$H NMR (300 MHz, CD$_3$OD) δ 7.60-7.40 (m, 2H), 7.40-7.20 (m, 2H), 7.00-6.80 (m, 2H), 4.77 (br s, 2H), 4.75-4.40 (m, 3H), 3.86 (s, 3H), 3.80 (s, 3H), 3.44 (s, 3H), 3.42 (s, 3H), 3.05 (br s, 2H), 2.00-1.70 (m, 9H). MS (ESI) m/z: 745 (M+1)$^+$.

Compound 97

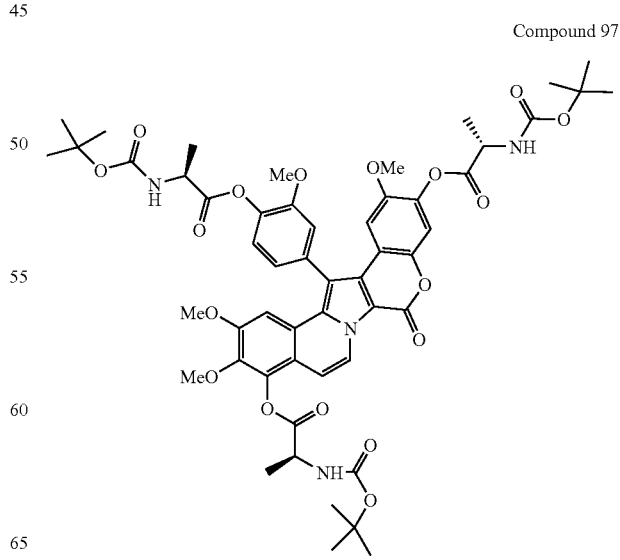

General procedure E (starting from 46, reaction time 30 h) and chromatography on silica gel (hexane:EtOAc, 1:1) to afford 97 as a yellow solid (16 mg, 88%).

$^1$H NMR (300 MHz, CDCl$_3$) δ 9.23 (d, J=7.6 Hz, 1H), 7.40-7.05 (m, 6H), 6.78 (d, J=8.4 Hz, 1H), 5.20-5.00 (m, 3H), 4.80-4.50 (m, 3H), 3.86 (s, 3H), 3.81 (s, 3H), 3.48 (s, 3H), 3.43 (s, 3H), 1.68 (d, J=7.1 Hz, 3H), 1.62 (d, J=7.2 Hz, 3H), 1.55 (d, J=7.1 Hz, 3H), 1.49 (s, 18H), 1.46 (s, 9H). $^{13}$C NMR (75 MHz, CDCl$_3$) δ 171.9, 171.6, 171.3, 155.3, 155.0, 154.9, 153.1, 152.2, 147.6, 145.5, 145.4, 141.6, 140.0, 139.5, 138.8, 134.5, 133.2, 128.3, 128.2, 123.9, 123.6, 123.5, 121.0, 118.3, 115.8, 115.1, 112.1, 109.0, 106.8, 106.2, 104.2, 80.3, 80.1 (2C), 60.8, 56.2, 55.8, 55.6, 49.6, 49.3 (2C), 28.3 (9C), 18.6 (2C), 18.3. MS (ESI) m/z: 1043 (M)$^+$. Rf: 0.42 (hexane: EtOAc, 1:1).

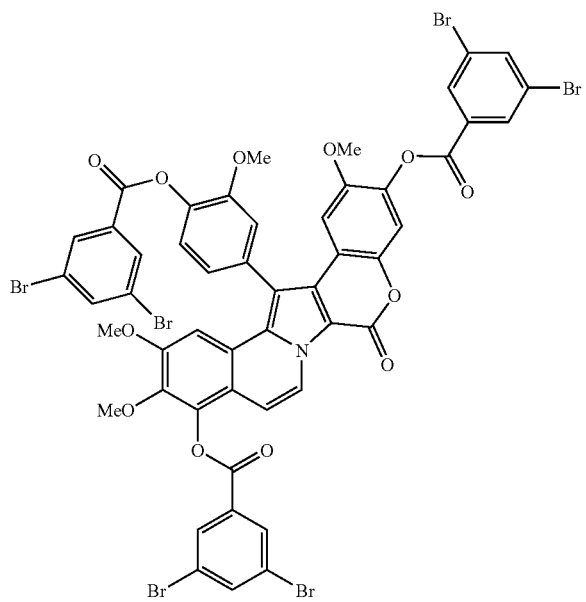

Compound 98

General procedure E (starting from 141, reaction time 18 h) and chromatography on silica gel (CH$_2$Cl$_2$) to afford 98 as a white solid (4 mg, 66%).

$^1$H NMR (300 MHz, CDCl$_3$) δ 9.25 (d, J=7.6 Hz, 1H), 8.39 (d, J=1.8 Hz, 2H), 8.32 (d, J=1.8 Hz, 2H), 8.27 (d, J=1.8 Hz, 2H), 8.01 (t, J=1.8 Hz, 1H), 7.97 (t, J=1.8 Hz, 1H), 7.94 (t, J=1.8 Hz, 1H), 7.43 (d, J=8.0 Hz, 1H), 7.40-7.25 (m, 3H), 7.19 (s, 1H), 7.09 (d, J=7.6 Hz, 1H), 6.91 (s, 1H), 3.90 (s, 3H), 3.86 (s, 3H), 3.60 (s, 3H), 3.52 (s, 3H). $^{13}$C NMR (75 MHz, CDCl$_3$) δ 162.3, 162.1, 162.0, 154.9, 153.3, 152.4, 147.7, 145.5, 141.9, 140.1, 139.5, 139.4, 139.0, 138.8, 134.8, 133.2, 132.2, 132.1, 132.0, 131.9, 131.8, 130.9, 128.8, 128.3, 124.0, 123.7, 123.6, 123.5, 123.3, 123.2, 121.0, 118.1, 116.1, 115.2, 112.2, 109.1, 106.5, 106.3, 104.5, 61.0, 56.3, 55.9, 55.8. MS (APCI) m/z: 1315 (M)$^+$. Rf: 0.73 (CH$_2$Cl$_2$).

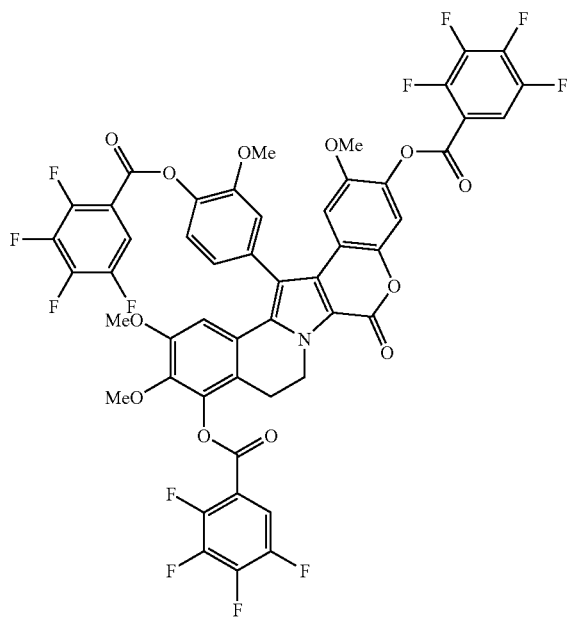

Compound 99

General procedure D (starting from 1,2,3,4,5-tetrafluorobenzoic acid) and chromatography on silica gel (CH$_2$Cl$_2$: MeOH, 200:1) to afford 99 as a white solid (35 mg, 71%).

$^1$H NMR (300 MHz, CDCl$_3$) δ 7.90-7.70 (m, 3H), 7.38 (d, J=8.0 Hz, 1H), 7.30-7.15 (m, 3H), 6.76 (s, 2H), 5.00-4.80 (br s, 1H), 4.80-4.60 (br s, 1H), 3.85 (s, 3H), 3.83 (s, 3H), 3.48 (s, 3H), 3.47 (s, 3H), 3.05 (br s, 2H). $^{13}$C NMR (75 MHz, CDCl$_3$) δ 159.9, 155.2, 152.3, 152.2, 147.7, 145.2, 141.4, 141.3, 139.7, 138.6, 135.0, 127.2, 124.0, 123.6, 123.0, 119.2, 116.7, 116.0, 115.3, 115.1, 114.2, 113.9, 112.1, 108.3, 105.8, 61.2, 56.6, 56.1, 55.9, 42.1, 22.6. MS (ESI) m/z: 1059 (M)$^+$. Rf: 0.46 (CH$_2$Cl$_2$).

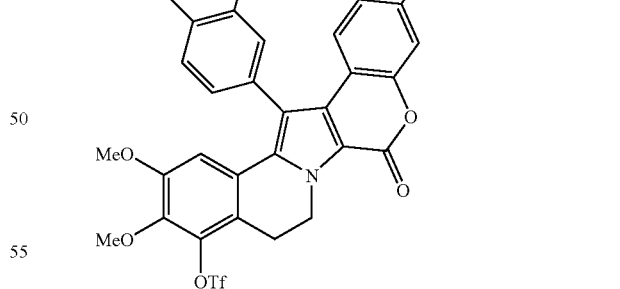

Compound 100

General procedure I (starting from 1) and chromatography on silica gel (CH$_2$Cl$_2$) to afford 100 as a white solid (30 mg, 85%).

$^1$H NMR (300 MHz, CDCl$_3$) δ 7.49 (d, J=8.6 Hz, 1H), 7.30-7.20 (m, 3H), 6.63 (s, 1H), 6.62 (s, 1H), 5.00-4.90 (m, 1H), 4.80-4.60 (m, 1H), 3.96 (s, 3H), 3.94 (s, 3H), 3.47 (s, 3H), 3.37 (s, 3H), 3.25-3.15 (m, 2H). $^{13}$C NMR (75 MHz, CDCl$_3$) δ 154.2, 152.7, 152.0, 147.9, 144.4, 141.7, 140.3, 138.7, 137.2, 136.5, 134.1, 126.1, 123.7, 123.4, 122.4, 120.7, 119.3, 117.8, 116.4, 115.4, 112.1, 109.0, 105.7, 61.4, 56.7, 55.8, 55.5, 41.8, 22.6. MS (ESI) m/z: 927 (M)⁺. Rf: 0.57 (CH$_2$Cl$_2$).

Compound 101

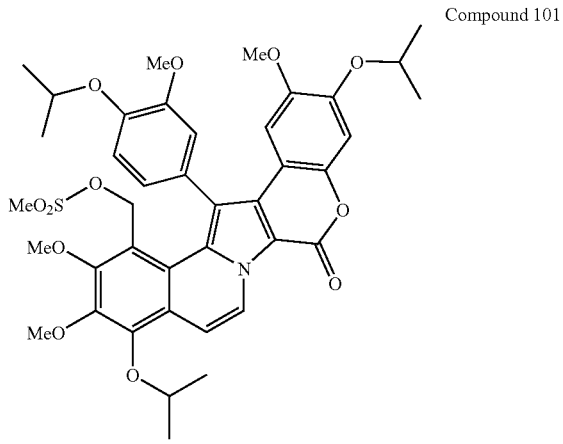

General procedure G (starting from methanesulfonic acid 5-isopropoxy-6,7-dimethoxy-3-isoquinolin-8-ylmethyl ester) and chromatography on silica gel (hexane:EtOAc, from 3:1 to 1:1) to afford 101 as a white solid (4 mg, 19%).

¹H NMR (300 MHz, CDCl$_3$) δ 9.22 (d, J=7.5 Hz, 1H), 7.38 (d, J=7.5 Hz, 1H), 7.26 (s, 1H), 7.05 (s, 2H), 7.00-6.90 (m, 2H), 4.80-4.50 (m, 3H), 3.95 (s, 5H), 3.85 (s, 3H), 3.75 (s, 3H), 3.54 (s, 2H), 2.92 (s, 3H), 1.50-1.30 (m, 18H). ¹³C NMR (75 MHz, CDCl$_3$) δ 155.4, 154.3, 151.0, 147.8, 146.8, 146.6, 146.4, 146.2, 140.7, 140.2, 134.7, 128.9, 128.8, 124.3, 124.0, 123.7, 123.1, 120.2, 116.5, 116.2, 115.4, 109.8, 107.7, 105.7, 103.4, 77.2, 71.7, 71.4, 68.6, 61.6, 60.6, 57.6, 56.0, 55.8, 22.8, 22.0, 21.8. MS (ESI) m/z: 722 (M−$^i$Pr)⁺. Rf: 0.50 (hexane:EtOAc, 1:1).

Compound 102

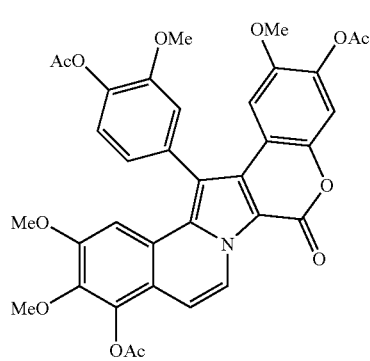

General procedure L (starting from 2 and Ac$_2$O) and chromatography on silica gel (hexane:EtOAc, 1:1) to afford 102 as a white solid (5.4 mg, 96%).

¹H NMR (300 MHz, CDCl$_3$) δ 9.24 (d, J=7.6 Hz, 1H), 7.40-7.00 (m, 6H), 6.81 (s, 1H), 3.89 (s, 3H), 3.83 (s, 3H), 3.48 (s, 3H), 3.45 (s, 3H), 2.49 (s, 3H), 2.37 (s, 3H), 2.32 (s, 3H). ¹³C NMR (75 MHz, CDCl$_3$) δ 168.8, 168.7, 155.0, 153.2, 152.4, 147.8, 145.5, 141.9, 140.3, 139.8, 139.0, 134.3, 133.3, 128.4, 124.1, 123.6, 123.4, 121.0, 118.2, 115.7, 115.1, 112.2, 112.1, 109.0, 106.6, 106.1, 104.1, 60.8, 56.2, 55.7, 55.6, 20.6 (3C). MS (ESI) m/z: 678 (M+23)⁺. Rf: 0.38 (hexane:EtOAc, 1:1).

Compound 103

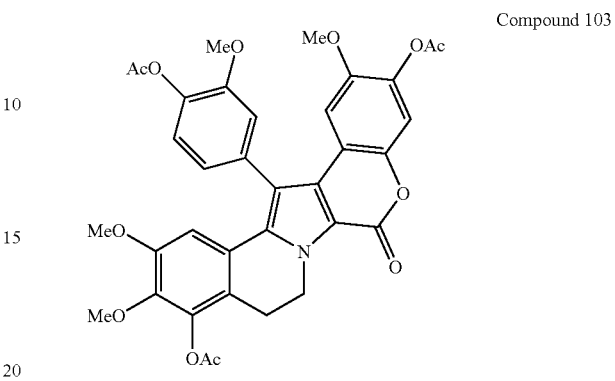

General procedure L (starting from 1 and Ac$_2$O) and chromatography on silica gel (hexane:EtOAc, 1:2) to afford 103 as a white solid (12 mg, 99%).

¹H NMR (300 MHz, CDCl$_3$) δ 7.30-7.05 (m, 4H), 6.68 (s, 2H), 4.95-4.80 (m, 1H), 4.80-4.60 (m, 1H), 3.83 (s, 3H), 3.81 (s, 3H), 3.42 (s, 3H), 3.38 (s, 3H), 3.00-2.95 (m, 2H), 2.40 (s, 3H), 2.35 (s, 3H), 2.31 (s, 3H). ¹³C NMR (75 MHz, CDCl$_3$) δ 168.9, 168.8, 168.7, 155.1, 152.2, 151.8, 147.7, 144.9, 141.6, 141.2, 140.0, 138.9, 134.9, 134.1, 127.2, 123.9, 123.2, 122.6, 119.1, 116.0, 115.8, 114.8, 114.7, 111.9, 107.5, 105.4, 60.8, 56.2, 55.7, 55.4, 41.9, 22.2, 20.6 (2C), 20.5. MS (ESI) m/z: 680 (M+23)⁺. Rf: 0.32 (hexane:EtOAc, 1:1).

Compound 104

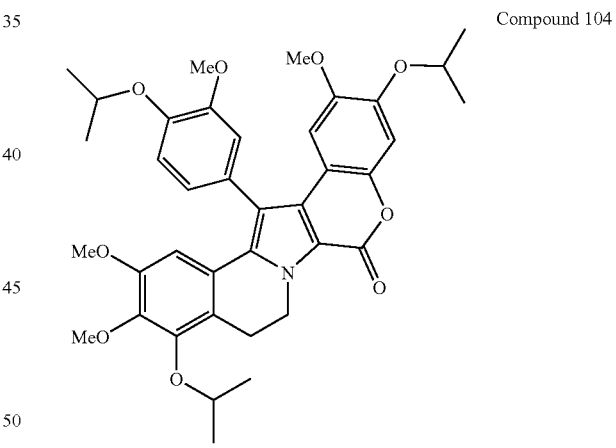

General procedure H (starting from 6,7-dimethoxy-5-isopropoxy-3,4-dihydroisoquinoline) and chromatography on silica gel (hexane:CH$_2$Cl$_2$:Et$_2$O, from 5:5:1 to 5:5:2) to afford 104 as a white solid (1.58 g, 56%).

¹H NMR (300 MHz, CDCl$_3$) δ 7.15-7.00 (m, 3H), 6.91 (s, 1H), 6.63 (s, 1H), 6.59 (s, 1H), 4.73 (t, J=7.0 Hz, 2H), 4.65-4.50 (m, 3H), 3.82 (s, 6H), 3.41 (s, 3H), 3.33 (s, 3H), 3.14 (t, J=6.8 Hz, 2H), 1.39 (t, J=6.3 Hz, 12H), 1.31 (d, J=6.1 Hz, 6H). ¹³C NMR (75 MHz, CDCl$_3$) δ 155.6, 151.7, 151.3, 148.6, 147.0, 146.9, 146.5, 145.9, 142.5, 135.5, 128.6, 128.1, 123.4, 123.0, 121.1, 116.9, 115.6, 114.6, 113.8, 110.3, 104.9, 104.8, 103.5, 75.7, 71.8, 71.4, 60.5, 56.2, 55.4, 55.1, 42.3, 22.7, 21.9, 21.8. MS (ESI) m/z: 658 (M+1)⁺. Rf: 0.56 (hexane:EtOAc, 1:1).

Compound 105

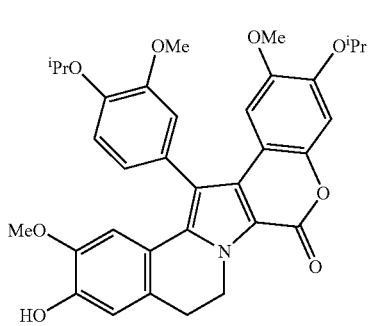

General procedure J (starting from 163, reaction time 22 h) and chromatography on silica gel (hexane:EtOAc, 1:1) to afford 105 (10 mg, 56%).

$^1$H NMR (300 MHz, CDCl$_3$) δ 7.12-7.03 (m, 3H), 6.92 (s, 1H), 6.81 (s, 1H), 6.69 (s, 1H), 6.67 (s, 1H), 4.85-4.69 (m, 2H), 4.64-4.40 (m, 2H), 3.82 (s, 3H), 3.43 (s, 3H), 3.39 (s, 3H), 3.08 (t, J=6.6 Hz, 2H), 1.42-1.37 (m, 12H). $^{13}$C NMR (75 MHz, CDCl$_3$) δ 155.6, 151.3, 147.0, 146.9, 146.5, 146.0, 145.8, 145.1, 136.0, 129.3, 128.7, 128.2, 127.5, 125.0, 123.4, 119.7, 116.9, 114.6, 114.2, 110.4, 108.3, 104.9, 103.5, 71.8, 71.4, 56.2, 55.5, 55.3, 42.4, 28.5, 21.9 (2C), 21.8 (2C). MS (ESI) m/z: 608 (M+23)$^+$, 586 (M+1)$^+$. Rf: 0.30 (hexane: EtOAc, 1:1).

Compound 106

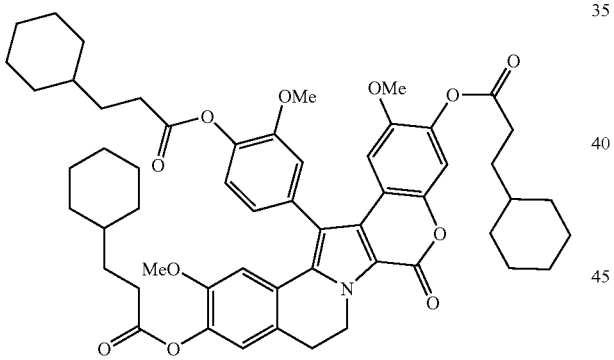

General procedure D (starting from 109 and cyclohexanepropionic acid) and chromatography on silica gel (CH$_2$Cl$_2$:MeOH, from 100:1 to 50:1) to afford 106 as a white solid (33 mg, 72%).

$^1$H NMR (300 MHz, CDCl$_3$) δ 7.20 (d, J=7.9 Hz, 1H), 7.14-7.07 (m, 3H), 6.94 (s, 1H), 6.79 (s, 1H), 6.70 (s, 1H), 4.92-4.84 (m, 1H), 4.79-4.70 (m, 1H), 3.80 (s, 3H), 3.42 (s, 3H), 3.35 (s, 3H), 3.11 (t, J=6.7 Hz, 2H), 2.64-2.54 (m, 6H), 1.81-1.60 (m, 21H), 1.39-1.12 (m, 12H), 0.98-0.91 (m, 6H). $^{13}$C NMR (75 MHz, CDCl$_3$) δ 172.1, 171.9, 171.8, 155.1, 152.3, 149.9, 147.7, 144.9, 140.1, 139.5, 139.0, 135.1, 133.8, 127.1, 125.9, 125.5, 123.9, 123.1, 122.6, 115.9 (2C), 114.8, 114.6, 111.9, 109.7, 105.4, 56.2, 55.7, 55.5, 42.4, 37.2 (3C), 37.1 (3C), 32.9 (6C), 32.2 (3C), 31.6 (3C), 28.0, 26.5 (3C), 26.2 (3C). MS (APCI) m/z: 916 (M+1)$^+$. Rf: 0.17 (hexane: EtOAc, 4:1).

Compound 107

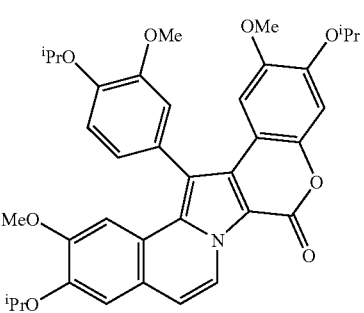

General procedure E (starting from 110, reaction time 2 h) and chromatography on silica gel (hexane:EtOAc, 2:1) to afford 107 (283 mg, 94%).

$^1$H NMR (300 MHz, CDCl$_3$) δ 9.24 (d, J=7.3 Hz, 1H), 7.29-7.17 (m, 2H), 7.12-7.10 (m, 2H), 7.04-7.02 (m, 2H), 6.98 (s, 1H), 6.76 (s, 1H), 4.70-4.56 (m, 3H), 3.84 (s, 3H), 3.44 (s, 3H), 3.43 (s, 3H), 1.44-1.39 (m, 18H). $^{13}$C NMR (75 MHz, CDCl$_3$) δ 155.3, 151.2, 150.0, 148.3, 147.7, 147.0, 146.4, 146.3, 134.2, 129.2, 128.6, 124.6, 123.8, 122.9, 118.8, 116.7, 114.9, 112.1, 110.8, 110.2, 109.8, 107.6, 105.5, 105.3, 103.2, 71.6, 71.3, 71.0, 56.0, 55.3, 55.0, 21.8 (3C), 21.7, 21.7, 21.6. MS (ESI) m/z: 648 (M+23)$^+$, 626 (M+1)$^+$. Rf: 0.35 (hexane:EtOAc, 2:1).

Compound 108

General procedure L (starting from 109 and Ac$_2$O) and chromatography on silica gel (CH$_2$Cl$_2$:MeOH, from 50:1 to 40:1) to afford 108 as a white solid (38 mg, 76%).

$^1$H NMR (300 MHz, CDCl$_3$) δ 7.22 (d, J=7.9 Hz, 1H), 7.15-7.09 (m, 3H), 6.95 (s, 1H), 6.79 (s, 1H), 6.69 (s, 1H), 4.92-4.71 (m, 2H), 3.81 (s, 3H), 3.43 (s, 3H), 3.35 (s, 3H), 3.12 (t, J=6.7 Hz, 2H), 2.35 (s, 3H), 2.31 (s, 3H), 2.30 (s, 3H). $^{13}$C NMR (75 MHz, CDCl$_3$) δ 169.0, 168.8, 168.6, 155.1, 152.2, 149.9, 147.7, 144.9, 140.0, 139.4, 138.9, 135.0, 134.0, 127.1, 125.9, 125.7, 123.9, 123.2, 122.6, 116.0, 115.9, 114.9, 114.6, 112.0, 109.7, 105.4, 56.2, 55.7, 55.5, 42.5, 28.1, 20.6 (3C). MS (ESI) m/z: 628 (M+1)⁺. Rf: 0.32 (CH₂Cl₂:MeOH, 100:1).

71.3, 71.2, 56.1, 55.4, 55.0, 42.3, 28.5, 22.0 (2C), 21.8, 21.8, 21.7 (2C). MS (ESI) m/z: 628 (M+1)⁺. Rf: 0.28 (hexane:CH₂Cl₂:Et₂O, 5:5:2).

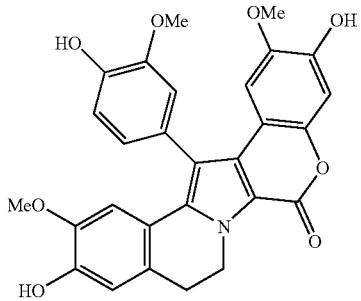

Compound 109

General procedure A (starting from 110) and chromatography on silica gel (CH₂Cl₂:MeOH, from 20:1 to 10:1 to 5:1) to afford 109 as a pale brown solid (1.11 g, 97%).

¹H NMR (300 MHz, DMSO-d₆) δ9.64 (s, 1H), 9.41 (s, 1H), 9.24 (s, 1H), 7.01 (s, 1H), 6.99 (d, J=8.1 Hz, 1H), 6.88 (d, J=8.4 Hz, 1H), 6.78 (s, 1H), 6.73 (s, 1H), 6.67 (s, 1H), 6.59 (s, 1H), 4.58 (t, J=6.5 Hz, 2H), 3.73 (s, 3H), 3.34 (s, 3H), 3.25 (s, 3H), 2.99 (t, J=6.4 Hz, 2H). ¹³C NMR (75 MHz, DMSO-d₆) δ 154.3, 148.5, 147.1, 146.9, 146.5, 146.0, 145.7, 144.4, 135.9, 127.7, 127.1, 125.5, 123.4, 118.1, 116.3, 115.3, 114.7, 114.3, 112.2, 109.2, 108.8, 105.1, 103.6, 56.0, 55.0, 54.7, 42.0, 27.5. MS (ESI) m/z: 524 (M+23)⁺. Rf: 0.55 (CH₂Cl₂:MeOH 10:1).

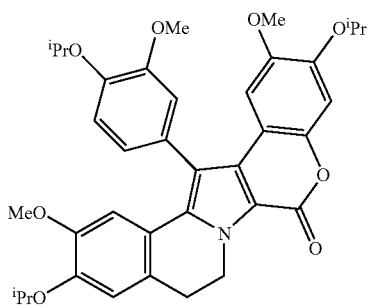

Compound 110

General procedure H (starting from 6-Isopropoxy-7-methoxy-3,4-dihydroisoquinoline) and chromatography on silica gel (hexane:CH₂Cl₂:Et₂O, 5:5:2) to afford 110 as a pale yellow solid (1.27 g, 47%).

¹H NMR (300 MHz, CDCl₃) δ 7.08-7.04 (m, 3H), 6.92 (s, 1H), 6.76-6.74 (m, 2H), 6.67 (s, 1H), 4.87-4.71 (m, 2H), 4.65-4.48 (m, 3H), 3.82 (s, 3H), 3.42 (s, 3H), 3.33 (s, 3H), 3.09 (t, J=6.6 Hz, 2H), 1.41-1.36 (m, 18H). ¹³C NMR (75 MHz, CDCl₃) δ 155.5, 151.2, 148.5, 147.2, 146.9, 146.8, 146.4, 145.8, 135.9, 128.5, 128.1, 126.3, 123.3, 120.1, 116.8, 114.8, 114.6, 114.5, 113.6, 110.3, 109.1, 104.8, 103.4, 71.7,

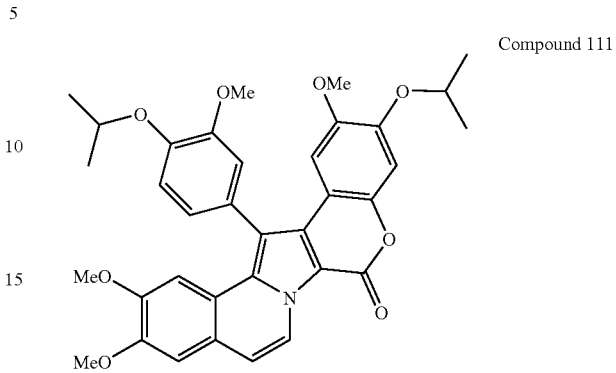

Compound 111

General procedure E (starting from 162, reaction time 3 h) and chromatography on silica gel (hexane:EtOAc, 1:1) to afford 111 as a white solid (176.3 mg, 94%).

¹H NMR (300 MHz, CDCl₃) δ 9.25 (d, J=7.3 Hz, 1H), 7.19-7.04 (m, 6H), 6.97 (s, 1H), 6.76 (s, 1H), 4.66-4.56 (m, 2H), 3.99 (s, 3H), 3.84 (s, 3H), 3.47 (s, 3H), 3.45 (s, 3H), 1.44-1.40 (m, 12H). ¹³C NMR (75 MHz, CDCl₃) δ 155.5, 151.3, 150.0, 149.1, 147.8, 147.1, 146.6, 146.5, 134.3, 129.4, 128.6, 124.7, 123.9, 123.3, 119.1, 116.8, 115.0, 112.2, 111.0, 109.9, 107.8, 107.3, 105.4, 105.3, 103.4, 71.7, 71.4, 56.1, 55.9, 55.9, 55.4, 55.1, 21.9, 21.8. MS (ESI) m/z: 598 (M+1)⁺. Rf: 0.50 (hexane:EtOAc, 1:1).

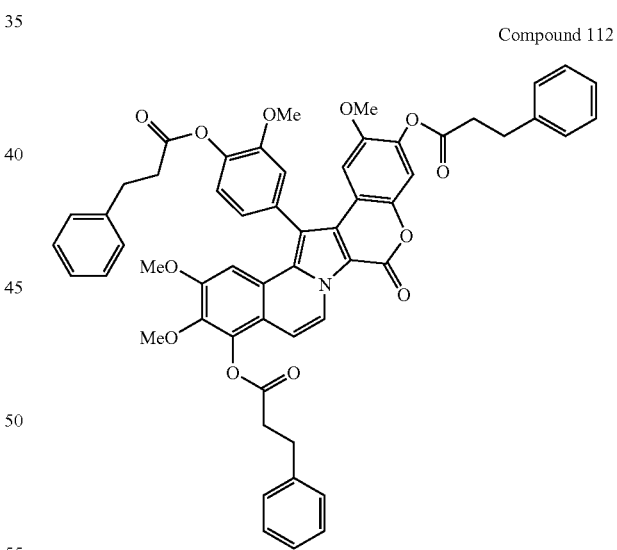

Compound 112

General procedure E (starting from 116, reaction time 23 h) and chromatography on silica gel (hexane:EtOAc, from 2:1 to 1:1) to afford 112 (17 mg, 99%) as a white solid.

¹H NMR (300 MHz, CDCl₃) δ 9.11 (d, J=7.5 Hz, 1H), 7.50-7.00 (m, 20H), 6.78 (s, 1H), 6.71 (d, J=7.5 Hz, 1H), 3.80 (s, 3H), 3.78 (s, 3H), 3.47 (s, 3H), 3.40 (s, 3H), 3.20-2.80 (m, 12H). ¹³C NMR (75 MHz, CDCl₃) δ 170.8, 170.7, 155.0, 153.1, 152.3, 147.7, 145.4, 141.8, 140.2, 140.1, 140.0, 139.9, 139.7, 138.9, 134.2, 133.2, 128.7, 128.6, 128.5, 128.4, 128.3, 126.7, 126.5, 126.4, 124.0, 123.3, 123.2, 120.9, 118.2, 115.6,

Compound 113

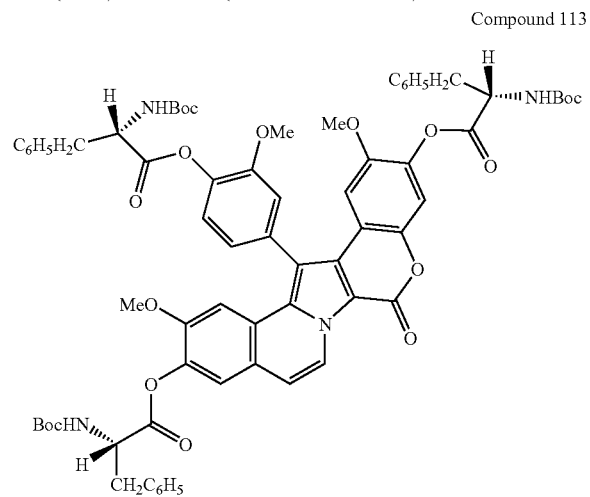

General procedure E (starting from 121, reaction time 22 h) and chromatography on silica gel (CH$_2$Cl$_2$:MeOH, 80:1) to afford 113 (43 mg, 86%) as a white solid.

$^1$H NMR (300 MHz, CDCl$_3$) δ 9.22 (d, J=7.3 Hz, 1H), 7.37-7.20 (m, 20H), 7.08-7.03 (m, 2H), 6.80 (d, J=2.2 Hz, 1H), 5.29-5.02 (m, 3H), 4.90-4.88 (m, 3H), 3.85 (s, 3H), 3.44 (s, 6H), 3.41-3.23 (m, 6H), 1.46 (s, 9H), 1.43 (s, 18H). $^{13}$C NMR (75 MHz, CDCl$_3$) δ 170.1, 170.0, 169.9, 155.1 (2C), 154.9, 152.3, 150.9, 147.6, 145.3, 140.5, 139.9, 139.3, 135.8 (2C), 134.5, 133.4, 125.0 (9C), 128.6 (6C), 128.1, 128.0, 127.1 (2C), 124.0, 123.7, 123.6, 123.1, 120.7, 115.8, 115.1, 112.8, 112.3, 112.1, 109.1, 106.4, 106.1, 80.1 (3C), 56.2 (2C), 55.7, 55.6, 55.5, 54.4, 38.1 (3C), 28.2 (9C). MS (ESI) m/z: 1263 (M+23)$^+$, 1241 (M+1)$^+$. Rf: 0.56 (CH$_2$Cl$_2$:MeOH, 50:1).

Compound 114

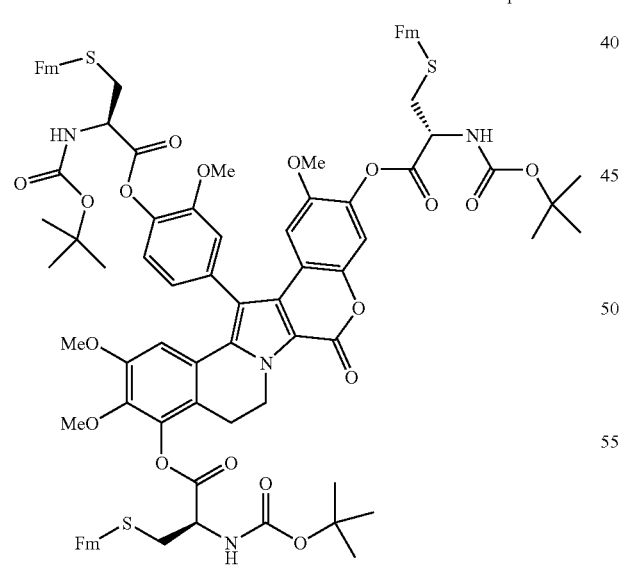

General procedure D (starting from 1 and (L)-N-Boc-Cys (Fm)) and chromatography on silica gel (hexane:EtOAc, 1:1) to afford 114 as a white solid (140 mg, 88%).

$^1$H NMR (300 MHz, CDCl$_3$) δ 7.85-7.65 (m, 12H), 7.45-7.25 (m, 12H), 7.25-7.05 (m, 4H), 6.64 (t, J=2.9 Hz, 2H), 5.50-5.30 (m, 3H), 4.90-4.70 (m, 4H), 4.60 (br s, 1H), 4.25-4.10 (m, 3H), 3.75 (s, 3H), 3.72 (s, 3H), 3.35 (s, 3H), 3.33 (s, 3H), 3.30-3.10 (m, 12H), 2.95 (m, 2H), 1.48 (s, 18H), 1.46 (s, 9H). $^{13}$C NMR (75 MHz, CDCl$_3$) δ 169.3, 169.1, 155.1, 154.9, 151.9, 151.7, 147.4, 145.7, 145.5, 144.8, 141.1, 141.0, 140.9, 139.5, 138.4, 134.7, 134.4, 127.7, 127.6, 127.5, 127.0, 126.9, 124.8, 124.7, 124.6, 123.7, 123.2, 122.6, 120.0, 119.9, 119.8, 119.3, 116.2, 115.6, 114.8, 114.7, 111.9, 107.7, 105.4, 80.5, 80.4, 80.3, 60.8, 56.1, 55.6, 55.5, 53.6, 53.4, 46.9, 41.9, 37.3, 37.2, 37.1, 35.6, 35.2, 31.9, 29.6, 28.3, 22.2. MS (ESI) m/z: 1698 (M+23)$^+$, 1676 (M+1)$^+$. Rf: 0.19 (hexane:EtOAc, 2:1).

Compound 115

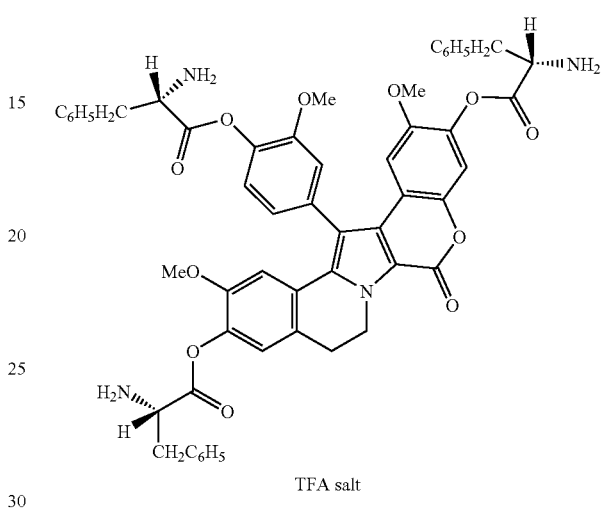

TFA salt

General procedure B (starting from 121) to afford 115 as a white solid (17 mg, quant.).

$^1$H NMR (300 MHz, CD$_3$OD) δ 7.44-7.35 (m, 17H), 7.26 (d, J=8.1 Hz, 1H), 7.10 (d, J=1.6 Hz, 1H), 7.06 (s, 1H), 6.88 (d, J=3.5 Hz, 1H), 6.78 (d, J=3.5 Hz, 1H), 4.79-4.70 (m, 3H), 4.63 (t, J=6.7 Hz, 2H), 3.89 (s, 3H), 3.53-3.26 (m, 6H), 3.44 (s, 3H), 3.36 (s, 3H), 3.16 (t, J=6.7 Hz, 2H). MS (ESI) m/z: 965 (M+23)$^+$, 943 (M+1)$^+$.

Compound 116

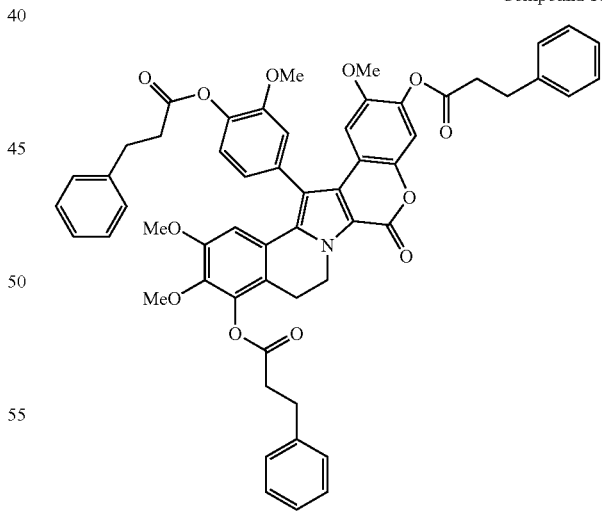

General procedure F (starting from 1 and hydrocinnamoyl chloride) and chromatography on silica gel (hexane:EtOAc, from 2:1 to 1:1) to afford 116 as a white solid (32 mg, 74%).

$^1$H NMR (300 MHz, CDCl$_3$) δ 7.40-7.20 (m, 15H), 7.15-7.05 (m, 3H), 7.02 (s, 1H), 6.66 (s, 2H), 4.80-4.70 (m, 1H), 4.70-4.50 (m, 1H), 3.78 (s, 3H), 3.73 (s, 3H), 3.39 (s, 3H), 3.38 (s, 3H), 3.20-2.80 (m, 12H), 2.71 (t, J=6.4 Hz, 2H). $^{13}$C NMR (75 MHz, CDCl$_3$) δ 170.8, 170.7, 170.6, 155.0, 152.2, 151.8, 147.6, 144.9, 141.5, 141.1, 140.2, 140.1, 140.0, 139.9, 138.9, 134.8, 134.0, 128.6, 128.5, 128.4, 128.3, 128.3, 128.2, 127.1, 126.6, 126.4, 126.3, 123.8, 123.2, 122.5, 119.1, 115.9, 115.7, 114.7, 114.6, 111.8, 107.5, 105.4, 60.7, 56.2, 55.7, 55.5, 41.8, 35.5, 35.4, 35.3, 30.9, 30.8, 30.8, 21.9. MS (ESI) m/z: 950 (M+23)$^+$, 928 (M+1)$^+$. Rf: 0.37 (hexane:EtOAc, 2:1).

Compound 117

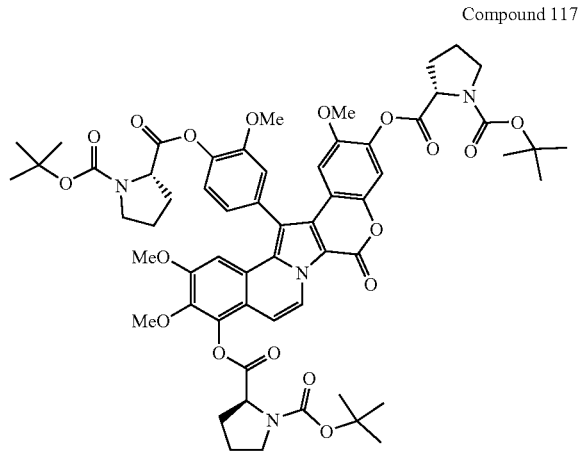

General procedure E (starting from 124, reaction time 31 h) and chromatography on silica gel (CH$_2$Cl$_2$:MeOH, from 50:1 to 30:1) to afford 117 as a brownish solid (40 mg, 67%).

$^1$H NMR (300 MHz, CDCl$_3$) δ 9.21 (d, J=7.3 Hz, 1H), 7.50-7.00 (m, 6H), 6.85-6.70 (m, 1H), 4.80-4.40 (m, 3H), 3.86 (s, 3H), 3.80 (s, 3H), 3.75-3.50 (m, 6H), 3.47 (s, 3H), 3.42 (s, 3H), 2.50-2.20 (m, 6H), 2.20-1.85 (m, 6H), 1.52 (s, 9H), 1.49 (s, 9H), 1.47 (s, 9H). $^{13}$C NMR (75 MHz, CDCl$_3$) δ 171.5, 170.9, 170.8, 155.0, 154.6, 154.4, 154.3, 153.8, 153.7, 152.4, 147.7, 145.5, 141.6, 140.1, 139.7, 134.4, 133.2, 124.2, 123.6, 123.4, 123.2, 121.0, 118.7, 115.7, 115.2, 112.3, 111.9, 107.5, 106.6, 106.1, 104.1, 80.2, 80.1, 79.9, 60.7, 59.0, 58.9, 56.1, 55.8, 55.7, 55.5, 46.6, 46.5, 46.4, 28.5, 28.4, 28.2, 24.5, 24.4, 24.3, 23.6, 23.5, 23.4. MS (ESI) m/z: 1143 (M+23)$^+$. Rf: 0.32 (CH$_2$Cl$_2$:MeOH, 50:1).

Compound 118

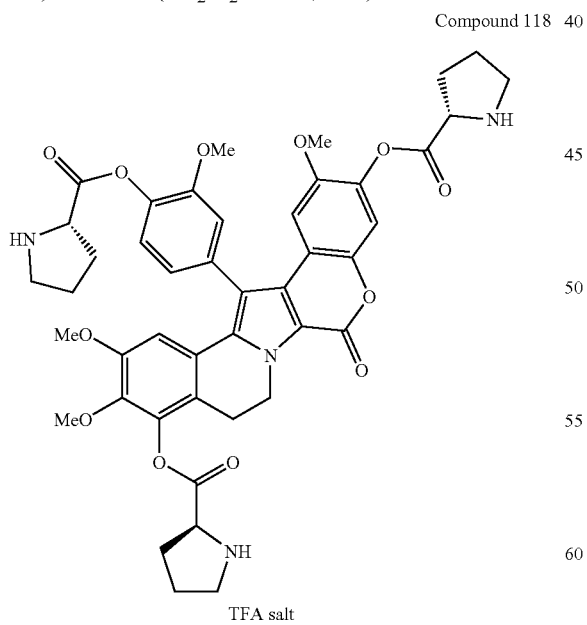

TFA salt

General procedure B (starting from 124) to afford 118 as a white solid (25 mg, quant.).

$^1$H NMR (300 MHz, CD$_3$OD) δ 7.49 (d, J=7.8 Hz, 1H), 7.41 (s, 1H), 7.30-7.20 (m, 2H), 6.81 (d, J=7.9 Hz, 1H), 6.76 (d, J=9.7 Hz, 1H), 4.90-4.70 (m, 5H), 3.87 (s, 3H), 3.81 (s, 3H), 3.60-3.40 (m, 12H), 3.08 (br t, 2H), 2.70-2.30 (m, 6H), 2.30-2.00 (m, 6H). MS (ESI) m/z: 823 (M+1)$^+$.

Compound 119

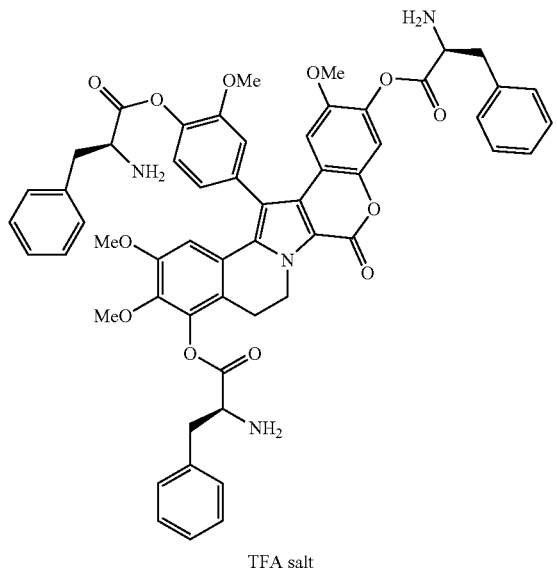

TFA salt

General procedure B (starting from 125) to afford 119 as a white solid (28 mg, 99%).

$^1$H NMR (300 MHz, CD$_3$OD) δ 7.50-7.35 (m, 16H), 7.30-7.20 (m, 2H), 7.15-7.10 (m, 1H), 6.82-6.75 (m, 2H), 4.85-4.55 (m, 5H), 3.88 (s, 3H), 3.81 (s, 3H), 3.60-3.40 (m, 12H), 2.94 (br s, 2H). MS (ESI) m/z: 973 (M)$^+$.

Compound 120

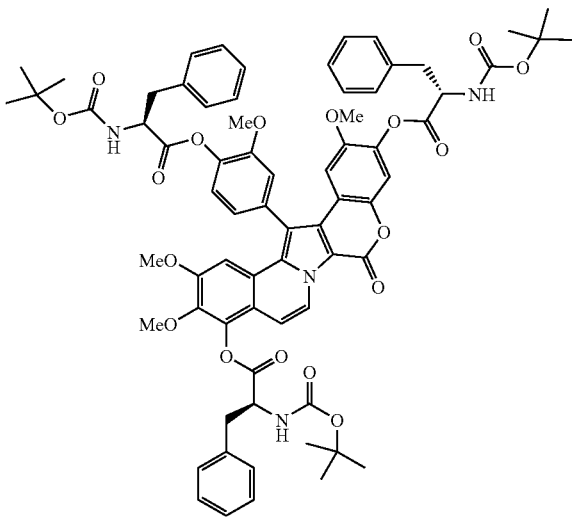

General procedure E (starting from 125, reaction time 31 h) and chromatography on silica gel (CH$_2$Cl$_2$:MeOH, 50:1) to afford 120 as a yellow solid (54 mg, 80%).

$^1$H NMR (300 MHz, CDCl$_3$) δ 9.12 (dd, J=7.5, 2.5 Hz, 1H), 7.40-7.20 (m, 19H), 7.10-7.00 (m, 2H), 6.79 (d, J=4.0 Hz, 1H), 5.20-4.80 (m, 6H), 3.86 (s, 3H), 3.85 (s, 3H), 3.48 (s, 3H), 3.44 (s, 3H), 3.40-3.20 (m, 6H), 1.46 (s, 18H), 1.43 (s, 9H). $^{13}$C NMR (75 MHz, CDCl$_3$) δ 170.6, 170.0, 169.8, 155.3, 155.1, 155.0, 154.8, 153.1, 152.2, 147.5, 145.3 (2C), 141.7, 139.8, 139.2 (2C), 138.8, 135.8, 135.7, 135.6, 134.6, 133.1 (2C), 129.5 (3C), 129.4 (3C), 128.8 (2C), 128.6 (2C), 128.1, 127.3, 127.2, 123.9, 123.6, 123.3, 120.9, 118.2, 115.8, 115.1, 112.0, 108.9, 106.9, 106.1, 104.2, 80.4, 80.2, 80.0, 60.8, 56.2, 56.1, 55.7, 54.7, 54.3 (2C), 38.1 (2C), 37.8, 28.2 (9C). MS (ESI) m/z: 1293 (M+23)⁺. Rf: 0.32 (CH₂Cl₂:MeOH, 60:1).

Compound 121

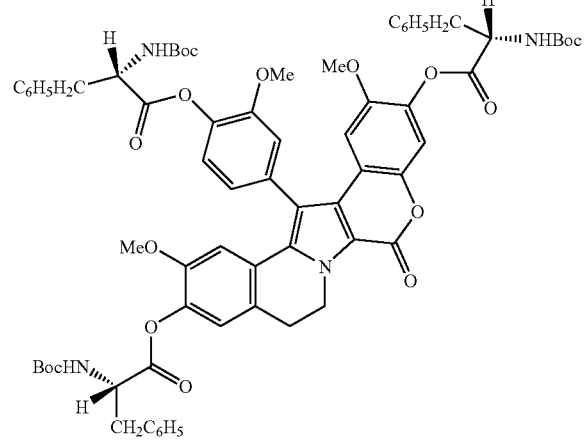

General procedure D (starting from 109 and Boc-L-Phe-OH) and chromatography on silica gel (CH₂Cl₂:MeOH, 100:1) to afford 121 as a white solid (87 mg, 68%).
¹H NMR (300 MHz, CDCl₃) δ 7.34-7.26 (m, 15H), 7.16 (br s, 2H), 7.10 (s, 1H), 7.05 (s, 1H), 6.91 (s, 1H), 6.78-6.68 (m, 2H), 4.99 (t, J=8.6 Hz, 2H), 4.88-4.72 (m, 6H), 3.81 (s, 3H), 3.41 (s, 3H), 3.34 (s, 3H), 3.30-3.12 (m, 8H), 1.44 (s, 9H), 1.43 (s, 18H). ¹³C NMR (75 MHz, CDCl₃) δ 170.1, 169.9 (2C), 155.0, 154.9, 152.0, 149.7, 147.5, 144.7, 139.6, 139.0, 138.4, 135.8 (2C), 134.8, 134.2, 129.4 (9C), 129.2, 128.5 (6C), 127.1 (2C), 126.9, 125.9, 125.7, 123.8, 123.1, 122.5, 116.1, 115.8, 114.9, 114.7, 111.8, 109.7, 105.4, 80.0 (3C), 56.1, 55.6, 55.4, 54.3 (3C), 42.3, 38.0 (3C), 28.2 (9C), 27.9. MS (ESI) m/z: 1265 (M+23)⁺. Rf: 0.65 (CH₂Cl₂:MeOH, 30:1).

Compound 122

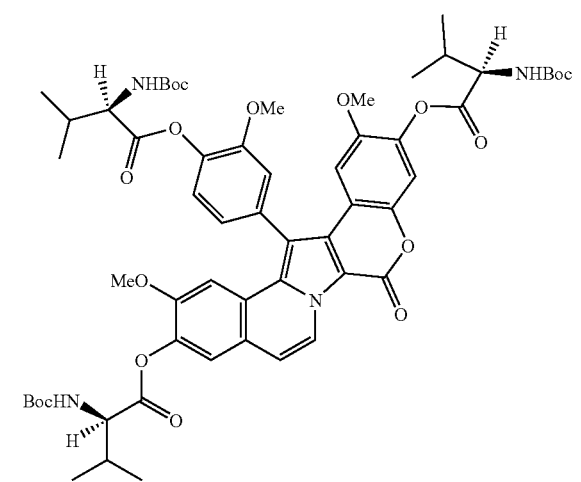

General procedure E (starting from 134, reaction time 22 h) and chromatography on silica gel (CH₂Cl₂:MeOH, 50:1) to afford 122 (47 mg, 94%) as a white solid.
¹H NMR (300 MHz, CDCl₃) δ 9.26 (d, J=7.3 Hz, 1H), 7.42 (s, 1H), 7.31-7.26 (m, 2H), 7.23-7.18 (m, 3H), 7.09 (d, J=7.5 Hz, 1H), 6.80 (d, J=7.5 Hz, 1H), 5.09-5.06 (m, 3H), 4.57-4.50 (m, 3H), 3.80 (s, 3H), 3.43 (s, 6H), 2.45-2.34 (m, 3H), 1.50 (s, 9H), 1.47 (s, 18H), 1.14-1.00 (m, 18H). ¹³C NMR (75 MHz, CDCl₃) δ 170.4 (b), 155.7, 154.9, 152.3, 150.9, 147.6, 145.4, 140.6, 140.0, 139.4, 134.5, 133.4, 128.1, 124.0, 123.8, 123.6, 123.1, 120.8, 115.8, 115.1, 112.8, 112.2, 112.2, 109.1, 106.4, 106.1, 80.0 (3C), 58.5 (2C), 56.0, 55.6, 55.5, 55.4, 30.0 (3C), 28.3 (9C), 19.2, 19.1 (2C), 17.2, 17.1 (2C). MS (ESI) m/z: 1119 (M+23)⁺, 1097 (M+1)⁺. Rf: 0.33 (CH₂Cl₂:MeOH, 100:1).

Compound 123

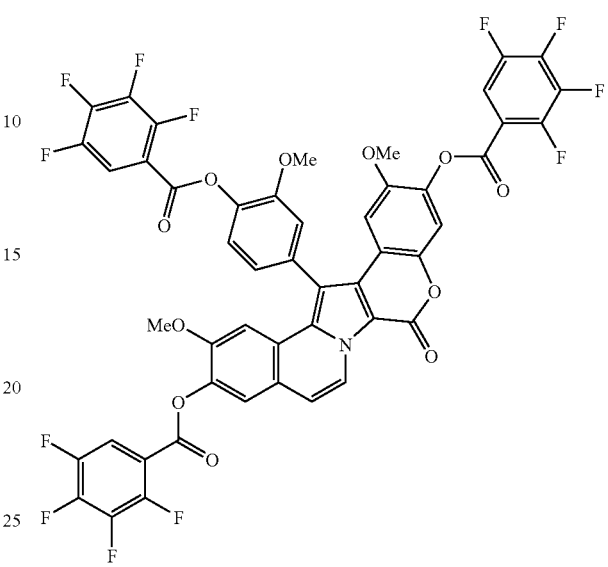

General procedure E (starting from 139, reaction time 7 h) and chromatography on silica gel (CH₂Cl₂:MeOH, 100:1) to afford 123 (15 mg, 75%) as a white solid.
¹H NMR (300 MHz, CDCl₃) δ 9.24 (d, J=7.5 Hz, 1H), 7.84-7.75 (m, 3H), 7.54 (s, 1H), 7.45 (d, J=8.4 Hz, 1H), 7.37-7.35 (m, 2H), 7.30 (s, 1H), 7.26 (s, 1H), 7.08 (d, J=7.3 Hz, 1H), 6.90 (s, 1H), 3.87 (s, 3H), 3.52 (s, 3H), 3.52 (s, 3H). ¹³C NMR (75 MHz, CDCl₃) δ 159.7 (3C), 154.8, 152.3, 150.8, 148.2, 147.6, 145.4, 140.3, 139.8, 139.2, 135.0, 133.4, 128.0, 124.0, 123.9, 123.8, 123.7, 123.2, 120.7, 116.2, 115.3, 113.8, 113.6, 112.8, 112.4, 112.1, 109.2, 106.6, 106.3, 56.4, 55.9, 55.8. MS (ESI) m/z: 1050 (M+23)⁺, 1028 (M+1)⁺. Rf: 0.63 (CH₂Cl₂).

Compound 124

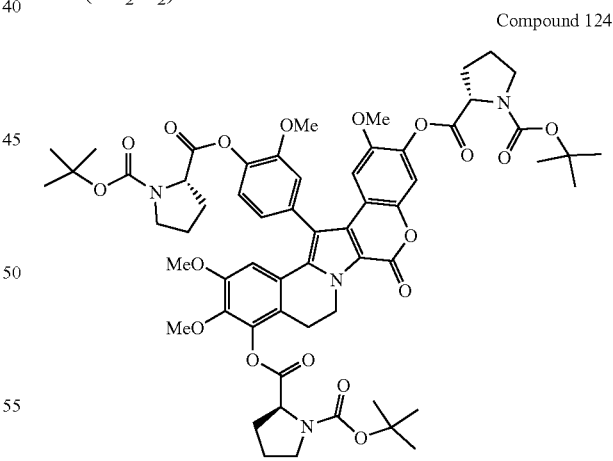

General procedure D (starting from 1 and (L)-N-Boc-Pro) and chromatography on silica gel (CH₂Cl₂:MeOH, from 50:1 to 20:1) to give 124 as a white solid (105 mg, 99%).
¹H NMR (300 MHz, CDCl₃) δ 7.20-7.10 (m, 2H), 7.10-7.00 (m, 2H), 6.70-6.60 (m, 2H), 4.90 (br s, 1H), 4.70-4.40 (m, 4H), 3.78 (s, 6H), 3.70-3.40 (m, 6H), 3.39 (s, 3H), 3.36 (s, 3H), 3.20-2.95 (m, 2H), 2.50-2.20 (m, 6H), 2.15-1.85 (m, 6H), 1.48 (s, 18H), 1.46 (s, 9H). ¹³C NMR (75 MHz, CDCl₃) δ 171.3, 170.9, 170.7, 155.0, 154.4, 153.8, 152.2, 151.7, 147.6, 144.8, 141.4, 141.0, 139.8, 138.7, 134.3, 127.1, 124.0, 123.4, 123.2, 122.6, 119.9, 119.0, 116.0, 115.7, 114.7, 112.1, 111.6, 107.5, 105.4, 80.2, 80.0, 79.9, 60.6, 58.9, 58.8, 56.1, 55.7, 55.6, 55.5, 46.6, 46.5, 46.4, 42.0, 28.3, 24.4, 24.3, 23.6, 23.5, 23.4, 23.3, 22.0. MS (ESI) m/z: 1145 (M+23)$^+$, 1124 (M+1)$^+$. Rf: 0.64 (CH$_2$Cl$_2$:MeOH, 20:1).

Compound 125

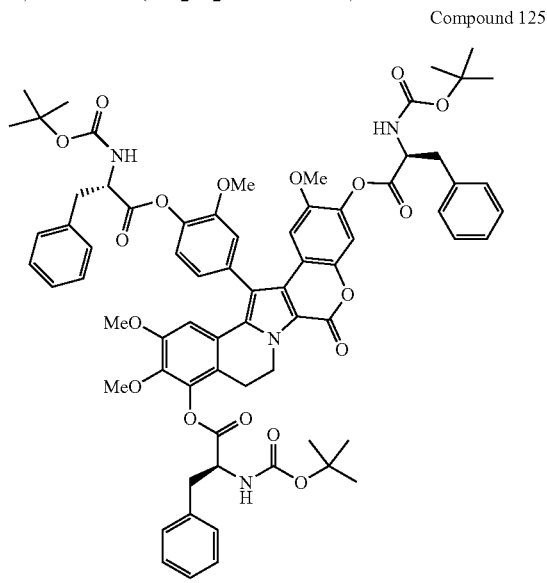

General procedure D (starting from 1 and (L)-Boc-Phe) and chromatography on silica gel (CH$_2$Cl$_2$:MeOH, from 50:1 to 30:1) to afford 125 as a brown solid (119 mg, 99%).

$^1$H NMR (300 MHz, CDCl$_3$) δ 7.50-7.25 (m, 15H), 7.20-7.10 (m, 3H), 7.03 (s, 1H), 5.10-5.00 (m, 3H), 5.00-4.80 (m, 3H), 4.75-4.50 (m, 2H), 3.83 (s, 3H), 3.82 (s, 3H), 3.78 (s, 6H), 3.40 (s, 3H), 3.37 (s, 3H), 3.35-3.00 (m, 6H), 2.95-2.85 (m, 2H), 1.44 (s, 9H), 1.43 (s, 9H), 1.42 (s, 9H). $^{13}$C NMR (75 MHz, CDCl$_3$) δ 170.4, 169.9 (2C), 155.2, 154.9, 152.1, 151.8, 147.5, 144.8, 141.3, 141.0, 139.6, 138.4, 135.8, 135.6, 134.7, 134.3, 129.5 (3C), 129.4 (2C), 129.2 (2C), 128.7 (2C), 128.5 (2C), 128.4 (2C), 127.2, 127.1, 126.9, 123.7, 123.2, 122.6, 119.4, 116.2, 115.6, 114.8, 114.7, 111.8, 107.6, 105.4, 80.3, 80.1, 80.0, 60.7, 56.1, 55.6, 55.5, 54.3, 53.4, 52.1, 41.8, 38.1 (2C), 37.8, 28.2 (9C), 22.0. MS (ESI) m/z: 1295 (M+23)$^+$, 1273 (M+1)$^+$. Rf: 0.21 (CH$_2$Cl$_2$:MeOH, 50:1).

Compound 126

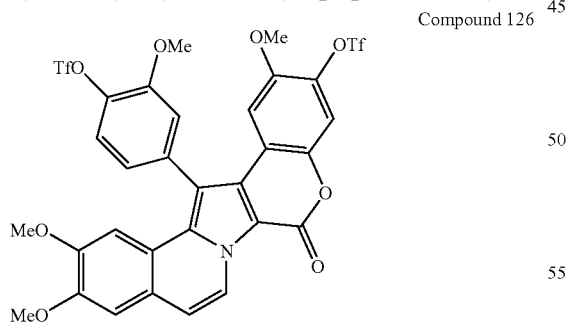

General procedure I (starting from 26) and chromatography on silica gel (CH$_2$Cl$_2$) to afford 126 as a pale yellow solid (24.2 mg, quant.).

$^1$H NMR (300 MHz, CDCl$_3$) δ 9.16 (d, J=7.3 Hz, 1H), 7.54 (d, J=8.1 Hz, 1H), 7.40-7.25 (m, 2H), 7.20 (s, 1H), 7.11 (br s, 2H), 6.98 (s, 1H), 6.76 (s, 1H), 3.99 (s, 3H), 3.98 (s, 3H), 3.50 (s, 3H), 3.46 (s, 3H). $^{13}$C NMR (75 MHz, CDCl$_3$) δ 154.4, 152.6, 150.7, 149.8, 147.9, 144.9, 138.8, 137.7, 137.4, 134.3, 129.6, 127.5, 127.2, 125.0, 124.1, 123.7, 122.9, 118.6 (2C, t, J$_{C-F}$=172.7, 164.5 Hz), 116.3, 113.7, 112.0, 110.2, 107.7, 106.5, 104.7, 56.7, 56.0, 55.8, 55.2. MS (ESI) m/z: 778 (M+1)$^+$. Rf: 0.36 (CH$_2$Cl$_2$).

Compound 127

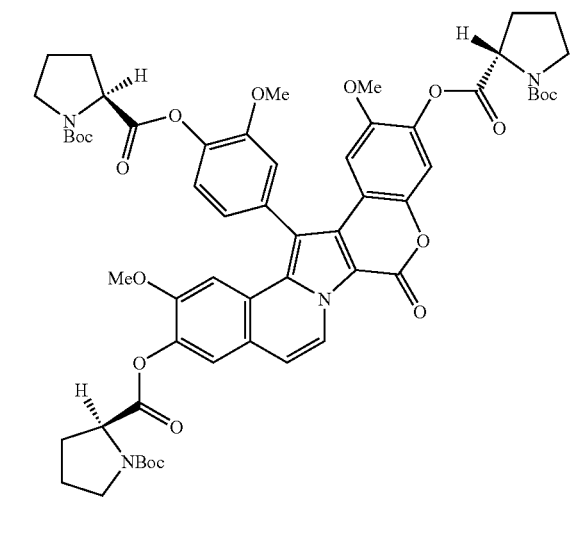

General procedure E (starting from 140, reaction time 17 h) and chromatography on silica gel (CH$_2$Cl$_2$:MeOH, 30:1) to afford 127 (30 mg, 67%) as a white solid.

$^1$H NMR (300 MHz, CDCl$_3$) δ 9.27-9.23 (m, 1H), 7.47-7.36 (m, 1H), 7.26-7.08 (m, 6H), 6.84-6.78 (m, 1H), 4.56-4.49 (m, 3H), 3.80 (s, 3H), 3.66-3.47 (m, 6H), 3.43 (s, 6H), 2.40-2.29 (m, 6H), 2.04-1.98 (m, 6H), 1.49 (s, 27H). MS (ESI) m/z: 1091 (M+1)$^+$. Rf: 0.31 (CH$_2$Cl$_2$:MeOH 30:1).

Compound 128

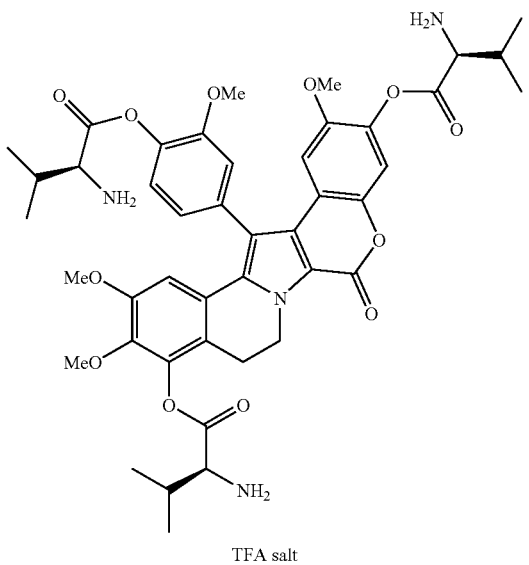

TFA salt

General procedure B (starting from 131) to afford 128 as a white solid (25 mg, 99%).

$^1$H NMR (300 MHz, CD$_3$OD) δ 7.50-7.40 (m, 2H), 7.30-7.20 (m, 2H), 6.82 (d, J=5.4 Hz, 1H), 6.79 (d, J=7.9 Hz, 1H), 4.90-4.70 (m, 2H), 4.44 (d, J=3.4 Hz, 1H), 4.32 (dd, J=4.2, 1.6 Hz, 1H), 4.24 (d, J=4.3 Hz, 1H), 3.86 (s, 3H), 3.81 (s, 3H), 3.44 (s, 3H), 3.43 (s, 3H), 3.15-3.00 (m, 2H), 2.65-2.40 (m, 3H), 1.30-1.15 (m, 18H). MS (ESI) m/z: 851 (M+23)$^+$, 829 (M+1)$^+$.

Compound 129

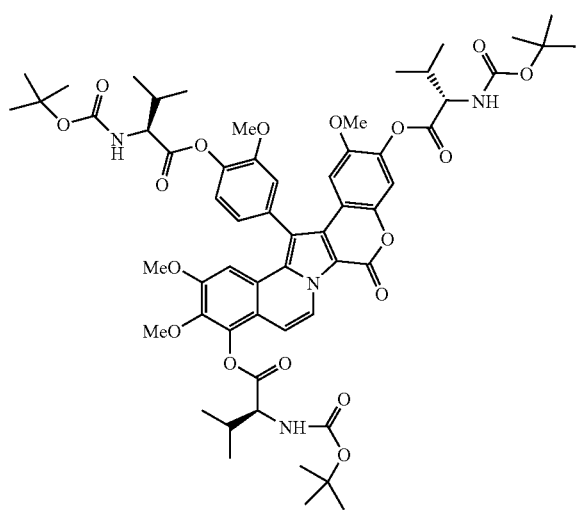

General procedure E (starting from 131, reaction time 24 h) and chromatography on silica gel (CH$_2$Cl$_2$:MeOH, from 50:1 to 30:1) to afford 129 as a yellow solid (53 mg, 79%).

$^1$H NMR (300 MHz, CDCl$_3$) δ 9.21 (d, J=7.6 Hz, 1H), 7.40-7.05 (m, 6H), 6.78 (d, J=9.1 Hz, 1H), 5.15-5.05 (m, 3H), 4.65-4.50 (m, 3H), 3.86 (s, 3H), 3.81 (s, 3H), 3.48 (s, 3H), 3.42 (s, 3H), 2.50-2.30 (m, 3H), 1.49 (s, 18H), 1.46 (s, 9H), 1.25-0.95 (m, 18H). $^{13}$C NMR (75 MHz, CDCl$_3$) δ 170.2 (3C), 155.9, 155.7, 154.9, 153.1, 152.2, 147.6, 145.4, 145.3, 141.7, 139.9, 139.4, 138.7, 134.5, 133.1, 128.3 (2C), 124.0, 123.6, 123.5, 121.0, 118.3, 115.8, 115.1, 112.1, 109.0, 106.9, 106.1, 104.2, 80.3, 80.0 (2C), 60.7, 59.0, 58.6 (2C), 56.0, 55.7, 55.6, 31.3, 31.1, 30.9, 28.3 (9C), 19.3, 19.2, 19.0, 17.5, 17.2, 17.1. MS (ESI) m/z: 1149 (M+23)$^+$. Rf: 0.19 (CH$_2$Cl$_2$:MeOH, 50:1).

Compound 130

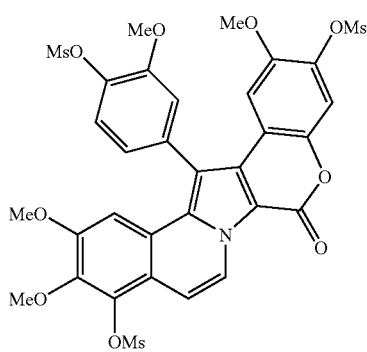

General procedure E (starting from 136, reaction time 3 d) and chromatography on silica gel (CH$_2$Cl$_2$:MeOH, from 50:1 to 30:1) to afford 130 as a brownish solid (105 mg, 99%).

$^1$H NMR (300 MHz, CDCl$_3$) δ 9.15 (d, J=7.6 Hz, 1H), 7.59 (d, J=8.0 Hz, 1H), 7.37 (d, J=7.5 Hz, 1H), 7.35-7.25 (m, 3H), 7.08 (s, 1H), 6.75 (s, 1H), 3.99 (s, 3H), 3.96 (s, 3H), 3.49 (s, 3H), 3.47 (s, 3H), 3.42 (s, 3H), 3.37 (s, 3H), 3.19 (s, 3H). $^{13}$C NMR (75 MHz, CDCl$_3$) δ 154.3, 153.1, 152.9, 148.0, 145.1, 142.6, 138.3, 138.2, 137.7, 135.7, 132.6, 127.6, 125.8, 123.8, 123.6, 121.0, 119.8, 116.6, 115.7, 113.7, 111.8, 109.1, 107.7, 106.4, 104.9, 61.5, 56.6, 55.8, 55.6, 39.7, 39.3, 38.6. MS (ESI) m/z: 764 (M+1)$^+$. Rf: 0.54 (CH$_2$Cl$_2$:MeOH, 50:1).

Compound 131

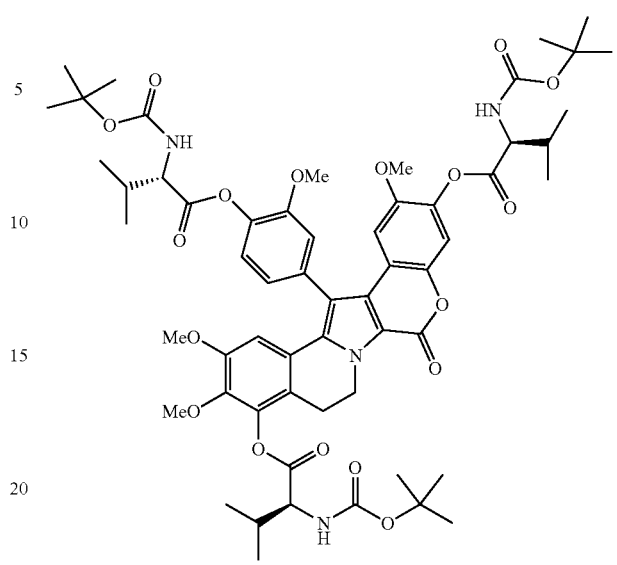

General procedure D (starting from 1 and (L)-Boc-Valine) and chromatography on silica gel (CH$_2$Cl$_2$:MeOH, from 50:1 to 30:1) to afford 131 as a yellow solid (105 mg, 99%).

$^1$H NMR (300 MHz, CDCl$_3$) δ 7.30-7.10 (m, 2H), 7.08 (s, 2H), 6.63 (t, J=8.9 Hz, 2H), 5.30-5.10 (m, 3H), 4.70 (br s, 1H), 4.66 (br s, 1H), 4.60-4.45 (m, 3H), 3.78 (s, 3H), 3.77 (s, 3H), 3.38 (s, 3H), 3.37 (s, 3H), 3.00 (br t, 2H), 2.45-2.30 (m, 3H), 1.48 (s, 9H), 1.47 (s, 9H), 1.45 (s, 9H), 1.15-0.95 (m, 18H). $^{13}$C NMR (75 MHz, CDCl$_3$) δ 170.6, 170.4 (2C), 155.7, 155.6, 154.9, 152.0, 151.8, 147.4, 144.8, 141.2, 141.0, 139.6, 138.5, 134.7, 134.3, 127.0, 126.9, 123.8, 123.2, 122.6, 119.4, 116.1, 115.6, 114.8, 114.7, 111.8, 107.6, 105.4, 80.1, 80.0, 79.9, 60.6, 58.8, 58.5, 58.4, 56.0, 55.6, 55.4, 41.8, 31.3, 31.1, 30.8, 28.3 (9C), 22.2, 19.2, 19.1, 19.0, 17.4, 17.1, 17.0. MS (ESI) m/z: 1151.7 (M+23)$^+$, 1129.8 (M+1)$^+$. Rf: 0.70 (CH$_2$Cl$_2$:MeOH, 20:1).

Compound 132

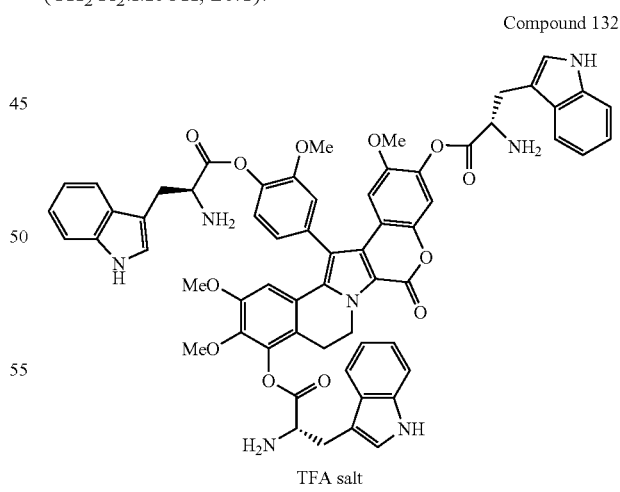

General procedure B (starting from 131) to afford 132 as a brownish solid (50 mg, quant.).

$^1$H NMR (300 MHz, CD$_3$OD) δ 7.90-7.40 (m, 19H), 6.80-6.70 (m, 2H), 4.90-4.50 (m, 5H), 3.90 (s, 3H), 3.79 (s, 3H), 3.60-3.30 (m, 12H), 2.72 (br s, 2H). MS (ESI) m/z: 1090 (M)$^+$.

Compound 133

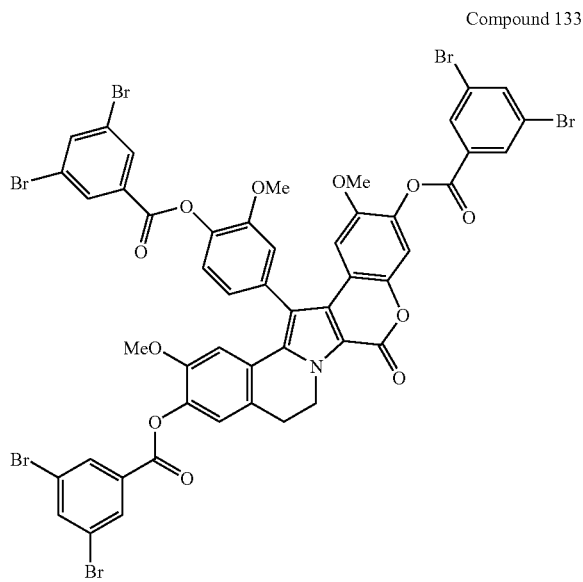

General procedure D (starting from 109 and 3,5-dibromobenzoic acid) and chromatography on silica gel (CH$_2$Cl$_2$:MeOH, from 200:1 to 100:1) to afford 133 as a white solid (43 mg, 67%).

$^1$H NMR (300 MHz, CDCl$_3$) δ 8.28 (d, J=1.8 Hz, 2H), 8.26 (d, J=1.8 Hz, 2H), 8.24 (d, J=1.8 Hz, 2H), 7.95-7.92 (m, 3H), 7.34 (d, J=8.1 Hz, 1H), 7.26 (s, 1H), 7.24-7.20 (m, 2H), 7.08 (s, 1H), 6.88 (s, 1H), 6.81 (s, 1H), 4.94-4.89 (m, 1H), 4.81-4.77 (m, 1H), 3.83 (s, 3H), 3.49 (s, 3H), 3.43 (s, 3H), 3.17 (t, J=6.7 Hz, 2H). $^{13}$C NMR (75 MHz, CDCl$_3$) δ 169.9, 154.9, 151.9, 149.1, 147.6, 147.4, 144.7, 139.4, 138.3, 135.8, 134.4, 129.4, 129.2, 128.5, 127.1, 126.4, 126.3, 123.6, 123.3, 119.5, 116.3, 114.9, 114.6, 114.4, 111.7, 110.9, 108.4, 105.4, 79.9, 79.9 (2C), 56.0, 55.8, 55.6, 55.4, 54.3 (2C), 42.4, 38.0 (2C), 28.4, 28.2 (6C). MS (APCI) m/z: 1288 (M+1)$^+$. Rf: 0.72 (CH$_2$Cl$_2$).

Compound 134

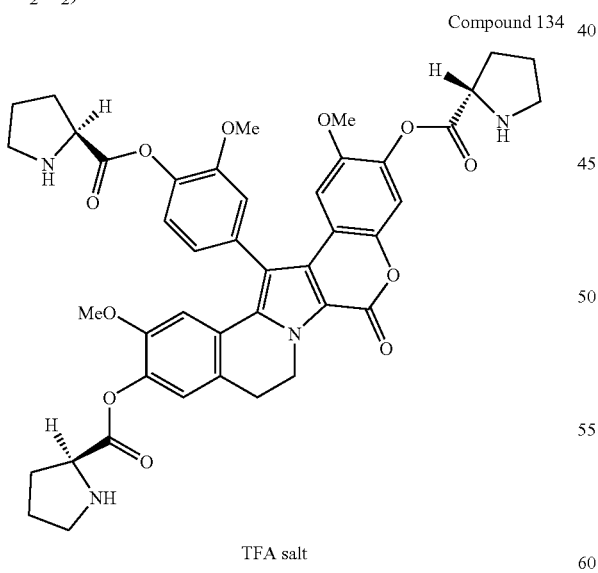

TFA salt

General procedure B (starting from 140) to afford 134 as a white solid (17 mg, quant.).

$^1$H NMR (300 MHz, CD$_3$OD) δ 7.49-7.44 (m, 2H), 7.29-7.17 (m, 3H), 6.88-6.75 (m, 2H), 4.79-4.68 (m, 3H), 3.89 (s, 3H), 3.52-3.38 (m, 12H), 3.15 (br t, 2H), 2.63-2.35 (m, 6H), 2.25-2.15 (m, 6H). MS (ESI) m/z: 793 (M+1)$^+$.

Compound 135

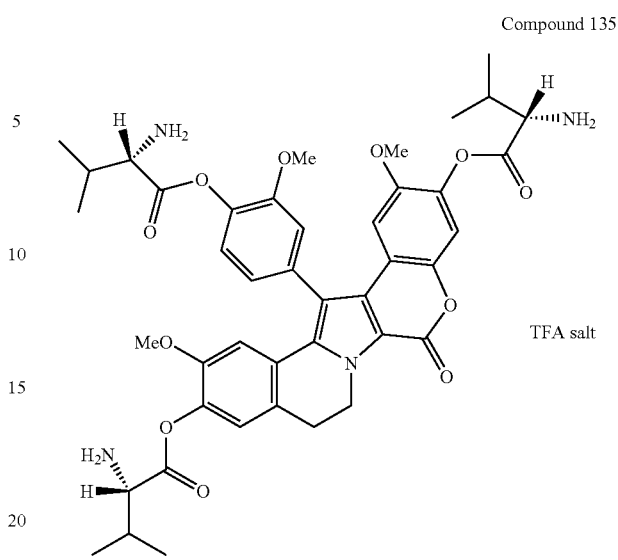

TFA salt

General procedure B (starting from 144) to afford 135 as a white solid (16 mg, quant.).

$^1$H NMR (300 MHz, CD$_3$OD) δ 7.47-7.44 (m, 2H), 7.28 (d, J=8.1 Hz, 1H), 7.19 (s, 1H), 7.15 (s, 1H), 6.90-6.78 (m, 2H), 4.77 (br t, 2H), 4.32 (s, 1H), 4.24 (s, 2H), 3.87 (s, 3H), 3.45 (s, 3H), 3.37 (s, 3H), 3.17 (br t, 2H), 2.54-2.46 (m, 3H), 1.26-1.17 (m, 18H). MS (ESI) m/z: 799 (M+1)$^+$.

Compound 136

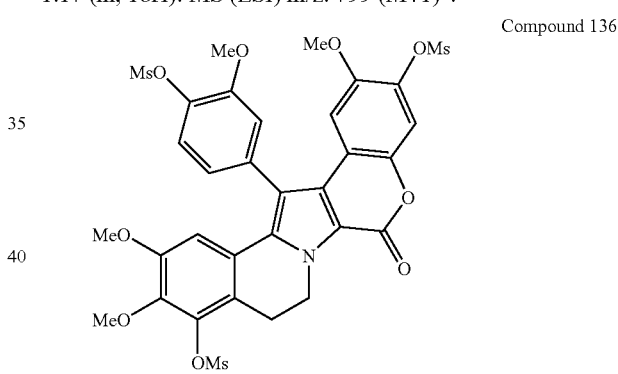

To a solution of 1 (25 mg, 0.047 mmol) in anhydrous CH$_2$Cl$_2$ (2 mL) under Argon at 0° C., Et$_3$N (39 μL, 0.28 mmol) and methanesulfonyl chloride (22 μL, 0.28 mmol) were added. The resulting mixture was stirred at 23° C. for 2 h, then quenched with H$_2$O and extracted with CH$_2$Cl$_2$ (3×20 mL).

The combined organic phases were washed with saturated aqueous solution of NaHCO$_3$, dried over anhydrous Na$_2$SO$_4$, filtered, and evaporated under vacuum. The resulting residue was purified on silica gel (CH$_2$Cl$_2$:MeOH, 50:1) to afford 136 as a brownish solid (35 mg, 97%).

$^1$H NMR (300 MHz, CDCl$_3$) δ 7.51 (d, J=8.0 Hz, 1H), 7.30-7.15 (m, 3H), 6.66 (s, 1H), 6.63 (s, 1H), 5.00-4.90 (m, 1H), 4.75-4.50 (m, 1H), 3.92 (s, 3H), 3.89 (s, 3H), 3.45 (s, 3H), 3.37 (s, 3H), 3.35 (s, 3H), 3.32 (s, 3H), 3.30-3.20 (m, 2H), 3.17 (s, 3H). $^{13}$C NMR (75 MHz, CDCl$_3$) δ 154.5, 152.8, 151.9, 148.0, 144.7, 141.8, 141.0, 138.0, 137.0, 135.6, 134.4, 126.3, 125.6, 123.5, 123.1, 121.7, 117.0, 115.5, 115.3, 113.6, 108.2, 105.7, 61.3, 56.5, 55.8, 55.5, 42.0, 39.4, 39.2, 38.6, 23.3. MS (APCI) m/z: 766 (M+1)$^+$. Rf: 0.54 (CH$_2$Cl$_2$:MeOH, 50:1).

Compound 137

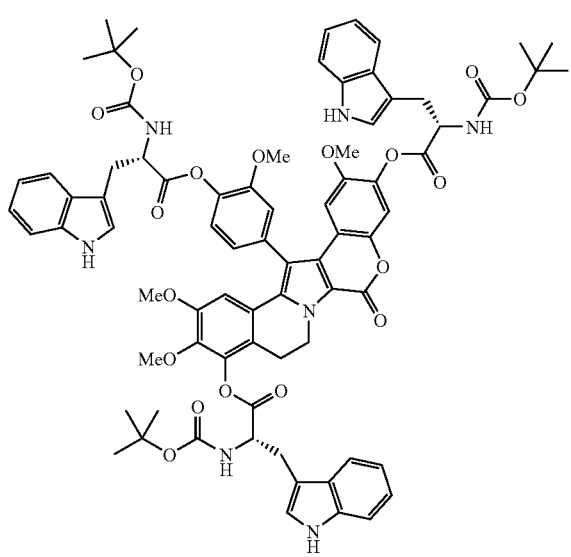

General procedure D (starting from 1 and (L)-N-Boc-Trp) and chromatography on silica gel (CH$_2$Cl$_2$:MeOH, from 30:1 to 20:1) to afford 137 as a brown solid (130 mg, 99%).

$^1$H NMR (300 MHz, CDCl$_3$) δ 8.51 (s, 2H), 8.42 (br s, 1H), 7.70-7.60 (m, 3H), 7.45-7.30 (m, 3H), 7.30-6.95 (m, 9H), 6.87 (s, 1H), 6.70-6.55 (m, 2H), 5.30-5.15 (m, 2H), 5.10-4.90 (m, 3H), 4.80-4.40 (m, 2H), 3.76 (s, 6H), 3.60-3.30 (m, 12H), 2.70 (br s, 2H), 1.45 (s, 27H). $^{13}$C NMR (75 MHz, CDCl$_3$) δ 170.8, 170.4 (2C), 155.2, 154.9, 152.0, 151.7, 147.5, 144.6, 141.4, 141.0, 139.6, 138.5, 136.1 (2C), 134.7, 134.1, 127.7, 127.6, 126.8, 123.8, 123.4, 123.1 (2C), 122.6, 122.2, 119.7, 119.6 (2C), 118.7, 118.6, 116.0, 115.6, 114.6, 111.7, 111.3 (2C), 109.8, 109.4, 107.6, 105.4, 80.2, 80.0 (2C), 60.8, 56.1, 55.6, 55.5, 54.4 (2C), 53.4, 41.7, 28.2 (9C+3C), 21.7. MS (ESI) m/z: 1412 (M+23)$^+$, 1391 (M+1)$^+$. Rf: 0.22 (CH$_2$Cl$_2$:MeOH, 30:1).

Compound 138

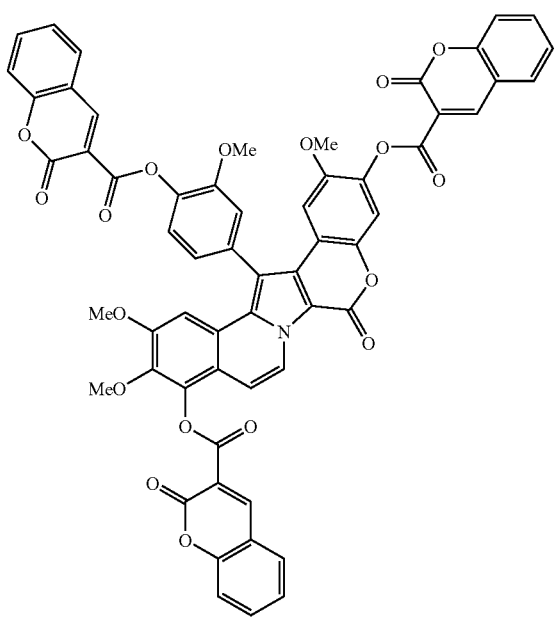

General procedure E (starting from 149, reaction time 2 d) and chromatography on silica gel (CH$_2$Cl$_2$:MeOH, from 100:1 to 50:1) to afford 138 as a white solid (29 mg, 83%).

$^1$H NMR (300 MHz, CDCl$_3$) δ 9.17 (d, J=7.6 Hz, 1H), 8.85 (d, J=4.5 Hz, 2H), 8.78 (s, 1H), 7.80-7.60 (m, 6H), 7.55-7.20 (m, 11H), 7.18 (s, 1H), 6.89 (s, 1H), 3.94 (s, 3H), 3.90 (s, 3H), 3.60 (s, 3H), 3.53 (s, 3H). $^{13}$C NMR (75 MHz, CDCl$_3$) δ 161.2, 160.6, 160.3, 156.4, 156.2, 155.5, 155.4, 155.3, 154.8, 153.3, 152.4, 150.5, 150.4, 150.1, 147.7, 145.4, 141.8, 139.9, 139.4, 138.7, 135.1, 135.0, 134.9, 134.7, 133.2, 129.9, 129.8, 129.7, 128.2, 125.1, 125.0, 124.9, 124.1, 123.7, 123.4, 120.9, 118.2, 117.8, 117.7, 117.7, 116.9, 116.7, 116.5, 115.9, 115.4, 112.3, 112.1, 109.0, 106.9, 106.3, 104.4, 61.0, 56.4, 56.1, 55.9. MS (ESI) m/z: 1046 (M+1)$^+$. Rf: 0.50 (CH$_2$Cl$_2$:MeOH, 50:1).

Compound 139

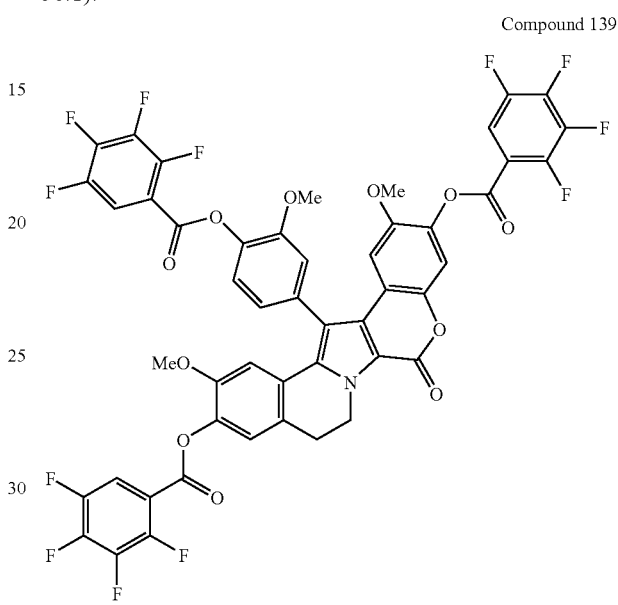

General procedure D (starting from 1 and 2,3,4,5-tetrafluorobenzoic acid) and chromatography on silica gel (CH$_2$Cl$_2$:MeOH, 200:1) to afford 139 as a white solid (33 mg, 64%).

$^1$H NMR (300 MHz, CDCl$_3$) δ 7.81-7.74 (m, 3H), 7.36 (d, J=8.1 Hz, 1H), 7.25 (s, 1H), 7.23 (s, 1H), 7.19 (s, 1H), 7.10 (s, 1H), 6.86 (s, 1H), 6.78 (s, 1H), 4.97-4.91 (m, 1H), 4.82-4.77 (m, 1H), 3.83 (s, 3H), 3.48 (s, 3H), 3.41 (s, 3H), 3.17 (t, J=6.5 Hz, 2H). $^{13}$C NMR (75 MHz, CDCl$_3$) δ 159.6 (3C), 154.9, 152.1, 149.7, 147.5, 144.9, 139.5, 138.9, 138.3, 134.9, 134.7, 126.9, 126.2, 126.1, 123.7, 123.3, 122.5, 116.5, 115.9, 115.2, 114.9, 113.8, 113.5, 111.9, 109.9, 105.6, 56.3, 55.9, 55.7, 42.5, 28.1. MS (APCI) m/z: 1030 (M+1)$^+$. Rf: 0.50 (CH$_2$Cl$_2$:MeOH, 200:1).

Compound 140

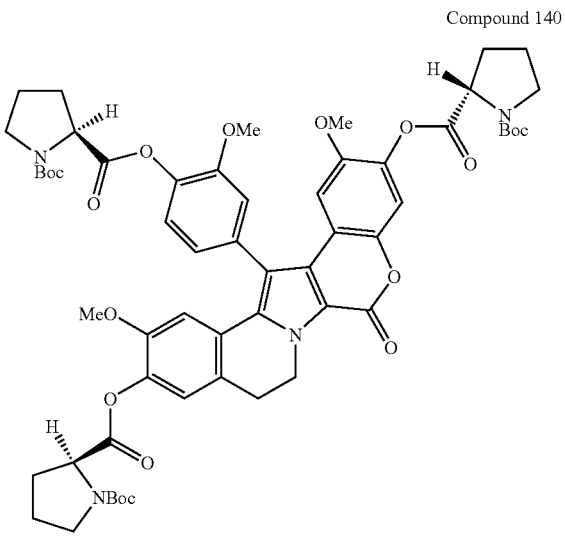

General procedure D (starting from 109 and Boc-L-Pro-OH) and chromatography on silica gel (CH$_2$Cl$_2$:MeOH, from 100:1 to 50:1) to afford 140 as a white solid (74 mg, 68%).

$^1$H NMR (300 MHz, CDCl$_3$) δ 7.16-7.13 (m, 2H), 7.06-7.03 (m, 2H), 6.90 (s, 1H), 6.78-6.63 (m, 2H), 4.95-4.62 (m, 2H), 4.56-4.46 (m, 3H), 3.78 (s, 3H), 3.69-3.43 (m, 6H), 3.40 (s, 3H), 3.33 (s, 3H), 3.11 (br t, 2H), 2.40-2.26 (m, 6H), 2.08-1.90 (m, 6H), 1.47 (s, 27H). $^{13}$C NMR (75 MHz, CDCl$_3$) δ 171.0, 170.8, 170.7, 155.0, 154.3, 153.7, 153.7 (2C), 152.1, 149.7, 147.6, 144.8, 139.8, 139.3, 138.7, 134.1, 125.9, 125.6, 124.0, 123.4, 123.1 (2C), 122.7, 122.2, 116.0, 114.7, 111.6, 109.6, 105.3, 80.1, 80.0, 79.8, 58.9 (2C), 56.1, 55.7, 55.6, 55.5, 46.5, 46.3 (2C), 42.4, 31.5, 30.9, 29.9, 28.3 (9C), 28.0, 24.2, 23.4, 22.5. MS (ESI) m/z: 1115 (M+23)$^+$, 1093 (M+1)$^+$. Rf: 0.18 (CH$_2$Cl$_2$:MeOH, 50:1).

Compound 141

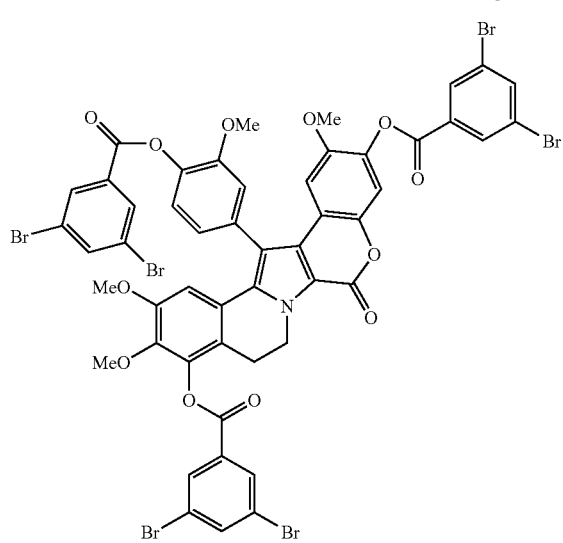

General procedure D (starting from 1 and 3,5-dibromobenzoic acid) and chromatography on silica gel (CH$_2$Cl$_2$:MeOH, 200:1) to afford 141 as a white solid (61 mg, 98%).

$^1$H NMR (300 MHz, CDCl$_3$) δ 8.32 (d, J=1.7 Hz, 2H), 8.30 (d, J=1.8 Hz, 2H), 8.26 (d, J=1.7 Hz, 2H), 7.98 (t, J=1.7 Hz, 1H), 7.96 (t, J=1.7 Hz, 1H), 7.93 (t, J=1.8 Hz, 1H), 7.36 (d, J=7.8 Hz, 1H), 7.25-7.19 (m, 3H), 6.78 (s, 1H), 6.77 (s, 1H), 5.00-4.60 (br s, 2H), 3.84 (s, 3H), 3.82 (s, 3H), 3.48 (s, 6H), 3.10-3.00 (m, 2H). $^{13}$C NMR (75 MHz, CDCl$_3$) δ 162.3, 152.5, 152.2, 147.9, 145.2, 141.6, 140.0, 139.5, 139.2, 138.9, 135.1, 134.8, 132.5, 132.2, 129.1, 127.3, 124.0, 123.7, 123.6, 123.5, 123.4, 123.0, 119.3, 116.7, 116.0, 115.1, 112.2, 108.1, 105.8, 61.2, 56.5, 56.1, 55.9, 42.2, 22.6. MS (APCI) m/z: 1319 (M+1)$^+$. Rf: 0.58 (CH$_2$Cl$_2$).

Compound 142

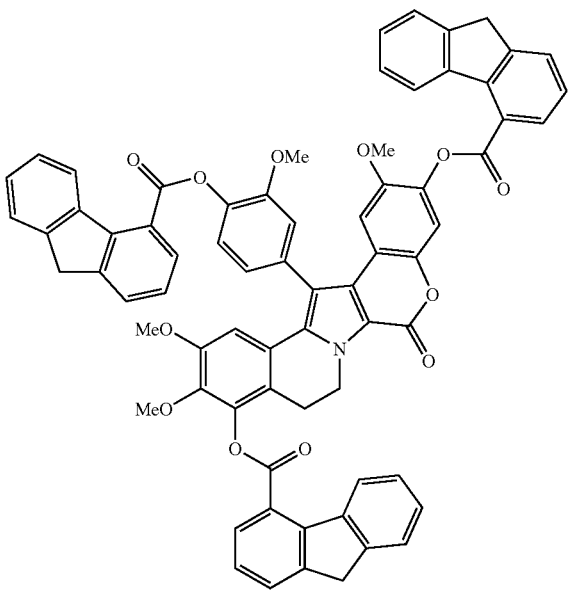

General procedure K (starting from 1 and 4-fluorenecarboxylic acid) and chromatography on silica gel (CH$_2$Cl$_2$:MeOH, from 200:1 to 100:1) to afford 142 as a white solid (36 mg, 69%).

$^1$H NMR (300 MHz, CDCl$_3$) δ 8.60-8.40 (m, 3H), 8.30-8.10 (m, 3H), 7.90-7.70 (m, 3H), 7.65-7.55 (m, 3H), 7.55-7.25 (m, 13H), 6.92 (s, 1H), 6.91 (s, 1H), 5.10-4.70 (br s, 2H), 4.00 (s, 2H), 3.99 (s, 2H), 3.96 (s, 2H), 3.93 (s, 3H), 3.91 (s, 3H), 3.60 (s, 3H), 3.58 (s, 3H), 3.18 (br s, 2H). $^{13}$C NMR (75 MHz, CDCl$_3$) δ 166.0, 165.9, 155.1, 152.6, 152.1, 148.0, 145.4, 145.2, 145.1, 145.0, 144.3, 144.2, 144.1, 141.9, 141.8, 141.5, 141.3, 140.4, 140.0, 139.9, 139.8, 139.2, 135.0, 134.3, 129.5, 129.4, 129.3, 129.0, 127.8, 127.7, 127.6, 127.3, 127.0, 126.8, 126.7, 126.2, 126.1, 126.0, 125.4, 125.3, 125.1, 125.0, 124.7, 124.5, 124.1, 123.5, 122.9, 119.6, 116.2, 116.0, 114.9, 112.1, 107.7, 105.6, 61.0, 56.3, 55.8, 55.7, 42.0, 37.0 (3C), 22.5. MS (APCI) m/z: 1108 (M)$^+$. Rf: 0.34 (CH$_2$Cl$_2$).

Compound 143

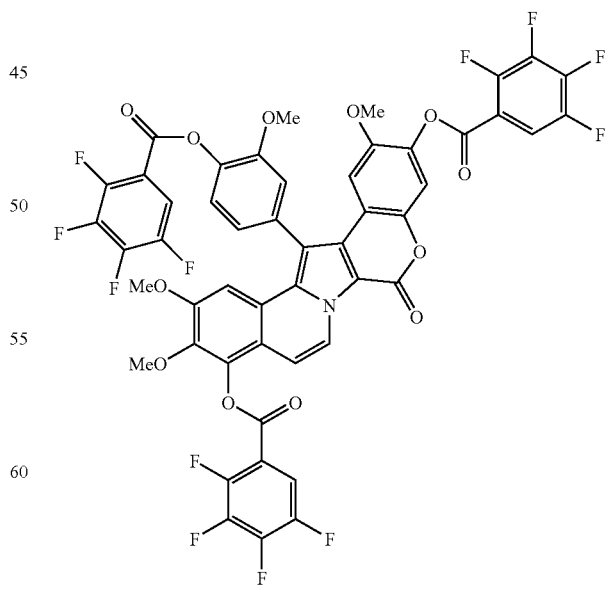

General procedure E (starting from 99, reaction time 63 h) and chromatography on silica gel (CH$_2$Cl$_2$:MeOH, 200:1) to afford 143 as a white solid (27 mg, 93%).

$^1$H NMR (300 MHz, CDCl$_3$) δ 9.22 (d, J=7.5 Hz, 1H), 7.95-7.70 (m, 3H), 7.46 (d, J=8.2 Hz, 1H), 7.40-7.35 (m, 2H), 7.25 (s, 1H), 7.18 (s, 1H), 7.11 (d, J=7.6 Hz, 1H), 6.88 (s, 1H), 3.92 (s, 3H), 3.87 (s, 3H), 3.58 (s, 3H), 3.51 (s, 3H). $^{13}$C NMR (75 MHz, CDCl$_3$) δ 154.7, 153.3, 152.3, 147.6, 145.4, 143.1, 141.7, 139.7, 139.2, 138.5, 135.0, 133.1, 128.2, 123.9, 123.7, 123.6, 120.9, 117.9, 116.1, 115.3, 113.8, 112.1, 109.1, 106.4, 106.3, 104.6, 61.0, 56.4, 55.9, 55.7. MS (APCI) m/z: 1058 (M+1)$^+$. Rf: 0.54 (CH$_2$Cl$_2$).

Compound 144

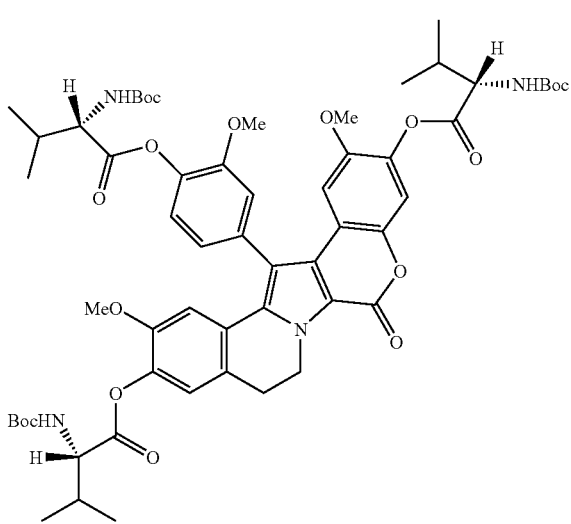

General procedure D (starting from 109 and Boc-L-Val-OH) and chromatography on silica gel (CH$_2$Cl$_2$:MeOH, from 100:1 to 50:1) to afford 144 as a white solid (87 mg, 79%).

$^1$H NMR (300 MHz, CDCl$_3$) δ 7.26-7.13 (m, 2H), 7.09 (s, 2H), 6.96 (s, 1H), 6.76 (d, J=7.5 Hz, 1H), 6.68 (d, J=9.5 Hz, 1H), 5.08-5.05 (m, 3H), 4.91-4.69 (m, 2H), 4.52-4.46 (m, 3H), 3.77 (s, 3H), 3.40 (s, 3H), 3.32 (s, 3H), 3.18 (br t, 2H), 2.42-2.38 (m, 3H), 1.48 (s, 9H), 1.45 (s, 18H), 1.11-0.98 (m, 18H). $^{13}$C NMR (75 MHz, CDCl$_3$) δ 170.3 (3C), 155.6, 154.9, 152.1, 149.7, 147.5, 144.8, 139.7, 139.1, 138.5, 134.9, 134.2, 126.9, 126.0, 125.7, 123.8, 123.1, 122.5, 116.1, 115.8, 115.0, 114.6, 111.9, 109.6, 105.4, 79.9 (3C), 58.5, 56.0, 55.6, 55.3, 55.3, 53.4, 42.4, 31.2 (3C), 28.3 (9C), 28.0, 19.1 (2C), 17.1 (4C). MS (ESI) m/z: 1121 (M+23)$^+$, 1099 (M+1)$^+$. Rf: 0.35 (CH$_2$Cl$_2$:MeOH, 50:1).

Compound 145

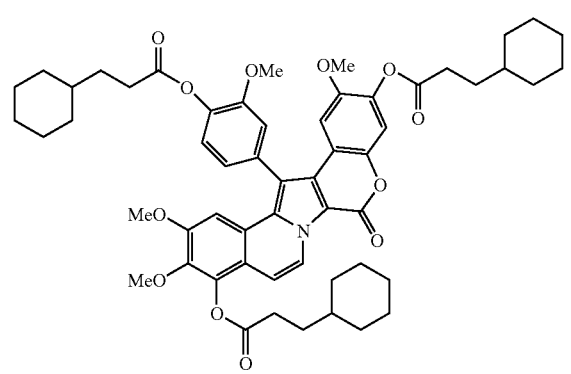

General procedure E (starting from 148, reaction time 24 h) and chromatography on silica gel (CH$_2$Cl$_2$:MeOH, 200:1) to afford 145 as a white solid (27 mg, 87%).

$^1$H NMR (300 MHz, CDCl$_3$) δ 9.22 (d, J=7.5 Hz, 1H), 7.35-7.00 (m, 6H), 6.81 (s, 1H), 3.87 (s, 3H), 3.82 (s, 3H), 3.49 (s, 3H), 3.45 (s, 3H), 2.76 (t, J=7.6 Hz, 2H), 2.70-2.55 (m, 4H), 1.90-1.60 (m, 18H), 1.50-1.10 (m, 15H), 1.05-0.80 (m, 6H). $^{13}$C NMR (75 MHz, CDCl$_3$) δ 172.0, 171.9, 171.8, 155.0, 153.2, 152.4, 147.8, 145.5, 141.8, 140.4, 139.9, 139.1, 134.1, 133.3, 128.4, 124.1, 123.6, 123.3, 121.0, 118.3, 116.5, 115.5, 115.0, 112.2, 108.9, 106.6, 106.1, 104.0, 60.8, 56.2, 55.7, 55.6, 37.2, 37.1, 37.0, 33.0 (4C), 32.9 (4C), 32.4, 32.3, 32.2, 31.6, 31.5, 26.5, 26.2 (6C). MS (ESI) m/z: 944 (M)$^+$. Rf: 0.35 (CH$_2$Cl$_2$).

Compound 146

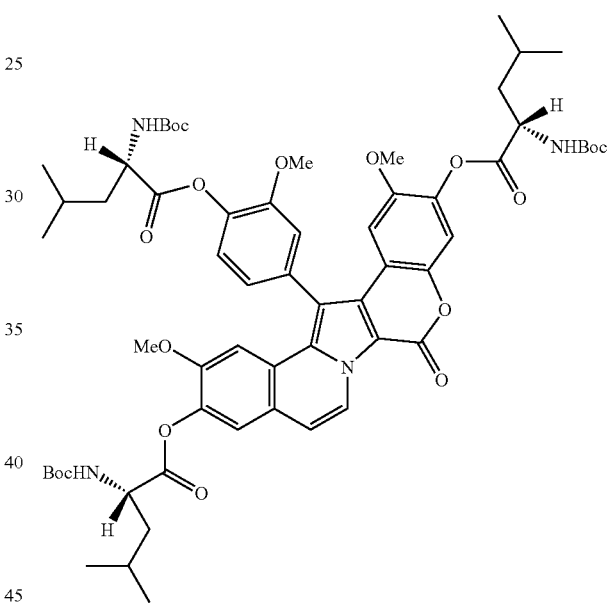

General procedure E (starting from 153, reaction time 35 h) and chromatography on silica gel (CH$_2$Cl$_2$:MeOH, 100:1) to afford 146 (38 mg, 73%) as a white solid.

$^1$H NMR (300 MHz, CDCl$_3$) δ 9.22 (d, J=7.3 Hz, 1H), 7.42 (s, 1H), 7.32 (d, J=7.9 Hz, 1H), 7.25-7.17 (m, 4H), 7.05 (d, J=7.7 Hz, 1H), 6.79 (d, J=5.9 Hz, 1H), 4.98-4.96 (m, 3H), 4.62-4.56 (m, 3H), 3.80 (s, 3H), 3.44 (s, 3H), 3.43 (s, 3H), 1.87-1.64 (m, 9H), 1.49 (s, 9H), 1.46 (s, 18H), 1.06-0.99 (m, 18H). $^{13}$C NMR (75 MHz, CDCl$_3$) δ 171.4 (4C), 155.3, 155.0, 152.3, 150.9, 147.7, 145.4, 140.7, 140.1, 139.6, 134.4, 128.1, 124.0, 123.8, 123.6, 123.2, 120.7, 115.8, 115.1, 112.8, 112.3, 112.2, 109.1, 106.4, 106.2, 80.0 (3C), 56.2 (2C), 55.8 (2C), 55.7, 52.2, 41.7 (2C), 41.5, 28.3 (9C), 24.8 (3C), 23.0, 22.9 (3C), 21.9. MS (ESI) m/z: 1161 (M+23)$^+$, 1139 (M+1)$^+$. Rf: 0.45 (CH$_2$Cl$_2$:MeOH, 50:1).

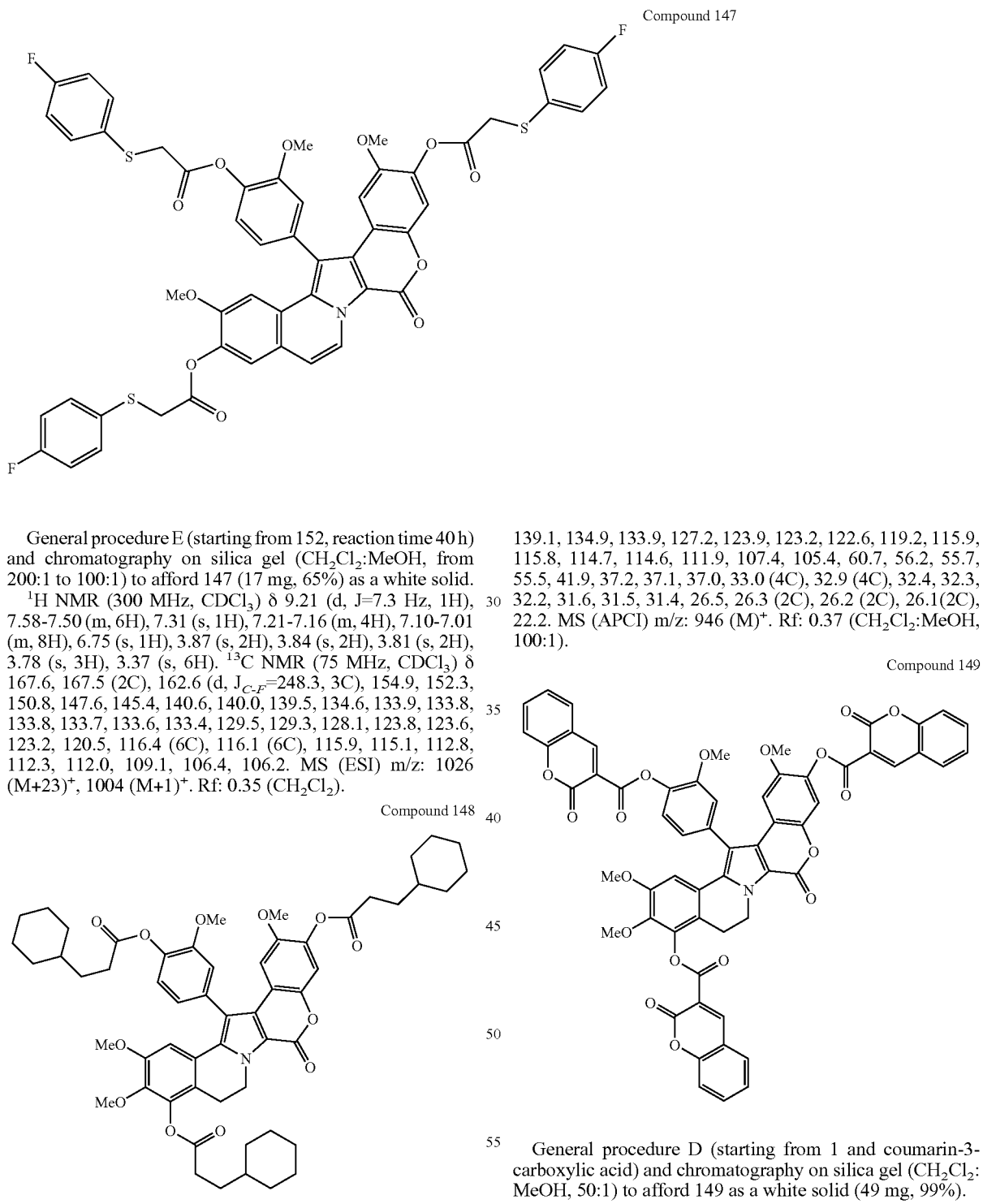

Compound 147

Compound 148

Compound 149

General procedure E (starting from 152, reaction time 40 h) and chromatography on silica gel (CH$_2$Cl$_2$:MeOH, from 200:1 to 100:1) to afford 147 (17 mg, 65%) as a white solid.

$^1$H NMR (300 MHz, CDCl$_3$) δ 9.21 (d, J=7.3 Hz, 1H), 7.58-7.50 (m, 6H), 7.31 (s, 1H), 7.21-7.16 (m, 4H), 7.10-7.01 (m, 8H), 6.75 (s, 1H), 3.87 (s, 2H), 3.84 (s, 2H), 3.81 (s, 2H), 3.78 (s, 3H), 3.37 (s, 6H). $^{13}$C NMR (75 MHz, CDCl$_3$) δ 167.6, 167.5 (2C), 162.6 (d, J$_{C-F}$=248.3, 3C), 154.9, 152.3, 150.8, 147.6, 145.4, 140.6, 140.0, 139.5, 134.6, 133.9, 133.8, 133.8, 133.7, 133.6, 133.4, 129.5, 129.3, 128.1, 123.8, 123.6, 123.2, 120.5, 116.4 (6C), 116.1 (6C), 115.9, 115.1, 112.8, 112.3, 112.0, 109.1, 106.4, 106.2. MS (ESI) m/z: 1026 (M+23)$^+$, 1004 (M+1)$^+$. Rf: 0.35 (CH$_2$Cl$_2$).

General procedure D (starting from 1 and 3-cyclohexylpropionic acid) and chromatography on silica gel (CH$_2$Cl$_2$:MeOH, 100:1) to afford 148 as a white solid (43 mg, 95%).

$^1$H NMR (300 MHz, CDCl$_3$) δ 7.30-7.05 (m, 4H), 6.68 (s, 2H), 5.00-4.80 (m, 1H), 4.80-4.70 (m, 1H), 3.82 (s, 3H), 3.80 (s, 3H), 3.42 (s, 3H), 3.39 (s, 3H), 3.00-2.90 (m, 2H), 2.70-2.50 (m, 6H), 1.90-1.60 (m, 21H), 1.50-1.10 (m, 12H), 1.05-0.90 (m, 6H). $^{13}$C NMR (75 MHz, CDCl$_3$) δ 171.9, 171.9, 171.8, 155.1, 152.3, 151.8, 147.7, 144.9, 141.6, 141.2, 140.1, 139.1, 134.9, 133.9, 127.2, 123.9, 123.2, 122.6, 119.2, 115.9, 115.8, 114.7, 114.6, 111.9, 107.4, 105.4, 60.7, 56.2, 55.7, 55.5, 41.9, 37.2, 37.1, 37.0, 33.0 (4C), 32.9 (4C), 32.4, 32.3, 32.2, 31.6, 31.5, 31.4, 26.5, 26.3 (2C), 26.2 (2C), 26.1(2C), 22.2. MS (APCI) m/z: 946 (M)$^+$. Rf: 0.37 (CH$_2$Cl$_2$:MeOH, 100:1).

General procedure D (starting from 1 and coumarin-3-carboxylic acid) and chromatography on silica gel (CH$_2$Cl$_2$:MeOH, 50:1) to afford 149 as a white solid (49 mg, 99%).

$^1$H NMR (300 MHz, CDCl$_3$) δ 8.82 (s, 1H), 8.80 (s, 1H), 8.77 (s, 1H), 7.80-7.60 (m, 6H), 7.25-7.15 (m, 7H), 7.15-7.05 (m, 3H), 6.78 (s, 1H), 6.76 (s, 1H), 5.00-4.80 (br s, 1H), 4.80-4.60 (br s, 1H), 3.86 (s, 3H), 3.85 (s, 3H), 3.50 (s, 3H), 3.48 (s, 3H), 3.20-3.05 (br s, 2H). $^{13}$C NMR (75 MHz, CDCl$_3$) δ 161.2, 160.5, 160.4, 156.4, 156.3, 156.2, 155.5, 155.4, 154.9, 152.2, 151.9, 150.5, 150.4, 150.0, 149.1, 147.7, 144.9, 141.4, 141.1, 139.7, 138.6, 135.1, 135.0, 134.9, 134.8, 134.5, 129.9, 129.8, 129.7, 129.5, 127.0, 125.1, 125.0, 124.9, 123.9, 123.3, 122.7, 119.3, 117.8, 116.9, 116.8, 116.6, 116.3, 115.7, 114.9, 112.0, 107.9, 105.6, 61.0, 56.4, 56.0, 55.8, 41.9, 22.3. MS (ESI) m/z: 1048 (M+1)+. Rf: 0.50 (CH$_2$Cl$_2$:MeOH, 50:1).

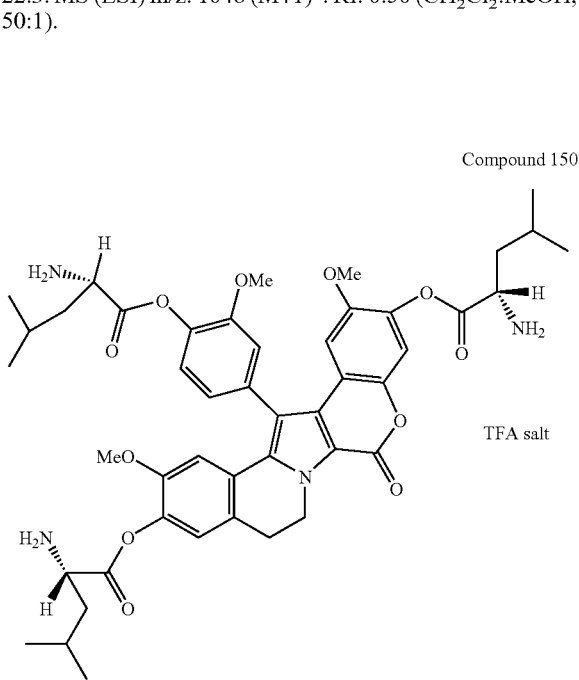

Compound 150

TFA salt

General procedure B (starting from 153) to afford 150 as a white solid (14 mg, 88%).

$^1$H NMR (300 MHz, CD$_3$OD) δ 7.47-7.41 (m, 2H), 7.29-7.24 (m, 2H), 7.16 (s, 1H), 6.87 (d, J=8.2 Hz, 1H), 6.80 (d, J=10.1 Hz, 1H), 4.42-4.29 (m, 3H), 3.92-3.87 (m, 2H), 3.85 (s, 3H), 3.45 (s, 3H), 3.37 (s, 3H), 3.18 (t, J=6.2 Hz, 2H), 2.14-1.61 (m, 9H), 1.12-0.98 (m, 18H). MS (ESI) m/z: 841 (M+1)+.

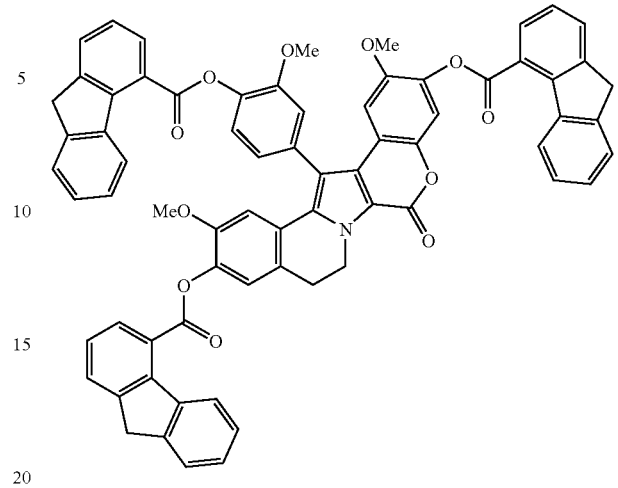

Compound 151

General procedure D (starting from 109 and 9H-fluorene-4-carboxylic acid) and chromatography on silica gel (CH$_2$Cl$_2$:MeOH, 200:1) to afford 151 as a white solid (26 mg, 48%).

$^1$H NMR (300 MHz, CDCl$_3$) δ 8.56-8.52 (m, 2H), 8.46-8.43 (m, 1H), 8.18-8.11 (m, 3H), 7.77-7.74 (m, 3H), 7.58-7.56 (m, 3H), 7.50-7.30 (m, 13H), 7.21 (s, 1H), 7.04 (s, 1H), 6.93 (s, 1H), 5.04-4.95 (m, 1H), 4.92-4.83 (m, 1H), 3.96 (s, 6H), 3.93 (s, 3H), 3.62 (s, 3H), 3.54 (s, 3H), 3.25 (t, J=6.5 Hz, 2H). $^{13}$C NMR (75 MHz, CDCl$_3$) δ 166.1, 166.0, 166.0, 155.2, 152.6, 150.2, 148.0, 145.2, 145.2, 145.1, 144.2, 144.2, 144.2, 141.5, 141.3, 140.4, 139.9, 139.8, 139.2, 135.2, 134.3, 129.5, 129.3, 129.1, 129.0, 127.7, 127.3, 126.9, 126.8, 126.1, 126.1, 126.0, 125.9, 125.4, 125.1, 125.1, 125.0, 124.7, 124.6, 124.1, 123.4, 122.8, 116.3, 116.1, 115.1, 114.8, 112.2, 109.9, 105.7, 56.3, 55.9, 55.7, 42.6, 37.0 (3C), 28.2. MS (ESI) m/z: 1100 (M+23)+. Rf: 0.47 (CH$_2$Cl$_2$).

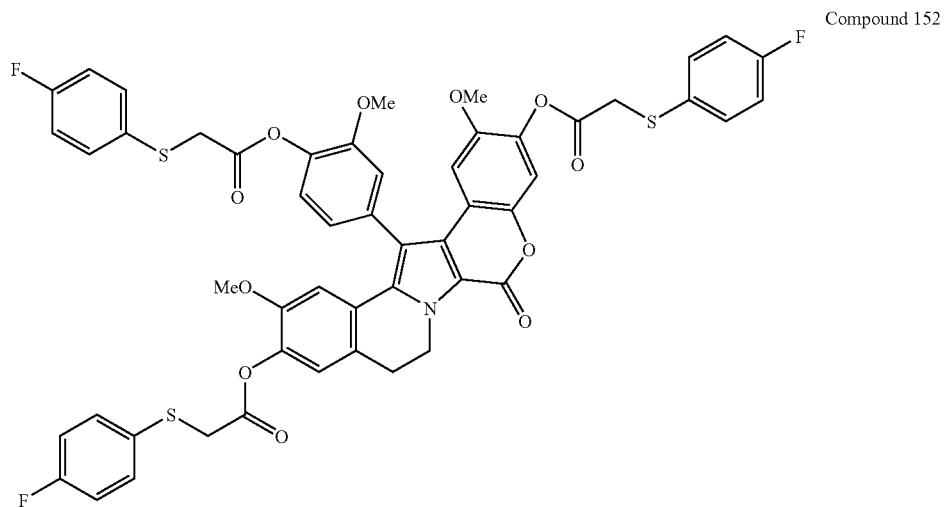

Compound 152

General procedure D (starting from 109 and fluorphenylsulfanylacetic acid) and chromatography on silica gel (hexane:EtOAc, 60:40) to give 152 as a white solid (47 mg, 94%).

¹H NMR (300 MHz, CDCl₃) δ 7.57-7.49 (m, 6H), 7.16-7.00 (m, 10H), 6.86 (s, 1H), 6.74 (s, 1H), 6.64 (s, 1H), 4.89-4.85 (m, 1H), 4.75-4.70 (m, 1H), 3.85 (s, 2H), 3.79 (s, 4H), 3.75 (s, 3H), 3.34 (s, 3H), 3.28 (s, 3H), 3.09 (t, J=6.6 Hz, 2H). ¹³C NMR (75 MHz, CDCl₃) δ 167.7, 167.5, 167.4, 164.2, 160.9, 154.9, 152.1, 149.7, 147.5, 144.8, 139.7, 139.2, 138.6, 134.9, 134.3, 133.8, 133.7, 133.6, 133.6, 129.3, 129.3, 126.9, 125.9, 125.8, 123.6, 123.1, 122.3, 116.4 (6C), 116.2, 116.1 (6C), 115.8, 115.0, 114.7, 111.7, 109.7, 105.5, 56.1, 55.6, 55.4, 42.4, 37.5 (3C), 27.8. MS (ESI) m/z: 1006 (M+1)⁺. Rf: 0.40 (hexane:EtOAc, 60:40).

General procedure D (starting from 109 and Boc-L-Leu-OH.H₂O) and chromatography on silica gel (hexane:EtOAc, 2:1) to give 153 as a white solid (77 mg, 68%).

¹H NMR (300 MHz, CDCl₃) δ 7.24-7.08 (m, 4H), 6.99 (s, 1H), 6.76 (d, J=7.0 Hz, 1H), 6.69 (d, J=8.4 Hz, 1H), 4.94-4.86 (m, 3H), 4.78-4.68 (m, 1H), 4.63-4.50 (m, 2H), 4.37-4.26 (m, 2H), 3.78 (s, 3H), 3.41 (s, 3H), 3.34 (s, 3H), 3.12 (br t, 2H), 1.90-1.60 (m, 9H), 1.45 (s, 27H), 1.05-0.95 (m, 18H). ¹³C NMR (75 MHz, CDCl₃) δ 177.6 (2C), 171.4, 155.6, 155.4, 155.1, 152.1, 149.7, 147.6, 144.8, 139.8, 139.2, 138.7, 135.0, 134.1, 127.0, 127.0, 126.0, 125.7, 123.8, 123.1, 122.5, 116.1, 115.8, 114.9, 114.7, 111.9, 109.7, 105.5, 80.0 (3C), 56.1, 55.7, 55.5, 53.1, 52.2 (2C), 42.4, 41.5 (3C), 28.3 (9C), 28.0, 24.7 (2C), 22.9, 22.8 (4C), 21.8 (2C). MS (ESI) m/z: 1163 (M+23)⁺, 1141 (M+1)⁺. Rf: 0.26 (hexane:EtOAc, 2:1).

Compound 153

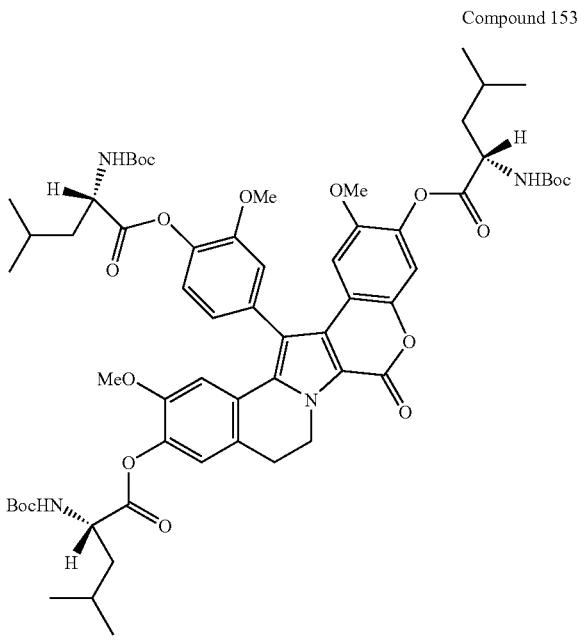

Compound 154

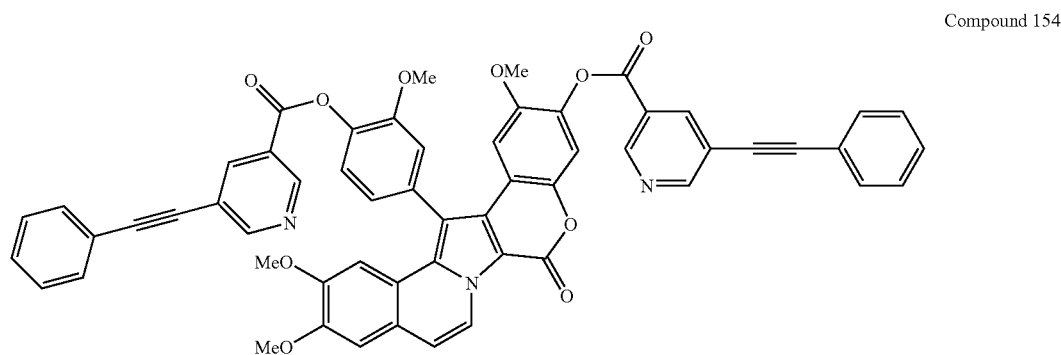

General procedure D (starting from 26 and 5-(2-phenyleth-1-ynyl)nicotinic acid) and chromatography on silica gel (CH$_2$Cl$_2$:EtOAc, 4:1) to give 154 as a pale yellow solid (31.0 mg, 88%).

$^1$H NMR (300 MHz, CDCl$_3$) δ 9.34-9.28 (m, 3H), 9.00-8.97 (m, 2H), 8.63-8.57 (m, 2H), 7.60-7.55 (m, 5H), 7.47-7.31 (m, 9H), 7.28 (s, 1H), 7.15-7.12 (m, 2H), 6.96 (s, 1H), 4.02 (s, 3H), 3.85 (s, 3H), 3.60 (s, 3H), 3.54 (s, 3H). $^{13}$C NMR (75 MHz, CDCl$_3$) δ 162.8, 162.6, 156.0, 154.9, 152.3, 150.4, 149.9, 149.6, 147.6, 145.5, 139.9 (3C), 139.3, 135.1, 134.2, 131.8, 129.2, 129.1, 128.5 (2C), 128.2, 124.7, 124.7, 123.9 (2C), 123.1, 122.0 (2C), 120.8, 118.9, 116.3, 115.5, 113.1, 112.1, 110.9, 108.4, 107.5, 106.3, 105.1, 94.1 (2C), 84.7 (2C), 56.3, 56.0, 55.9, 55.7. MS (ESI) m/z: 946 (M+23)$^+$, 924 (M+1)$^+$. Rf: 0.48 (CH$_2$Cl$_2$:EtOAc, 4:1).

General procedure D (starting from 109 and Boc-L-Ala-OH) and chromatography on silica gel (hexane:EtOAc, from 2:1 to 1:1) to give 156 as a white solid (81 mg, 80%).

$^1$H NMR (300 MHz, CDCl$_3$) δ 7.25-7.09 (m, 4H), 6.97 (s, 1H), 6.75 (d, J=7.7 Hz, 1H), 6.67 (d, J=10.1 Hz, 1H), 5.12 (br s, 2H), 4.89-4.85 (m, 1H), 4.70-4.55 (m, 3H), 3.78 (s, 3H), 3.40 (s, 3H), 3.33 (s, 3H), 2.03 (br t, 2H), 1.58 (d, J=7.1 Hz, 3H), 1.52 (d, J=7.1 Hz, 6H), 1.47 (s, 9H), 1.45 (s, 18H). $^{13}$C NMR (75 MHz, CDCl$_3$) δ 171.4, 155.0, 152.0, 149.7, 147.4, 144.8, 139.7, 139.1, 138.6, 135.0, 134.1, 126.9, 126.8, 126.0, 125.9, 125.7, 123.7, 123.1, 122.4, 116.1, 115.8, 114.9, 114.7, 111.7, 109.6, 105.4, 79.9, 60.3, 56.1, 55.7, 55.7, 55.5, 55.4, 49.2, 42.3, 28.2, 27.9, 21.0, 18.5, 14.1. MS (ESI) m/z: 1037 (M+23)$^+$, 1015 (M+1)$^+$. Rf: 0.44 (hexane:EtOAc, 1:1).

Compound 155

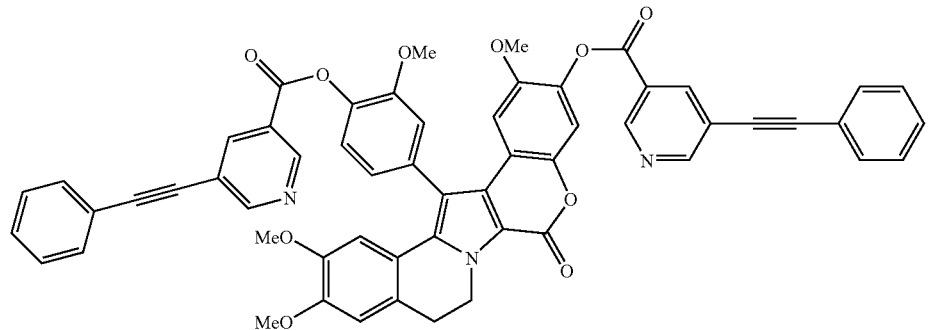

General procedure D (starting from 95 and 5-(2-phenyleth-1-ynyl)nicotinic acid) and chromatography on silica gel (CH$_2$Cl$_2$:EtOAc, 4:1) to give 155 as a pale yellow solid (37.0 mg, 98%).

$^1$H NMR (300 MHz, CDCl$_3$) δ 9.32 (br d, J=1.9 Hz, 1H), 9.28 (br d, J=1.9 Hz, 1H), 8.99-8.97 (m, 2H), 8.60 (t, J=1.9 Hz, 1H), 8.6 (t, J=1.9 Hz, 1H), 7.59-7.55 (m, 4H), 7.40-7.36 (m, 7H), 7.26-7.21 (m, 3H), 6.84 (s, 1H), 6.80 (s, 1H), 6.75 (s, 1H), 4.95-4.75 (m, 2H), 3.92 (s, 3H), 3.82 (s, 3H), 3.51 (s, 3H), 3.50 (s, 3H), 3.16 (t, J=6.6 Hz, 2H). $^{13}$C NMR (75 MHz, CDCl$_3$) δ 162.7, 156.0, 155.0, 152.1, 149.8, 149.2, 147.7, 147.6, 144.9, 139.9, 139.8, 139.6, 138.4, 135.9, 134.8, 131.7, 129.2, 129.1, 128.5, 128.5, 127.4, 126.5, 124.8 (2C), 123.7, 123.5, 122.0 (2C), 120.7, 119.6, 116.5, 115.0, 114.7, 114.5, 111.9, 111.0, 108.5, 105.6, 94.0, 93.9, 84.7 (2C), 56.2, 55.9, 55.8, 55.5, 42.5, 28.6. MS (ESI) m/z: 926 (M+1)$^+$. Rf: 0.48 (CH$_2$Cl$_2$:EtOAc, 4:1).

Compound 156

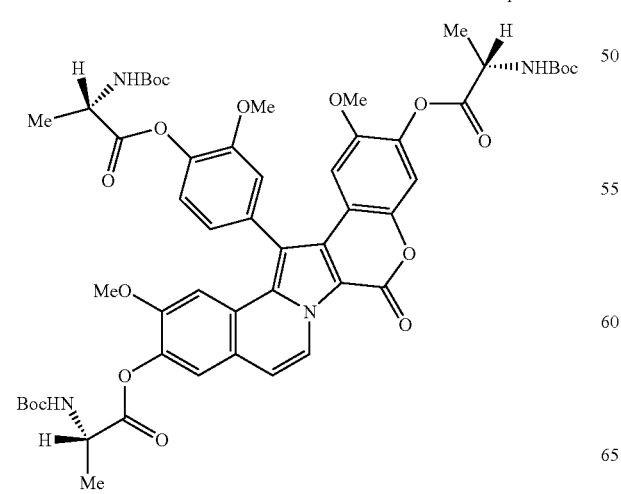

Compound 157

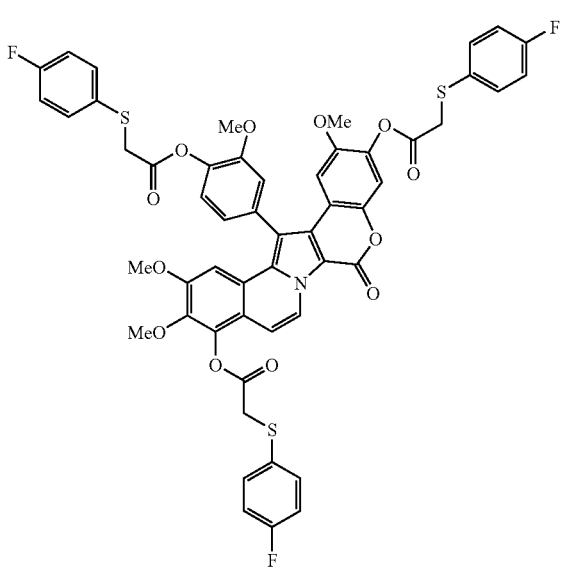

General procedure E (starting from 161, reaction time 24 h) and chromatography on silica gel (hexane:EtOAc, 3:2) to give 157 as a yellow solid (27.1 mg, quant.).

$^1$H NMR (300 MHz, CDCl$_3$) δ 9.16 (d, J=7.8 Hz, 1H), 7.60-7.50 (m, 6H), 7.22-7.20 (m, 1H), 7.10-7.00 (m, 10H), 6.75 (s, 2H), 3.93 (s, 2H), 3.87 (s, 2H), 3.82 (s, 3H), 3.80 (s, 2H), 3.79 (s, 3H), 3.45 (s, 3H), 3.37 (s, 3H). $^{13}$C NMR (75 MHz, CDCl$_3$) δ 167.8, 167.7, 167.7, 164.6, 164.5, 161.3, 161.2, 155.1, 153.4, 152.5, 147.8, 145.6, 142.1, 140.3, 139.8, 138.9, 134.8, 134.1, 134.0, 133.4, 128.5, 124.0, 123.9, 123.7, 121.2, 118.3, 116.9, 116.6, 116.5, 116.4, 116.1, 115.4, 115.4, 112.3, 112.2, 112.1, 109.2, 106.7, 106.5, 104.5, 61.2, 56.5, 55.9, 55.8, 37.8. MS (APCI) m/z: 1034 (M+1)$^+$. Rf: 0.63 (hexane:EtOAc, 3:2).

Compound 158
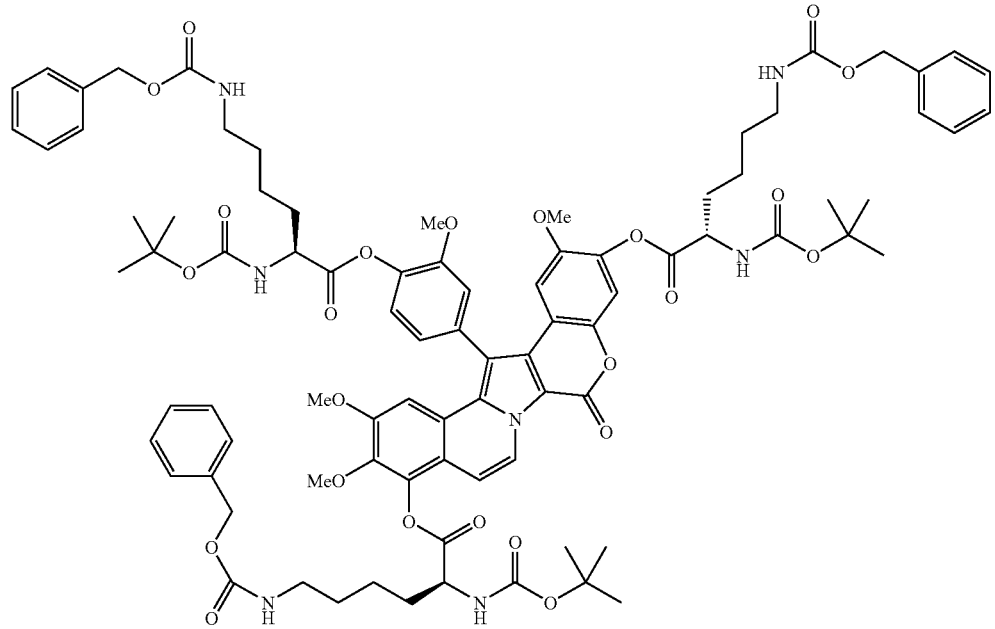
General procedure E (starting from 74, reaction time 6 d) and chromatography on silica gel (hexane:EtOAc, 2:3) to give 158 as a yellow solid (48.3 mg, 68%).
$^1$H NMR (300 MHz, CDCl$_3$) δ 9.20 (d, J=7.5 Hz, 1H), 7.33-7.06 (m, 21H), 6.77 (d, J=8.4 Hz, 1H), 5.09 (s, 6H), 4.94-4.91 (m, 3H), 4.56 (m, 3H), 3.85 (s, 3H), 3.79 (s, 3H), 3.48 (s, 3H), 3.41 (s, 3H), 3.25-3.24 (m, 6H), 2.19-1.82 (m, 6H), 1.62-1.50 (m, 12H), 1.46-1.45 (m, 27H). $^{13}$C NMR (75 MHz, CDCl$_3$) δ 171.5, 170.9 (2C), 156.8 (3C), 156.0, 155.7, 155.1, 153.3 (2C), 152.5, 147.8, 145.6 (2C), 141.9, 140.2, 139.6 (2C), 139.1 (2C), 136.8, 136.7, 136.2, 134.8, 133.5 (2C), 128.8, 128.3, 124.3, 123.9, 123.7, 121.2, 118.5, 116.1, 115.4, 112.3, 109.2, 107.1, 106.4, 104.6, 80.6, 80.4 (2C), 66.9 (3C), 61.1, 56.5, 56.0 (2C), 54.0, 53.7 (2C), 40.8, 40.7 (2C), 32.3, 32.0 (2C), 29.8 (3C), 28.6 (9C), 22.6, 22.5 (2C). MS (ESI) m/z: 1638 (M+23)$^+$. Rf: 0.44 (hexane:EtOAc, 2:3).
Compound 159
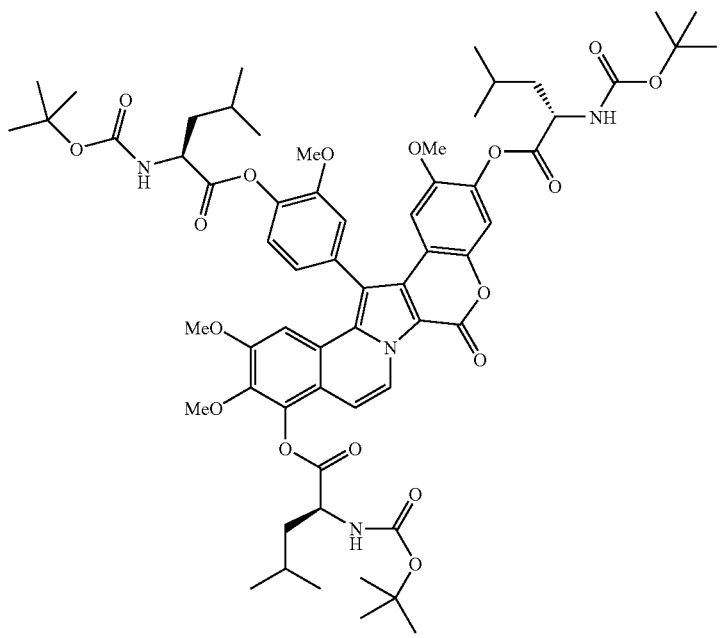

General procedure E (starting from 76, reaction time 6 d) and chromatography on silica gel (hexane:EtOAc, 2:1) to give 159 as a yellow solid (27.9 mg, 69%).

$^1$H NMR (300 MHz, CDCl$_3$) δ 9.22 (d, J=7.6 Hz, 1H), 7.32-7.08 (m, 6H), 6.80-6.77 (m, 1H), 5.01-4.98 (m, 3H), 6.60 (m, 3H), 3.84 (s, 3H), 3.81 (s, 3H), 3.48 (s, 3H), 3.43 (s, 3H), 1.91-1.62 (m, 9H), 1.50-1.46 (m, 27H), 1.06-0.99 (m, 18H). $^{13}$C NMR (75 MHz, CDCl$_3$) δ 171.9, 171.4, 155.6, 155.5, 155.3, 155.0, 153.2, 152.3, 147.6, 145.5, 145.4, 141.7, 140.1, 139.6, 139.0, 134.5, 133.2 (2C), 128.3, 124.0, 123.6, 123.5, 121.0, 118.4, 115.8, 115.1, 112.1, 109.0, 107.0, 106.2, 104.2, 80.4, 80.1 (2C), 56.2, 55.8, 55.7, 55.6, 52.6, 52.2 (2C), 41.7, 41.5, 41.3, 28.3 (9C), 24.8 (3C), 23.0, 22.9 (3C), 21.9, 21.8. MS (ESI) m/z: 1191 (M+23)$^+$. Rf: 0.55 (hexane:EtOAc, 2:1).

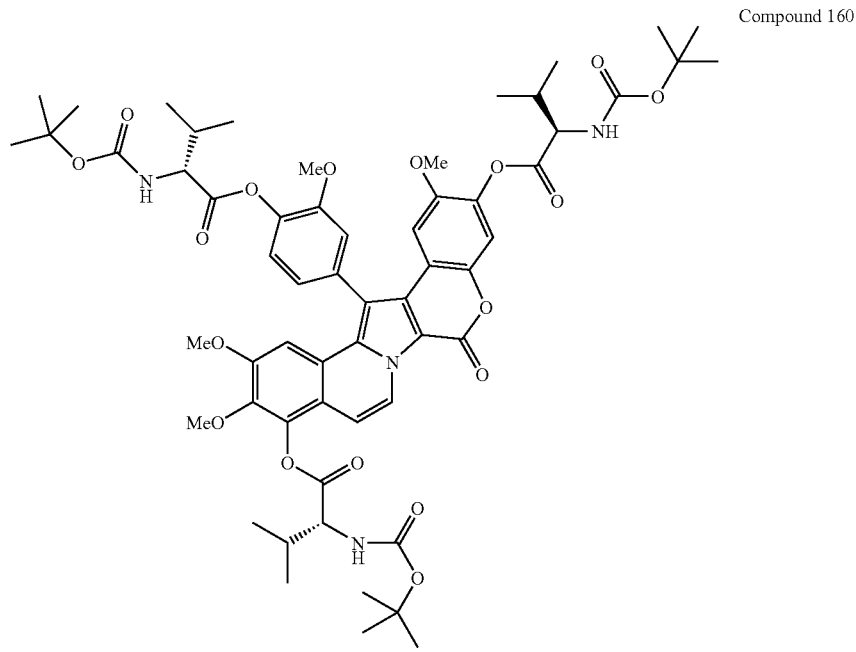

Compound 160

General procedure E (starting from 75, reaction time 3 d) and chromatography on silica gel (hexane:EtOAc, 2:1) to give 160 as a yellow solid (37.8 mg, 77%).

$^1$H NMR (300 MHz, CDCl$_3$) δ 9.22 (d, J=7.6 Hz, 1H), 7.33-7.09 (m, 6H), 6.78 (d, J=8.8 Hz, 1H), 5.12-5.06 (m, 3H), 4.63-4.53 (m, 3H), 3.86 (s, 3H), 3.81 (s, 3H), 3.49 (s, 3H), 3.43 (s, 3H), 2.46-2.35 (m, 3H), 1.49-1.44 (m, 27H), 1.31-1.01 (m, 18H). $^{13}$C NMR (75 MHz, CDCl$_3$) δ 170.4 (3C), 155.9, 155.7, 154.9, 153.1 (2C), 152.2, 147.6, 145.4 (2C), 141.7, 139.9, 138.7, 134.6, 133.2 (2C), 124.0, 123.6, 123.5, 121.0, 118.3, 115.8, 115.1, 112.1 (2C), 109.0, 106.9, 106.1, 104.2, 80.3, 79.9 (2C), 60.7, 59.0, 58.5 (2C), 56.0, 55.7, 55.6, 31.3, 31.1, 30.9, 28.3 (9C), 19.3, 19.2, 19.0, 17.5, 17.2, 17.1. MS (ESI) m/z: 1149 (M+23)$^+$, 1127 (M+1)$^+$. Rf: 0.42 (hexane:EtOAc, 2:1).

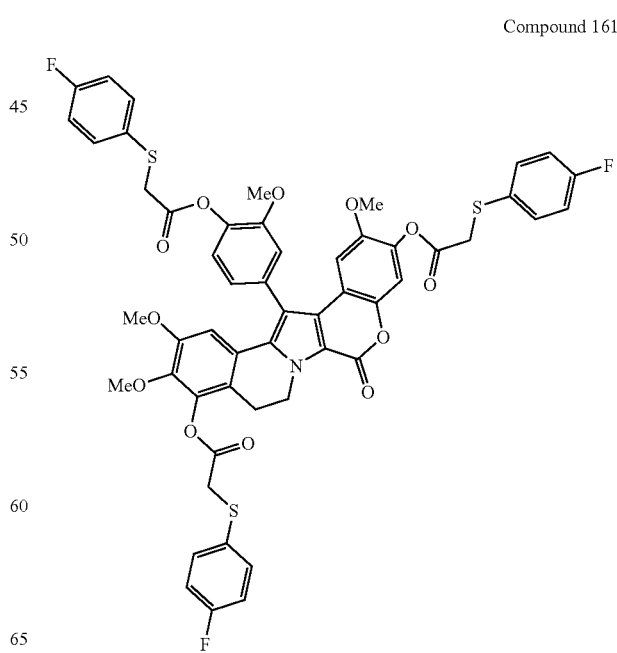

Compound 161

General procedure D (starting from 1 and 2-[(4-fluorophenyl)thio]acetic acid) and chromatography on silica gel (hexane:EtOAc, 3:2) to give a yellow solid which contained 2-[(4-fluorophenyl)thio]acetic acid. The solid was dissolved in CH$_2$Cl$_2$ (20 mL) and washed with NaOH 1 M (20 mL) to give 161 as a pale yellow solid (52.3 mg, 54%).

$^1$H NMR (300 MHz, CDCl$_3$) δ 7.57-7.49 (m, 6H), 7.16-7.00 (m, 10H), 6.64 (s, 1H), 6.63 (s, 1H), 4.80-4.76 (m, 1H), 4.70-4.55 (m, 1H), 3.87 (s, 2H), 3.85 (s, 2H), 3.79 (s, 2H), 3.77 (s, 3H), 3.74 (s, 3H), 3.35 (s, 3H), 3.34 (s, 3H), 2.90 (br t, 2H). $^{13}$C NMR (75 MHz, CDCl$_3$) δ 167.6, 167.5, 167.4, 164.2, 160.9, 154.8, 152.1, 151.8, 147.5, 144.8, 141.3, 141.1, 139.7, 138.6, 134.7, 134.3, 133.7 (2C), 133.6, 133.5, 133.4, 129.3 (2C), 126.9, 123.5, 123.2, 122.6, 119.0, 116.5, 116.3, 116.2, 116.1, 116.0, 115.6, 114.7, 111.6, 107.6, 105.5, 60.8, 56.2, 55.6, 55.4, 41.8, 37.5, 37.4, 37.3, 29.6. MS (ESI) m/z: 1057 (M+23)$^+$, 1035 (M+1)$^+$. Rf: 0.71 (hexane:EtOAc, 1:1).

Compound 162

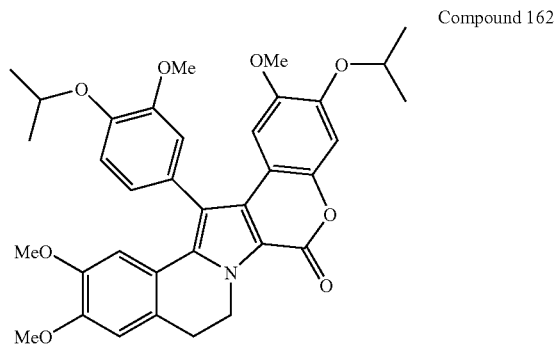

General procedure G (starting from 6,7-Dimethoxy-3,4-dihydroisoquinoline) and chromatography on silica gel (hexane:EtOAc, 2:1) to afford 162 as a pale yellow solid (274.8 mg, 47%).

$^1$H NMR (300 MHz, CDCl$_3$) δ 7.11-7.03 (m, 3H), 6.91 (s, 1H), 6.75 (s, 1H), 6.73 (s, 1H), 6.67 (s, 1H), 4.83-4.61 (m, 2H), 4.59-4.51 (m, 2H), 3.89 (s, 3H), 3.82 (s, 3H), 3.42, 3.36 (s, 3H), 3.12 (t, J=6.8 Hz, 2H), 1.39-1.36 (m, 12H). $^{13}$C NMR (75 MHz, CDCl$_3$) δ 155.2, 152.0, 148.6, 147.1, 146.6, 146.1, 145.5, 135.5, 128.2, 127.8, 126.3, 123.1, 119.7, 116.6, 114.5, 114.4, 113.3, 110.7, 110.0, 108.3, 104.5, 103.0, 71.4, 71.0, 55.9, 55.6, 55.1, 54.7, 42.0, 28.3, 21.6, 21.5, 21.5, 21.4. MS (ESI) m/z: 600 (M+1)$^+$. Rf: 0.17 (hexane:EtOAc, 2:1).

Compound 163

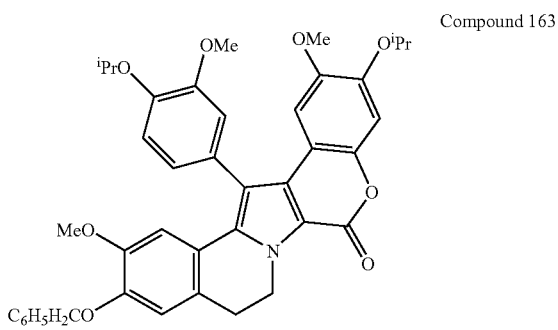

General procedure G (starting from 6-Benzyloxy-7-methoxy-3,4-dihydroisoquinoline) and chromatography on silica gel (hexane:EtOAc, 2:1) to afford 163 as a pale yellow solid (42.5 mg, 34%).

$^1$H NMR (300 MHz, CDCl$_3$) δ 7.43-7.29 (m, 5H), 7.09-7.03 (m, 3H), 6.90 (s, 1H), 6.76 (s, 1H), 6.75 (s, 1H), 6.66 (s, 1H), 5.14 (s, 2H), 4.79-4.50 (m, 4H), 3.82 (s, 3H), 3.42 (s, 3H), 3.37 (s, 3H), 3.04 (t, J=6.8 Hz, 2H), 1.39-1.36 (m, 12H). $^{13}$C NMR (75 MHz, CDCl$_3$) δ 155.6, 151.2, 148.0, 148.0, 147.0, 146.9, 146.5, 145.9, 136.6, 135.8, 128.6, 128.5, 128.2, 128.0, 127.1, 126.4, 125.4, 123.4, 120.5, 116.9, 114.9, 114.5, 113.7, 113.3, 110.3, 109.0, 108.5, 104.8, 103.4, 71.7, 71.4, 70.9, 56.1, 55.4, 55.1, 42.3, 28.6, 21.8 (4C). MS (ESI) m/z: 676 (M)$^+$. Rf: 0.30 (hexane:EtOAc, 2:1).

Compound 164

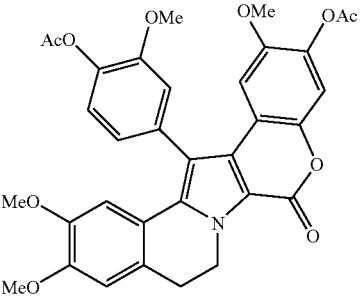

General procedure L (starting from 95) to afford 164 as a brown solid (7 mg, quant.).

$^1$H NMR (300 MHz, CDCl$_3$) δ 7.23-7.09 (m, 4H), 6.76 (s, 1H), 6.72 (s, 1H), 6.69 (s, 1H), 4.90-4.74 (m, 2H), 4.30 (t, J=6.6 Hz, 2H), 3.90 (s, 3H), 3.80 (s, 3H), 3.43 (s, 3H), 3.16 (s, 3H), 3.14 (t, J=6.6 Hz, 2H), 2.34 (s, 3H), 2.31 (s, 2H). $^{13}$C NMR (75 MHz, CDCl$_3$) δ 168.7, 152.1, 149.1, 147.7 (2C), 139.9, 138.8, 134.3, 130.9, 128.8, 126.4, 126.3, 123.8, 123.3, 119.7, 116.2, 114.8 (2C), 111.9, 111.0, 108.5, 105.5, 56.2, 55.9, 55.7, 55.4, 42.5, 29.7 (2C), 29.4. MS (ESI) m/z: 600 (M+1)$^+$. Rf: 0.27 (EtOAc:hexane, 2:1).

Compound 165

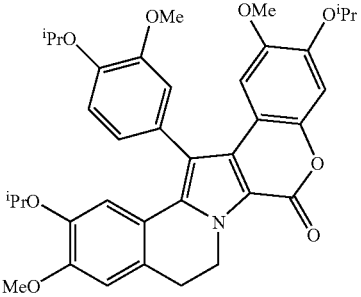

General procedure G (starting from 7-Isopropoxy-6-methoxy-3,4-dihydroisoquinoline) and chromatography on silica gel (hexane:EtOAc, 50:50) to afford 165 as a pale yellow solid (84.6 mg, 23%).

$^1$H NMR (300 MHz, CDCl$_3$) δ 7.08-7.00 (m, 3H), 6.86 (s, 1H), 6.74 (s, 2H), 6.60 (s, 1H), 4.78-4.71 (m, 2H), 4.60-4.41 (m, 2H), 3.88-3.77 (m, 1H), 3.83 (s, 3H), 3.80 (s, 3H), 3.40 (s, 3H), 3.08 (t, J=6.8 Hz, 2H), 1.40 (d, J=6.1 Hz, 6H), 1.33 (d, J=6.0 Hz, 6H), 1.10 (d, J=6.1 Hz, 3H), 1.07 (d, J=6.1 Hz, 3H). $^{13}$C NMR (75 MHz, CDCl$_3$) δ 155.5, 151.1, 149.9, 147.0, 146.8, 146.4, 145.8, 145.7, 135.8, 128.3, 128.2, 126.4, 123.2, 119.9, 116.2, 114.7, 114.3, 113.5, 111.9, 111.4, 110.3, 104.8, 103.3, 71.5, 71.3, 70.7, 55.9, 55.8, 55.3, 42.3, 28.6, 21.9, 21.8, 21.7, 21.5(2C), 20.9. MS (ESI) m/z: 650 (M+23)⁺, 628 (M+1)⁺. Rf: 0.41 (hexane:EtOAc, 50:50).

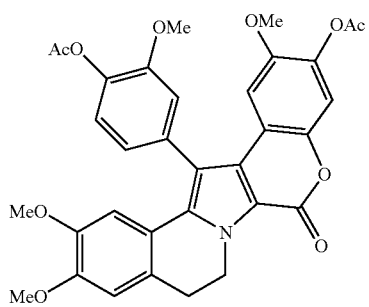

Compound 166

General procedure L (starting from 26) and chromatography on silica gel (CH₂Cl₂:MeOH, 20:1) to afford 166 (7 mg, quant.).

¹H NMR (300 MHz, CDCl₃) δ 9.30 (d, J=7.6 Hz, 1H), 7.31-7.26 (m, 5H), 7.23-7.10 (m, 2H), 6.84 (s, 1H), 4.00 (s, 3H), 3.83 (s, 3H), 3.51 (s, 3H), 3.46 (s, 3H), 2.37 (s, 2H), 2.32 (s, 2H). MS (ESI) m/z: 620 (M+23)⁺, 598 (M+1)⁺. Rf: 0.60 (CH₂Cl₂:MeOH, 10:1).

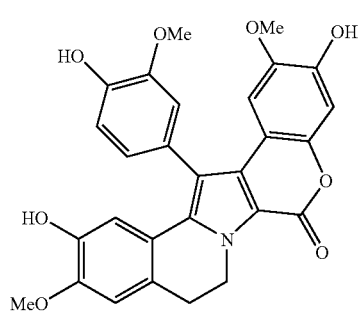

Compound 167

General procedure A (starting from 165) and chromatography on silica gel (CH₂Cl₂:MeOH, 20:1) to afford 167 as a beige solid (35.3 mg, 55%).

¹H NMR (300 MHz, DMSO-d₆) δ 9.66 (br s, 1H), 9.26 (br s, 1H), 8.85 (br s, 1H), 6.99-6.94 (m, 3H), 6.83 (dd, J=7.8, 1.7 Hz, 1H), 6.78 (s, 1H), 6.66 (s 1H), 6.46 (s, 1H), 4.62 (br t, J=5.9 Hz, 2H), 3.79 (s, 3H), 3.73 (s, 3H), 3.33 (s, 3H), 3.06 (br t, J=5.9 Hz, 2H). ¹³C NMR (75 MHz, DMSO-d₆) δ 154.3, 148.4, 148.0, 146.8, 146.5, 145.6, 144.8, 144.4, 135.4, 127.9, 125.5, 125.3, 123.3, 119.7, 116.4, 114.8, 114.5, 112.8, 112.4, 111.9, 108.8, 105.0, 103.5, 55.9, 55.6, 55.0, 42.0, 28.0. MS (ESI) m/z: 524 (M+23)⁺, 502 (M+1)⁺. Rf: 0.25 (CH₂Cl₂:MeOH, 20:1).

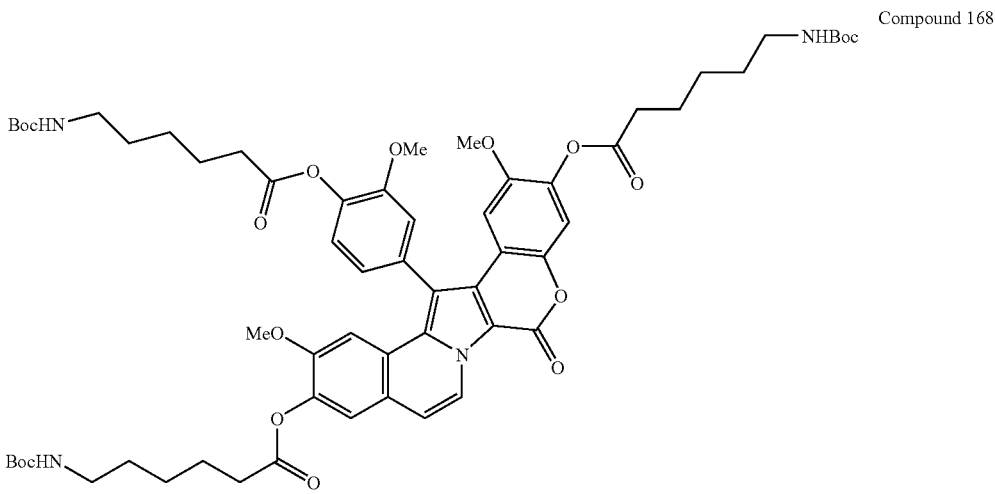

Compound 168

General procedure D (starting from 3 and 6-(BOC-amino) caproic acid) and chromatography on silica gel (CH₂Cl₂:MeOH, 40:1) to afford 168 as a white solid (608 mg, 89%).

¹H NMR (300 MHz, CDCl₃) δ 9.24 (d, J=7.3 Hz, 1H), 7.38 (s, 1H), 7.29-7.13 (m, 5H), 7.07 (d, J=7.5 Hz, 1H), 6.80 (s, 1H), 4.56 (bs, 3H), 3.82 (s, 3H), 3.44 (s, 6H), 3.20-3.13 (m, 6H), 2.66-2.56 (m, 6H), 1.84-1.75 (m, 6H), 1.60-1.44 (m, 39H). ¹³C NMR (75 MHz, CDCl₃) δ 171.4, 171.2, 155.9, 155.0, 152.4, 151.0, 147.7, 145.4, 140.9, 140.3, 139.8, 134.1, 133.5, 128.2, 124.0, 123.8, 123.6, 123.5, 123.0, 120.6, 115.5, 115.0, 112.7, 112.2, 112.1, 108.9, 106.3, 106.1, 79.0(3C), 56.2, 55.7, 55.6, 40.3(3C), 33.8(2C), 33.7, 29.7(3C), 28.4 (9C), 26.2, 26.1(2C), 24.5(2C), 24.5. MS (ESI) m/z: 1162 (M+23)⁺. Rf: 0.30 (CH₂Cl₂:MeOH, 40:1).

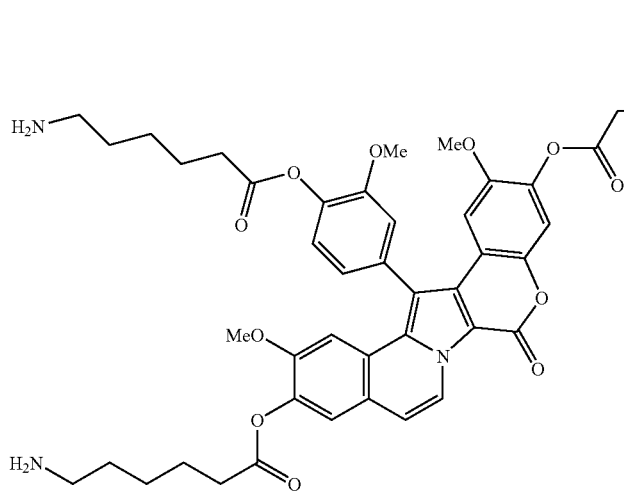

Compound 169

HCl salt

General procedure C (starting from 168) to afford 169 as a white solid (389 mg, 93%).

$^1$H NMR (300 MHz, CD$_3$OD) δ 9.07 (d, J=7.3 Hz, 1H), 7.49 (s, 2H), 7.39 (d, J=8.1 Hz, 1H), 7.31-7.28 (m, 2H), 7.16-7.11 (m, 2H), 6.86 (s, 1H), 3.88 (s, 3H), 3.46 (s, 6H), 3.02-2.94 (m, 6H), 2.73-2.60 (m, 6H), 1.88-1.75 (m, 12H), 1.54-1.52 (m, 6H). MS (ESI) m/z: 839 (M+1)$^+$.

Compound 170

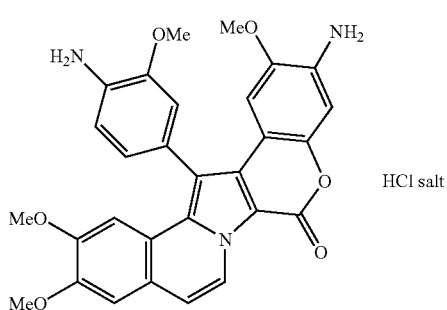

HCl salt

Me$_3$SiCl (12 mL, 0.095 mmol) was added to a suspension of 57 (7.0 mg, 0.0136 mmol) in MeOH (2 mL). The solution was stirred at 23° C. for 1 hour. The solvent was evaporated to dryness and CH$_2$Cl$_2$ (2×1 mL) was added in order to remove all the solvent to give 170 as a light orange solid (8 mg, quant.).

$^1$H NMR (300 MHz, CD$_3$OD) δ 7.70 (d, J=7.3 Hz, 1H), 7.47 (s, 1H), 7.42 (s, 1H), 7.32 (d, J=7.3 Hz, 1H), 6.96 (s, 1H), 6.79 (s, 1H), 6.56 (s, 1H), 4.90-4.79 (m, 4H), 3.98 (s, 3H), 3.85 (s, 3H), 3.57 (s 3H), 3.34 (s, 3H).

Compound 171

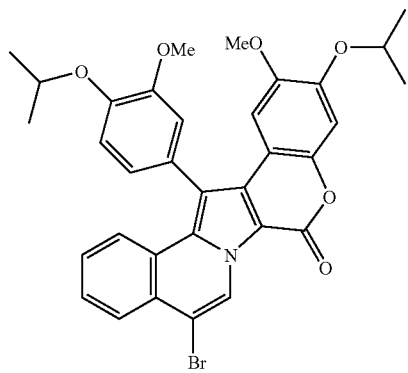

General procedure G (starting from 4-bromoisoquinoline) and chromatography on silica gel (hexane:CH$_2$Cl$_2$:Et$_2$O, 6:4:1) to provide 171 as a yellow solid (41 mg, 16%).

$^1$H NMR (300 MHz, CDCl$_3$) δ 9.61 (s, 1H), 8.11 (d, J=7.8 Hz, 1H), 7.76 (d, J=8.4 Hz, 1H), 7.59 (t, J=7.7 Hz, 1H), 7.34 (t, J=7.8 Hz, 1H), 7.17 (d, J=8.0 Hz, 1H), 7.12-7.05 (m, 2H), 6.96 (s, 1H), 6.64 (s, 1H), 4.70 (hp, J=6.0 Hz, 1H), 4.57 (hp, J=6.0 Hz, 1H), 3.83 (s, 3H), 3.44 (s, 3H), 1.51 (d, J=6.2 Hz, 3H), 1.44 (d, J=6.0 Hz, 3H), 1.40 (d, J=7.8 Hz, 6H). $^{13}$C NMR (75 MHz, CDCl$_3$) δ 155.4, 151.5, 148.1, 147.5, 146.7, 146.6, 133.3, 129.8, 128.8, 128.4, 127.6, 127.0, 125.5, 125.0, 124.6, 123.2, 116.6, 114.8, 114.2, 113.5, 109.5, 108.8, 108.4, 105.4, 103.2, 71.5, 56.1, 55.4, 22.3, 21.9, 21.8, 21.7. Rf: 0.46 (hexane:CH$_2$Cl$_2$:Et$_2$O, 6:4:1).

Compound 172

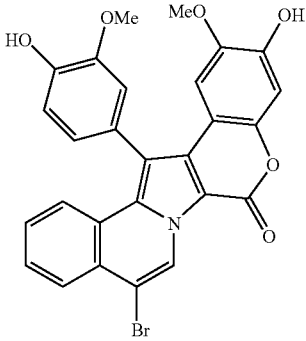

General procedure A (starting from 171) and chromatography on silica gel (CH$_2$Cl$_2$:MeOH from 30:1 to 10:1) to afford 172 as a yellow solid (20 mg, 74%).

$^1$H NMR (300 MHz, (CD$_3$)$_2$SO, 40° C.) δ 9.85 (s, 1H), 9.38 (s, 1H), 9.36 (s, 1H), 8.03 (d, J=8.4 Hz, 1H), 7.79 (d, J=8.2 Hz, 1H), 7.70 (t, J=7.3 Hz, 1H), 7.54 (t, J=7.3 Hz, 1H), 7.20-7.05 (m, 2H), 6.96 (d, J=7.8 Hz, 1H), 6.87 (s, 1H), 6.55 (s, 1H), 3.74 (s, 3H), 3.37 (s, 3H). $^{13}$C NMR (75 MHz, (CD$_3$)$_2$SO, 60° C.) δ 154.1, 148.8, 148.1, 147.1, 146.2, 144.7, 132.2, 129.4, 129.1, 128.6, 127.2, 126.2, 124.4, 123.9, 123.0, 116.7, 114.5, 113.5, 107.7, 107.3, 105.8, 103.6, 72.0, 55.9, 55.0. MS (APCI) m/z: 534 (M+2)$^+$, 532 (M)$^+$. Rf: 0.50 (CH$_2$Cl$_2$:MeOH, 20:1).

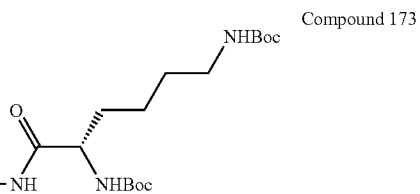

Compound 173

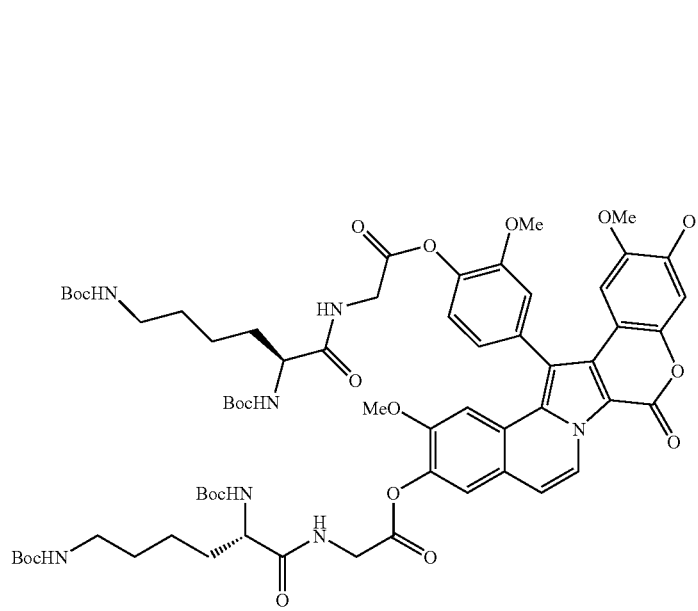

General procedure D (starting from 3 and Boc-Lys(Boc) Gly-OH) and chromatography on silica gel (CH$_2$Cl$_2$:MeOH, 30:1) to afford 173 as a pale yellow solid (98 mg, 74%).

$^1$H NMR (300 MHz, CDCl$_3$) δ 8.62 (d, J=7.3 Hz, 1H), 7.70-7.40 (m, 3H), 7.30-7.00 (m, 6H), 6.80-6.60 (m, 2H), 6.40 (d, J=7.1 Hz, 1H), 5.67 (br s, 2H), 5.41 (br s, 1H), 4.91 (br s, 1H), 4.82 (br s, 2H), 4.50-4.20 (m, 9H), 3.90 (s, 3H), 3.42 (s, 6H), 3.05 (br s, 6H), 1.90-1.60 (m, 6H), 1.50-1.30 (m, 66H). $^{13}$C NMR (75 MHz, CDCl$_3$) δ 173.2, 172.8, 167.8, 167.7, 156.3, 156.1, 155.9, 154.1, 152.1, 150.6, 147.5, 144.7, 140.0, 139.6, 138.9, 134.4, 132.9, 127.4, 123.7, 123.4, 123.3, 121.9, 121.0, 115.4, 112.2, 111.9, 108.2, 106.0, 105.7, 79.9, 78.9, 56.4, 55.7, 55.5, 54.3, 53.4, 40.9, 39.8, 31.9, 29.6, 28.4, 28.3, 28.2, 27.7, 22.5. MS (APCI) m/z: 1678 (M+23)$^+$. Rf: 0.21 (CH$_2$Cl$_2$:MeOH, 30:1).

Compound 174

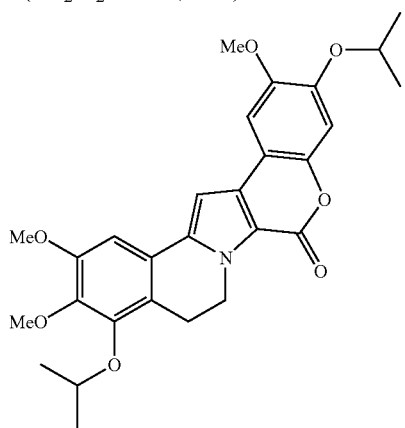

General procedure H (starting from 6,7-dimethoxy-5-isopropoxy-3,4-dihydroisoquinoline) and chromatography on silica gel Merck Si60 (230-400 mesh) (CH$_2$Cl$_2$:MeOH, 100:1) to afford 174 as a clear oil (150 mg, 43%).

$^1$H NMR (300 MHz, CDCl$_3$) δ 7.16 (s, 1H), 7.00 (s, 1H), 6.92 (s, 1H), 6.81 (s, 1H), 4.70-4.50 (m, 4H), 3.95 (s, 6H), 3.88 (s, 3H), 3.10 (t, J=6.7 Hz, 2H), 1.41 (d, J=6.2 Hz, 6H), 1.31 (d, J=6.2 Hz, 6H). $^{13}$C NMR (75 MHz, CDCl$_3$) δ 155.4, 152.7, 148.9, 147.6, 147.2, 145.9, 143.2, 139.7, 130.9, 122.8, 120.4, 115.1, 109.9, 104.6, 103.6, 103.4, 96.0, 75.6, 71.5, 60.6, 56.4, 56.1, 42.0, 22.6, 22.5, 21.8. MS (ESI) m/z: 494 (M+1)$^+$. Rf: 0.40 (CH$_2$Cl$_2$:MeOH, 100:1).

Compound 175

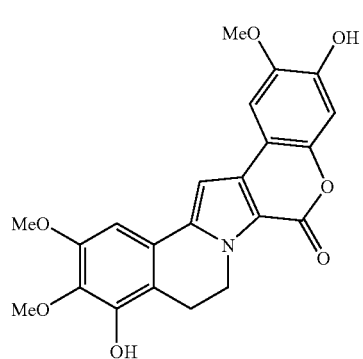

General procedure A (starting from 174) and chromatography on silica gel Merck Si60 (230-400 mesh) (CH$_2$Cl$_2$:MeOH, 50:1) to afford 175 as a brown solid (15 mg, 62%).

$^1$H NMR (300 MHz, CDCl$_3$) δ 7.16 (s, 1H), 6.99 (s, 1H), 6.84 (s, 1H), 6.81 (s, 1H), 5.99 (s, 1H), 5.84 (s, 1H), 4.70 (t, J=6.9 Hz, 2H), 4.01 (s, 3H), 3.96 (s, 6H), 3.11 (t, J=6.9 Hz, 2H). $^{13}$C NMR (75 MHz, CDCl$_3$) δ 155.4, 151.3, 146.6, 146.4, 146.0, 143.9, 139.6, 136.1, 130.9, 123.1, 115.3, 112.4, 109.9, 103.7, 103.4, 100.1, 96.0, 61.2, 56.4, 56.0, 41.9, 21.3. MS (ESI) m/z: 410 (M+1)$^+$. Rf: 0.44 (CH$_2$Cl$_2$:MeOH, 20:1).

Compound 176

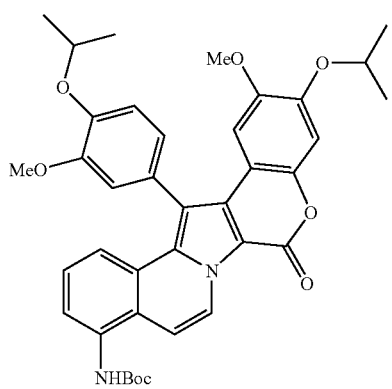

General procedure H (starting from 5-Boc-aminoisoquinoline) and chromatography on silica gel Merck Si60 (230-400 mesh) (CH$_2$Cl$_2$:MeOH:Et$_3$N, 100:1:0.5) to afford 176 as a brown solid (120 mg, 10%).

$^1$H NMR (300 MHz, CDCl$_3$) δ 9.61 (s, 1H), 8.11 (d, J=7.8 Hz, 1H), 7.76 (d, J=8.4 Hz, 1H), 7.59 (t, J=7.7 Hz, 1H), 7.34 (t, J=7.8 Hz, 1H), 7.17 (d, J=8.0 Hz, 1H), 7.12-7.05 (m, 2H), 6.96 (s, 1H), 6.64 (s, 1H), 4.70 (hp, J=6.0 Hz, 1H), 4.57 (hp, J=6.0 Hz, 1H), 3.83 (s, 3H), 3.44 (s, 3H), 1.51 (d, J=6.2 Hz, 3H), 1.44 (d, J=6.0 Hz, 3H), 1.40 (d, J=7.8 Hz, 6H). MS (ESI) m/z: 653 (M+1)$^+$. Rf: 0.33 (CH$_2$Cl$_2$:MeOH, 100:1).

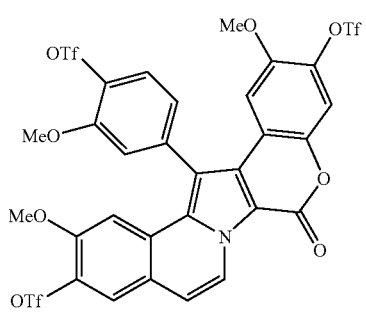

Compound 177

General procedure I (starting from 3) and chromatography on silica gel (CH$_2$Cl$_2$) and triturated with Et$_2$O (50 mL) to afford 177 as a white solid (434.7 mg, 82%).

$^1$H NMR (300 MHz, CDCl$_3$) δ 9.31 (d, J=7.3 Hz, 1H), 7.62 (s, 1H), 7.57 (d, J=8.5 Hz, 1H), 7.35-7.32 (m, 3H), 7.16 (d, J=7.6 Hz, 1H), 7.14 (s, 1H), 6.74 (s, 1H), 3.97 (s, 3H), 3.50 (s, 6H). $^{13}$C NMR (75 MHz, CDCl$_3$) δ 154.3, 152.9, 150.9, 148.1, 145.0, 139.4, 139.0, 138.1, 136.7, 132.7, 127.3, 124.9, 124.0, 123.8, 123.7, 121.0, 120.8, 117.5, 116.5, 115.8, 113.2, 112.3, 109.9, 106.8, 106.4, 56.8, 55.9, 55.7. MS (ESI) m/z: 896 (M+1)$^+$. Rf: 0.32 (hexane:EtOAc, 6:1).

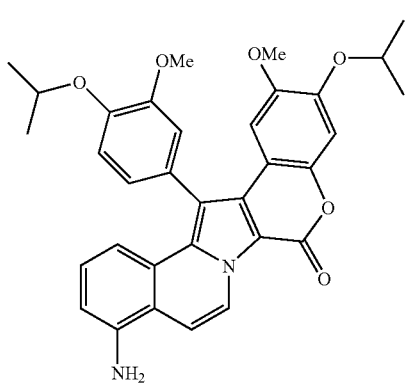

Compound 178

AlCl$_3$ (12 mg, 0.092 mmol) was added to a solution of 176 (20 mg, 0.030 mmol) in anhydrous CH$_2$Cl$_2$ (2 mL) under Argon atmosphere. The reaction mixture was stirred for 2.5 hours at 23° C. The mixture was quenched with H$_2$O (10 mL, pH=4-5), extracted with CH$_2$Cl$_2$ (3×10 mL), dried over anhydrous Na$_2$SO$_4$ and evaporated under reduced pressure. The resulted residue was subjected to flash chromatography on silica gel Merck Si60 (230-400 mesh) (CH$_2$Cl$_2$:MeOH, 30:1) to provide 178 as a white solid (7 mg, 42%).

$^1$H NMR (300 MHz, CDCl$_3$) δ 9.28 (d, J=7.7 Hz, 1H), 7.25-7.05 (m, 6H), 6.97 (s, 1H), 6.82 (d, J=7.7 Hz, 1H), 6.65 (s, 1H), 4.69 (hp, J=6.2 Hz, 1H), 4.57 (hp, J=6.2 Hz, 1H), 4.12 (bs, 2H), 3.82 (s, 3H), 3.43 (s, 3H), 1.49 (d, J=5.9 Hz, 3H), 1.43 (d, J=5.9 Hz, 3H), 1.40 (d, J=6.2 Hz, 6H). MS (ESI) m/z: 553 (M+1)$^+$. Rf: 0.55 (CH$_2$Cl$_2$:MeOH, 30:1).

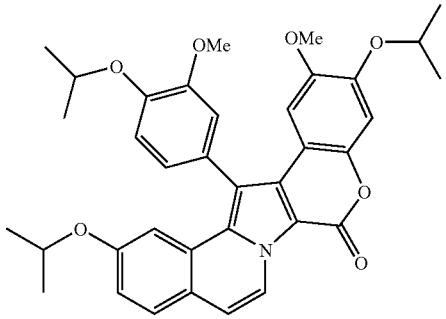

Compound 179

General procedure H (starting from 7-isopropylisoquinoline) and chromatography on reverse silica gel RP-18 (CH$_3$CN:H$_2$O, 4:1 then CH$_3$CN) to afford 179 as a yellow oil (6 mg, 2%).

$^1$H NMR (300 MHz, CDCl$_3$) δ 9.20 (d, J=7.3 Hz, 1H), 7.61 (d, J=7.3 Hz, 1H), 7.17-7.05 (m, 6H), 6.98 (s, 1H), 6.70 (s, 1H), 4.65-4.58 (m, 2H), 4.1-3.95 (m, 1H), 3.83 (s, 3H), 3.44 (s, 3H), 1.47 (d, J=6.1 Hz, 6H), 1.40 (d, J=6.1 Hz, 6H), 1.17-1.12 (m, 6H). MS (ESI) m/z: 596 (M+1)$^+$. Rf: 0.31 (CH$_3$CN, RP-18).

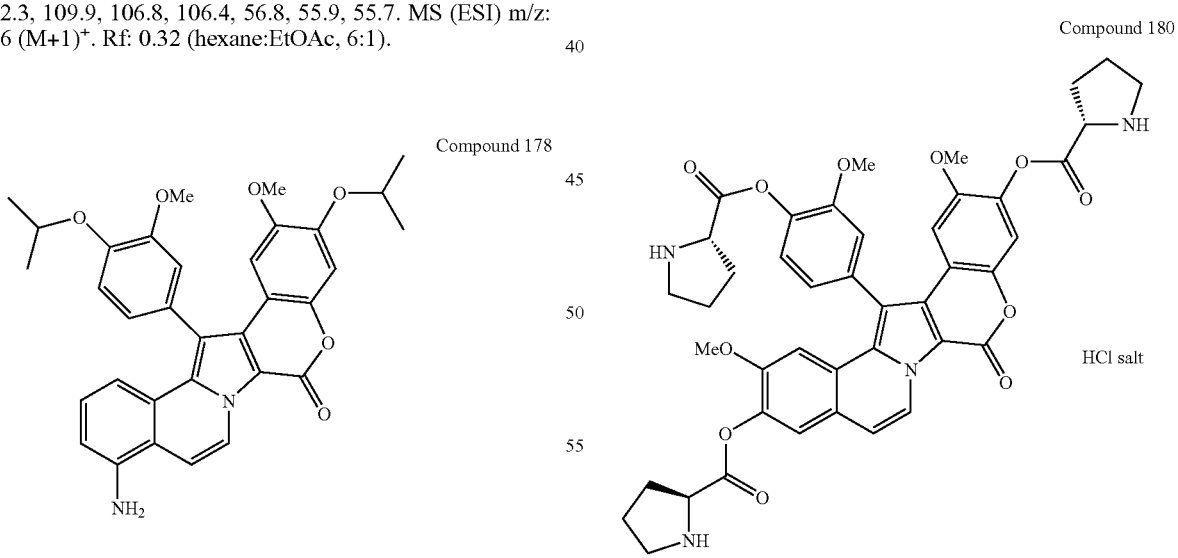

Compound 180

General procedure C (starting from 127) to afford 180 as a pale yellow solid (156 mg, 88%).

$^1$H NMR (300 MHz, CD$_3$OD) δ 9.17 (dd, J=7.6, 2.6 Hz, 1H), 7.69 (d, J=2.7 Hz, 1H), 7.65-7.55 (m, 2H), 7.50-7.20 (m, 4H), 6.90 (d, J=10.6 Hz, 1H), 4.80-4.60 (m, 3H), 3.92 (s, 3H), 3.91 (s, 3H), 3.60-3.40 (m, 12H), 2.70-2.30 (m, 6H), 2.30-10 (m, 6H). MS (ESI) m/z: 791 (M+1)$^+$.

Compound 181

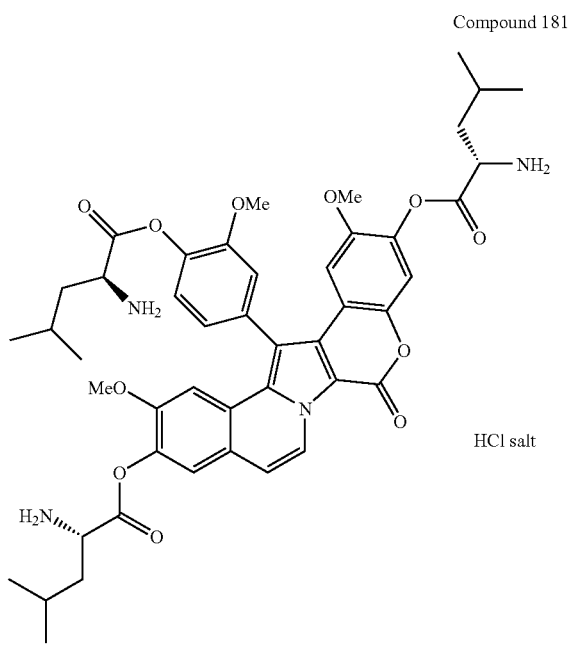

HCl salt

General procedure C (starting from 146) to afford 181 as a white solid (390 mg, 84%).

¹H NMR (300 MHz, CD₃OD) δ 9.26 (d, J=7.5 Hz, 1H), 7.69 (s, 1H), 7.60-7.50 (m, 2H), 7.45-7.30 (m, 4H), 6.92 (d, J=6.6 Hz, 1H), 4.50-4.30 (m, 3H), 3.88 (s, 3H), 3.48 (s, 6H), 2.20-1.70 (m, 6H), 1.20-1.00 (m, 18H). MS (ESI) m/z: 840 (M+1)⁺.

Compound 182

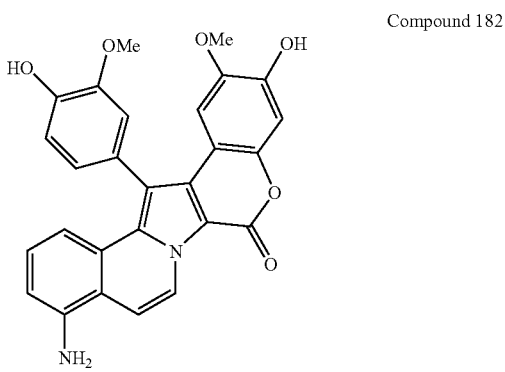

General procedure A (starting from 178) and chromatography on silica gel Merck Si60 (230-400 mesh) (CH₂Cl₂:MeOH, 30:1) to afford 182 as a white solid (3.8 mg, 76%).

¹H NMR (300 MHz, CD₃OD) δ 9.15 (d, J=7.7 Hz, 1H), 7.20-7.15 (m, 2H), 7.10-6.95 (m, 4H), 6.89 (s, 1H), 6.82 (d, J=7.7 Hz, 1H), 6.57 (s, 1H), 3.81 (s, 3H), 3.44 (s, 3H). MS (ESI) m/z: 469 (M+1)⁺. Rf: 0.12 (CH₂Cl₂:MeOH, 40:1).

Compound 183

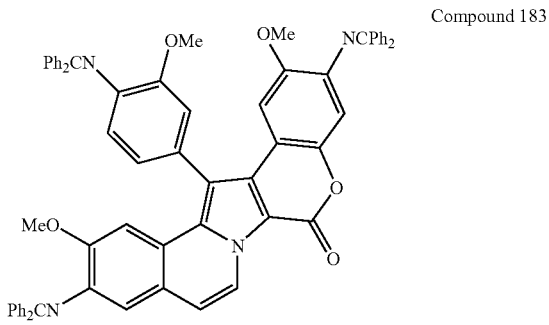

A suspension of 177 (0.33 g, 0.37 mmol), Pd(OAc)₂ (12.5 mg, 0.055 mmol), BINAP (69.2 mg, 0.111 mmol) in anhydrous toluene (5 mL) was stirred at 23° C. under Argon atmosphere for 5 min. Then benzophenone imine (218 mL, 1.30 mmol) was added and the mixture was stirred at 110° C. for 7 days. The reaction was cool down to 23° C., H₂O (20 mL) was added, was extracted with CH₂Cl₂ (3×20 mL), dried over anhydrous Na₂SO₄, filtered and evaporated to dryness. The residue was purified by chromatography on silica gel (hexane:EtOAc, 2:1) to give 183 (29.0 mg, 8%) as a yellow solid.

¹H NMR (300 MHz, CDCl₃) δ 9.11 (d, J=7.5 Hz, 1H), 7.78-7.70 (m, 4H), 7.48-7.13 (m, 26H), 7.07-6.97 (m, 3H), 6.86-6.80 (m, 3H), 6.67 (s, 1H), 6.64 (s, 1H), 3.69 (s, 3H), 3.28 (s, 3H), 3.26 (s, 3H). ¹³C NMR (75 MHz, CDCl₃) δ 170.4, 169.3, 155.5, 150.3, 150.0, 146.4, 146.0, 142.8, 141.9, 140.9, 139.4, 139.0, 137.0, 136.4, 134.2, 131.1, 130.9, 129.6, 129.4, 128.8, 128.6, 128.5, 128.2, 127.9, 127.9 (4C), 124.1, 123.8, 122.7, 121.7, 121.1, 117.5, 114.4, 113.1, 112.6, 111.9, 109.2, 105.4, 105.2, 55.7, 55.6, 55.3. MS (ESI) m/z: 989 (M+1)⁺. Rf: 0.50 (Hex:EtOAc, 2:1).

Compound 184

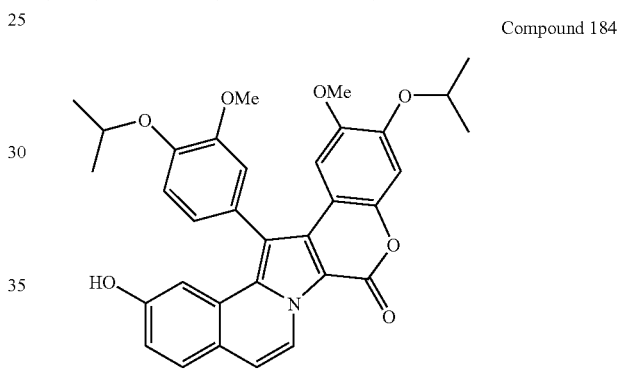

General procedure G (starting from 7-hydroxy-isoquinoline) and chromatography on silica gel (CH₂Cl₂:EtOAc, 200:1) to afford 184 as a white solid (112.5 mg, 9%).

¹H NMR (300 MHz, (CD₃)₂SO) δ 10.0 (br s, 1H), 8.84 (d, J=7.0 Hz, 1H), 7.61 (d, J=8.8 Hz, 1H), 7.09-7.01 (m, 3H), 6.71 (s, 2H), 6.6 (s, 1H), 6.5 (s, 1H), 4.64 (m, 1H), 4.42 (m, 1H), 3.33 (s, 3H), 3.31 (s, 3H), 1.27 (d, J=5.7 Hz, 6H), 1.13 (d, J=5.7 Hz, 6H). ¹³C NMR (75 MHz, (CD₃)₂SO) δ 158.9, 157.0, 155.4, 149.2, 147.6, 147.2, 147.1, 145.7, 133.8, 128.6, 124.5, 121.5, 121.3, 118.6, 114.6, 114.5, 113.9, 110.8, 110.0, 108.3, 106.9, 101.5, 92.8, 83.8, 70.5, 70.1, 55.9, 54.9, 54.8, 21.7 (2C). MS (ESI) m/z: 575 (M+1)⁺. Rf: 0.23 (CH₂Cl₂:EtOAc, 200:1).

Compound 185

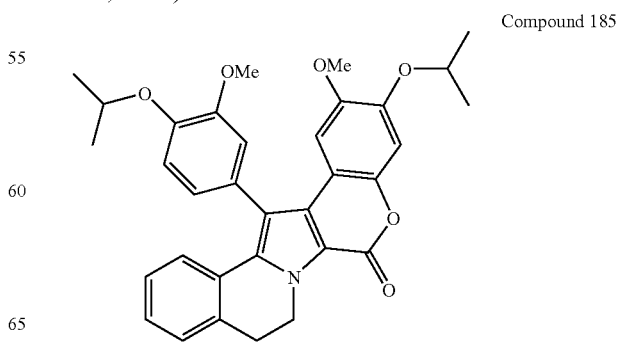

General procedure H (starting from 3,4-dihydroisoquinoline) and chromatography on silica gel (CH$_2$Cl$_2$ and then hexane:EtOAc, 2:1) to afford 185 as a pale yellow solid (243 mg, 21%).

$^1$H NMR (300 MHz, CDCl$_3$) δ 7.28-7.00 (m, 7H), 6.91 (s, 1H), 6.63 (s, 1H), 4.80-4.78 (m, 2H), 4.64 (sep, J=6.0 Hz, 1H), 4.53 (sep, J=6.0 Hz, 1H), 3.81 (s, 3H), 3.42 (s, 3H), 317 (t, J=6.5 Hz, 2H), 1.39-1.37 (m, 12H). MS (ESI) m/z: 541 (M+1)$^+$. Rf: 0.50 (hexane:EtOAc, 2:1).

Compound 186

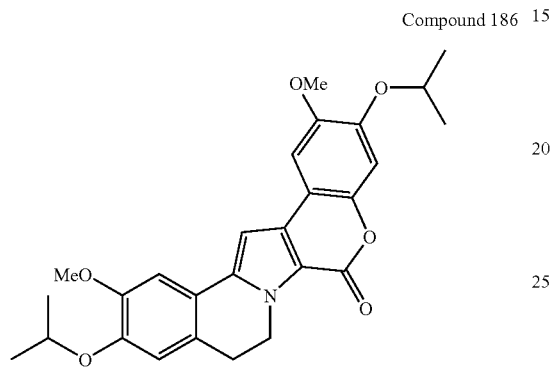

General procedure H (starting from 6-isopropoxy-7-methoxy-3,4-dihydroisoquinoline) and chromatography on silica gel Merck Si60 (230-400 mesh) (CH$_2$Cl$_2$:MeOH, from 100:1 to 20:1) to afford 186 as a brown solid (861 mg, 29%).

$^1$H NMR (300 MHz, CDCl$_3$) δ 7.17 (s, 1H), 7.15 (s, 1H), 6.90 (s, 1H), 6.78 (s, 1H), 6.77 (s, 1H), 4.68 (t, J=6.7 Hz, 2H), 4.62-4.50 (m, 2H), 3.94 (s, 3H), 3.93 (s, 3H), 3.06 (t, J=6.7 Hz, 2H), 1.40 (d, J=6.0 Hz, 12H). $^{13}$C NMR (75 MHz, CDCl$_3$) δ 155.4, 149.6, 148.1, 147.6, 147.2, 145.9, 140.1, 131.1, 125.6, 120.0, 115.0, 114.9, 110.0, 108.1, 104.6, 103.6, 95.3, 71.5, 56.4, 56.2, 42.2, 28.2, 22.0, 21.8. MS (ESI) m/z: 464 (M+1)$^+$. Rf: 0.44 (hexane:AcOEt, 1:1).

Compound 187

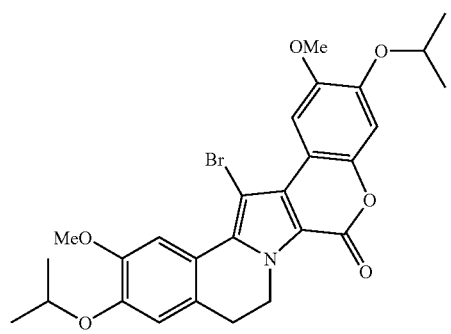

N-Bromosuccinimide (21 mg, 0.12 mmol) was added in one portion to a solution of 186 (50 mg, 0.10 mmol) in AcOEt (1 mL) under Argon atmosphere. The solution was stirred at 23° C. for 15 minutes, then diluted with AcOEt, quenched with H$_2$O and washed succesively with HCl 0.1N (2×10 mL) and NaOH 0.1N (2×10 mL).

After drying over Na$_2$SO$_4$, the solvent was evaporated under vacuum to afford 187 as a brown solid (56 mg, 96%).

$^1$H NMR (300 MHz, CDCl$_3$) δ 8.19 (s, 1H), 8.12 (s, 1H), 6.89 (s, 1H), 6.81 (s, 1H), 4.73 (t, J=6.2 Hz, 2H), 4.65-4.50 (m, 2H), 3.94 (s, 3H), 3.93 (s, 3H), 3.02 (t, J=6.5 Hz, 2H), 1.41 (d, J=6.0 Hz, 6H), 1.40 (d, J=6.0 Hz, 6H). $^{13}$C NMR (75 MHz, CDCl$_3$) δ 154.7, 148.8, 148.0, 147.6, 146.5, 145.9, 135.2, 127.3, 127.0, 119.2, 114.6, 114.0, 109.6, 109.5, 104.7, 103.2, 86.5, 71.4, 56.3, 56.2, 42.5, 28.8, 22.0, 21.8. MS (ESI) m/z: 564 (M+23)$^+$. Rf: 0.58 (hexane:AcOEt, 1:1).

Compound 188

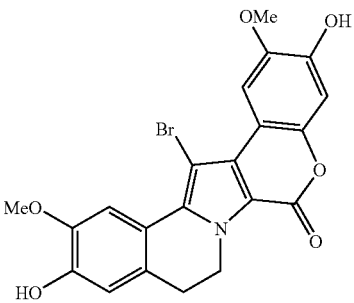

General procedure A (starting from 187) and chromatography on silica gel Merck Si60 (230-400 mesh) (CH$_2$Cl$_2$:MeOH, from 100:1 to 40:1) to afford 188 as a brown solid (15 mg, 40%).

$^1$H NMR (300 MHz, CDCl$_3$) δ 8.23 (s, 1H), 8.11 (s, 1H), 6.87 (s, 1H), 6.79 (s, 1H), 4.67 (t, J=6.6 Hz, 2H), 3.96 (s, 3H), 3.94 (s, 3H), 2.97 (t, J=6.6 Hz, 2H). MS (ESI) m/z: 458 (M+1)$^+$. Rf: 0.14 (CH$_2$Cl$_2$:MeOH, 50:1).

Compound 189

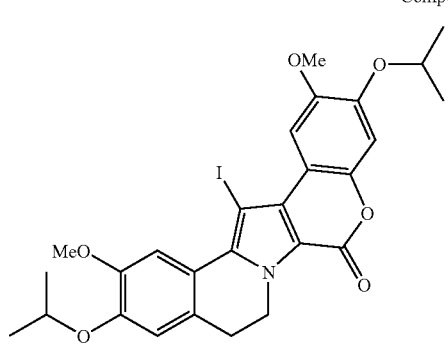

N-Iodosuccinimide (77 mg, 0.32 mmol) was added in one portion to a solution of 186 (100 mg, 0.21 mmol) in CH$_2$Cl$_2$ (4 mL) under Argon atmosphere. The solution was stirred at 23° C. for 30 minutes, then diluted with AcOEt, quenched with H$_2$O and washed succesively with NaOH 0.1N (2×10 mL) and H$_2$O (2×10 mL).

After drying over Na$_2$SO$_4$, the solvent was evaporated under vacuum to afford 189 as a brown solid (120 mg, 95%).

$^1$H NMR (300 MHz, CDCl$_3$) δ 8.48 (s, 1H), 8.25 (s, 1H), 6.87 (s, 1H), 6.81 (s, 1H), 4.74 (t, J=6.2 Hz, 2H), 4.65-4.50 (m, 2H), 3.97 (s, 3H), 3.94 (s, 3H), 2.99 (t, J=6.4 Hz, 2H), 1.41 (d, J=6.0 Hz, 6H), 1.40 (d, J=6.0 Hz, 6H). $^{13}$C NMR (75 MHz, CDCl$_3$) δ 154.5, 148.4, 148.0, 147.5, 145.9, 137.5, 129.4, 127.7, 119.5, 115.7, 114.6, 110.0, 103.7, 103.2, 71.3, 56.3, 42.5, 29.0, 22.0, 21.8. MS (ESI) m/z: 590 (M+1)$^+$. Rf: 0.49 (hexane:AcOEt, 1:1).

Compound 190

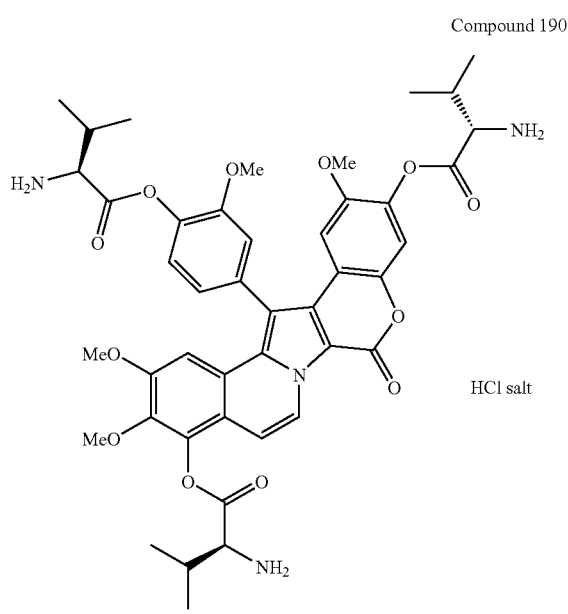

HCl salt

Compound 191

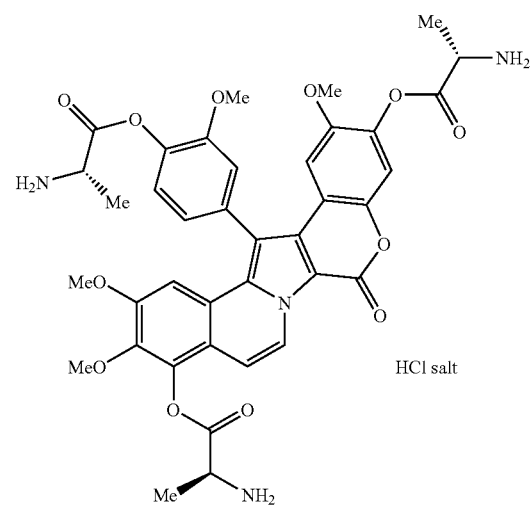

HCl salt

General procedure C (starting from 97) to afford 191 as a white solid (1.15 g, 94%).

$^1$H NMR (300 MHz, CD$_3$OD) δ 9.16 (d, J=7.7 Hz, 1H), 7.60-7.50 (m, 2H), 7.40-7.25 (m, 3H), 7.22 (d, J=7.4 Hz, 1H), 6.88 (d, J=9.1 Hz, 1H), 4.70-4.60 (m, 1H), 4.60-4.50 (m, 1H), 4.50-4.35 (m, 1H), 3.91 (s, 3H), 3.90 (s, 3H), 3.54 (d, J=2.1 Hz, 3H), 3.48 (d, J=2.1 Hz, 3H), 1.90-1.70 (m, 9H). MS (ESI) m/z: 743 (M+1)$^+$.

Compound 192

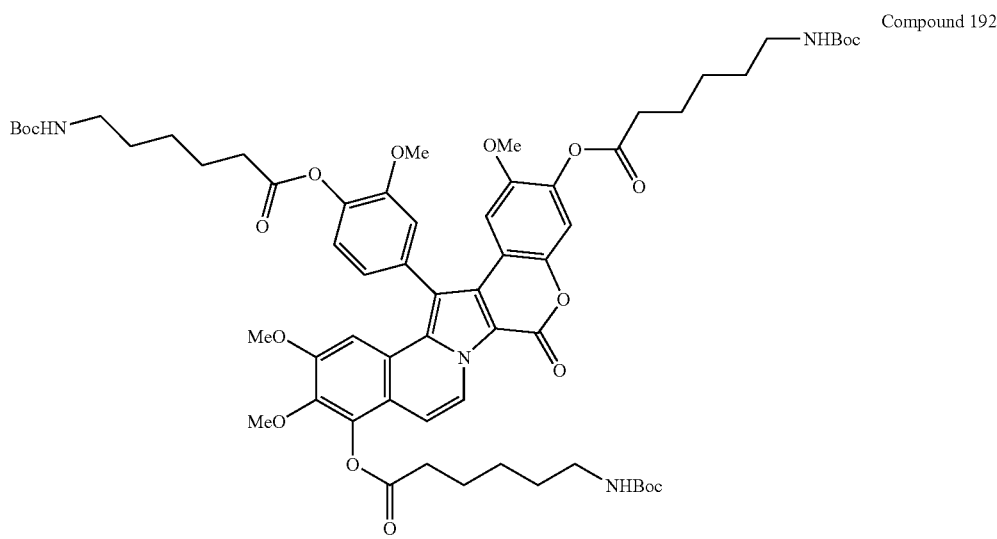

General procedure C (starting from 129) to afford 190 as a white solid (197 mg, 80%).

$^1$H NMR (300 MHz, CD$_3$OD) δ 9.23 (d, J=7.5 Hz, 1H), 7.60-7.50 (m, 2H), 7.45-7.30 (m, 3H), 7.24 (d, J=7.4 Hz, 1H), 6.92 (d, J=10.4 Hz, 1H), 4.60 (d, J=3.7 Hz, 1H), 4.36 (d, J=4.3 Hz, 1H), 4.27 (d, J=4.3 Hz, 1H), 3.90 (d, J=1.2 Hz, 3H), 3.89 (d, J=2.4 Hz, 3H), 3.54 (d, J=3.8 Hz, 3H), 3.48 (d, J=3.5 Hz, 3H), 2.70-2.40 (m, 3H), 1.35-1.15 (m, 18H). MS (ESI) m/z: 827 (M+1)$^+$.

General procedure D (starting from 2 and 6-(BOC-amino) caproic acid) and chromatography on silica gel (hexane:EtOAc, 50:50) to afford 192 as a white solid (2.02 g, 92%).

$^1$H NMR (300 MHz, CDCl$_3$) δ 9.17 (d, J=7.5 Hz, 1H), 7.30-7.20 (m, 3H), 7.09 (s, 1H), 7.08 (s, 1H), 7.02 (d, J=7.5 Hz, 1H), 6.78 (s, 1H), 4.61 (bs, 3H), 3.85 (s, 3H), 3.82 (s, 3H), 3.48 (s, 3H), 3.43 (s, 3H), 3.20-3.10 (m, 6H), 2.74 (t, J=7.3 Hz, 2H), 2.63 (t, J=7.3 Hz, 2H), 2.56 (t, J=7.3 Hz, 2H), 1.90-1.70 (m, 6H), 1.60-1.40 (m, 39H). $^{13}$C NMR (75 MHz, CDCl$_3$) δ 171.4, 171.3, 171.2, 155.9, 154.9, 153.2, 152.4, 147.7, 145.4, 141.7, 140.3, 139.8, 139.0, 134.1, 133.2, 128.3, 124.0, 123.5, 123.3, 120.9, 118.2, 115.5, 115.0, 112.1, 108.8, 106.5, 106.1, 104.0, 79.0, 60.7, 56.2, 55.7, 55.6, 40.3, 33.8, 33.7, 29.7, 28.4, 26.2, 26.0, 24.7, 24.5, 24.4. MS (ESI) m/z: 1191 (M+23)$^+$. Rf: 0.19 (hexane:AcOEt, 1:1).

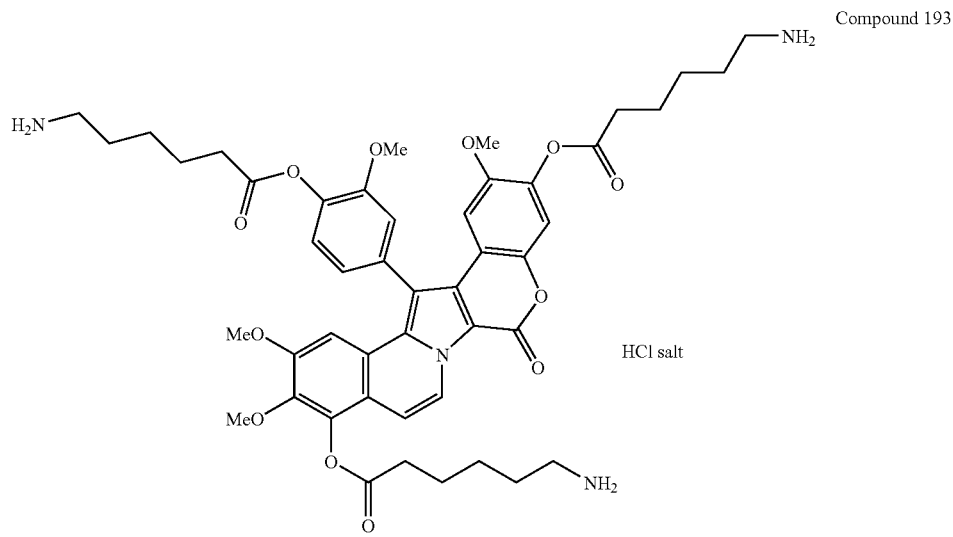

Compound 193
HCl salt

General procedure C (starting from 192) to afford 193 as a white solid (1.45 g, 90%).

$^1$H NMR (300 MHz, CD$_3$OD) δ 9.08 (d, J=8.5 Hz, 1H), 7.44 (d, J=1.7 Hz, 1H), 7.39 (d, J=8.0 Hz, 1H), 7.26 (dd, J=8.1, 1.7 Hz, 1H), 7.20-7.10 (m, 3H), 6.85 (s, 1H), 3.86 (s, 3H), 3.84 (s, 6H), 3.50 (s, 3H), 3.44 (s, 3H), 3.05-2.90 (m, 6H), 2.83 (t, J=7.3 Hz, 2H), 2.71 (t, J=7.3 Hz, 2H), 2.61 (t, J=7.3 Hz, 2H), 1.90-1.50 (m, 18H). MS (ESI) m/z: 869 (M+1)$^+$.

Compound 194

General procedure G (starting from 7-Hydroxy-8-bromo-isoquinoline) and chromatography on silica gel (CH$_2$Cl$_2$:EtOAc, 10:1) to afford 194 as a pale yellow solid (9 mg, 2%).

$^1$H NMR (300 MHz, CDCl$_3$) δ 9.21 (d, J=6.7 Hz, 1H), 7.63 (d, J=6.7 Hz, 1H), 7.18-7.05 (m, 5H), 6.96 (s, 1H), 6.62 (s, 1H), 4.72-4.55 (m, 2H), 3.84 (s, 3H), 3.44 (s, 3H), 1.5-1.40 (m, 12H). Rf: 0.51 (CH$_2$Cl$_2$:EtOAc, 10:1).

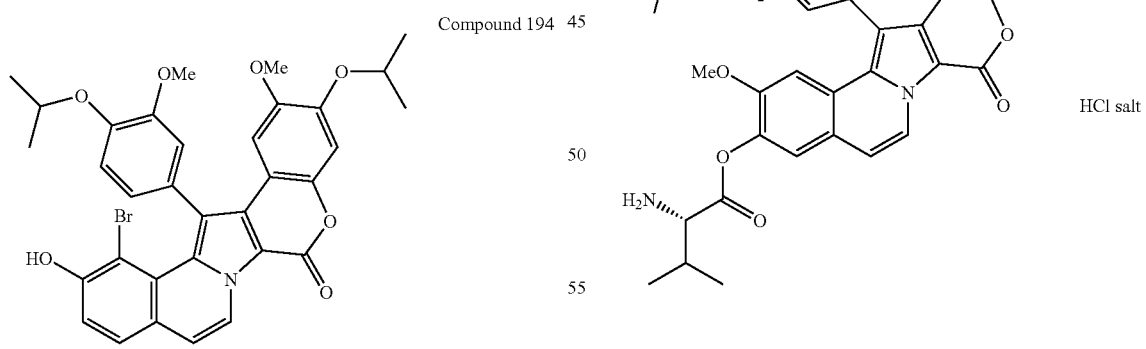

Compound 195
HCl salt

General procedure C (starting from 38) to afford 195 as a pale yellow solid (654 mg, 83%).

$^1$H NMR (300 MHz, CD$_3$OD) δ 9.20-9.15 (m, 1H), 7.67 (s, 1H), 7.65-7.55 (m, 2H), 7.50-7.20 (m, 4H), 6.91 (d, J=8.4 Hz, 1H), 4.40-4.25 (m, 3H), 3.91 (d, J=3.8 Hz, 3H), 3.49 (s, 6H), 2.70-2.40 (m, 3H), 1.40-1.20 (m, 18H). MS (ESI) m/z: 797 (M+1)$^+$.

Compound 196

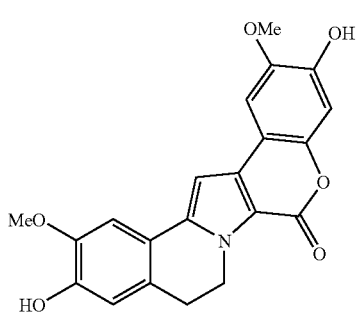

General procedure A (starting from 186) and chromatography on silica gel Merck Si60 (230-400 mesh) (CH$_2$Cl$_2$:MeOH, 40:1) to afford 196 as a brown solid (25 mg, 62%).
$^1$H NMR (300 MHz, CDCl$_3$) δ 7.17 (s, 2H), 7.00 (s, 1H), 6.86 (s, 1H), 6.76 (s, 1H), 5.83 (bs, 1H), 5.78 (bs, 1H), 4.70 (t, J=6.4 Hz, 2H), 4.01 (s, 3H), 3.99 (s, 3H), 3.07 (t, J=6.7 Hz, 2H). $^{13}$C NMR (75 MHz, CDCl$_3$) δ 156.7, 147.9, 147.6, 146.6, 145.9, 141.7, 132.7, 132.6, 126.9, 119.4, 115.5, 114.7, 110.1, 108.3, 104.8, 104.2, 95.6, 56.6, 56.4, 42.7, 28.4. MS (ESI) m/z: 380 (M+1)$^+$. Rf: 0.22 (CH$_2$Cl$_2$:MeOH, 40:1).

Compound 197

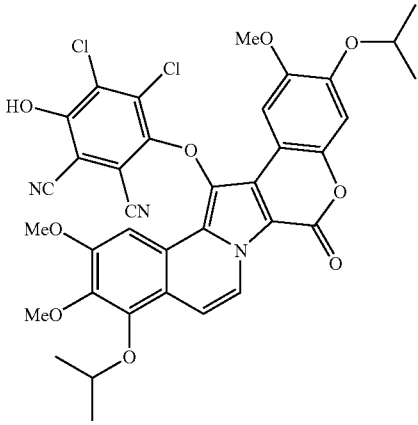

General procedure E (starting from 186 and 16 h of reaction time) and chromatography on silica gel Merck Si60 (230-400 mesh) (CH$_2$Cl$_2$:MeOH from 50:1 to 10:1) to afford 197 as a beige solid (52 mg, 66%).
$^1$H NMR (300 MHz, CD$_3$OD) δ 8.77 (d, J=7.7 Hz, 1H), 7.28 (d, J=7.3 Hz, 1H), 7.20 (s, 1H), 6.81 (s, 1H), 6.63 (s, 1H), 4.75-4.55 (m, 2H), 3.96 (s, 3H), 3.70 (s, 3H), 3.49 (s, 3H), 1.50-1.40 (m, 6H), 1.35-1.25 (m, 6H). $^{13}$C NMR (75 MHz, CD$_3$OD+CDCl$_3$) δ 155.3, 154.0, 151.7, 148.3, 147.0, 146.4, 146.2, 143.7, 142.9, 133.1, 129.3, 129.2, 129.0, 126.8, 122.9, 121.8, 120.4, 119.3, 116.3, 114.0, 111.4, 108.3, 107.1, 104.9, 104.6, 103.1, 100.0, 99.7, 97.9, 76.4, 71.5, 60.5, 55.4, 22.4, 21.5, 21.3. MS (ESI) m/z: 740 (M+23)$^+$, 718 (M+1)$^+$. Rf: 0.14 (CH$_2$Cl$_2$:MeOH, 10:1).

Compound 198

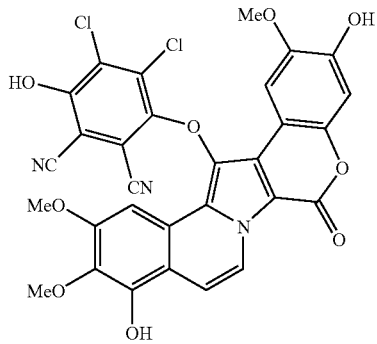

General procedure A (starting from 197) and chromatography on silica gel Merck Si60 (230-400 mesh) (CH$_2$Cl$_2$:MeOH, 5:1) to afford 198 as a brown solid (15 mg, 42%).
$^1$H NMR (300 MHz, CD$_3$OD) δ 8.81 (d, J=7.5 Hz, 1H), 7.31 (d, J=7.5 Hz, 1H), 6.98 (s, 1H), 6.72 (s, 1H), 6.70 (s, 1H), 3.88 (s, 3H), 3.69 (s, 3H), 3.60 (s, 3H). MS (ESI) m/z: 634 (M+1)$^+$. Rf: 0.22 (CH$_2$Cl$_2$:MeOH, 5:1).

Compound 199

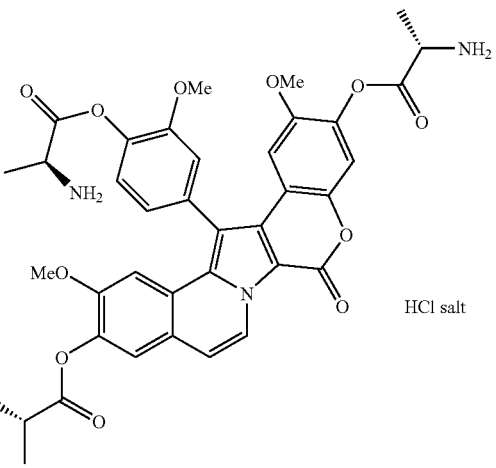

HCl salt

General procedure C (starting from 41) to afford 199 as a pale yellow solid (537 mg, 80%).
$^1$H NMR (300 MHz, CD$_3$OD) δ 9.18 (d, J=7.5 Hz, 1H), 7.67 (s, 1H), 7.60-7.50 (m, 2H), 7.45-7.35 (m, 1H), 7.35-7.25 (m, 3H), 6.91 (d, J=8.0 Hz, 1H), 4.60-4.40 (m, 3H), 3.90 (d, J=2.5 Hz, 3H), 3.49 (s, 3H), 3.48 (s, 3H), 1.85-1.60 (m, 9H). MS (ESI) m/z: 713 (M+1)$^+$.

Compound 200

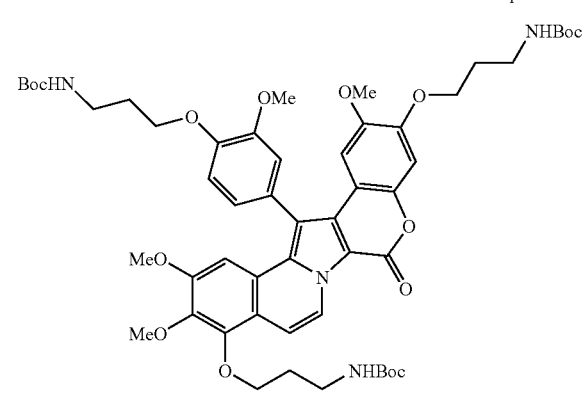

A suspension of 2 (100 mg, 0.18 mmol), Cs$_2$CO$_3$ (246 mg, 0.75 mmol) in anhydrous DMF (2 mL) was stirred at 23° C. under Argon atmosphere for 10 minutes, then 3-(BOC-amino)propyl bromide (180 mg, 0.75 mmol) was added and the mixture was heated at 50° C. overnight. The resulting solution was cooled to 23° C., quenched with H$_2$O, diluted with EtOAc (50 mL) and washed with H$_2$O (2×20 mL).

The combined organic layers were dried over anhydrous Na$_2$SO$_4$, filtered, and the solvent removed under vaccum. The residue was purified by chromatography on silica gel (CH$_2$Cl$_2$:MeOH, 30:1) to afford 200 as a white solid (180 mg, 95%).
$^1$H NMR (300 MHz, CDCl$_3$) δ 9.21 (d, J=7.7 Hz, 1H), 7.36 (d, J=7.7 Hz, 1H), 7.20-7.10 (m, 3H), 6.97 (s, 1H), 6.93 (s, 1H), 6.70 (s, 1H), 5.50-5.40 (m, 2H), 4.97 (bs, 1H), 4.18 (t, J=6.4 Hz, 4H), 4.12 (t, J=5.8 Hz, 2H), 3.91 (s, 3H), 3.87 (s, 3H), 3.47 (s, 3H), 3.44 (s, 3H), 3.44-3.10 (m, 6H), 2.15-2.00 (m, 6H), 1.48 (s, 9H), 1.45 (s, 9H), 1.44 (s, 9H). MS (ESI) m/z: 1023 (M+1)$^+$. Rf: 0.15 (hexane:AcOEt, 1:1).

Compound 201

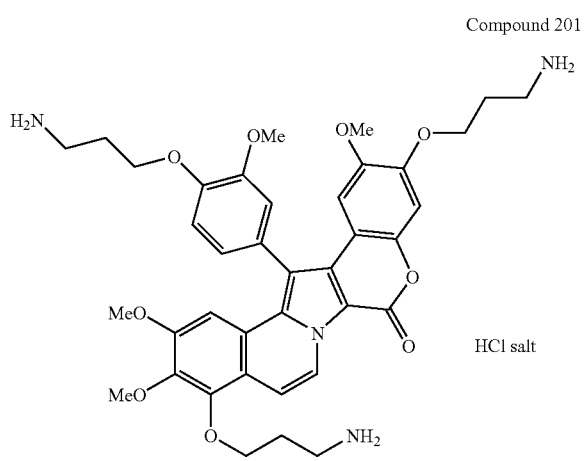

HCl salt

General procedure C (starting from 200) to afford 201 as a white solid (110 mg, 85%).

$^1$H NMR (300 MHz, CD$_3$OD) δ 9.18 (d, J=7.5 Hz, 1H), 7.47 (d, J=7.5 Hz, 1H), 7.37 (d, J=8.0 Hz, 1H), 7.28 (d, J=1.8 Hz, 1H), 7.23 (dd, J=8.0, 1.8 Hz, 1H), 7.10 (s, 1H), 7.07 (s, 1H), 6.80 (s, 1H), 4.28 (t, J=5.7 Hz, 4H), 4.21 (t, J=5.5 Hz, 2H), 3.91 (s, 3H), 3.88 (s, 6H), 3.47 (s, 3H), 3.46 (s, 3H), 3.30-2.25 (m, 4H), 3.19 (t, J=7.0 Hz, 2H), 2.30-2.15 (m, 6H). MS (ESI) m/z: 701 (M+1)$^+$.

Compound 202

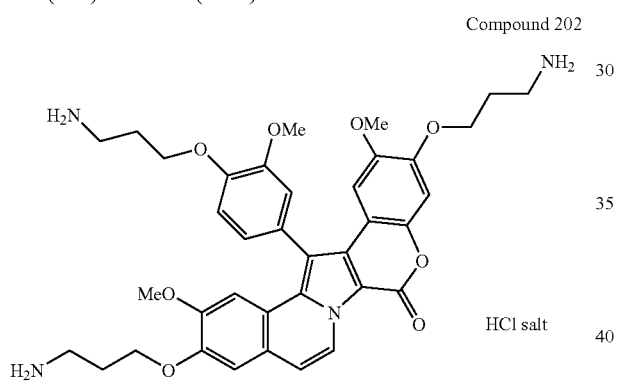

HCl salt

General procedure C (starting from 203) to afford 202 as a pink solid (80 mg, 80%).

$^1$H NMR (300 MHz, CD$_3$OD) δ 9.02 (d, J=7.3 Hz, 1H), 7.40-7.30 (m, 3H), 7.30-7.15 (m, 3H), 6.96 (s, 1H), 6.77 (s, 1H), 4.27 (t, J=5.7 Hz, 4H), 4.35-4-15 (m, 2H), 3.90 (s, 3H), 3.47 (s, 3H), 3.46 (s, 3H), 3.40-3.20 (m, 6H), 2.20-2.10 (m, 6H), 1.58 (s, 9H), 1.48 (s, 9H), 1.44 (s, 9H). MS (ESI) m/z: 671 (M+1)$^+$.

Compound 203

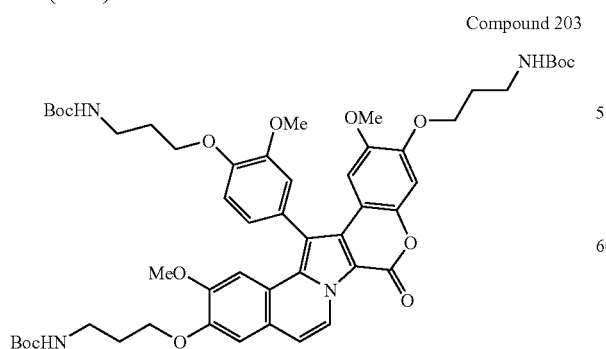

A suspension of 3 (100 mg, 0.20 mmol), Cs$_2$CO$_3$ (293 mg, 0.90 mmol) in anhydrous DMF (2 mL) was stirred at 23° C. under argon atmosphere for 30 minutes, then 3-(BOC-amino) propyl bromide (214 mg, 0.90 mmol) was added and the mixture was heated at 40° C. for 4 hours. The resulting solution was cooled to 23° C., quenched with H$_2$O, diluted with EtOAc (50 mL) and washed with H$_2$O (2×20 mL).

The combined organic layers were dried over anhydrous Na$_2$SO$_4$, filtered, and the solvent removed under vaccum. The residue was purified by chromatography on silica gel (CH$_2$Cl$_2$:MeOH, 30:1) to give 203 as a white solid (144 mg, 74%).

$^1$H NMR (300 MHz, CD$_3$OD) δ 9.24 (d, J=7.3 Hz, 1H), 7.25-7.10 (m, 4H), 7.08 (s, 1H), 7.04 (d, J=7.3 Hz, 1H), 6.93 (s, 1H), 6.72 (s, 1H), 5.50-5.40 (m, 3H), 4.30-4.10 (m, 6H), 3.87 (s, 3H), 3.47 (s, 3H), 3.46 (s, 3H), 3.30-2.10 (m, 6H), 2.30-2.15 (m, 6H). MS (ESI) m/z: 971 (M+1)$^+$. Rf: 0.73 (CH$_2$Cl$_2$:MeOH, 30:1).

Compound 204

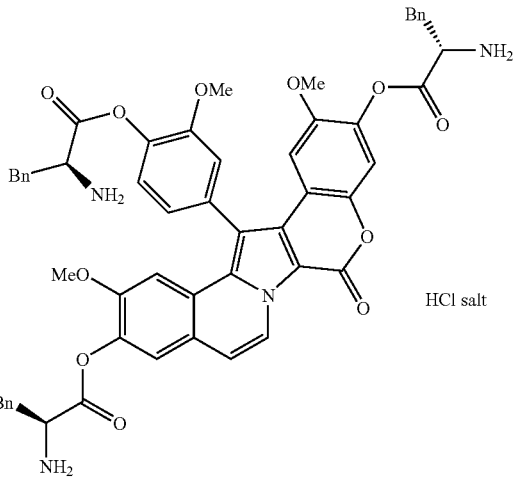

HCl salt

General procedure C (starting from 113) to afford 204 as a pale yellow solid (781 mg, 81%).

$^1$H NMR (300 MHz, CD$_3$OD) δ 9.17 (d, J=7.3 Hz, 1H), 7.60-7.25 (m, 21H), 7.17 (d, J=3.1 Hz, 1H), 6.89 (d, J=3.1 Hz, 1H), 4.80-4.60 (m, 3H), 3.94 (s, 3H), 3.60-3.40 (m, 12H). MS (ESI) m/z: 941 (M+1)$^+$.

Compound 205

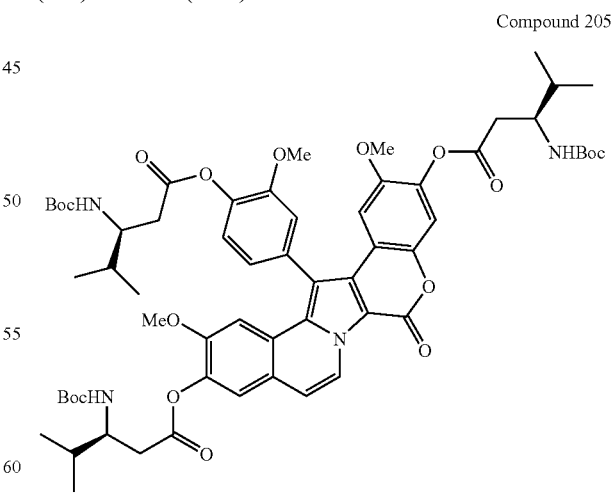

General procedure D (starting from 3 and Boc-L-Leu-OH) and chromatography on silica gel (hexane:EtOAc, 3:2) to afford 205 as a yellow oil (100 mg, 88%).

$^1$H NMR (300 MHz, CDCl$_3$) δ 9.24 (d, J=7.5 Hz, 1H), 7.45 (s, 1H), 7.33 (d, J=8.0 Hz, 1H), 7.25-7.15 (m, 4H), 7.06 (d,

J=7.5 Hz, 1H), 6.79 (d, J=7.1 Hz, 1H), 5.10-4.90 (m, 3H), 4.10-3.90 (m, 3H), 3.82 (s, 3H), 3.44 (s, 6H), 2.90-2.70 (m, 6H), 2.00-1.90 (m, 3H), 1.45 (s, 27H), 1.10-0.90 (m, 18H). MS (ESI) m/z: 1161 (M+23)⁺. Rf: 0.17 (hexane:EtOAc, 2:1).

General procedure C (starting from 120) to afford 207 as a white solid (225 mg, 80%).

¹H NMR (300 MHz, CD₃OD) δ 9.09 (d, J=7.3 Hz, 1H), 7.60-7.30 (m, 18H), 7.20 (s, 1H), 7.13 (s, 1H), 7.12 (s, 1H), 6.87 (d, J=2.9 Hz, 1H), 4.76 (t, J=6.6 Hz, 2H), 4.62 (d, J=6.6 Hz, 1H), 4.00-3.85 (m, 6H), 3.70-3.35 (m, 12H). MS (ESI) m/z: 971 (M+1)⁺.

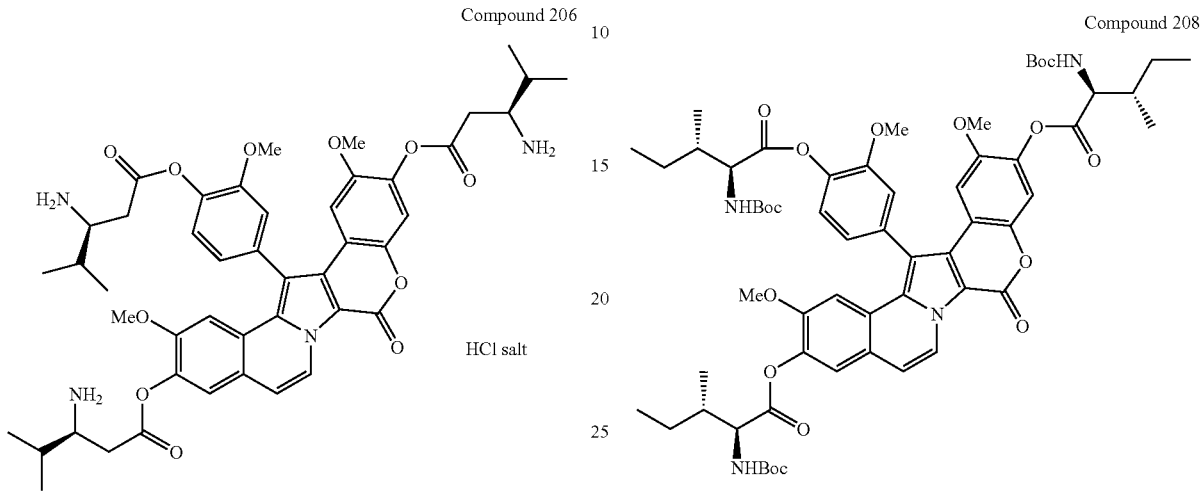

General procedure C (starting from 205) to afford 206 as a white solid (66 mg, 85%).

¹H NMR (300 MHz, CD₃OD) δ 9.23 (d, J=7.7 Hz, 1H), 7.64 (s, 1H), 7.55-7.45 (m, 2H), 7.40-7.30 (m, 4H), 6.91 (s, 1H), 3.87 (s, 3H), 3.70-3.50 (m, 3H), 3.46 (s, 6H), 3.20-2.90 (m, 6H), 2.20-2.05 (m, 3H), 1.20-1.05 (m, 18H). MS (ESI) m/z: 839 (M+1)⁺.

General procedure D (starting from 3 and Boc-L-Ile-OH) and chromatography on silica gel (hexane:EtOAc, 2:1) to afford 208 as a yellow solid (537 mg, 94%).

¹H NMR (300 MHz, CDCl₃) δ 9.26 (d, J=7.5 Hz, 1H), 7.42 (s, 1H), 7.35-7.15 (m, 5H), 7.09 (d, J=7.5 Hz, 1H), 6.79 (d, J=7.0 Hz, 1H), 5.10-5.05 (m, 3H), 4.60-4.55 (m, 3H), 3.79 (s, 3H), 3.43 (s, 6H), 2.20-2.05 (m, 3H), 1.70-1.60 (m, 3H), 1.49 (s, 9H), 1.47 (s, 9H), 1.45 (s, 9H), 1.40-1.20 (s, 6H), 1.15-0.90 (m, 18H). MS (ESI) m/z: 1162 (M+23)⁺. Rf: 0.45 (hexane:EtOAc, 2:1).

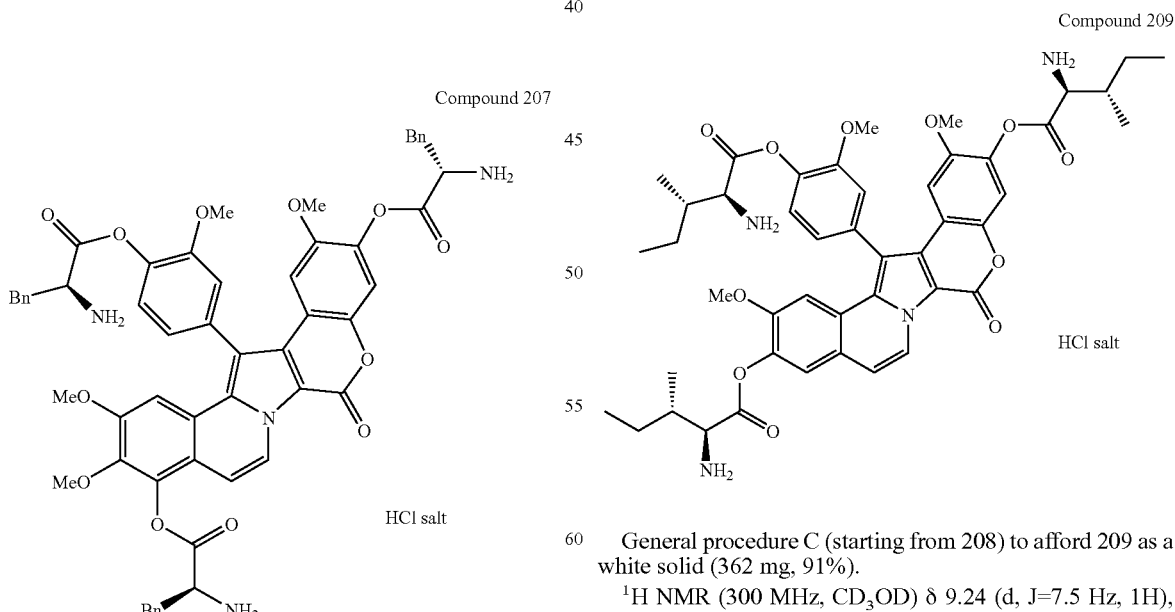

General procedure C (starting from 208) to afford 209 as a white solid (362 mg, 91%).

¹H NMR (300 MHz, CD₃OD) δ 9.24 (d, J=7.5 Hz, 1H), 7.67 (s, 1H), 7.60-7.50 (m, 2H), 7.45-7.30 (m, 4H), 6.92 (d, J=9.8 Hz, 1H), 4.40 (d, J=3.4 Hz, 1H), 4.37 (d, J=3.6 Hz, 1H), 4.33 (d, J=3.6 Hz, 1H), 3.88 (s, 3H), 3.49 (s, 3H), 3.48 (s, 6H), 2.30-2.10 (m, 3H), 1.90-1.70 (m, 3H), 1.60-1.40 (m, 3H), 1.30-1.00 (m, 18H). MS (ESI) m/z: 839 (M+1)⁺.

Compound 210

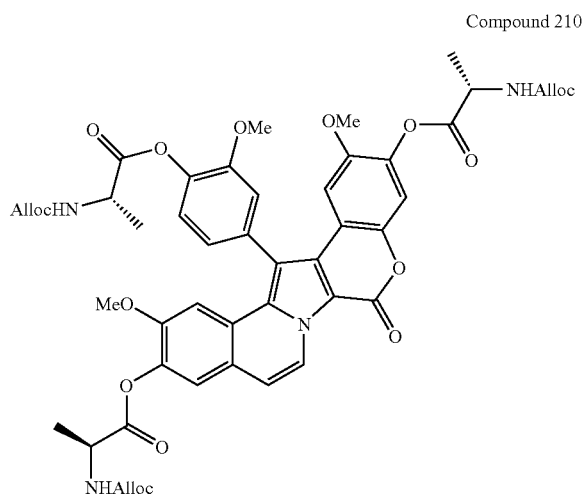

General procedure D (starting from 3 and Alloc-Ala-OH) and chromatography on silica gel (CH$_2$Cl$_2$:MeOH, 80:1) to afford 210 as a white solid (29 mg, 74%).

$^1$H NMR (300 MHz, CDCl$_3$) δ 9.15-9.05 (m, 1H), 7.40-7.20 (m, 4H), 7.17 (d, J=6.5 Hz, 1H), 7.07 (s, 1H), 6.95-6.85 (m, 1H), 6.77 (d, J=5.8 Hz, 1H), 6.00-5.80 (m, 3H), 5.50-5.20 (m, 9H), 4.80-4.50 (m, 9H), 3.84 (d, J=2.9 Hz, 3H), 3.44 (s, 6H), 1.70-1.50 (m, 9H). Rf: 0.14 (CH$_2$Cl$_2$:MeOH, 80:1).

Compound 211

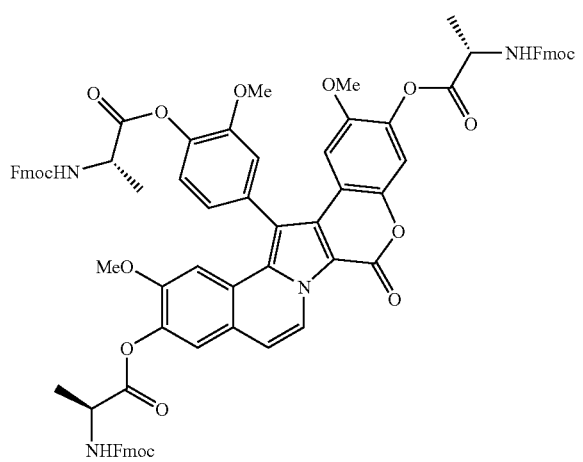

To a suspension of 3 (20 mg, 0.04 mmol), Fmoc-Ala-OH (93 mg, 0.30 mmol) in CH$_2$Cl$_2$ anh. (2 mL) under Argon atmosphere at 0° C. was added HATU (114 mg, 0.30 mmol) and N-Methylmorpholine (0.053 mL, 0.48 mmol).

The mixture was stirred at 23° C. overnight. The resulting pale brown solution was diluted with CH$_2$Cl$_2$ (20 mL), washed with KHCO$_3$ 10% (20 mL), saturated aqueous solution of Na$_2$SO$_4$ (20 mL), and brine (20 mL).

The organic phase was dried over anhydrous Na$_2$SO$_4$ and the solvent removed under vaccum. The residue was purified by chromatography on silica gel (CH$_2$Cl$_2$:MeOH, 100:1) to give 211 as a white solid (32 mg, 84%).

$^1$H NMR (300 MHz, CDCl$_3$) δ 9.26 (d, J=7.7 Hz, 1H), 7.80-7.70 (m, 6H), 7.65-7.55 (m, 6H), 7.50-7.25 (m, 15H), 7.25-7.15 (m, 3H), 7.19 (d, J=6.9 Hz, 1H), 6.80-6.75 (m, 1H), 5.45-5.35 (m, 3H), 4.80-4.65 (m, 3H), 4.50-4.40 (m, 6H), 4.30-4.20 (m, 3H), 3.81 (s, 3H), 3.43 (s, 6H), 1.75-1.55 (m, 9H). MS (ESI) m/z: 1401 (M+23)$^+$. Rf: 0.15 (CH$_2$Cl$_2$:MeOH, 100:1).

Compound 212

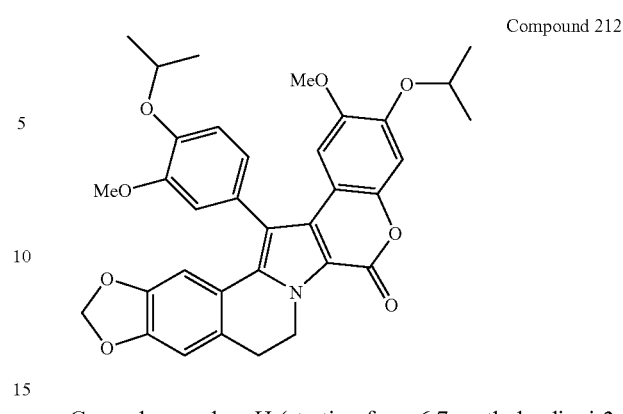

General procedure H (starting from 6,7-methylendioxi-3,4-dihidroisoquinoline) and chromatography on silica gel Merck-60 (230-400 mesh) (5:5:2 hexane-DCM-Et$_2$O) to provide 212 as a yellow solid (144 mg, 660%).

$^1$H NMR (300 MHz, CDCl$_3$) δ 7.10-6.95 (m, 3H), 6.90 (s, 1H), 6.74 (s, 1H), 6.62 (s, 1H), 6.58 (s, 1H), 5.89 (s, 2H), 4.80-4.50 (m, 4H), 3.82 (s, 3H), 3.41 (s, 3H), 3.08 (t, J=6.5 Hz, 2H), 1.50-1.25 (m, 12H). MS (ESI) m/z: 588.2 (M+5)$^+$. Rf: 0.27 (hexane:EtOAc, 1:1).

Compound 213

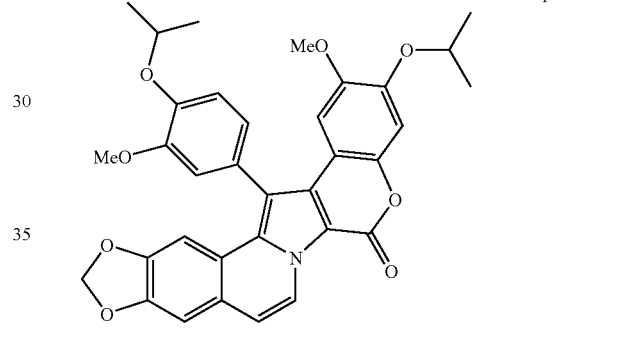

General procedure E (starting from 212, reaction time 3 h) and chromatography on silica gel (hexane:EtOAc, 1:1) to give 213 (19 mg, 33%).

$^1$H NMR (300 MHz, CDCl$_3$) δ 9.23 (d, J=6.5 Hz, 1H), 7.20-6.90 (m, 7H), 6.63 (s, 1H), 6.00-5.95 (m, 2H), 4.80-4.50 (m, 2H), 3.83 (s, 3H), 3.43 (s, 3H), 1.50-1.20 (m, 12H). MS (ESI) m/z: 582.2 (M+1)$^+$. Rf: 0.48 (hexane:EtOAc, 1:1).

Compound 214

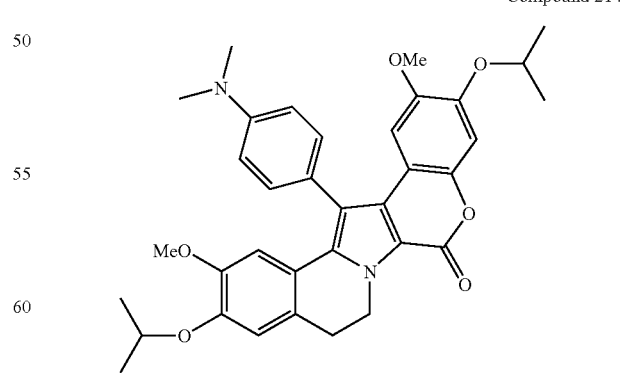

General procedure M (starting from 4-dimethylaminophenyl boronic acid) and chromatography on silica gel (Hexane:EtOAc 3:1 to 2:1) to provide 214 (13 mg, 28%).

¹H NMR (300 MHz, CDCl₃) δ 7.35 (m, 2H), 6.89 (m, 3H), 6.76 (m, 3H), 4.78 (t, J=6.7 Hz, 2H), 4.54 (m, 2H), 3.44 (s, 3H), 3.33 (s, 3H), 3.08 (t, J=6.7 Hz, 2H), 2.98 (s, 6H), 1.37 (d, J=6.2 Hz, 6H), 1.36 (d, J=6.2 Hz, 6H). ¹³C NMR (75 MHz, CDCl₃) δ 155.8, 150.5, 148.6, 147.2, 146.9, 146.6, 145.9, 136.2, 131.9, 128.5, 126.3, 123.0, 120.6, 115.5, 114.7, 113.7, 113.4, 110.8, 109.4, 105.2, 103.6, 71.5, 71.4, 55.6, 55.2, 42.4, 40.8, 29.3, 28.7, 22.1, 21.9. MS (ESI) m/z: 583.5 (M+1)⁺. Rf: 0.50 (hexane:EtOAc, 1:1).

¹H NMR (300 MHz, CDCl₃) δ 9.21 (d, J=7.3 Hz, 1H), 7.39 (m, 2H), 7.30 (s, 1H), 7.08 (s, 1H), 7.00 (d, J=7.3 Hz, 1H), 6.96 (s, 1H), 6.84 (m, 3H), 4.69 (hp, J=6.2 Hz, 1H), 4.57 (hp, J=6.2 Hz, 1H), 3.48 (s, 3H), 3.47 (s, 3H), 2.92 (s, 3H), 1.43 (d, J=6.2 Hz, 6H), 1.40 (d, J=6.2 Hz, 6H). MS (ESI) m/z: 867.4 (M+1)⁺. Rf: 0.25 (Hexane:EtOAc 1:1).

Compound 217

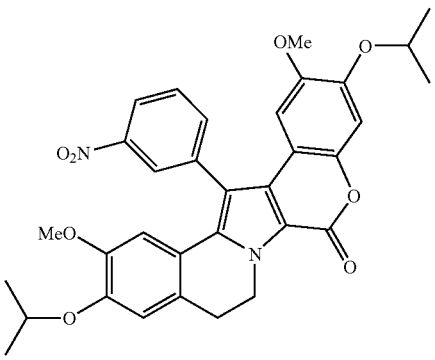

Compound 215

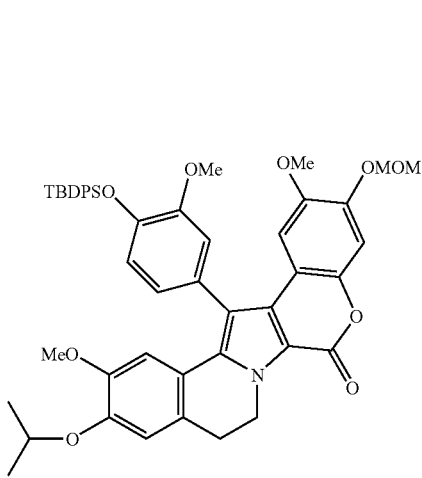

General procedure H (starting from 6-isopropoxy-7-methoxy-3,4-dihydroisoquinoline) and chromatography on silica gel (Hexane:CH₂Cl₂:Et₂O 5:5:2) to provide 215 as white solid (21 mg, 21%).

¹H NMR (300 MHz, CDCl₃) δ 7.73 (m, 4H), 7.44-7.35 (m, 6H), 7.20 (s, 1H), 6.94-6.80 (m, 3H), 6.75 (s, 1H), 6.71 (s, 1H), 6.67 (s, 1H), 5.23 (s, 2H), 4.84 (m, 1H), 4.68 (m, 1H), 4.56 (hp, J=6.0 Hz, 1H), 3.60 (s, 3H), 3.49 (s, 3H), 3.40 (s, 3H), 3.31 (s, 3H), 3.06 (m, 2H), 1.37 (d, J=6.0 Hz, 6H), 1.13 (s, 9H). MS (ESI) m/z: 826.3 (M+1)⁺. Rf: 0.40 (Hexane/CH₂Cl₂/Et₂O 5:5:2).

General procedure M (starting from 3-nitrophenyl boronic acid) and chromatography on silica gel (Hexane:EtOAc 2:1) to provide 217 (33 mg, 67%) and LLSA-3,4-di(OiPr)-14(I) (10 mg, 20%).

¹H NMR (300 MHz, CDCl₃) δ 8.45 (s, 1H), 8.35 (d, J=8.1 Hz, 1H), 7.96 (d, J=7.7 Hz, 1H), 7.78 (dd, J=7.7, 8.1 Hz, 1H), 6.92 (s, 1H), 6.79 (s, 1H), 6.44 (s, 1H), 6.36 (s, 1H), 4.80 (dt, J=6.5, 6.3 Hz, 2H), 4.55 (m, 2H), 3.37 (s, 3H), 3.24 (s, 3H), 3.10 (t, J=6.5 Hz, 2H), 1.37 (d, J=6.1 Hz, 6H), 1.36 (d, J=6.1 Hz, 6H). ¹³C NMR (75 MHz, CDCl₃) δ 155.4, 148.9, 148.6, 148.0, 147.6, 146.7, 146.2, 138.2, 137.9, 136.1, 130.1, 127.8, 127.1, 126.4, 122.7, 119.3, 115.0, 114.3, 112.0, 109.7, 109.2, 104.6, 103.9, 71.6, 71.5, 55.6, 55.2, 42.5, 29.7, 22.0, 21.8. MS (ESI) m/z: 585.4 (M+1)⁺. Rf: 0.60 (Hexane:EtOAc 1:1).

Compound 218

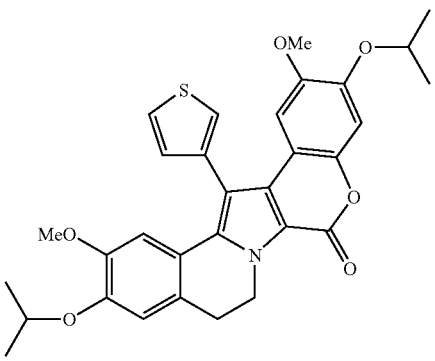

Compound 216

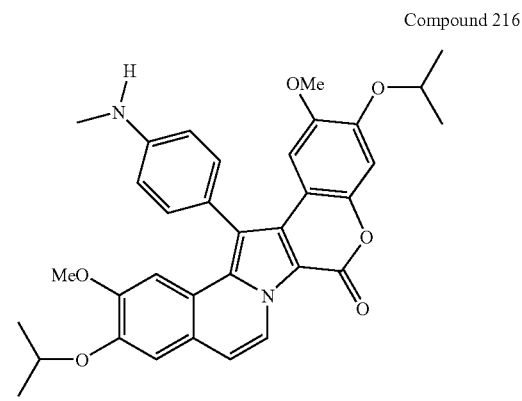

General procedure E (starting from 214, reaction time 6 h) and chromatography on silica gel (Hexane:EtOAc 1:1) to provide 216 (8 mg, 80%).

General procedure M (starting from 3-thiopheneboronic acid) and chromatography on silica gel (Hexane:EtOAc 2:1) to provide 218 (18 mg, 39%).

¹H NMR (300 MHz, CDCl₃) δ 7.60 (dd, J=3.1, 5.0 Hz, 1H), 7.44 (dd, J=1.3, 3.1 Hz, 1H), 7.26 (dd, J=1.3, 5.0 Hz, 1H), 6.91 (s, 1H), 6.76 (s, 1H), 6.71 (s, 1H), 6.63 (s, 1H), 4.77 (m, 2H), 4.54 (m, 2H), 3.50 (s, 3H), 3.41 (s, 3H), 3.09 (t, J=6.6 Hz, 2H), 1.38 (d, J=6.0 Hz, 6H), 1.37 (d, J=6.0 Hz, 6H). ¹³C NMR (75 MHz, CDCl₃) δ 155.6, 148.7, 147.4, 147.0, 146.6, 145.9, 136.5, 135.5, 130.3, 128.8, 126.9, 126.3, 125.2, 120.0, 114.5, 113.9, 110.3, 108.9, 108.7, 104.4, 103.4, 71.4, 71.3, 55.4, 55.1, 42.4, 29.7, 28.6, 22.0, 21.8. MS (ESI) m/z: 546.5 (M+1)⁺. Rf: 0.65 (Hexane:EtOAc 1:1).

Compound 219

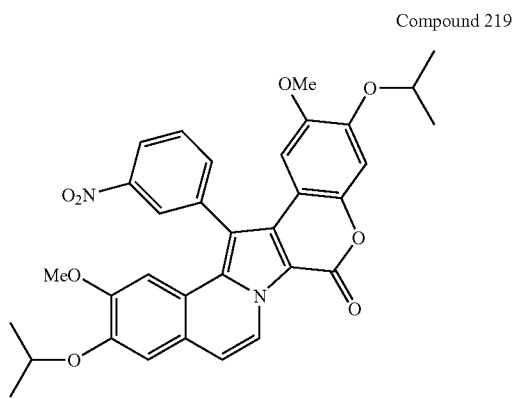

General procedure E (starting from 217, reaction time 5 h) and chromatography on silica gel (Hexane:EtOAc 2:1) to provide 219 (26 mg, quantitative).

$^1$H NMR (300 MHz, CDCl$_3$) δ 9.27 (d, J=7.4 Hz, 1H), 8.56 (m, 1H), 8.43 (m, 1H), 8.07 (d, J=7.7 Hz, 1H), 7.88 (dd, J=7.7, 8.0 Hz, 1H), 7.12 (s, 1H), 7.07 (d, J=7.4 Hz, 1H), 6.97 (s, 1H), 6.84 (s, 1H), 6.45 (s, 1H), 4.70 (hp, J=6.1 Hz, 1H), 4.57 (hp, J=6.1 Hz, 1H), 3.37 (s, 3H), 3.34 (s, 3H), 1.42 (d, J=6.1 Hz, 6H), 1.39 (d, J=6.1 Hz, 6H). $^{13}$C NMR (75 MHz, CDCl$_3$) δ 155.3, 150.5, 149.0, 148.4, 148.9, 146.8, 146.7, 138.7, 138.5, 134.1, 130.3, 129.2, 127.0, 125.1, 123.2, 123.1, 118.3, 112.9, 110.8, 109.2, 108.5, 108.0, 105.1, 103.8, 71.6, 71.4, 55.5, 55.1, 29.7, 21.9, 21.8. MS (ESI) m/z: 583.2 (M+1)$^+$. Rf: 0.60 (Hexane:EtOAc 1:1).

Compound 220

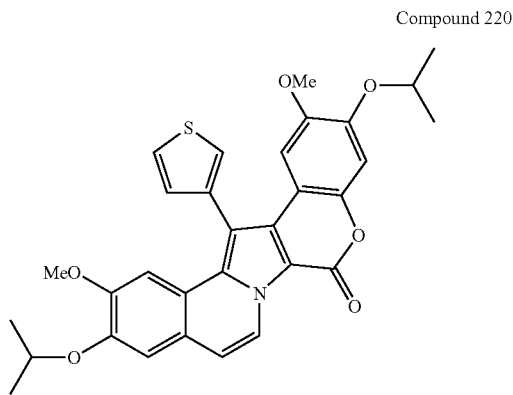

General procedure E (starting from 218, reaction time 5 h) and chromatography on silica gel (Hexane: EtOAc 2:1) to provide 220 (13 mg, 99%).

$^1$H NMR (300 MHz, CDCl$_3$) δ 9.20 (d, J=7.4 Hz, 1H), 7.70 (dd, J=3.0, 4.8 Hz, 1H), 7.56 (dd, J=1.3, 3.0 Hz, 1H), 7.34 (dd, J=1.3, 4.8 Hz, 1H), 7.16 (s, 1H), 7.09 (s, 1H), 7.02 (d, J=7.4 Hz, 1H), 6.96 (s, 1H), 6.71 (s, 1H), 4.70 (hp, J=6.2 Hz, 1H), 4.57 (d, J=6.2 Hz, 1H), 3.52 (s, 6H), 1.43 (d, J=6.2 Hz, 6H), 1.40 (d, J=6.2 Hz, 6H). $^{13}$C NMR (125 MHz, CDCl$_3$) δ 155.5, 150.2, 148.5, 147.9, 146.6, 135.8, 134.8, 130.8, 130.0, 127.2, 125.9, 124.7, 123.2, 118.9, 112.4, 110.3, 109.8, 108.1, 105.2, 104.9, 103.3, 71.4, 71.2, 55.4, 55.1, 29.7, 21.9, 21.8. MS (ESI) m/z: 544.2 (M+1)$^+$. Rf: 0.65 (Hexane:EtOAc 1:1).

Compound 221

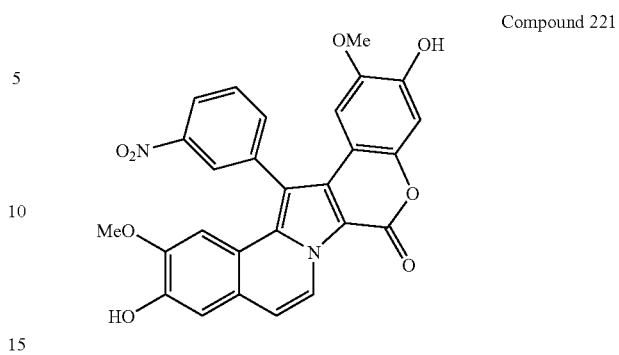

General procedure A (starting from 219) and chromatography on silica gel (CH$_2$Cl$_2$:MeOH 50:1) to provide 221 (14 mg, 88%).

$^1$H NMR (300 MHz, CDCl$_3$/CD$_3$OD) δ 9.14 (d, J=7.3 Hz, 1H), 8.52 (m, 1H), 8.46 (d, J=8.4 Hz, 1H), 8.08 (d, J=7.9 Hz, 1H), 7.92 (dd, J=7.9, 8.4 Hz, 1H), 7.14 (s, 1H), 7.06 (d, J=7.3 Hz, 1H), 6.90 (s, 1H), 6.82 (s, 1H), 6.42 (s, 1H), 3.37 (s, 3H), 3.36 (s, 3H). MS (ESI) m/z: 499.4 (M+1)$^+$. Rf: 0.15 (CH$_2$Cl$_2$:MeOH 50:1).

Compound 222

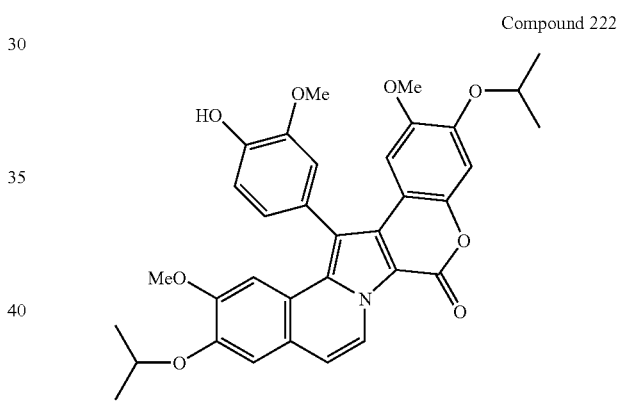

A suspension of 3 (50 mg, 0.10 mmol) and Cs$_2$CO$_3$ (34 mg, 0.105 mmol) in anhydrous DMF (2 mL) under Argon atmosphere was heated at 40° C. for 30 minutes. Isopropylmagnesium bromide (0.014 mL, 0.15 mmol) was added dropwise via syringe to the reaction mixture. The resulting yellow suspension was stirred at 40° C. for 16 hours. The reaction mixture was cooled to 23° C. and evaporated in vacuo. The residue was disolved in CH$_2$Cl$_2$, filtered, and the solvent removed under vacuum. The residue was purified by chromatography on silica gel (hexane:EtoAc 2:1 to 1:1) to afford 222 (30 mg, 51%).

$^1$H NMR (300 MHz, CDCl$_3$) δ 9.21 (d, J=7.3 Hz, 1H), 7.28-7.08 (m, 5H), 7.01 (d, J=7.3 Hz, 1H), 6.96 (s, 1H), 6.74 (s, 1H), 5.89 (s, 1H), 4.69 (hp, J=6.0 Hz, 1H), 4.57 (hp, J=6.2 Hz, 1H), 3.88 (s, 3H), 3.46 (s, 3H), 3.45 (s, 3H), 1.43 (d, J=6.0 Hz, 6H), 1.40 (d, J=6.2 Hz, 6H). $^{13}$C NMR (75 MHz, CDCl$_3$) δ 155.6, 150.2, 148.5, 147.9, 147.3, 146.6, 145.7, 134.4, 129.5, 124.7, 123.1, 119.0, 115.2, 113.9, 112.3, 111.1, 110.5, 110.0, 107.8, 105.7, 105.6, 103.5, 71.4, 71.2, 56.2, 55.5, 55.2, 29.7, 21.9, 21.8. MS (ESI) m/z: 584.2 (M+1)$^+$. Rf: 0.40 (Hexane/EtOAc 1:1).

Compound 223

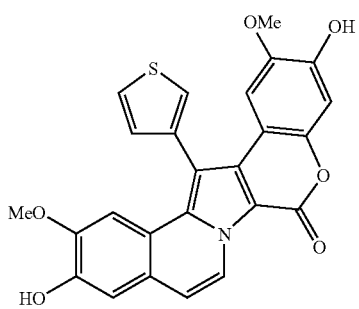

General procedure A (starting from 220) and chromatography on silica gel (Hexane/EtOAc 1:1) to provide 223 (1.5 mg, 38%).

$^1$H NMR (300 MHz, CDCl$_3$/CD$_3$OD) δ 9.06 (d, J=7.4 Hz, 1H), 7.70 (dd, J=3.0, 4.8 Hz, 1H), 7.53 (dd, J=1.3, 3.0 Hz, 1H), 7.30 (dd, J=1.3, 4.8 Hz, 1H), 7.10 (s, 1H), 7.09 (s, 1H), 6.98 (d, J=7.4 Hz, 1H), 6.90 (s, 1H), 6.63 (s, 1H), 3.52 (s, 3H), 3.51 (s, 3H). $^{13}$C NMR (75 MHz, CDCl$_3$/CD$_3$OD) δ 156.4, 148.6, 148.1, 147.5, 147.0, 144.9, 136.1, 135.8, 130.9, 130.8, 127.6, 126.2, 125.7, 123.1, 118.7, 112.7, 111.4, 109.6, 107.9, 105.2, 105.0, 102.9, 102.8, 55.5, 55.2. MS (ESI) m/z: 460.0 (M+1)$^+$. Rf: 0.20 (CH$_2$Cl$_2$:MeOH 50:1).

Compound 224

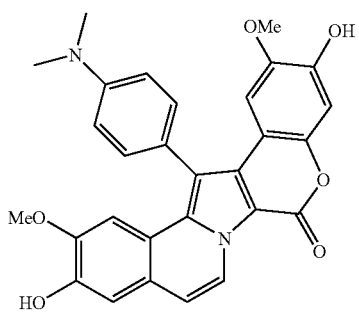

General procedure A (starting from 214) and chromatography on silica gel (CH$_2$Cl$_2$:MeOH 50:1 to 20:1) to provide 224 (11 mg, 50%).

$^1$H NMR (500 MHz, CDCl$_3$/CD$_3$OD) δ 7.43 (s, 1H), 7.31 (m, 2H), 6.91 (m, 2H), 6.81 (s, 1H), 6.72 (s, 1H), 6.70 (s, 1H), 4.67 (t, J=6.7 Hz, 2H), 3.43 (s, 3H), 3.33 (s, 3H), 3.02 (t, J=6.7 Hz, 2H), 2.96 (s, 6H). $^{13}$C NMR (125 MHz, CDCl$_3$/CD$_3$OD) δ 156.9, 151.1, 146.8, 146.6, 146.5, 146.4, 145.0, 137.5, 132.3, 129.7, 127.6, 123.6, 119.8, 115.4, 115.1, 114.0, 113.4, 110.5, 109.6, 105.3, 103.9, 55.7, 55.4, 42.8, 41.1, 28.7. MS (ESI) m/z: 499.2 (M+1)$^+$. Rf: 0.15 (CH$_2$Cl$_2$:MeOH 40:1).

Compound 225

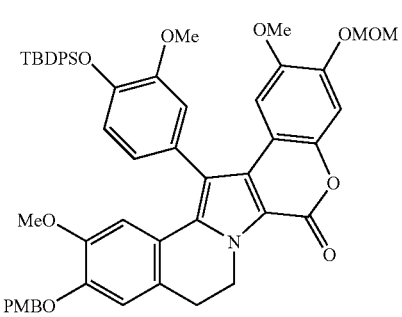

A suspension of 227 (63 mg, 0.080 mmol) and Cs$_2$CO$_3$ (29 mg, 0.088 mmol) in anhydrous DMF under Argon atmosphere at room temperature for 30 minutes. 4-methoxybenzyl chloride (0.088 mmol) was added dropwise via syringe to the reaction mixture. The resulting suspension was stirred at room temperature overnight. The progress of the reaction was followed by TLC (CH$_2$Cl$_2$/EtOAc 10:1). The reaction mixture was evaporated in vacuo. The residue was purified by chromatography on silica gel (CH$_2$Cl$_2$/EtOAc 10:1) to obtain 225 (9 mg, 12%).

$^1$H NMR (300 MHz, CDCl$_3$) δ 7.73 (m, 4H), 7.46-7.35 (m, 8H), 7.34 (s, 1H), 6.93-6.80 (m, 5H), 6.76 (s, 1H), 6.71 (s, 1H), 6.67 (s, 1H), 5.65 (s, 1H), 5.22 (s, 2H), 5.08 (s, 2H), 4.82 (m, 1H), 4.63 (m, 1H), 3.81 (s, 3H), 3.60 (s, 3H), 3.49 (s, 3H), 3.40 (s, 3H), 3.32 (s, 3H), 3.04 (m, 2H), 1.13 (s, 9H). MS (ESI) m/z: 904.0 (M+1)$^+$. Rf: 0.65 (CH$_2$Cl$_2$/EtOAc 10:1).

Compound 226

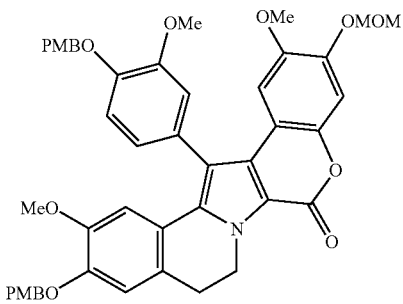

A suspension of 227 (63 mg, 0.080 mmol) and Cs$_2$CO$_3$ (29 mg, 0.088 mmol) in anhydrous DMF under Argon atmosphere at room temperature for 30 minutes. 4-methoxybenzyl chloride (0.088 mmol) was added dropwise via syringe to the reaction mixture. The resulting suspension was stirred at room temperature overnight. The progress of the reaction was followed by TLC (CH$_2$Cl$_2$/EtOAc 10:1). The reaction mixture was evaporated in vacuo. The residue was purified by chromatography on silica gel (CH$_2$Cl$_2$/EtOAc 10:1) to obtain 226 (33 mg, 48%).

$^1$H NMR (300 MHz, CDCl$_3$) δ 7.40-7.33 (m, 8H), 7.25 (s, 1H), 7.21-7.00 (m, 3H), 6.92-6.88 (m, 4H), 6.77 (s, 1H), 6.69 (s, 1H), 6.64 (s, 1H), 5.22 (s, 2H), 5.19 (s, 2H), 5.07 (s, 2H), 4.82 (m, 1H), 4.64 (m, 1H), 3.85 (s, 3H), 3.82 (s, 3H), 3.81 (s, 3H), 3.49 (s, 3H), 3.36 (s, 3H), 3.27 (s, 3H), 3.05 (m, 2H). MS (ESI) m/z: 786.0 (M+1)$^+$. Rf: 0.50 (CH$_2$Cl$_2$/EtOAc 10:1).

Compound 227

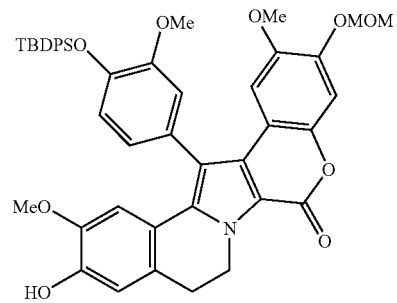

General procedure G (starting from 6-hydroxy-7-methoxy-3,4-dihydroisoquinoline and iodo-acetic acid 2-[4-(tert-butyl-diphenyl-silannyloxy)-3-methoxy-phenylethynyl]-4-methoxy-5-methoxymethoxy-phenyl ester) and chromatography on silica gel (Hexane:CH$_2$Cl$_2$:Et$_2$O 5:5:2) to provide 227 slightly impure (103 mg, 20%). To obtain a pure product, this compound was submitted to chromatography on LiChroprep® NH$_2$ (EtOAc) (24 mg, 5%).

$^1$H NMR (300 MHz, CDCl$_3$) δ 7.74 (m, 4H), 7.47-7.35 (m, 6H), 7.20 (s, 1H), 6.94-6.70 (m, 4H), 6.67 (m, 2H), 5.65 (s, 1H), 5.23 (s, 2H), 4.84 (m, 1H), 4.63 (m, 1H), 3.61 (s, 3H), 3.49 (s, 3H), 3.40 (s, 3H), 3.36 (s, 3H), 3.05 (m, 2H), 1.14 (s, 9H). $^{13}$C NMR (75 MHz, CDCl$_3$) δ 155.4, 151.1, 146.1, 145.9, 145.8, 145.7, 145.1, 144.9, 135.9, 135.1, 133.5, 133.4, 129.9, 128.3, 127.6, 127.4, 123.3, 120.3, 119.6, 115.1, 114.8, 114.1, 113.8, 111.9, 108.4, 105.3, 105.0, 95.5, 56.2, 55.7, 55.4, 55.3, 42.3, 29.6, 28.4, 26.7, 19.8. MS (APCI) m/z: 784.1 (M+1)⁺. Rf: 0.25 (CH$_2$Cl$_2$/MeOH 100:1).

Compound 228

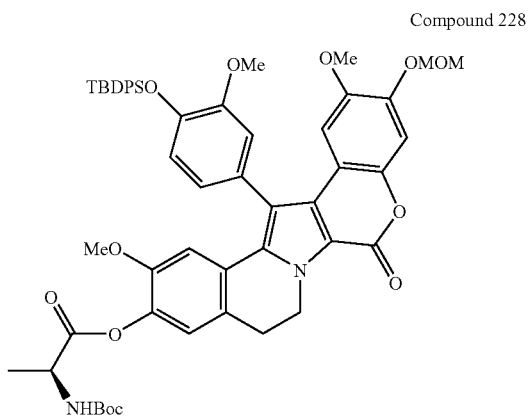

A suspension of 227 (25 mg, 0.031 mmol), Boc-L-Ala-OH (12 mg, 0.063 mmol), EDC·HCl (12 mg, 0.063 mmol) and DMAP (0.8 mg, 0.0063 mmol) in CH$_2$Cl$_2$ anh. (2 mL) was stirred under argon atmosphere at room temperature for 2 h. The resulting solution was diluted with CH$_2$Cl$_2$ (20 mL), washed with water (20 mL) and saturated NaHCO$_3$ aqueous solution (20 mL).

The organic phase was dried over anhydrous sodium sulfate and the solvent removed under vaccum to give 228 as a white solid (30 mg, quant.).

¹H NMR (300 MHz, CDCl$_3$) δ 7.73 (m, 4H), 7.44-7.35 (m, 6H), 7.20 (s, 1H), 6.96-6.80 (m, 5H), 6.65 (s, 1H), 5.22 (s, 2H), 5.09 (m, 1H), 4.90 (m, 1H), 4.63 (m, 1H), 3.61 (s, 3H), 3.49 (s, 3H), 3.39 (s, 3H), 3.27 (s, 3H), 3.07 (m, 2H), 1.55 (d, J=7.2 Hz, 3H), 1.47 (s, 9H), 1.13 (s, 9H). MS (ESI) m/z: 955.2 (M+1)⁺. Rf: 0.65 (Hexane/EtOAc 1:1).

Compound 229

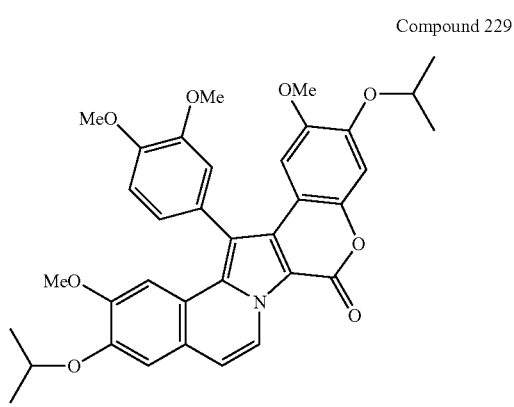

A suspension of 222 (25 mg, 0.043 mmol) and Cs$_2$CO$_3$ (21 mg, 0.064 mmol) in anhydrous DMF under Argon atmosphere was heated at 40° C. for 30 minutes. MeI (0.215 mmol) was added dropwise via syringe to the reaction mixture. The resulting yellow suspension was stirred at 40° C. for 3 hours. The progress of the reaction was followed by TLC (CH$_2$Cl$_2$/MeOH 8:0.2).

The reaction mixture was cooled to 23° C. and evaporated in vacuo. The residue was disolved in CH$_2$Cl$_2$, filtered, and the solvent removed under vacuum to afford 229 (22 mg, 85%).

¹H NMR (500 MHz, DMSO-d$_6$) δ 9.07 (d, J=7.4 Hz, 1H), 7.46 (s, 1H), 7.33 (d, J=7.4 Hz, 1H), 7.28 (d, J=8.2 Hz, 1H), 7.21 (d, J=2.5 Hz, 1H), 7.16 (dd, J=8.2, 2.5 Hz, 1H), 7.15 (s, 1H), 7.11 (s, 1H), 6.70 (s, 1H), 4.76 (hp, J=6.1 Hz, 1H), 4.69 (hp, J=6.1 Hz, 1H), 3.86 (s, 3H), 3.75 (s, 3H), 3.34 (s, 3H), 3.32 (s, 3H), 1.31 (d, J=6.1 Hz, 3H), 1.30 (d, J=6.1 Hz, 3H), 1.27 (d, J=6.1 Hz, 3H), 1.26 (d, J=6.1 Hz, 3H). ¹³C NMR (125 MHz, CDCl$_3$) δ 155.6, 150.1, 149.8, 149.0, 148.5, 147.9, 146.6, 146.5, 134.4, 129.5, 128.3, 124.7, 124.1, 123.2, 118.9, 114.3, 112.3, 111.9, 110.9, 110.3, 109.9, 107.8, 105.6, 105.4, 103.4, 71.4, 71.1, 56.3, 56.1, 55.5, 55.2, 29.7, 21.9, 21.8. MS (ESI) m/z: 598.4 (M+1)⁺. Rf: 0.65 (CH$_2$Cl$_2$/MeOH 8:0.2).

Compound 230

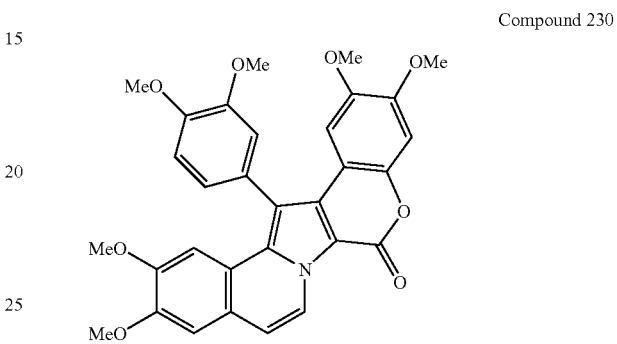

This compound is a by-product of the synthesis of 222.

¹H NMR (300 MHz, CDCl$_3$) δ 9.26 (d, J=7.5 Hz, 1H), 7.28-7.11 (m, 4H), 7.10 (s, 1H), 7.07 (d, J=7.5 Hz, 1H), 6.97 (s, 1H), 6.74 (s, 1H), 3.99 (s, 6H), 3.92 (s, 3H), 3.88 (s, 3H), 3.47 (s, 3H), 3.46 (s, 3H). MS (APCI) m/z: 842.2 (M+1)⁺. Rf: 0.35 (CH$_2$Cl$_2$/MeOH 9:0.2).

Compound 231

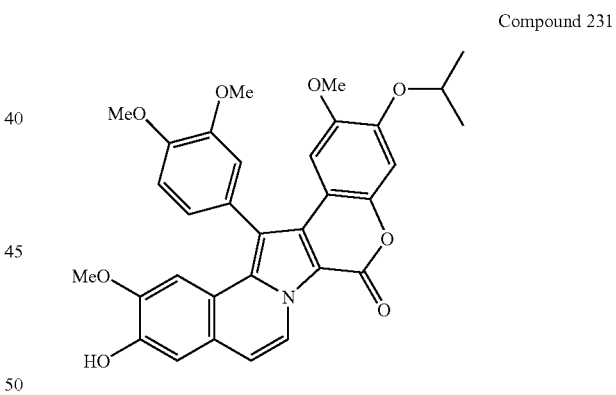

A suspension of 222 (22 mg, 0.037 mmol) and AlCl$_3$ (12 mg, 0.092 mmol) in anhydrous CH$_2$Cl$_2$ (1 mL) was stirred at room temperature for 2'5 h under Argon atmosphere. CH$_2$Cl$_2$ and MeOH were added and then the solvent was evaporated under reduced pressure. The residue was purified by preparative TLC (CH$_2$Cl$_2$/MeOH 9:0.5) to provide 231 (3 mg, 15%).

¹H NMR (500 MHz, DMSO-d$_6$) δ 9.98 (s, 1H), 9.03 (d, J=7.4 Hz, 1H), 7.29 (d, J=8.2 Hz, 1H), 7.25 (d, J=7.4 Hz, 1H), 7.21 (d, J=2.5 Hz, 1H), 7.20 (s, 1H), 7.16 (dd, J=8.2, 2.5 Hz, 1H), 7.14 (s, 1H), 7.10 (s, 1H), 6.69 (s, 1H), 4.69 (hp, J=6.1 Hz, 1H), 3.86 (s, 3H), 3.76 (s, 3H), 3.37 (s, 3H), 3.35 (s, 3H), 1.27 (d, J=6.1 Hz, 3H), 1.26 (d, J=6.1 Hz, 3H). ¹³C NMR (125 MHz, DMSO-d$_6$) δ 154.3, 149.9, 149.0, 148.6, 148.4, 147.5, 146.2, 146.1, 134.0, 128.6, 127.1, 124.7, 123.6, 122.0, 117.5, 114.6, 113.0, 112.6, 111.6, 110.7, 109.2, 106.7, 105.2, 103.2, 70.5, 56.0, 55.8, 54.8, 54.5, 29.0, 21.7, 21.6. MS (APCI) m/z: 556.1 (M+1)⁺. Rf: 0.30 (CH$_2$Cl$_2$/MeOH 9:0.2).

Compound 232

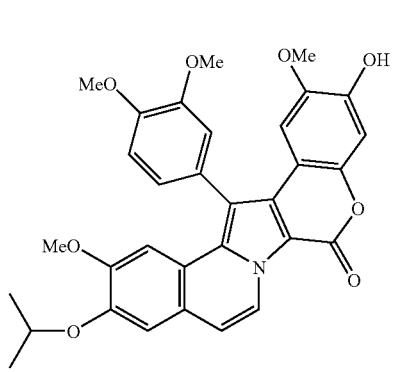

A suspension of 222 (22 mg, 0.037 mmol) and AlCl₃ (12 mg, 0.092 mmol) in anhydrous CH$_2$Cl$_2$ (1 mL) was stirred at room temperature for 2.5 h under Argon atmosphere. CH$_2$Cl$_2$ and MeOH were added and then the solvent was evaporated under reduced pressure. The residue was purified by preparative TLC (CH$_2$Cl$_2$/MeOH 9:0.5) to provide 232 (1 mg, 5%).

$^1$H NMR (500 MHz, DMSO-d$_6$) δ 9.88 (s, 1H), 9.06 (d, J=7.4 Hz, 1H), 7.46 (s, 1H), 7.30 (d, J=8.2 Hz, 1H), 7.29 (d, J=7.4 Hz, 1H), 7.21 (d, J=2.5 Hz, 1H), 7.16 (dd, J=8.2, 2.5 Hz, 1H), 7.10 (s, 1H), 6.88 (s, 1H), 6.68 (s, 1H), 4.76 (hp, J=6.1 Hz, 1H), 3.86 (s, 3H), 3.76 (s, 3H), 3.36 (s, 3H), 3.32 (s, 3H), 1.31 (d, J=6.1 Hz, 3H), 1.30 (d, J=6.1 Hz, 3H). MS (APCI) m/z: 556.1 (M+1)$^+$. Rf: 0.25 (CH$_2$Cl$_2$/MeOH 9:0.2).

Compound 233

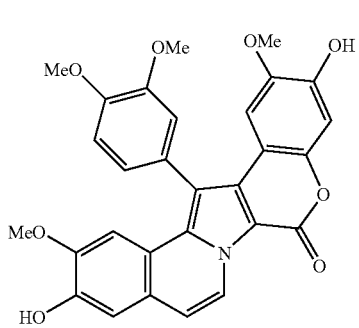

A suspension of 222 (22 mg, 0.037 mmol) and AlCl$_{13}$ (12 mg, 0.092 mmol) in anhydrous CH$_2$Cl$_2$ (1 mL) was stirred at room temperature for 2'5 h under Argon atmosphere. CH$_2$Cl$_2$ and MeOH were added and then the solvent was evaporated under reduced pressure. The residue was purified by preparative TLC (CH$_2$Cl$_2$/MeOH 9:0.5) to provide 233 (5 mg, 26%).

$^1$H NMR (500 MHz, DMSO-d$_6$) δ 9.97 (s, 1H), 9.86 (s, 1H), 9.02 (d, J=7.4 Hz, 1H), 7.29 (d, J=8.2 Hz, 1H), 7.23 (d, J=7.4 Hz, 1H), 7.21 (d, J=2.5 Hz, 1H), 7.20 (s, 1H), 7.16 (dd, J=8.2, 2.5 Hz, 1H), 7.09 (s, 1H), 6.87 (s, 1H), 6.67 (s, 1H), 3.86 (s, 3H), 3.76 (s, 3H), 3.36 (s, 3H), 3.35 (s, 3H). $^{13}$C NMR (125 MHz, DMSO-d$_6$) δ 154.3, 149.9, 149.0, 148.5, 148.3, 147.8, 146.3, 144.6, 134.0, 128.9, 127.3, 124.7, 123.6, 122.0, 117.4, 114.6, 113.1, 112.4, 111.5, 110.4, 108.2, 106.4, 105.6, 105.3, 103.7, 56.0, 55.8, 55.0, 54.5. MS (APCI) m/z: 514.1 (M+1)$^+$. Rf: 0.15 (CH$_2$Cl$_2$/MeOH 9:0.2).

Compound 234

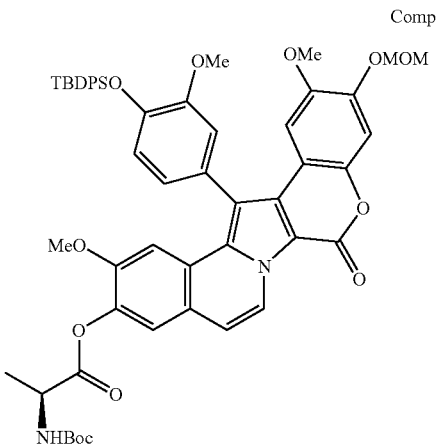

General procedure E (starting from 228, reaction time 28 h) and chromatography on silica gel (hexane:EtOAc 2:1) to afford 234 as a white solid (24 mg, 81%).

$^1$H NMR (300 MHz, CDCl$_3$) δ 9.20 (d, J=7.3 Hz, 1H), 7.75 (d, J=6.7 Hz, 4H), 7.48-7.37 (m, 6H), 7.25 (s, 1H), 7.03 (s, 1H), 7.00 (d, J=7.3 Hz, 1H), 6.92 (s, 2H), 6.73 (s, 1H), 5.24 (s, 2H), 5.12 (m, 1H), 4.62 (m, 1H), 3.64 (s, 3H), 3.50 (s, 3H), 3.43 (s, 3H), 3.37 (s, 3H), 1.58 (d, J=7.0 Hz, 3H), 1.25 (s, 9H), 1.15 (s, 9H). MS (APCI) m/z: 953.2 (M+1)$^+$. Rf: 0.25 (hexane/EtAcO, 2:1).

Compound 235

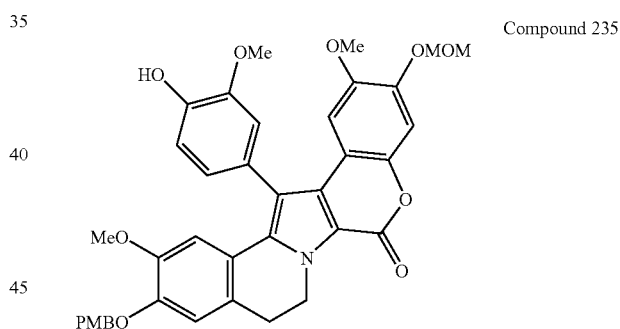

A suspension of 227 (63 mg, 0.080 mmol) and Cs$_2$CO$_3$ (29 mg, 0.088 mmol) in anhydrous DMF under Argon atmosphere at room temperature for 30 minutes. 4-methoxybenzyl chloride (0.088 mmol) was added dropwise via syringe to the reaction mixture. The resulting suspension was stirred at room temperature overnight. The progress of the reaction was followed by TLC (CH$_2$Cl$_2$/EtOAc 10:1).

The reaction mixture was evaporated in vacuo. The residue was purified by chromatography on silica gel (CH$_2$Cl$_2$/EtOAc 10:1) to obtain 235 (15 mg, 26%).

$^1$H NMR (300 MHz, CDCl$_3$) δ 7.35 (m, 2H), 7.22 (s, 1H), 7.14-7.06 (m, 2H), 6.98-6.88 (m, 3H), 6.78 (s, 1H), 6.72 (s, 1H), 6.69 (s, 1H), 5.76 (s, 1H), 5.22 (s, 2H), 5.09 (s, 2H), 4.82 (m, 1H), 4.64 (m, 1H), 3.86 (s, 3H), 3.80 (s, 3H), 3.49 (s, 3H), 3.47 (s, 3H), 3.37 (s, 3H), 3.05 (m, 2H). MS (ESI) m/z: 664.4 (M+1)$^+$. Rf: 0.30 (CH$_2$Cl$_2$/EtOAc 10:1).

Compound 236

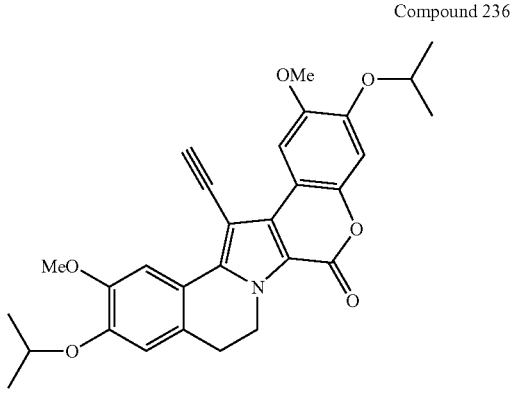

To a stirred solution of 189 (80 mg, 0.135 mmol), PdCl$_2$(PPh$_3$)$_2$ (5 mg, 0.006 mmol) and CuI (8 mg, 0.04 mmol) in 5:1 DMF-Et$_3$N (1.2 mL) under argon atmosphere at room temperature, trimethylsilylacetylene (0.04 mL, 0.27 mmol) was added via syringe. The reaction mixture was heated in a sealed tube at 90° C. for 5 hours, then the mixture was cooled to room temperature and quenched with water (10 mL). The mixture was diluted with ethyl acetate (20 mL) and washed with water (2×10 mL) and brine (2×10 mL). The organic layer was dried over anhydrous sodium sulfate and concentrated under reduced pressure.

To a solution of the resulting oil in methanol/dichloromethane (3:2, 5 mL)), potassium carbonate (20 mg, 0.142 mmol) was added in portions at room temperature under argon atmosphere. After 2 hours, a saturated aqueous solution of NH$_4$Cl was added. The aqueous phase was extracted with CH$_2$Cl$_2$ (twice, 20 mL) and the organic phase was dried over anhydrous sodium sulfate. The solvent was evaporated under reduced pressure and the residue was purified by chromatography on silica gel (Hexane/EtOAc 2:1) to obtain 236 (20 mg, 26%).

$^1$H NMR (300 MHz, CDCl$_3$) δ 8.24 (s, 1H), 8.16 (s, 1H), 6.91 (s, 1H), 6.80 (s, 1H), 4.71 (t, J=6.6 Hz, 2H), 4.60 (m, 2H), 3.92 (s, 6H), 3.64 (s, 1H), 3.06 (t, J=6.6 Hz, 2H), 1.41 (d, J=6.0 Hz, 12H). $^{13}$C NMR (75 MHz, CDCl$_3$) δ 155.3, 149.4, 148.6, 148.2, 147.2, 146.3, 141.7, 131.5, 126.7, 119.8, 114.8, 114.0, 110.4, 109.6, 105.3, 103.4, 82.9, 79.9, 71.7, 56.5, 56.3, 42.7, 28.5, 22.3, 22.1. MS (ESI) m/z: 488.5 (M+1)$^+$. Rf: 0.45 (Hexane/EtOAc 2:1).

Compound 237

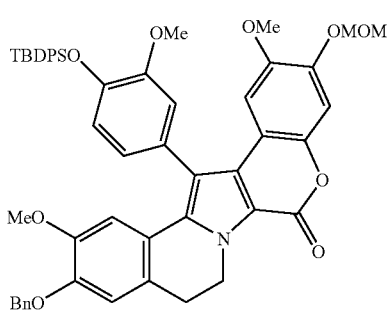

General Procedure H (starting from iodo-acetic acid 2-[4-(tert-butyl-diphenyl-silannyloxy)-3-methoxy-phenylethynyl]-4-methoxy-5-methoxymethoxy-phenyl ester and 6-Benzyloxy-7-methoxy-3,4-dihydroisoquinoline) and chromatography on silica gel (5:5:2 hexane-dichloromethane-ether) to afford 237 as a white solid (273 mg, 20%).

$^1$H NMR (300 MHz, CDCl$_3$) δ 7.74 (m, 4H), 7.45-7.30 (m, 14H), 7.20 (s, 1H), 6.94 (m, 1H), 6.84 (m, 1H), 6.74 (m, 1H), 6.68 (s, 1H), 5.23 (s, 2H), 5.16 (s, 2H), 4.82 (m, 1H), 4.64 (m, 1H), 3.61 (s, 3H), 3.50 (s, 3H), 3.41 (s, 3H), 3.35 (s, 3H), 3.03 (m, 2H), 1.14 (s, 9H). $^{13}$C NMR (75 MHz, CDCl$_3$) δ 155.5, 151.1, 148.1, 146.1, 145.9, 145.7, 145.0, 136.7, 135.7, 135.4, 135.1, 133.4, 129.9, 129.6, 128.6, 128.2, 128.0, 127.8, 127.7, 127.5, 127.2, 126.4, 123.3, 120.6, 120.3, 115.2, 115.1, 113.4, 112.0, 109.2, 105.4, 105.0, 95.6, 71.0, 56.2, 55.7, 55.4, 55.2, 42.4, 28.6, 26.7, 19.8. MS (ESI) m/z: 875 (M+1)$^+$. Rf: 0.45 (hexane:dichloromethane:Et$_2$O, 5:5:2).

Compound 238

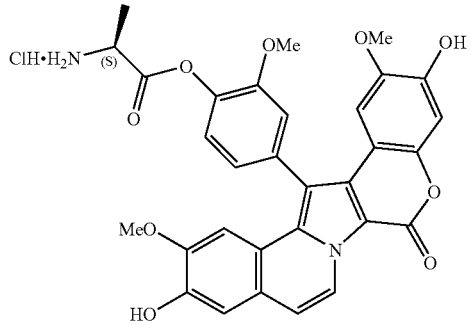

General Procedure C (starting from the corresponding protected lamellarin) to afford 238 as a yellow solid (5 mg, 15%).

$^1$H NMR (300 MHz, CD$_3$OD) δ 9.10 (d, J=7.3 Hz, 1H), 7.43 (d, J=7.3 Hz, 1H), 7.40 (d, J=1.9 Hz, 1H), 7.30 (dd, J=7.3, 1.9 Hz, 1H), 7.16 (s, 1H), 7.14-7.12 (m, 2H), 6.86 (s, 1H), 6.73 (d, J=7.3 Hz, 1H), 4.61 (br s, 1H), 3.84 (s, 3H), 3.49 (s, 6H), 1.63 (d, J=7.3 Hz, 1H). MS (ESI) m/z: 572 (M+1)$^+$.

Compound 239

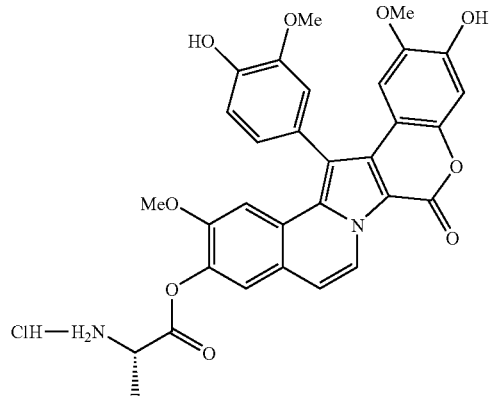

To a solution of 234 (10 mg, 0.016 mmol) in anhydrous THF (1 mL) at −78° C., 0.03 mL of a 1M TBAF solution in THF and 0.7M acetic acid solution were added. The mixture was stirred for 15 min at −78° C. Sodium bicarbonate saturated solution was added (5 drops), the mixture was diluted with dichloromethane (2 mL), dried over sodium sulfate and concentrated to dryness. To the resulting residue, a cold 3.0M solution of HCl in ethyl acetate (1 mL) was added and the mixture was stirred at 0° C. for 1 hour. The reaction was concentrated and the residue was washed with hexane and dichloromethane to afford 239 as a white solid (4 mg, 63% yield).

$^1$H NMR (300 MHz, CD$_3$OD) δ 8.99 (d, J=7.8 Hz, 1H), 7.50 (d, J=2.0 Hz, 1H), 7.48 (d, J=8.8 Hz, 1H), 7.30 (dd, J=2.0, 7.8 Hz, 1H), 7.15-7.00 (m, 3H), 6.77 (s, 1H), 6.68 (d, J=7.3 Hz, 1H), 4.52 (q, J=7.3 Hz, 1H), 3.89 (s, 3H), 3.50 (s, 3H), 3.56 (s, 3H), 3.49 (s, 3H), 1.81 (d, J=7.3 Hz, 3H). MS (ESI) m/z: 571 (M+1)$^+$.

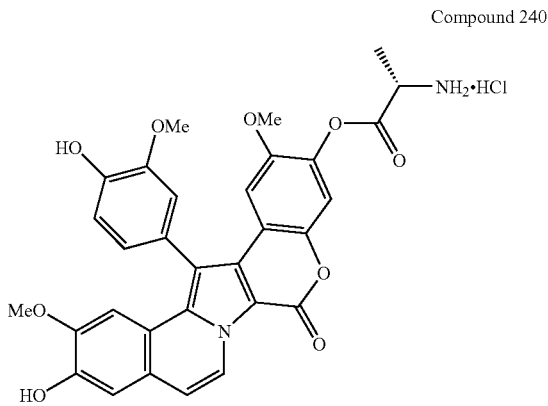

Compound 240

To a solution of the corresponding protected lamellarin (47 mg, 0.047 mmol) in anhydrous THF (5 mL) at −78° C., 0.14 mL of a 1M TBAF solution in THF and 0.7M acetic acid solution were added. The mixture was stired 15 min at −78° C. Sodium bicarbonate saturated solution was added (5 drops), the mixture was diluted with dichloromethane (2 mL), dried over sodium sulfate and concentrated to dryness. To the resulting residue, a cold 3.0M solution of HCl in ethyl acetate (1.3 mL) was added and the mixture was stirred at 0° C. for 1 hour. The reaction was concentrated and the residue was washed with hexane and dichloromethane to afford 240 as a white solid (4 mg, 14%).

$^1$H NMR (300 MHz, CD$_3$OD) δ 9.10 (d, J=7.5 Hz, 1H), 7.48 (m, 2H), 7.33 (m, 1H), 7.15 (m, 3H), 6.85 (s, 1H), 6.71 (d, J=7.5 Hz, 1H), 4.51 (m, 1H), 3.87 (s, 3H), 3.50 (s, 3H), 3.49 (s, 3H), 1.80 (d, J=7.3 Hz, 1H). MS (ESI) m/z: 572 (M+1)$^+$.

Example 2

Bioassays for Antitumoral Activity

The finality of these assays is to interrupt the growth of an "in vitro" tumor cell culture by means a continued exhibition of the cells to the sample to be testing.

Cell Lines

| NAME | N° ATCC | SPECIES | TISSUE | CHARACTERISTICS |
|---|---|---|---|---|
| K-562 | CCL-243 | human | leukemia | erythroleukemia (pleural effusion) |
| A-549 | CCL-185 | human | lung | lung carcinoma "NSCL" |
| SK-MEL-28 | HTB-72 | human | melanoma | malignant melanoma |
| HT-29 | HTB-38 | human | colon | colon adenocarcinoma |
| LoVo | CCL-229 | human | colon | colon adenocarcinoma |
| LoVo-Dox | | human | colon | colon adenocarcinoma (MDR) |
| DU-145 | HTB-81 | human | prostate | prostate carcinoma, not androgen receptors |
| LNCaP | CRL-1740 | human | prostate | prostate adenocarcinoma, with androgen receptors |
| SK-BR-3 | HTB-30 | human | breast | breast adenocarcinoma, Her2/neu+, (pleural effusion) |
| IGROV | | human | ovary | ovary adenocarcinoma |
| IGROV-ET | | human | ovary | ovary adenocarcinoma, characterized as ET-743 resistant cells |
| HeLa | CCL-2 | human | cervix | cervix epitheloid carcinoma |
| HeLa-APL | CCL-3 | human | cervix | cervix epitheloid carcinoma, characterized as aplidine resistant cells |
| PANC-1 | CRL-1469 | human | pancreas | pancreatic epitheloid carcinoma |

Inhibition of Cell Growth by Colorimetric Assay.

A colorimetric type of assay, using sulforhodamine B (SRB) reaction has been adapted for a quantitative measurement of cell growth and viability (following the technique described by P. A. Skehan, et al., *J. Natl. Cancer Inst.* 1990, 82, 1107-1112).

This form of assay employs 96 well cell culture microplates of 9 mm diameter (T. Mosmann et al., *J. of Immunological Methods* 1983, 65, 55-63; G. T. Faircloth et al., *J. of Tissue and Culture Methods* 1988, 11, 201-205).

Most of the cell lines are obtained from American Type Culture Collection (ATCC) derived from different human cancer types.

The values for mean +/− SD of data from triplicate wells are calculated. Some parameters for cellular responses can be calculated: GI=growth inhibition, TGI=total growth inhibition (cytostatic effect) and LC=cell killing (cytotoxic effect).

Tables 1 illustrates data on the biological activity of the compounds of the present invention.

TABLE 1

| | | Activity data (Molar) | | | | | | | |
|---|---|---|---|---|---|---|---|---|---|
| | | DU-145 | LN-caP | SKOV-3 | IGROV | IGROV-ET | SK-BR-3 | MEL-28 | H-MEC-1 |
| 1 | GI50 | 8.24E−06 | 2.77E−07 | 1.37E−05 | 4.93E−07 | 4.44E−07 | 2.37E−06 | 2.24E−06 | 6.06E−07 |
| | TGI | 1.18E−05 | 1.44E−06 | 1.88E−05 | 1.76E−06 | 1.20E−06 | 1.09E−05 | 5.04E−06 | 1.38E−06 |
| | LC50 | 1.70E−05 | 7.85E−06 | 1.88E−05 | 1.88E−05 | 1.88E−05 | 1.88E−05 | 1.13E−05 | 5.72E−06 |
| 2 | GI50 | 6.40E−08 | 7.27E−08 | 1.40E−07 | 8.80E−07 | 1.98E−06 | 3.14E−07 | 3.02E−07 | 6.65E−07 |
| | TGI | 1.40E−07 | 3.98E−07 | 5.10E−06 | 5.17E−06 | 8.12E−06 | 2.36E−06 | 3.66E−06 | 1.89E−05 |
| | LC50 | 1.89E−05 | 1.44E−06 | 1.89E−05 | 1.89E−05 | 1.89E−05 | 1.88E−05 | 1.89E−05 | 1.89E−05 |
| 3 | GI50 | 1.90E−08 | 1.23E−07 | 5.37E−08 | 2.36E−07 | 2.14E−07 | 1.06E−07 | 8.81E−08 | 1.13E−07 |
| | TGI | 7.97E−08 | 3.98E−07 | 2.40E−07 | 1.06E−06 | 1.16E−06 | 7.67E−07 | 1.77E−06 | 3.14E−06 |
| | LC50 | 2.00E−05 | 1.06E−06 | 1.58E−05 | 2.00E−05 | 2.00E−05 | 7.69E−06 | 1.13E−05 | 1.55E−05 |

TABLE 1-continued

Activity data (Molar)

|   |      |          |          |          |          |          |          |          |          |
|---|------|----------|----------|----------|----------|----------|----------|----------|----------|
| 4 | GI50 | 2.18E−07 | 3.32E−07 |          | 4.02E−07 | 5.99E−07 | 3.38E−07 |          |          |
|   | TGI  | 6.67E−07 | 7.85E−07 |          | 2.00E−06 | 1.64E−06 | 7.03E−07 |          |          |
|   | LC50 | 2.14E−06 | 1.85E−06 |          | 1.13E−05 | 1.31E−05 | 1.47E−06 |          |          |
| 5 | GI50 | 3.56E−08 | 2.23E−07 |          | 2.47E−07 | 2.12E−07 | 2.41E−07 | 6.29E−08 |          |
|   | TGI  | 1.19E−07 | 1.05E−06 |          | 8.55E−07 | 1.06E−06 | 5.95E−07 | 2.49E−07 |          |
|   | LC50 | 5.75E−07 | 3.62E−06 |          | 4.54E−06 | 6.09E−06 | 3.54E−06 | 1.12E−06 |          |
| 6 | GI50 | 3.55E−07 | 5.78E−07 |          | 9.63E−07 | 1.39E−06 | 5.48E−07 | 3.86E−07 |          |
|   | TGI  | 1.46E−06 | 7.96E−06 |          | 7.96E−06 | 7.96E−06 | 2.56E−06 | 1.74E−06 |          |
|   | LC50 | 7.96E−06 | 7.96E−06 |          | 7.96E−06 | 7.96E−06 | 7.96E−06 | 7.96E−06 |          |
| 7 | GI50 | 9.93E−07 | 4.25E−07 |          | 1.23E−06 | 1.86E−06 | 1.14E−06 | 6.52E−07 |          |
|   | TGI  | 2.31E−06 | 1.36E−06 |          | 2.67E−06 | 4.58E−06 | 2.61E−06 | 1.64E−06 |          |
|   | LC50 | 5.41E−06 | 3.61E−06 |          | 5.79E−06 | 8.14E−06 | 5.98E−06 | 3.75E−06 |          |
| 8 | GI50 | 7.03E−07 | 6.54E−07 |          | 4.45E−07 | 3.35E−06 | 9.15E−07 | 4.07E−07 |          |
|   | TGI  | 2.60E−06 | 2.47E−06 |          | 2.17E−06 | 1.12E−05 | 3.04E−06 | 2.20E−06 |          |
|   | LC50 | 9.43E−06 | 7.21E−06 |          | 1.12E−05 | 1.12E−05 | 9.19E−06 | 1.12E−05 |          |
| 9 | GI50 | 5.43E−08 | 1.74E−07 |          | 1.82E−07 | 1.32E−07 | 1.74E−07 | 1.34E−07 |          |
|   | TGI  | 1.69E−07 | 4.22E−07 |          | 9.09E−07 | 9.80E−07 | 3.74E−07 | 5.16E−07 |          |
|   | LC50 | 6.15E−07 | 1.38E−06 |          | 3.00E−06 | 4.93E−07 | 8.06E−07 | 2.11E−06 |          |
| 11| GI50 | 3.53E−08 |          |          | 2.67E−07 | 5.53E−06 | 1.87E−07 | 2.00E−07 |          |
|   | TGI  | 1.51E−07 |          |          | 1.14E−06 | 1.11E−05 | 1.20E−06 | 1.18E−06 |          |
|   | LC50 | 2.78E−06 |          |          | 5.88E−06 | 1.11E−05 | 6.66E−06 | 6.18E−06 |          |
| 12| GI50 | 2.49E−07 |          |          | 1.42E−06 | 1.09E−05 | 6.98E−07 | 1.77E−06 |          |
|   | TGI  | 1.43E−06 |          |          | 3.38E−06 | 1.09E−05 | 3.45E−06 | 5.98E−06 |          |
|   | LC50 | 7.07E−06 |          |          | 8.01E−06 | 1.09E−05 | 1.09E−05 | 1.09E−05 |          |
| 13| GI50 | 8.32E−07 |          |          | 1.29E−06 | 1.96E−06 | 4.54E−08 | 3.11E−06 |          |
|   | TGI  | 3.64E−06 |          |          | 4.79E−06 | 7.86E−06 | 1.13E−07 | 1.09E−05 |          |
|   | LC50 | 1.24E−05 |          |          | 1.24E−05 | 1.24E−05 | 1.02E−05 | 1.24E−05 |          |
| 14| GI50 | 5.17E−07 |          |          | 4.90E−07 | 7.45E−07 | 4.24E−08 | 1.42E−06 |          |
|   | TGI  | 2.19E−06 |          |          | 2.44E−06 | 4.97E−06 | 9.88E−08 | 1.40E−05 |          |
|   | LC50 | 1.40E−05 |          |          | 1.40E−05 | 1.40E−05 | 1.40E−05 | 1.40E−05 |          |

|   |      | A-549    | K-562    | PANC-1   | HT-29    | LOVO     | LOVO-DOX | HELA     | HELA-APL |
|---|------|----------|----------|----------|----------|----------|----------|----------|----------|
| 1 | GI50 | 1.88E−06 | 8.15E−07 | 2.20E−06 | 1.88E−05 | 1.18E−05 | 8.01E−07 |          |          |
|   | TGI  | 1.88E−06 | 2.11E−06 | 7.94E−06 | 1.88E−05 | 5.76E−05 | 7.13E−06 |          |          |
|   | LC50 | 1.88E−06 | 2.97E−06 | 1.88E−05 | 1.88E−05 | 1.88E−05 | 1.88E−05 |          |          |
| 2 | GI50 | 6.74E−07 | 1.17E−07 | 9.88E−07 | 8.31E−06 | 3.98E−07 | 6.04E−07 |          |          |
|   | TGI  | 1.89E−05 | 2.25E−06 | 6.97E−06 | 1.89E−05 | 3.02E−06 | 3.83E−06 |          |          |
|   | LC50 | 1.89E−05 | 1.89E−05 | 1.89E−05 | 1.89E−05 | 1.60E−05 | 1.89E−05 |          |          |
| 3 | GI50 | 2.04E−08 | 8.69E−08 | 2.48E−07 | 5.33E−06 | 3.98E−07 | 4.20E−07 |          |          |
|   | TGI  | 1.14E−06 | 7.91E−07 | 2.20E−06 | 1.90E−05 | 9.65E−06 | 1.67E−06 |          |          |
|   | LC50 | 1.55E−05 | 8.15E−06 | 2.00E−05 | 2.00E−05 | 2.00E−06 | 2.00E−05 |          |          |
| 4 | GI50 | 5.43E−07 | 3.96E−07 | 4.80E−07 | 2.50E−06 | 4.68E−07 | 2.00E−06 | 3.38E−07 | 2.38E−07 |
|   | TGI  | 1.21E−06 | 9.37E−07 | 1.34E−06 | 6.03E−06 | 1.08E−06 | 5.95E−06 | 6.85E−07 | 6.81E−07 |
|   | LC50 | 1.00E−05 | 4.44E−06 | 5.99E−06 | 1.46E−05 | 4.36E−06 | 1.78E−05 | 1.39E−06 | 1.95E−06 |
| 5 | GI50 | 1.21E−07 | 7.70E−08 | 4.18E−07 | 1.70E−06 | 3.45E−07 | 4.09E−07 | 1.24E−07 | 3.10E−07 |
|   | TGI  | 1.02E−06 | 1.10E−06 | 1.64E−06 | 3.24E−06 | 1.06E−06 | 1.10E−06 | 1.12E−06 | 1.71E−06 |
|   | LC50 | 4.65E−06 | 7.40E−06 | 4.51E−06 | 6.16E−06 | 4.14E−06 | 3.40E−06 | 3.10E−06 | 5.55E−06 |
| 6 | GI50 | 4.97E−07 | 4.82E−07 | 2.46E−06 | 7.96E−06 | 2.79E−06 | 3.84E−06 | 5.84E−07 | 3.41E−06 |
|   | TGI  | 7.96E−06 | 5.38E−06 | 7.96E−06 | 7.96E−06 | 7.96E−06 | 7.96E−06 | 7.96E−06 | 7.96E−06 |
|   | LC50 | 7.96E−06 | 7.96E−06 | 7.96E−06 | 7.96E−06 | 7.96E−06 | 7.96E−06 | 7.96E−06 | 7.96E−06 |
| 7 | GI50 | 9.69E−07 | 5.96E−07 | 1.36E−06 | 8.71E−07 | 2.00E−06 | 3.66E−06 | 8.30E−07 | 1.85E−06 |
|   | TGI  | 2.96E−06 | 2.68E−06 | 3.31E−06 | 3.31E−06 | 5.05E−06 | 8.14E−06 | 1.91E−06 | 3.66E−06 |
|   | LC50 | 8.14E−06 | 8.14E−06 | 8.04E−06 | 8.14E−06 | 8.14E−06 | 8.14E−06 | 4.42E−06 | 7.24E−06 |
| 8 | GI50 | 7.44E−07 | 2.25E−07 | 2.31E−07 | 3.77E−07 | 1.48E−06 | 8.34E−06 | 2.76E−07 | 7.30E−06 |
|   | TGI  | 6.34E−06 | 1.57E−06 | 8.65E−07 | 1.12E−05 | 4.68E−06 | 1.12E−05 | 1.41E−06 | 1.12E−05 |
|   | LC50 | 1.12E−05 | 7.49E−06 | 1.12E−05 | 1.12E−05 | 1.12E−05 | 1.12E−05 | 7.92E−06 | 1.12E−05 |
| 9 | GI50 | 3.23E−07 | 4.73E−08 | 2.00E−07 | 1.61E−06 | 2.43E−07 | 3.88E−07 | 1.07E−07 | 2.82E−07 |
|   | TGI  | 1.15E−06 | 3.11E−07 | 1.56E−06 | 3.28E−06 | 5.84E−07 | 1.14E−06 | 4.59E−07 | 1.23E−06 |
|   | LC50 | 6.76E−06 | 4.18E−06 | 4.91E−06 | 6.66E−06 | 2.30E−06 | 3.63E−06 | 4.06E−06 | 3.83E−06 |
| 11| GI50 | 1.28E−07 |          | 2.14E−07 | 3.84E−08 | 4.24E−08 | 1.11E−05 | 2.08E−07 | 5.23E−06 |
|   | TGI  | 1.54E−06 |          | 1.76E−06 | 1.75E−07 | 1.16E−06 | 1.11E−05 | 1.35E−06 | 1.11E−05 |
|   | LC50 | 1.11E−05 |          | 1.11E−05 | 8.23E−06 | 1.04E−05 | 1.11E−05 | 1.11E−05 | 1.11E−05 |
| 12| GI50 | 1.20E−06 |          | 1.62E−06 | 8.11E−08 | 1.83E−06 | 1.09E−05 | 1.66E−06 | 3.66E−06 |
|   | TGI  | 6.64E−06 |          | 8.94E−06 | 8.41E−07 | 7.41E−06 | 1.09E−05 | 7.50E−06 | 1.09E−05 |
|   | LG50 | 1.09E−05 |          | 1.09E−05 | 1.09E−05 | 1.09E−05 | 1.09E−05 | 1.09E−05 | 1.09E−05 |
| 13| GI50 | 9.06E−07 |          | 2.43E−06 | 3.22E−06 | 7.54E−06 | 6.75E−06 | 1.83E−06 | 2.60E−06 |
|   | TGI  | 1.24E−05 |          | 1.24E−05 | 6.39E−06 | 2.35E−06 | 3.42E−06 | 9.63E−06 | 1.21E−05 |
|   | LC50 | 1.24E−05 |          | 1.24E−05 | 1.24E−05 | 9.02E−06 | 1.24E−05 | 1.24E−05 | 1.24E−05 |
| 14| GI50 | 5.55E−07 |          | 1.18E−06 | 2.47E−06 | 5.97E−07 | 4.97E−07 | 1.83E−06 | 2.60E−06 |
|   | TGI  | 1.40E−05 |          | 1.40E−05 | 7.26E−06 | 2.47E−06 | 1.45E−06 | 9.63E−06 | 1.21E−05 |
|   | LC50 | 1.40E−05 |          | 1.40E−05 | 1.40E−05 | 1.40E−05 | 1.40E−05 | 1.24E−05 | 1.24E−05 |

TABLE 1-continued

Activity data (Molar)

|    |      | DU-145   | LN-caP   | SKOV-3   | IGROV    | IGROV-ET | SK-BR-3  | MEL-28   | H-MEC-1  |
|----|------|----------|----------|----------|----------|----------|----------|----------|----------|
| 15 | GI50 | 6.85E-08 | 5.60E-08 |          | 8.62E-08 | 6.87E-06 | 5.61E-08 | 4.82E-08 |          |
|    | TGI  | 3.08E-06 | 6.09E-07 |          | 2.03E-06 | 1.10E-05 | 6.35E-07 | 1.64E-06 |          |
|    | LC50 | 1.10E-05 | 3.93E-06 |          | 9.76E-06 | 1.10E-05 | 5.84E-06 | 7.24E-06 |          |
| 16 | GI50 | 5.27E-08 | 1.31E-07 |          | 2.26E-07 | 2.78E-07 | 2.07E-07 | 1.38E-07 |          |
|    | TGI  | 2.98E-07 | 2.65E-07 |          | 4.78E-07 | 5.00E-07 | 4.11E-07 | 3.04E-07 |          |
|    | LC50 | 2.80E-06 | 5.34E-07 |          | 1.59E-06 | 8.97E-07 | 8.16E-07 | 6.69E-07 |          |
| 17 | GI50 | 4.87E-08 | 1.32E-07 |          | 1.05E-07 | 1.62E-07 | 8.03E-08 | 5.18E-08 |          |
|    | TGI  | 2.28E-07 | 2.81E-07 |          | 4.05E-07 | 5.44E-07 | 2.86E-07 | 1.71E-07 |          |
|    | LC50 | 2.30E-06 | 5.99E-07 |          | 4.93E-06 | 8.78E-06 | 1.22E-06 | 7.66E-07 |          |
| 18 | GI50 | 5.05E-07 | 3.59E-07 | 1.22E-06 | 1.31E-06 | 2.00E-06 | 4.58E-07 | 5.24E-07 | 4.94E-07 |
|    | TGI  | 1.41E-06 | 1.27E-06 | 2.82E-06 | 3.21E-06 | 5.14E-06 | 2.14E-06 | 1.44E-06 | 8.46E-07 |
|    | LC50 | 7.04E-06 | 4.27E-06 | 6.51E-06 | 7.91E-06 | 1.23E-05 | 1.05E-05 | 4.43E-06 | 2.93E-06 |
| 19 | GI50 | 5.32E-07 | 9.41E-08 | 7.58E-07 | 4.06E-07 | 7.61E-07 | 1.65E-07 | 2.73E-07 | 8.07E-07 |
|    | TGI  | 2.16E-06 | 1.41E-06 | 2.31E-06 | 2.51E-06 | 2.54E-06 | 2.28E-06 | 1.53E-06 | 2.42E-06 |
|    | LC50 | 6.85E-06 | 5.37E-06 | 6.57E-06 | 9.34E-06 | 1.13E-05 | 1.40E-05 | 4.99E-06 | 7.16E-06 |
| 20 | GI50 | 5.00E-07 |          |          | 5.16E-06 | 5.93E-06 | 5.48E-08 | 2.24E-06 |          |
|    | TGI  | 2.36E-06 |          |          | 7.46E-06 | 1.53E-05 | 2.38E-07 | 1.53E-05 |          |
|    | LC50 | 1.53E-05 |          |          | 1.53E-05 | 1.53E-05 | 1.53E-05 | 1.53E-05 |          |
| 21 | GI50 | 3.53E-07 | 1.90E-07 | 8.49E-07 | 3.15E-07 | 9.01E-07 | 3.42E-07 | 2.87E-07 | 2.81E-07 |
|    | TGI  | 7.03E-07 | 3.83E-07 | 1.17E-05 | 6.64E-07 | 5.18E-06 | 5.99E-07 | 4.97E-07 | 5.09E-07 |
|    | LC50 | 1.17E-05 | 7.75E-07 | 1.17E-05 | 9.02E-06 | 1.17E-05 | 1.17E-05 | 8.60E-07 | 9.22E-07 |
| 22 | GI50 | 7.43E-07 | 5.64E-07 | 2.01E-07 | 7.87E-07 | 2.89E-06 | 2.57E-07 | 3.32E-07 | 8.56E-07 |
|    | TGI  | 8.10E-06 | 1.82E-06 | 2.22E-06 | 8.54E-06 | 1.36E-05 | 1.81E-06 | 3.56E-06 | 2.91E-06 |
|    | LC50 | 1.36E-05 | 1.36E-05 | 1.36E-05 | 1.36E-05 | 1.36E-05 | 7.16E-06 | 1.36E-05 | 1.04E-05 |
| 23 | GI50 | 1.76E-07 | 1.68E-07 | 1.18E-08 | 3.30E-07 | 1.86E-06 | 3.91E-08 | 6.99E-08 | 2.19E-07 |
|    | TGI  | 1.62E-06 | 5.34E-07 | 3.20E-07 | 1.92E-06 | 5.82E-06 | 3.03E-06 | 8.15E-06 | 6.87E-06 |
|    | LC50 | 5.82E-06 | 2.34E-06 | 1.97E-06 | 5.82E-06 | 5.82E-06 | 2.85E-06 | 3.09E-06 | 2.87E-06 |
| 24 | GI50 | 9.13E-07 | 9.34E-07 | 1.67E-06 | 1.23E-06 | 1.31E-06 | 6.53E-07 | 1.38E-06 | 8.06E-07 |
|    | TGI  | 2.94E-06 | 1.91E-06 | 3.39E-06 | 4.82E-06 | 7.13E-06 | 1.93E-06 | 2.81E-06 | 2.20E-06 |
|    | LC50 | 7.13E-06 | 3.89E-06 | 6.90E-06 | 7.13E-06 | 7.13E-06 | 5.58E-06 | 5.74E-06 | 5.97E-06 |
| 26 | GI50 | 6.11E-07 | 7.11E-07 | 8.74E-07 | 5.04E-07 | 5.74E-07 | 9.66E-08 | 2.08E-06 | 7.98E-07 |
|    | TGI  | 2.94E-06 | 4.30E-06 | 5.53E-06 | 2.30E-06 | 2.08E-06 | 1.09E-06 | 7.79E-06 | 1.95E-05 |
|    | LC50 | 1.95E-05 | 1.47E-05 | 1.95E-05 | 1.30E-05 | 1.95E-05 | 1.36E-06 | 1.95E-05 | 1.95E-05 |
| 27 | GI50 | 9.76E-07 |          |          | 1.15E-06 | 1.04E-05 | 8.81E-07 | 4.47E-06 |          |
|    | TGI  | 3.95E-06 |          |          | 5.06E-06 | 1.52E-05 | 3.25E-06 | 9.35E-06 |          |
|    | LC50 | 1.26E-05 |          |          | 1.52E-05 | 1.52E-05 | 1.41E-05 | 1.52E-05 |          |
| 28 | GI50 | 3.15E-07 |          |          | 1.64E-06 | 1.14E-05 | 9.41E-07 | 2.24E-06 |          |
|    | TGI  | 1.47E-06 |          |          | 3.97E-06 | 1.14E-05 | 4.73E-06 | 7.28E-06 |          |
|    | LC50 | 7.32E-06 |          |          | 9.61E-06 | 1.14E-05 | 1.14E-05 | 1.14E-05 |          |

|    |      | A-549    | K-562    | PANC-1   | HT-29    | LOVO     | LOVO-DOX | HELA     | HELA-APL |
|----|------|----------|----------|----------|----------|----------|----------|----------|----------|
| 15 | GI50 | 5.41E-08 | 1.60E-06 | 1.54E-06 | 4.73E-08 | 1.68E-06 | 1.10E-05 | 5.79E-08 | 2.43E-06 |
|    | TGI  | 1.46E-06 | 3.91E-06 | 5.26E-06 | 1.11E-07 | 4.96E-06 | 1.10E-05 | 1.41E-06 | 5.53E-06 |
|    | LC50 | 1.10E-05 | 9.57E-06 | 1.10E-05 | 9.17E-06 | 1.10E-05 | 1.10E-05 | 7.81E-06 | 1.10E-05 |
| 16 | GI50 | 1.78E-07 | 1.83E-07 | 2.41E-07 | 4.11E-07 | 1.96E-07 | 4.20E-07 | 1.93E-07 | 2.29E-07 |
|    | TGI  | 5.02E-07 | 4.45E-07 | 7.56E-07 | 9.31E-07 | 3.47E-07 | 1.03E-06 | 3.68E-07 | 5.20E-07 |
|    | LC50 | 3.05E-06 | 2.23E-06 | 3.34E-06 | 5.00E-06 | 6.12E-07 | 4.42E-06 | 7.03E-07 | 2.38E-06 |
| 17 | GI50 | 2.07E-07 | 5.36E-08 | 2.06E-07 | 3.42E-07 | 2.16E-07 | 3.84E-07 | 1.09E-07 | 1.19E-07 |
|    | TGI  | 6.63E-07 | 2.77E-07 | 1.52E-06 | 6.86E-07 | 4.20E-07 | 1.33E-06 | 3.59E-07 | 3.53E-07 |
|    | LC50 | 8.48E-06 | 2.50E-06 | 8.53E-06 | 8.78E-06 | 8.16E-07 | 5.29E-06 | 8.78E-07 | 1.85E-06 |
| 18 | GI50 | 1.61E-06 | 5.58E-07 | 9.92E-07 | 8.19E-07 | 6.64E-07 | 1.08E-06 |          |          |
|    | TGI  | 4.00E-06 | 1.51E-06 | 3.70E-06 | 4.54E-06 | 2.37E-06 | 3.67E-06 |          |          |
|    | LC50 | 9.99E-06 | 8.64E-06 | 1.23E-05 | 1.23E-05 | 1.23E-05 | 1.21E-05 |          |          |
| 19 | GI50 | 6.05E-07 | 1.84E-06 | 2.45E-07 | 1.09E-07 | 7.22E-07 | 8.74E-07 |          |          |
|    | TGI  | 2.13E-06 | 4.62E-06 | 2.42E-06 | 2.10E-06 | 2.33E-06 | 2.72E-06 |          |          |
|    | LC50 | 6.32E-06 | 1.16E-05 | 9.50E-06 | 7.29E-06 | 6.60E-06 | 8.03E-06 |          |          |
| 20 | GI50 | 5.89E-07 |          | 1.24E-06 | 3.58E-06 | 4.36E-06 | 5.25E-07 | 1.17E-06 | 2.09E-06 |
|    | TGI  | 1.53E-05 |          | 1.53E-05 | 1.53E-05 | 8.83E-06 | 2.06E-06 | 1.53E-05 | 1.53E-05 |
|    | LC50 | 1.53E-05 |          | 1.53E-05 | 1.53E-05 | 1.53E-05 | 1.53E-05 | 1.53E-05 | 1.53E-05 |
| 21 | GI50 | 1.39E-06 | 2.86E-07 | 5.14E-07 | 5.12E-07 | 1.95E-06 | 4.97E-06 |          |          |
|    | TGI  | 4.62E-06 | 5.82E-07 | 1.81E-06 | 1.17E-05 | 4.97E-06 | 1.17E-05 |          |          |
|    | LC50 | 1.17E-05 | 2.39E-06 | 1.17E-05 | 1.17E-05 | 1.17E-05 | 1.17E-05 |          |          |
| 22 | GI50 | 8.90E-07 | 6.70E-07 | 9.76E-07 | 8.79E-07 | 4.84E-07 | 6.59E-06 |          |          |
|    | TGI  | 7.73E-06 | 4.77E-06 | 1.36E-05 | 1.36E-05 | 2.49E-06 | 1.36E-05 |          |          |
|    | LC50 | 1.36E-05 | 1.36E-05 | 1.36E-05 | 1.36E-05 | 1.36E-05 | 1.36E-05 |          |          |
| 23 | GI50 | 2.43E-07 | 2.48E-07 | 4.20E-07 | 2.90E-07 | 2.02E-07 | 1.61E-06 |          |          |
|    | TGI  | 3.24E-06 | 1.01E-06 | 3.33E-06 | 5.82E-06 | 1.40E-06 | 4.70E-06 |          |          |
|    | LC50 | 5.82E-06 | 3.36E-06 | 5.82E-06 | 5.82E-06 | 5.82E-06 | 5.82E-06 |          |          |
| 24 | GI50 | 1.55E-06 | 6.80E-07 | 1.34E-06 | 7.13E-06 | 7.49E-07 | 8.91E-07 |          |          |
|    | TGI  | 3.37E-06 | 1.91E-06 | 6.23E-06 | 7.13E-06 | 1.78E-06 | 3.66E-06 |          |          |
|    | LC50 | 7.13E-06 | 5.30E-06 | 7.13E-06 | 7.13E-06 | 4.28E-06 | 7.13E-06 |          |          |
| 26 | GI50 | 1.11E-06 | 7.85E-07 | 1.07E-06 | 9.17E-06 | 1.19E-06 | 8.67E-07 |          |          |
|    | TGI  | 8.10E-06 | 3.41E-06 | 8.80E-06 | 1.95E-05 | 1.00E-05 | 7.63E-06 |          |          |
|    | LC50 | 1.95E-05 | 1.61E-05 | 1.95E-05 | 1.95E-05 | 1.95E-05 | 1.95E-05 |          |          |

TABLE 1-continued

Activity data (Molar)

| | | | | | | | | | |
|---|---|---|---|---|---|---|---|---|---|
| 27 | GI50 | 5.49E−06 | | 4.41E−06 | 1.44E−07 | 2.70E−07 | 1.52E−05 | 4.04E−06 | 1.30E−05 |
| | TGI | 1.52E−05 | | 1.30E−05 | 2.17E−06 | 2.17E−06 | 1.52E−05 | 9.47E−06 | 1.52E−05 |
| | LC50 | 1.52E−05 | | 1.52E−05 | 1.52E−05 | 1.52E−05 | 1.52E−05 | 1.52E−05 | 1.52E−05 |
| 28 | GI50 | 1.39E−06 | | 1.91E−06 | 1.11E−07 | 6.34E−07 | 1.14E−05 | 2.76E−06 | 9.53E−06 |
| | TGI | 1.14E−05 | | 1.14E−05 | 1.20E−06 | 5.16E−06 | 1.14E−05 | 9.24E−06 | 1.14E−05 |
| | LC50 | 1.14E−05 | | 1.14E−05 | 1.14E−05 | 1.14E−05 | 1.14E−05 | 1.14E−05 | 1.14E−05 |

| | | DU-145 | LN-caP | SKOV-3 | IGROV | IGROV-ET | SK-BR-3 | MEL-28 | H-MEC-1 |
|---|---|---|---|---|---|---|---|---|---|
| 29 | GI50 | 1.98E−07 | 7.04E−08 | 1.79E−06 | 3.67E−07 | 5.65E−06 | 2.42E−07 | 1.55E−06 | 2.42E−08 |
| | TGI | 4.40E−07 | 1.69E−07 | 3.90E−06 | 1.66E−06 | 7.35E−06 | 5.25E−07 | 3.17E−06 | 5.26E−08 |
| | LC50 | 3.90E−06 | 3.96E−07 | 7.35E−06 | 7.35E−06 | 7.35E−06 | 7.03E−06 | 6.45E−06 | 2.90E−07 |
| 30 | GI50 | 5.38E−08 | 2.75E−07 | 3.48E−07 | 3.50E−07 | 4.50E−07 | 4.98E−07 | 2.51E−07 | 7.05E−08 |
| | TGI | 2.65E−07 | 1.27E−06 | 1.24E−06 | 1.47E−06 | 1.83E−06 | 1.61E−06 | 1.08E−06 | 2.41E−07 |
| | LC50 | 3.84E−06 | 4.90E−06 | 5.36E−06 | 6.99E−06 | 6.63E−06 | 6.39E−06 | 4.42E−06 | 8.40E−06 |
| 31 | GI50 | 3.01E−07 | 5.48E−07 | 5.24E−07 | 1.26E−06 | 1.39E−06 | 1.80E−06 | 4.82E−07 | 1.19E−07 |
| | TGI | 8.61E−07 | 1.45E−06 | 4.22E−06 | 7.62E−06 | 4.00E−06 | 7.62E−06 | 7.62E−06 | 2.60E−07 |
| | LC50 | 7.62E−06 | 3.43E−06 | 7.62E−06 | 7.62E−06 | 7.62E−06 | 7.62E−06 | 7.62E−06 | 5.65E−07 |
| 32 | GI50 | 1.11E−07 | 4.29E−07 | 1.86E−06 | 5.61E−07 | 6.66E−07 | 1.30E−06 | 1.35E−06 | 2.76E−07 |
| | TGI | 3.09E−07 | 1.67E−06 | 3.67E−06 | 2.06E−06 | 3.01E−06 | 3.19E−06 | 2.87E−06 | 7.23E−07 |
| | LC50 | 8.57E−07 | 5.08E−06 | 7.27E−06 | 6.12E−06 | 8.76E−06 | 7.82E−06 | 6.13E−06 | 5.37E−06 |
| 33 | GI50 | 1.86E−08 | 3.97E−08 | 3.91E−08 | 4.96E−08 | 7.81E−08 | 3.05E−08 | 4.11E−08 | 9.80E−09 |
| | TGI | 4.60E−08 | 1.55E−07 | 2.28E−07 | 5.00E−07 | 5.89E−07 | 1.68E−07 | 1.98E−07 | 2.14E−08 |
| | LC50 | 3.67E−07 | 4.23E−07 | 5.03E−06 | 4.76E−06 | 8.83E−06 | 1.44E−06 | 2.48E−06 | 4.63E−08 |
| 34 | GI50 | 1.96E−07 | 4.61E−07 | 1.27E−06 | 3.07E−07 | 2.07E−06 | 1.18E−06 | 1.36E−06 | 2.44E−07 |
| | TGI | 5.88E−07 | 1.57E−06 | 2.91E−06 | 2.11E−06 | 4.63E−06 | 3.25E−06 | 2.76E−06 | 6.53E−07 |
| | LC50 | 6.50E−06 | 4.11E−06 | 6.65E−06 | 8.74E−06 | 9.10E−06 | 8.95E−06 | 5.58E−06 | 3.44E−06 |
| 35 | GI50 | 3.21E−08 | 8.81E−08 | 1.13E−07 | 1.52E−07 | 1.92E−07 | 2.28E−07 | 5.46E−08 | 1.97E−08 |
| | TGI | 8.81E−08 | 4.68E−07 | 9.32E−07 | 9.07E−07 | 8.55E−07 | 6.89E−07 | 9.15E−07 | 4.03E−08 |
| | LC50 | 5.76E−07 | 2.22E−06 | 3.83E−06 | 4.05E−06 | 5.45E−06 | 4.03E−06 | 2.77E−06 | 8.26E−08 |
| 36 | GI50 | 1.08E−08 | 4.28E−08 | 3.92E−08 | 4.69E−08 | 7.65E−08 | 3.96E−08 | 3.19E−08 | 2.65E−09 |
| | TGI | 3.83E−08 | 1.56E−07 | 2.97E−07 | 4.09E−07 | 5.40E−07 | 2.21E−07 | 1.81E−07 | 8.60E−09 |
| | LC50 | 6.68E−07 | 4.24E−07 | 5.89E−06 | 7.95E−06 | 8.78E−06 | 2.94E−06 | 2.70E−06 | 1.35E−06 |
| 37 | GI50 | 6.77E−08 | 5.93E−07 | 1.62E−06 | 5.77E−07 | 3.59E−07 | 5.76E−08 | 6.23E−07 | 9.74E−08 |
| | TGI | 1.55E−06 | 2.18E−06 | 3.58E−06 | 2.17E−06 | 2.11E−06 | 2.12E−06 | 2.68E−06 | 1.26E−06 |
| | LC50 | 5.62E−06 | 5.05E−06 | 7.87E−06 | 5.89E−06 | 8.04E−06 | 1.06E−05 | 7.95E−06 | 4.73E−06 |
| 38 | GI50 | 5.12E−08 | 1.52E−07 | 6.84E−07 | 2.44E−07 | 1.29E−06 | 4.48E−07 | 1.65E−07 | 8.09E−08 |
| | TGI | 9.11E−06 | 5.09E−07 | 7.42E−06 | 1.07E−06 | 4.51E−06 | 4.08E−06 | 5.20E−07 | 9.11E−07 |
| | LC50 | 9.11E−06 | 3.90E−06 | 9.11E−06 | 9.11E−06 | 9.11E−06 | 9.11E−06 | 9.11E−06 | 9.11E−06 |
| 39 | GI50 | 1.80E−08 | 2.79E−06 | 6.34E−08 | 3.41E−08 | 5.50E−08 | 5.45E−08 | 3.39E−08 | 6.98E−09 |
| | TGI | 1.42E−07 | 2.52E−07 | 8.47E−06 | 9.31E−07 | 3.69E−07 | 1.46E−06 | 2.95E−07 | 8.47E−06 |
| | LC50 | 8.47E−06 | 8.47E−06 | 8.47E−06 | 8.47E−06 | 8.47E−06 | 8.47E−06 | 8.47E−06 | 8.47E−06 |
| 40 | GI50 | 1.62E−08 | 1.30E−07 | 2.84E−08 | 4.49E−08 | 8.52E−08 | 8.16E−07 | 4.12E−08 | |
| | TGI | 9.40E−08 | 4.47E−07 | 1.07E−07 | 3.91E−07 | 5.57E−07 | 3.25E−06 | 5.95E−07 | |
| | LC50 | 9.48E−06 | 4.38E−06 | 9.48E−06 | 5.04E−06 | 9.48E−06 | 9.48E−06 | 9.48E−06 | |
| 41 | GI50 | 6.79E−07 | 2.10E−06 | 5.95E−06 | 9.17E−08 | 1.88E−07 | 1.62E−06 | 1.86E−06 | |
| | TGI | 9.87E−06 | 6.47E−06 | 9.87E−06 | 4.92E−07 | 8.52E−07 | 4.85E−06 | 4.19E−06 | |
| | LC50 | 9.87E−06 | 9.87E−06 | 9.87E−06 | 4.70E−06 | 9.87E−06 | 9.87E−06 | 9.43E−06 | |
| 42 | GI50 | 3.65E−07 | 3.77E−07 | 1.24E−06 | 1.85E−07 | 2.38E−07 | 2.00E−06 | 1.23E−06 | |
| | TGI | 2.28E−06 | 1.41E−06 | 4.44E−06 | 5.60E−07 | 6.78E−07 | 4.01E−06 | 3.32E−06 | |
| | LC50 | 9.46E−06 | 4.91E−06 | 9.46E−06 | 2.83E−06 | 6.62E−06 | 8.04E−06 | 8.94E−06 | |

| | | A-549 | K-562 | PANC-1 | HT-29 | LOVO | LOVO-DOX |
|---|---|---|---|---|---|---|---|
| 29 | GI50 | 1.73E−06 | 4.81E−07 | 9.78E−07 | 1.84E−06 | 2.91E−06 | 7.35E−06 |
| | TGI | 3.63E−06 | 3.46E−06 | 4.23E−06 | 5.08E−06 | 7.35E−06 | 7.35E−06 |
| | LC50 | 7.35E−06 | 7.35E−06 | 7.35E−06 | 7.35E−06 | 7.35E−06 | 7.35E−06 |
| 30 | GI50 | 3.41E−07 | 2.04E−07 | 8.05E−07 | 2.81E−06 | 3.83E−07 | 6.83E−07 |
| | TGI | 1.27E−06 | 1.10E−06 | 2.18E−06 | 5.06E−06 | 1.06E−06 | 1.93E−06 |
| | LC50 | 6.64E−06 | 8.60E−06 | 5.64E−06 | 8.60E−06 | 3.77E−06 | 5.22E−06 |
| 31 | GI50 | 4.33E−07 | 4.10E−07 | 1.96E−06 | 7.62E−06 | 1.98E−06 | 1.49E−06 |
| | TGI | 1.42E−06 | 2.47E−06 | 7.62E−06 | 7.62E−06 | 5.35E−06 | 7.62E−06 |
| | LC50 | 4.60E−06 | 7.62E−06 | 7.62E−06 | 7.62E−06 | 7.62E−06 | 7.62E−06 |
| 32 | GI50 | 1.53E−06 | 6.73E−07 | 3.16E−06 | 2.66E−06 | 3.92E−07 | 6.71E−07 |
| | TGI | 3.34E−06 | 2.43E−06 | 1.38E−06 | 5.30E−06 | 1.65E−06 | 2.42E−06 |
| | LC50 | 7.33E−06 | 8.31E−06 | 8.76E−06 | 8.76E−06 | 6.31E−06 | 8.25E−06 |
| 33 | GI50 | 3.79E−08 | 5.96E−09 | 8.92E−08 | 1.34E−06 | 1.53E−07 | 1.98E−07 |
| | TGI | 1.54E−07 | 9.18E−07 | 1.06E−06 | 3.42E−06 | 3.33E−07 | 5.58E−07 |
| | LC50 | 8.83E−07 | 4.03E−06 | 8.44E−06 | 8.74E−06 | 7.26E−07 | 4.33E−06 |
| 34 | GI50 | 1.47E−06 | 1.04E−06 | 3.01E−07 | 1.16E−06 | 8.40E−07 | 9.10E−06 |
| | TGI | 3.71E−06 | 2.61E−06 | 9.92E−07 | 5.39E−06 | 4.02E−06 | 9.10E−06 |
| | LC50 | 9.10E−06 | 6.62E−06 | 9.10E−06 | 9.10E−06 | 9.10E−06 | 9.10E−06 |
| 35 | GI50 | 5.24E−08 | 8.08E−08 | 1.78E−07 | 1.18E−06 | 2.07E−07 | 2.17E−07 |
| | TGI | 2.59E−07 | 9.75E−07 | 1.21E−06 | 2.44E−06 | 7.05E−07 | 7.37E−07 |
| | LC50 | 6.09E−06 | 4.82E−06 | 3.67E−06 | 5.06E−06 | 2.60E−06 | 2.80E−06 |

TABLE 1-continued

Activity data (Molar)

| | | | | | | | | |
|---|---|---|---|---|---|---|---|---|
| 36 | GI50 | 3.28E−08 | 9.48E−09 | 1.69E−07 | 1.51E−06 | 1.58E−07 | 1.45E−07 | |
| | TGI | 1.54E−07 | 1.88E−07 | 1.13E−06 | 4.08E−06 | 3.21E−07 | 5.25E−07 | |
| | LC50 | 1.69E−06 | 5.70E−06 | 8.78E−06 | 8.78E−06 | 6.52E−07 | 8.78E−06 | |
| 37 | GI50 | 1.72E−06 | 1.24E−08 | 2.15E−06 | 9.12E−08 | 1.79E−06 | 2.10E−06 | |
| | TGI | 3.80E−06 | 1.97E−06 | 1.10E−05 | 2.00E−06 | 4.40E−06 | 4.60E−06 | |
| | LC50 | 8.38E−06 | 7.53E−06 | 1.10E−05 | 1.09E−05 | 1.08E−05 | 1.01E−05 | |
| 38 | GI50 | 1.34E−06 | 4.13E−08 | 4.99E−07 | 3.24E−08 | 9.11E−06 | 9.11E−06 | |
| | TGI | 4.78E−06 | 1.15E−06 | 9.11E−06 | 9.11E−08 | 9.11E−06 | 9.11E−06 | |
| | LC50 | 9.11E−06 | 9.11E−06 | 9.11E−06 | 9.11E−06 | 9.11E−06 | 9.11E−06 | |
| 39 | GI50 | 4.64E−08 | 3.59E−08 | 1.64E−07 | 3.04E−06 | 3.21E−07 | 3.23E−07 | |
| | TGI | 8.55E−07 | 1.08E−06 | 8.47E−06 | 8.47E−06 | 2.53E−06 | 1.81E−06 | |
| | LC50 | 8.47E−06 | 8.47E−06 | 8.47E−06 | 8.47E−06 | 8.47E−06 | 8.47E−06 | |
| 40 | GI50 | 3.16E−08 | 5.82E−08 | 2.54E−07 | 3.57E−06 | 2.23E−07 | 4.70E−07 | |
| | TGI | 2.70E−07 | 9.86E−07 | 3.27E−06 | 9.48E−06 | 8.84E−07 | 3.35E−06 | |
| | LC50 | 9.48E−06 | 4.61E−06 | 9.48E−06 | 9.48E−06 | 6.41E−06 | 9.48E−06 | |
| 41 | GI50 | 2.42E−06 | 1.77E−06 | 2.48E−06 | 3.24E−06 | 3.31E−06 | 4.20E−06 | |
| | TGI | 8.01E−06 | 3.76E−06 | 9.87E−06 | 8.89E−06 | 9.87E−06 | 9.87E−06 | |
| | LC50 | 9.87E−06 | 8.02E−06 | 9.87E−06 | 9.87E−06 | 9.87E−06 | 9.87E−06 | |
| 42 | GI50 | 7.35E−07 | 3.13E−07 | 7.32E−07 | 3.91E−06 | 4.63E−07 | 3.95E−07 | |
| | TGI | 2.99E−06 | 1.79E−06 | 4.06E−06 | 9.46E−06 | 3.63E−06 | 2.32E−06 | |
| | LC50 | 9.46E−06 | 5.42E−06 | 9.46E−06 | 9.46E−06 | 9.46E−06 | 9.46E−06 | |

| | | DU-145 | LN-caP | SKOV-3 | IGROV | IGROV-ET | SK-BR-3 | MEL-28 | H-MEC-1 |
|---|---|---|---|---|---|---|---|---|---|
| 43 | GI50 | 5.74E−08 | | 1.46E−07 | 4.18E−07 | 9.80E−08 | 2.12E−07 | 4.98E−07 | |
| | TGI | 3.01E−07 | | 1.14E−06 | 2.14E−06 | 3.24E−06 | 1.10E−06 | 1.21E−05 | |
| | LC50 | 1.21E−05 | | 1.21E−05 | 8.94E−06 | 1.21E−05 | 7.90E−06 | 1.21E−05 | |
| 44 | GI50 | 4.85E−08 | | 9.88E−08 | 1.06E−06 | 1.18E−06 | 1.22E−07 | 4.80E−07 | |
| | TGI | 2.73E−07 | | 1.15E−06 | 2.32E−06 | 3.58E−06 | 8.66E−07 | 3.21E−06 | |
| | LC50 | 7.60E−06 | | 7.60E−06 | 5.06E−06 | 7.60E−06 | 7.60E−06 | 7.60E−06 | |
| 45 | GI50 | 1.05E−07 | | 1.75E−06 | 1.57E−06 | 2.58E−06 | 4.14E−07 | 8.98E−07 | |
| | TGI | 5.49E−07 | | 2.20E−06 | 4.12E−06 | 8.07E−06 | 1.58E−06 | 1.15E−05 | |
| | LC50 | 1.15E−05 | | 1.15E−05 | 1.09E−05 | 1.15E−05 | 1.15E−05 | 1.15E−05 | |
| 46 | GI50 | 3.80E−07 | 2.09E−06 | 3.16E−06 | 2.77E−07 | 4.99E−07 | 1.93E−06 | 1.22E−06 | 1.95E−07 |
| | TGI | 2.19E−06 | 6.58E−06 | 9.57E−06 | 2.15E−06 | 3.03E−06 | 4.67E−06 | 9.57E−06 | 9.57E−06 |
| | LC50 | 8.54E−06 | 9.57E−06 | 9.57E−06 | 9.57E−06 | 9.57E−06 | 9.57E−06 | 9.57E−06 | 9.57E−06 |
| 46 | GI50 | 2.76E−09 | 6.29E−10 | 3.20E−09 | 2.54E−09 | 2.87E−09 | 1.67E−09 | 2.21E−09 | 4.19E−10 |
| | TGI | 5.71E−09 | 2.48E−09 | 9.57E−09 | 5.78E−09 | 6.57E−09 | 4.64E−09 | 4.17E−09 | 8.47E−10 |
| | LC50 | 9.57E−06 | 9.57E−09 | 9.57E−06 | 9.57E−06 | 9.57E−06 | 3.21E−08 | 7.87E−06 | 3.65E−09 |
| 47 | GI50 | 1.08E−06 | 8.84E−08 | | 7.64E−07 | 2.07E−06 | 2.29E−06 | 2.07E−06 | |
| | TGI | 4.61E−06 | 1.59E−06 | | 1.03E−05 | 1.03E−05 | 6.01E−06 | 1.03E−05 | |
| | LC50 | 1.03E−05 | 5.87E−06 | | 1.03E−05 | 1.03E−05 | 1.03E−05 | 1.03E−05 | |
| 53 | GI50 | 4.53E−06 | 4.01E−06 | | 1.38E−06 | 2.01E−05 | 1.99E−06 | 4.03E−06 | |
| | TGI | 1.23E−05 | 9.75E−06 | | 2.01E−05 | 2.01E−05 | 9.49E−06 | 1.55E−05 | |
| | LC50 | 2.01E−05 | 2.01E−05 | | 2.01E−05 | 2.01E−05 | 2.01E−05 | 2.01E−05 | |
| 54 | GI50 | 2.88E−06 | 1.71E−06 | | 8.84E−07 | 6.64E−06 | 1.05E−06 | 1.53E−06 | |
| | TGI | 7.16E−06 | 4.34E−06 | | 4.02E−06 | 1.72E−05 | 4.31E−06 | 5.70E−06 | |
| | LC50 | 1.72E−05 | 1.11E−05 | | 1.33E−06 | 1.72E−05 | 1.72E−05 | 1.72E−05 | |
| 57 | GI50 | 3.89E−06 | 2.16E−06 | | 8.47E−07 | 8.90E−07 | 3.17E−07 | 1.68E−06 | |
| | TGI | 1.22E−05 | 5.47E−06 | | 5.88E−06 | 6.43E−06 | 5.24E−06 | 1.26E−05 | |
| | LC50 | 1.95E−05 | 1.39E−05 | | 1.95E−05 | 1.95E−05 | 1.95E−05 | 1.95E−05 | |
| 59 | GI50 | 1.39E−06 | 1.37E−06 | | 8.99E−07 | 6.32E−07 | 3.72E−07 | 1.62E−06 | |
| | TGI | 2.60E−06 | 2.63E−06 | | 2.63E−06 | 2.04E−06 | 1.15E−06 | 3.04E−06 | |
| | LC50 | 4.86E−06 | 5.06E−06 | | 7.67E−06 | 5.98E−06 | 4.11E−06 | 5.67E−06 | |
| 60 | GI50 | 1.18E−06 | 5.50E−07 | | 6.82E−07 | 2.56E−06 | 4.91E−07 | 1.17E−06 | |
| | TGI | 2.65E−06 | 1.79E−06 | | 3.29E−06 | 6.16E−06 | 1.64E−06 | 4.14E−06 | |
| | LC50 | 5.97E−06 | 5.25E−06 | | 9.15E−06 | 9.15E−06 | 8.58E−06 | 9.15E−06 | |
| 63 | GI50 | 2.20E−06 | 1.13E−06 | 3.06E−06 | 9.75E−07 | 6.40E−07 | 1.57E−06 | 2.34E−06 | 2.72E−06 |
| | TGI | 5.08E−06 | 3.47E−06 | 5.84E−06 | 3.86E−06 | 2.86E−06 | 4.80E−06 | 4.87E−06 | 5.25E−06 |
| | LC50 | 1.17E−05 | 9.61E−06 | 1.11E−05 | 1.46E−05 | 1.52E−05 | 1.47E−05 | 1.01E−05 | 1.01E−05 |
| 66 | GI50 | 1.73E−06 | 8.90E−07 | 2.85E−06 | 1.35E−06 | 1.22E−06 | 4.34E−07 | 1.42E−06 | 1.52E−06 |
| | TGI | 3.65E−06 | 1.89E−06 | 6.28E−06 | 3.02E−06 | 2.90E−06 | 1.82E−06 | 2.55E−06 | 2.73E−06 |
| | LC50 | 7.12E−06 | 4.03E−06 | 7.12E−06 | 6.75E−06 | 6.87E−06 | 7.12E−06 | 4.55E−06 | 4.93E−06 |
| 77 | GI50 | 8.00E−07 | 7.51E−06 | 7.52E−06 | 5.92E−06 | 2.58E−07 | 3.53E−06 | 3.29E−06 | 2.71E−06 |
| | TGI | 3.96E−06 | 1.17E−05 | 1.17E−05 | 8.84E−06 | 1.17E−05 | 1.17E−05 | 1.01E−05 | 1.17E−05 |
| | LC50 | 1.17E−05 | 1.17E−05 | 1.17E−05 | 1.17E−05 | 1.17E−05 | 1.17E−05 | 1.17E−05 | 1.17E−05 |

| | | A-549 | K-562 | PANC-1 | HT-29 | LOVO | LOVO-DOX | HELA | HELA-APL |
|---|---|---|---|---|---|---|---|---|---|
| 43 | GI50 | 1.90E−06 | 1.18E−07 | 1.49E−06 | 1.21E−05 | 6.35E−07 | 9.37E−07 | | |
| | TGI | 1.21E−05 | 5.65E−07 | 6.57E−06 | 1.21E−05 | 3.72E−06 | 3.14E−06 | | |
| | LC50 | 1.21E−05 | 1.21E−05 | 1.21E−05 | 1.21E−05 | 1.21E−05 | 9.84E−06 | | |
| 44 | GI50 | 5.44E−06 | 1.82E−07 | 1.17E−06 | 7.60E−06 | 3.74E−07 | 6.08E−07 | | |
| | TGI | 7.60E−06 | 6.86E−07 | 4.35E−06 | 7.60E−06 | 3.18E−06 | 2.51E−06 | | |
| | LC50 | 7.60E−06 | 5.36E−06 | 7.60E−06 | 7.60E−06 | 7.60E−06 | 7.60E−06 | | |

TABLE 1-continued

Activity data (Molar)

| | | | | | | | | | |
|---|---|---|---|---|---|---|---|---|---|
| 45 | GI50 | 4.35E−06 | 3.15E−07 | 2.03E−06 | 1.15E−05 | 7.71E−07 | 7.78E−07 | | |
| | TGI | 1.15E−05 | 1.73E−06 | 9.75E−06 | 1.15E−05 | 6.71E−06 | 4.51E−06 | | |
| | LC50 | 1.15E−05 | 8.79E−06 | 1.15E−05 | 1.15E−05 | 1.15E−05 | 1.15E−05 | | |
| 46 | GI50 | 1.31E−06 | 2.25E−06 | 1.34E−06 | 2.28E−06 | 4.23E−06 | 6.57E−06 | | |
| | TGI | 9.57E−06 | 6.53E−06 | 9.57E−06 | 9.57E−06 | 9.57E−06 | 9.57E−06 | | |
| | LC50 | 9.57E−06 | 9.57E−06 | 9.57E−06 | 9.57E−06 | 9.57E−06 | 9.57E−06 | | |
| 46 | GI50 | 2.33E−06 | 5.98E−10 | 2.94E−09 | 1.03E−08 | 3.24E−09 | 1.50E−08 | | |
| | TGI | 9.57E−06 | 1.40E−09 | 1.15E−08 | 9.57E−06 | 9.32E−09 | 9.57E−08 | | |
| | LC50 | 9.57E−06 | 2.41E−09 | 9.57E−06 | 9.57E−06 | 9.57E−06 | 9.57E−06 | | |
| 47 | GI50 | 3.26E−06 | 5.64E−07 | 3.86E−06 | 1.25E−06 | 3.97E−06 | 8.09E−06 | 5.37E−07 | 5.75E−06 |
| | TGI | 1.03E−05 | 3.74E−06 | 1.03E−05 | 1.03E−05 | 1.03E−05 | 1.03E−05 | 4.79E−06 | 1.03E−05 |
| | LC50 | 1.03E−05 | 1.03E−05 | 1.03E−05 | 1.03E−05 | 1.03E−05 | 1.03E−05 | 1.03E−05 | 1.03E−05 |
| 53 | GI50 | 5.66E−06 | 1.03E−05 | 1.03E−06 | 2.17E−06 | 1.11E−05 | 2.01E−05 | 5.90E−07 | 2.01E−05 |
| | TGI | 2.01E−05 | 2.01E−05 | 9.67E−06 | 2.01E−05 | 2.01E−05 | 2.01E−05 | 1.23E−05 | 2.01E−05 |
| | LC50 | 2.01E−05 | 2.01E−05 | 2.01E−05 | 2.01E−05 | 2.01E−05 | 2.01E−05 | 2.01E−05 | 2.01E−05 |
| 54 | GI50 | 2.85E−06 | 3.76E−06 | 7.11E−07 | 1.52E−06 | 3.40E−06 | 1.25E−05 | 6.16E−07 | 3.83E−06 |
| | TGI | 1.51E−05 | 1.42E−05 | 2.59E−06 | 1.72E−05 | 8.94E−06 | 1.72E−05 | 2.71E−06 | 1.72E−05 |
| | LC50 | 1.72E−05 | 1.72E−05 | 1.72E−05 | 1.72E−05 | 1.72E−05 | 1.72E−05 | 1.72E−05 | 1.72E−05 |
| 57 | GI50 | 1.29E−06 | 2.69E−06 | 6.11E−07 | 3.49E−06 | 7.17E−07 | 8.28E−07 | 6.85E−07 | 3.68E−06 |
| | TGI | 1.95E−05 | 1.95E−05 | 9.70E−06 | 1.95E−05 | 5.30E−06 | 6.91E−06 | 5.67E−06 | 1.10E−05 |
| | LC50 | 1.95E−05 | 1.95E−05 | 1.95E−05 | 1.95E−05 | 1.95E−05 | 1.95E−05 | 1.95E−05 | 1.95E−05 |
| 59 | GI50 | 1.70E−06 | 1.64E−06 | 1.10E−06 | 1.97E−06 | 1.13E−06 | 5.28E−07 | 1.37E−06 | 1.88E−06 |
| | TGI | 3.29E−06 | 3.45E−06 | 3.48E−06 | 3.70E−06 | 2.53E−06 | 1.60E−06 | 2.98E−06 | 3.90E−06 |
| | LC50 | 6.36E−06 | 7.27E−06 | 8.81E−06 | 6.98E−06 | 5.67E−06 | 4.56E−06 | 6.44E−06 | 8.12E−06 |
| 60 | GI50 | 1.62E−06 | 6.97E−07 | 7.47E−07 | 2.42E−06 | 1.61E−06 | 2.82E−06 | 1.02E−06 | 3.49E−06 |
| | TGI | 4.63E−06 | 2.19E−06 | 4.40E−06 | 5.88E−06 | 3.58E−06 | 9.15E−06 | 2.51E−06 | 9.15E−06 |
| | LC50 | 9.15E−06 | 6.87E−06 | 9.15E−06 | 9.15E−06 | 7.94E−06 | 9.15E−06 | 6.13E−06 | 9.15E−06 |
| 63 | GI50 | 2.84E−06 | 2.90E−06 | 1.93E−06 | 2.92E−06 | 1.46E−06 | 9.09E−07 | | |
| | TGI | 5.57E−06 | 6.75E−06 | 5.05E−06 | 5.70E−06 | 3.68E−06 | 2.95E−06 | | |
| | LC50 | 1.09E−05 | 1.52E−05 | 1.32E−05 | 1.11E−05 | 9.11E−06 | 9.85E−06 | | |
| 66 | GI50 | 1.86E−06 | 9.82E−07 | 1.95E−06 | 2.77E−06 | 2.19E−06 | 1.91E−06 | | |
| | TGI | 3.46E−06 | 2.80E−06 | 7.12E−06 | 6.77E−06 | 7.12E−06 | 5.56E−06 | | |
| | LC50 | 6.43E−06 | 7.12E−06 | 7.12E−06 | 7.12E−06 | 7.12E−06 | 7.12E−06 | | |
| 77 | GI50 | 6.69E−06 | 2.13E−06 | 4.46E−06 | 1.17E−05 | 1.17E−05 | 1.02E−05 | | |
| | TGI | 1.17E−05 | 6.15E−06 | 1.17E−05 | 1.17E−05 | 1.17E−05 | 1.17E−05 | | |
| | LC50 | 1.17E−05 | 1.17E−05 | 1.17E−05 | 1.17E−05 | 1.17E−05 | 1.17E−05 | | |

| | | DU-145 | LN-caP | SKOV-3 | IGROV | IGROV-ET | SK-BR-3 | MEL-28 | H-MEC-1 |
|---|---|---|---|---|---|---|---|---|---|
| 84 | GI50 | 3.41E−06 | 7.10E−07 | 4.58E−06 | 2.41E−06 | 4.26E−06 | 4.60E−07 | 2.07E−06 | 6.82E−07 |
| | TGI | 8.36E−06 | 2.01E−06 | 9.90E−06 | 6.28E−06 | 8.25E−06 | 9.50E−07 | 3.86E−06 | 1.86E−06 |
| | LC50 | 9.90E−06 | 5.21E−06 | 9.90E−06 | 9.90E−06 | 9.90E−06 | 9.90E−06 | 7.21E−06 | 5.96E−06 |
| 92 | GI50 | 1.49E−05 | 1.67E−07 | 7.61E−06 | 3.13E−06 | 6.85E−06 | 4.35E−06 | 4.75E−06 | 1.42E−05 |
| | TGI | 1.49E−05 | 7.10E−07 | 1.49E−05 | 6.64E−06 | 1.49E−05 | 1.16E−05 | 1.01E−05 | 1.49E−05 |
| | LC50 | 1.49E−05 | 5.09E−06 | 1.49E−05 | 1.41E−05 | 1.49E−05 | 1.49E−05 | 1.49E−05 | 1.49E−05 |
| 93 | GI50 | 1.28E−05 | 4.08E−07 | 6.26E−06 | 3.37E−06 | 1.17E−05 | 4.95E−06 | 4.57E−06 | 1.28E−05 |
| | TGI | 1.28E−05 | 1.27E−06 | 1.28E−05 | 7.08E−06 | 1.28E−05 | 1.28E−05 | 1.28E−05 | 1.28E−05 |
| | LC50 | 1.28E−05 | 7.08E−06 | 1.28E−05 | 1.28E−05 | 1.28E−05 | 1.28E−05 | 1.28E−05 | 1.28E−05 |
| 94 | GI50 | 1.31E−06 | 6.73E−07 | 8.48E−06 | 1.83E−06 | 1.59E−06 | 3.35E−06 | 2.45E−06 | 1.59E−05 |
| | TGI | 1.59E−05 | 2.87E−06 | 1.59E−05 | 5.90E−06 | 1.59E−05 | 1.24E−05 | 7.31E−06 | 1.59E−05 |
| | LC50 | 1.59E−05 | 1.25E−05 | 1.59E−05 | 1.59E−05 | 1.59E−05 | 1.59E−05 | 1.59E−05 | 1.59E−05 |
| 96 | GI50 | 4.26E−06 | | 4.20E−06 | 1.20E−06 | 2.69E−06 | 4.17E−07 | 2.14E−06 | 3.81E−07 |
| | TGI | 9.20E−06 | | 9.20E−06 | 3.01E−06 | 5.60E−06 | 1.86E−06 | 4.43E−06 | 9.20E−06 |
| | LC50 | 9.20E−06 | | 9.20E−06 | 5.47E−06 | 9.20E−06 | 9.18E−06 | 9.20E−06 | 9.20E−06 |
| 97 | GI50 | 4.13E−06 | | 6.01E−06 | 1.86E−07 | 6.78E−07 | 1.23E−06 | 2.62E−07 | 3.37E−08 |
| | TGI | 9.59E−06 | | 9.59E−06 | 1.94E−06 | 3.33E−06 | 3.58E−06 | 4.71E−06 | 9.59E−08 |
| | LC50 | 9.59E−06 | | 9.59E−06 | 7.54E−06 | 9.59E−06 | 9.59E−06 | 9.59E−06 | 9.59E−06 |
| 99 | GI50 | 9.44E−06 | 4.46E−06 | 9.44E−06 | 3.07E−06 | 9.44E−06 | 9.44E−06 | 9.44E−06 | 4.06E−06 |
| | TGI | 9.44E−06 | 8.19E−06 | 9.44E−06 | 9.44E−06 | 9.44E−06 | 9.44E−06 | 9.44E−06 | 5.48E−06 |
| | LC50 | 9.44E−06 | 9.44E−06 | 9.44E−06 | 9.44E−06 | 9.44E−06 | 9.44E−06 | 9.44E−06 | 7.42E−06 |
| 101 | GI50 | 1.31E−05 | 8.25E−06 | 7.91E−07 | 1.19E−05 | 1.31E−05 | 1.31E−05 | 1.31E−05 | 4.66E−06 |
| | TGI | 1.31E−05 | 1.31E−05 | 2.34E−06 | 1.31E−05 | 1.31E−05 | 1.31E−05 | 1.31E−05 | 6.99E−06 |
| | LC50 | 1.31E−05 | 1.31E−05 | 5.71E−06 | 1.31E−05 | 1.31E−05 | 1.31E−05 | 1.31E−05 | 1.05E−05 |
| 109 | GI50 | 2.99E−06 | 1.16E−06 | 2.49E−06 | 1.80E−06 | 9.67E−06 | 3.45E−06 | 8.85E−07 | 9.17E−07 |
| | TGI | 1.54E−05 | 1.99E−06 | 1.18E−05 | 6.08E−06 | 1.99E−05 | 8.10E−06 | 2.57E−06 | 1.99E−05 |
| | LC50 | 1.99E−05 | 1.99E−05 | 1.99E−05 | 1.99E−05 | 1.99E−05 | 1.90E−05 | 1.08E−05 | 1.99E−05 |
| 115 | GI50 | 1.63E−06 | 6.70E−07 | 1.10E−06 | 1.07E−06 | 1.70E−06 | 1.87E−06 | 1.45E−06 | 2.13E−07 |
| | TGI | 4.29E−06 | 1.67E−06 | 2.38E−06 | 2.58E−06 | 5.38E−06 | 3.75E−06 | 2.65E−06 | 4.52E−07 |
| | LC50 | 7.78E−06 | 3.87E−06 | 5.13E−06 | 6.26E−06 | 7.78E−06 | 7.53E−06 | 4.83E−06 | 2.96E−06 |
| 118 | GI50 | 1.60E−06 | 9.87E−07 | 2.02E−06 | 9.70E−07 | 8.76E−07 | 6.39E−07 | 1.65E−06 | 1.45E−06 |
| | TGI | 3.00E−06 | 2.16E−06 | 4.08E−06 | 2.30E−06 | 2.33E−06 | 2.04E−06 | 3.00E−06 | 3.06E−06 |
| | LC50 | 5.64E−06 | 4.76E−06 | 8.22E−06 | 5.47E−06 | 6.17E−06 | 6.25E−06 | 5.49E−06 | 6.45E−06 |
| 126 | GI50 | 2.53E−06 | 1.25E−06 | 3.48E−06 | 2.26E−06 | 3.88E−06 | 2.11E−06 | 2.93E−06 | 7.46E−07 |
| | TGI | 6.49E−06 | 2.76E−06 | 6.98E−06 | 5.32E−06 | 7.87E−06 | 5.36E−06 | 5.27E−06 | 2.25E−06 |
| | LC50 | 1.29E−05 | 6.04E−06 | 1.29E−05 | 1.26E−05 | 1.29E−05 | 1.29E−06 | 9.48E−06 | 6.46E−06 |

TABLE 1-continued

Activity data (Molar)

| | | | | | | | | | |
|---|---|---|---|---|---|---|---|---|---|
| 128 | GI50 | 1.33E−06 | 1.26E−06 | | 6.39E−07 | 6.89E−07 | | 1.57E−06 | 1.53E−06 |
| | TGI | 2.48E−06 | 2.69E−06 | | 1.98E−06 | 2.26E−06 | | 3.03E−06 | 3.16E−06 |
| | LC50 | 4.62E−06 | 5.71E−06 | | 5.70E−06 | 7.59E−06 | | 5.86E−06 | 6.53E−06 |
| 134 | GI50 | 2.12E−06 | 4.58E−07 | 7.39E−07 | 9.43E−07 | 4.82E−07 | 2.10E−06 | 1.73E−06 | 2.13E−06 |
| | TGI | 4.47E−06 | 1.34E−06 | 1.85E−06 | 2.48E−06 | 2.14E−06 | 4.34E−06 | 3.23E−06 | 6.51E−06 |
| | LC50 | 8.81E−06 | 4.16E−06 | 4.26E−06 | 6.50E−06 | 7.58E−06 | 8.81E−06 | 6.04E−06 | 8.81E−06 |

| | | A-549 | K-562 | PANC-1 | HT-29 | LOVO | LOVO-DOX |
|---|---|---|---|---|---|---|---|
| 84 | GI50 | 2.66E−06 | 7.31E−07 | 5.01E−07 | 2.34E−06 | 4.48E−06 | 9.90E−06 |
| | TGI | 4.91E−06 | 3.30E−06 | 5.47E−06 | 9.90E−06 | 9.90E−06 | 9.90E−06 |
| | LC50 | 9.03E−06 | 9.90E−06 | 9.90E−06 | 9.90E−06 | 9.90E−06 | 9.90E−06 |
| 92 | GI50 | 1.49E−05 | 2.23E−06 | 5.42E−06 | 1.49E−05 | 7.52E−06 | 2.14E−06 |
| | TGI | 1.49E−05 | 1.38E−06 | 1.49E−05 | 1.49E−05 | 1.49E−05 | 5.96E−06 |
| | LC50 | 1.49E−05 | 1.49E−05 | 1.49E−05 | 1.49E−05 | 1.49E−05 | 1.49E−05 |
| 93 | GI50 | 8.64E−06 | 1.62E−06 | 1.28E−05 | 1.28E−05 | 1.28E−05 | 3.39E−06 |
| | TGI | 1.28E−05 | 2.65E−06 | 1.28E−05 | 1.28E−05 | 1.28E−05 | 1.17E−05 |
| | LC50 | 1.28E−05 | 4.36E−06 | 1.28E−05 | 1.28E−05 | 1.28E−05 | 1.28E−05 |
| 94 | GI50 | 7.19E−06 | 5.26E−07 | 2.12E−06 | 1.55E−05 | 5.70E−06 | 2.84E−06 |
| | TGI | 1.59E−05 | 1.82E−06 | 1.59E−05 | 1.59E−05 | 1.59E−05 | 8.25E−06 |
| | LC50 | 1.59E−05 | 4.32E−06 | 1.59E−05 | 1.59E−05 | 1.59E−05 | 1.59E−05 |
| 96 | GI50 | 4.97E−06 | 1.63E−06 | 1.68E−06 | 9.20E−06 | 2.28E−06 | 5.63E−07 |
| | TGI | 9.20E−06 | 4.43E−06 | 5.65E−06 | 9.20E−06 | 9.20E−06 | 2.07E−06 |
| | LC50 | 9.20E−06 | 9.20E−06 | 9.20E−06 | 9.20E−06 | 9.20E−06 | 9.20E−06 |
| 97 | GI50 | 9.59E−06 | 3.20E−06 | 4.47E−06 | 9.59E−06 | 5.28E−06 | 5.29E−06 |
| | TGI | 9.59E−06 | 6.86E−06 | 9.59E−06 | 9.59E−06 | 9.59E−06 | 9.59E−06 |
| | LC50 | 9.59E−06 | 9.59E−06 | 9.59E−06 | 9.59E−06 | 9.59E−06 | 9.59E−06 |
| 99 | GI50 | 9.44E−06 | 9.72E−07 | 9.44E−06 | 9.44E−06 | 9.44E−06 | 9.44E−06 |
| | TGI | 9.44E−06 | 1.48E−06 | 9.44E−06 | 9.44E−06 | 9.44E−06 | 9.44E−06 |
| | LC50 | 9.44E−06 | 2.26E−06 | 9.44E−06 | 9.44E−06 | 9.44E−06 | 9.44E−06 |
| 101 | GI50 | 1.31E−05 | 2.19E−06 | 1.31E−05 | 1.31E−05 | 1.31E−05 | 1.31E−05 |
| | TGI | 1.31E−05 | 3.53E−06 | 1.31E−05 | 1.31E−05 | 1.31E−05 | 1.31E−05 |
| | LC50 | 1.31E−05 | 5.73E−06 | 1.31E−05 | 1.31E−05 | 1.31E−05 | 1.31E−05 |
| 109 | GI50 | 5.94E−06 | 4.25E−07 | 5.70E−06 | 4.81E−06 | 9.17E−07 | 5.64E−06 |
| | TGI | 1.41E−05 | 1.99E−06 | 1.99E−05 | 1.99E−05 | 4.07E−06 | 1.35E−05 |
| | LG50 | 1.99E−05 | 1.99E−05 | 1.99E−05 | 1.99E−05 | 1.99E−05 | 1.99E−05 |
| 115 | GI50 | 1.65E−06 | 5.36E−07 | 2.47E−06 | 2.92E−06 | 7.03E−07 | 1.76E−06 |
| | TGI | 3.11E−06 | 2.47E−06 | 7.78E−06 | 6.46E−06 | 1.82E−06 | 4.78E−06 |
| | LC50 | 5.87E−06 | 7.78E−06 | 7.78E−06 | 7.78E−06 | 4.41E−06 | 7.78E−06 |
| 118 | GI50 | 1.80E−06 | 1.17E−06 | 1.08E−06 | 1.92E−06 | 1.35E−06 | 4.50E−07 |
| | TGI | 3.55E−06 | 2.77E−06 | 2.40E−06 | 3.56E−06 | 2.70E−06 | 1.30E−06 |
| | LC50 | 6.99E−06 | 6.57E−06 | 5.35E−06 | 6.59E−06 | 5.43E−06 | 3.86E−06 |
| 126 | GI50 | 2.98E−06 | 2.15E−06 | 2.19E−06 | 3.00E−06 | 2.56E−06 | 1.29E−05 |
| | TGI | 5.74E−06 | 4.32E−06 | 6.57E−06 | 9.22E−06 | 5.68E−06 | 1.29E−05 |
| | LC50 | 2.25E−06 | 8.69E−06 | 1.29E−05 | 1.29E−05 | 1.26E−05 | 1.29E−05 |
| 128 | GI50 | 1.61E−06 | 1.11E−06 | 8.88E−07 | 1.95E−06 | 8.54E−07 | 4.03E−07 |
| | TGI | 3.23E−06 | 2.98E−06 | 2.31E−06 | 3.54E−06 | 1.92E−06 | 1.49E−06 |
| | LC50 | 6.45E−06 | 8.01E−06 | 5.99E−06 | 6.44E−06 | 4.30E−06 | 4.66E−06 |
| 134 | GI50 | 2.55E−06 | 5.71E−07 | 2.17E−06 | 2.85E−06 | 2.05E−06 | 5.19E−07 |
| | TGI | 4.93E−06 | 4.93E−06 | 4.53E−06 | 8.81E−06 | 4.21E−06 | 1.99E−06 |
| | LC50 | 8.81E−06 | 8.81E−06 | 8.81E−06 | 8.81E−06 | 8.67E−06 | 7.79E−06 |

| | | DU-145 | LN-caP | IGROV | IGROV-ET | SK-BR-3 | MEL-28 | A-549 | K-562 |
|---|---|---|---|---|---|---|---|---|---|
| 135 | GI50 | 1.60E−06 | 7.83E−07 | 2.10E−06 | 5.86E−07 | 5.79E−07 | 1.67E−06 | 3.34E−06 | 1.07E−06 |
| | TGI | 3.78E−06 | 2.02E−06 | 4.68E−06 | 1.98E−06 | 2.61E−06 | 5.00E−06 | 8.76E−06 | 6.82E−06 |
| | LC50 | 8.76E−06 | 4.91E−06 | 8.76E−06 | 6.33E−06 | 8.76E−06 | 8.76E−06 | 8.76E−06 | 8.76E−06 |
| 169 | GI50 | 1.51E−08 | 3.73E−08 | 4.71E−08 | 4.18E−08 | 3.87E−08 | 4.64E−08 | 6.46E−08 | 6.80E−08 |
| | TGI | 9.01E−08 | 1.83E−06 | 1.92E−06 | 3.01E−06 | 1.32E−07 | 5.29E−07 | 1.14E−06 | 3.21E−06 |
| | LG50 | 1.05E−08 | 1.24E−06 | 1.05E−05 | 1.05E−05 | 1.05E−05 | 1.05E−05 | 9.74E−06 | 1.05E−05 |
| 173 | GI50 | 4.01E−08 | 8.15E−08 | 1.53E−07 | 1.45E−07 | | 1.52E−07 | 2.60E−07 | 1.11E−07 |
| | TGI | 1.34E−07 | 2.68E−06 | 8.09E−07 | 4.28E−07 | | 6.04E−06 | 6.04E−06 | 6.04E−06 |
| | LC50 | 7.49E−07 | 2.55E−06 | 6.04E−06 | 6.04E−06 | | 6.04E−06 | 6.04E−06 | 6.04E−06 |
| 180 | GI50 | 3.59E−08 | 5.30E−08 | 5.30E−08 | 6.91E−08 | 1.81E−08 | 1.34E−08 | 2.01E−08 | 4.00E−08 |
| | TGI | 8.42E−08 | 2.27E−07 | 3.19E−07 | 5.31E−07 | 5.41E−08 | 1.26E−07 | 2.33E−07 | 1.53E−06 |
| | LC50 | 1.11E−05 | 6.15E−07 | 1.11E−05 | 1.11E−05 | 1.19E−06 | 1.11E−05 | 7.26E−06 | 1.11E−05 |
| 181 | GI50 | 2.49E−08 | 5.93E−08 | 3.80E−08 | 5.00E−08 | 2.06E−08 | 1.68E−08 | 1.98E−08 | 3.28E−08 |
| | TGI | 5.94E−08 | 2.37E−07 | 2.31E−07 | 3.41E−07 | 5.92E−08 | 9.56E−08 | 2.09E−07 | 4.44E−07 |
| | LC50 | 1.05E−05 | 6.78E−07 | 3.20E−07 | 1.05E−05 | 8.62E−07 | 2.14E−06 | 8.18E−06 | 7.14E−06 |
| 182 | GI50 | 1.08E−06 | 1.75E−06 | 2.86E−06 | 3.16E−06 | 3.65E−07 | 1.08E−06 | 9.58E−06 | 3.16E−07 |
| | TGI | 2.13E−05 | 2.13E−05 | 2.13E−05 | 2.13E−05 | 1.25E−06 | 2.13E−05 | 2.13E−05 | 4.85E−06 |
| | LC50 | 2.13E−05 | 2.13E−05 | 2.13E−05 | 2.13E−05 | 1.20E−05 | 2.13E−05 | 2.13E−05 | 2.13E−05 |
| 188 | GI50 | 3.19E−06 | 3.30E−06 | 5.37E−06 | 2.51E−06 | 3.60E−06 | 1.14E−06 | 1.08E−05 | 9.08E−07 |
| | TGI | 2.18E−05 | 2.18E−05 | 2.02E−05 | 1.34E−05 | 1.15E−05 | 2.18E−05 | 2.18E−05 | 4.02E−06 |
| | LC50 | 2.18E−05 | 2.18E−05 | 2.18E−05 | 2.18E−05 | 2.18E−05 | 2.18E−05 | 2.18E−05 | 2.18E−05 |

TABLE 1-continued

Activity data (Molar)

| | | | | | | | | | |
|---|---|---|---|---|---|---|---|---|---|
| 190 | GI50 | 5.75E−08 | 4.86E−08 | 1.34E−07 | 1.02E−07 | 9.22E−08 | 9.15E−06 | 1.67E−07 | 7.18E−08 |
| | TGI | 2.63E−07 | 2.97E−07 | 8.95E−07 | 1.20E−06 | 3.83E−07 | 1.07E−05 | 1.66E−06 | 7.12E−06 |
| | LC50 | 1.07E−05 | 1.97E−06 | 8.32E−06 | 6.42E−06 | 2.63E−06 | 1.07E−05 | 1.07E−05 | 1.07E−05 |
| 191 | GI50 | 6.21E−08 | 2.44E−07 | 4.58E−07 | 5.88E−07 | 5.55E−07 | 3.63E−07 | 5.73E−07 | 1.29E−07 |
| | TGI | 2.28E−07 | 1.48E−06 | 2.77E−06 | 6.96E−06 | 3.66E−06 | 1.17E−05 | 1.17E−05 | 1.69E−06 |
| | LC50 | 1.17E−05 | 5.36E−06 | 1.17E−05 | 1.17E−05 | 1.17E−05 | 1.17E−05 | 1.17E−05 | 9.49E−06 |
| 193 | GI50 | 3.33E−08 | 1.18E−07 | 7.41E−08 | 1.36E−07 | 2.27E−07 | 1.01E−07 | 6.07E−07 | 1.23E−07 |
| | TGI | 1.28E−07 | 4.91E−07 | 4.10E−07 | 4.32E−07 | 5.67E−07 | 4.97E−07 | 1.02E−05 | 3.99E−07 |
| | LC50 | 4.38E−07 | 5.49E−06 | 3.48E−06 | 9.59E−06 | 1.02E−05 | 1.02E−05 | 1.02E−05 | 3.91E−06 |
| 195 | GI50 | 1.37E−08 | 2.21E−08 | 2.50E−08 | 4.17E−08 | 4.55E−08 | 4.41E−08 | 1.13E−07 | 1.17E−08 |
| | TGI | 2.84E−08 | 8.64E−08 | 1.45E−07 | 2.15E−07 | 8.98E−08 | 1.59E−07 | 1.15E−06 | 4.09E−08 |
| | LC50 | 5.85E−08 | 3.65E−07 | 8.55E−07 | 2.74E−06 | 8.40E−07 | 1.94E−06 | 1.10E−05 | 1.70E−07 |
| 196 | GI50 | 4.14E−07 | 3.98E−07 | 6.91E−07 | 8.49E−07 | 6.54E−07 | 6.75E−07 | 1.68E−06 | 2.34E−07 |
| | TGI | 1.65E−06 | 1.45E−06 | 2.49E−06 | 3.85E−06 | 1.65E−06 | 8.99E−06 | 2.64E−05 | 6.14E−07 |
| | LC50 | 1.12E−05 | 9.78E−06 | 1.65E−05 | 2.64E−05 | 2.64E−05 | 2.64E−05 | 2.64E−05 | 1.50E−06 |
| 199 | GI50 | 3.73E−09 | 1.58E−08 | 1.89E−08 | 3.13E−08 | 4.66E−08 | 3.26E−08 | 6.06E−08 | 1.12E−08 |
| | TGI | 9.93E−09 | 8.92E−08 | 9.62E−08 | 1.59E−07 | 9.74E−08 | 1.51E−07 | 1.33E−06 | 5.55E−08 |
| | LC50 | 3.72E−08 | 3.92E−07 | 8.73E−07 | 1.22E−06 | 8.28E−06 | 7.04E−06 | 1.22E−06 | 2.81E−07 |
| 204 | GI50 | 5.63E−09 | 7.90E−08 | 2.38E−08 | 1.80E−08 | 1.51E−07 | 2.68E−08 | 3.11E−08 | 7.48E−09 |
| | TGI | 1.74E−08 | 2.29E−07 | 1.13E−07 | 1.09E−07 | 3.90E−07 | 2.43E−07 | 1.00E−06 | 2.03E−07 |
| | LC50 | 4.47E−08 | 5.97E−07 | 5.26E−07 | 9.52E−06 | 1.09E−06 | 7.14E−06 | 9.52E−06 | 5.96E−07 |

| | | PANC-1 | HT-29 | LOVO | LOVO-DOX | HELA | HELA-APL |
|---|---|---|---|---|---|---|---|
| 135 | GI50 | 2.11E−06 | 1.15E−06 | 2.69E−06 | 3.80E−06 | | |
| | TGI | 5.53E−06 | 4.82E−06 | 8.76E−06 | 8.76E−06 | | |
| | LC50 | 8.76E−06 | 8.76E−06 | 8.76E−06 | 8.76E−06 | | |
| 169 | GI50 | 1.52E−07 | 2.97E−06 | 1.59E−07 | 2.58E−07 | 5.57E−08 | 7.05E−08 |
| | TGI | 1.05E−05 | 1.05E−05 | 4.18E−07 | 9.22E−07 | 1.39E−06 | 5.30E−07 |
| | LC50 | 1.05E−05 | 1.05E−05 | 1.42E−06 | 105E−05 | 4.42E−06 | 2.97E−06 |
| 173 | GI50 | 4.61E−07 | 6.04E−06 | 1.15E−06 | 5.02E−07 | 1.21E−07 | 4.44E−07 |
| | TGI | 6.04E−06 | 6.04E−06 | 2.57E−06 | 6.04E−06 | 6.04E−06 | 6.04E−06 |
| | LC50 | 6.04E−06 | 6.04E−06 | 5.72E−06 | 6.04E−06 | 6.04E−06 | 6.04E−06 |
| 180 | GI50 | 1.30E−07 | 1.11E−05 | 5.35E−07 | 1.04E−07 | 8.06E−08 | 1.30E−07 |
| | TGI | 1.11E−08 | 1.11E−05 | 2.01E−06 | 4.98E−07 | 1.99E−06 | 1.21E−06 |
| | LC50 | 1.11E−05 | 1.11E−05 | 8.51E−06 | 1.11E−05 | 1.11E−05 | 1.11E−05 |
| 181 | GI50 | 8.64E−08 | 3.06E−06 | 3.31E−07 | 9.45E−08 | 4.78E−08 | 6.67E−08 |
| | TGI | 2.09E−06 | 1.05E−05 | 1.10E−06 | 4.70E−07 | 6.32E−07 | 4.77E−07 |
| | LC50 | 1.05E−05 | 1.05E−05 | 1.05E−05 | 1.05E−05 | 1.05E−05 | 8.14E−06 |
| 182 | GI50 | 4.85E−06 | 2.13E−05 | 2.13E−05 | 1.21E−06 | 8.52E−06 | 4.46E−06 |
| | TGI | 2.13E−05 | 2.13E−05 | 2.13E−05 | 2.13E−05 | 2.13E−05 | 2.13E−05 |
| | LC50 | 2.13E−05 | 2.13E−05 | 2.13E−05 | 2.13E−05 | 2.13E−05 | 2.13E−05 |
| 188 | GI50 | 5.56E−06 | 2.18E−05 | 4.50E−06 | 1.30E−06 | 1.05E−06 | 9.84E−07 |
| | TGI | 2.18E−05 | 2.18E−05 | 2.18E−05 | 2.18E−05 | 3.69E−06 | 3.16E−06 |
| | LC50 | 2.18E−05 | 2.18E−05 | 2.18E−05 | 2.18E−05 | 2.18E−05 | 1.58E−05 |
| 190 | GI50 | 3.76E−07 | 2.99E−06 | 2.85E−07 | 3.10E−07 | 8.33E−08 | 8.99E−08 |
| | TGI | 3.50E−06 | 1.07E−05 | 1.20E−06 | 1.37E−06 | 1.31E−06 | 1.72E−06 |
| | LC50 | 1.07E−05 | 1.07E−05 | 5.46E−06 | 7.68E−06 | 3.93E−06 | 5.20E−06 |
| 191 | GI50 | 1.27E−06 | 6.18E−06 | 5.13E−07 | 7.85E−07 | 9.48E−07 | 9.40E−07 |
| | TGI | 9.66E−06 | 1.17E−05 | 1.70E−06 | 1.17E−05 | 2.96E−06 | 2.52E−06 |
| | LC50 | 1.17E−05 | 1.17E−05 | 7.90E−06 | 1.17E−05 | 8.63E−06 | 5.96E−06 |
| 193 | GI50 | 2.78E−07 | 1.02E−05 | 3.50E−07 | 3.13E−07 | 3.50E−07 | 7.97E−07 |
| | TGI | 3.60E−06 | 1.02E−05 | 8.47E−07 | 1.02E−05 | 1.02E−05 | 1.02E−05 |
| | LC50 | 1.02E−05 | 1.02E−05 | 1.02E−05 | 1.02E−05 | 1.02E−05 | 1.02E−05 |
| 195 | GI50 | 5.69E−08 | 2.15E−06 | 1.50E−07 | 1.06E−07 | 5.13E−08 | 8.76E−08 |
| | TGI | 3.63E−07 | 4.31E−06 | 3.42E−07 | 5.00E−07 | 2.04E−07 | 2.34E−07 |
| | LC50 | 3.11E−06 | 8.62E−06 | 7.83E−07 | 2.50E−06 | 6.33E−07 | 5.36E−07 |
| 196 | GI50 | 9.57E−07 | 8.46E−06 | 7.99E−07 | 5.17E−07 | 3.51E−07 | 1.17E−07 |
| | TGI | 7.25E−06 | 2.64E−05 | 3.53E−06 | 2.64E−05 | 1.93E−06 | 5.11E−07 |
| | LC50 | 2.64E−05 | 2.64E−05 | 2.64E−05 | 2.64E−05 | 2.64E−05 | 1.92E−06 |
| 199 | GI50 | 3.69E−08 | 2.14E−06 | 1.28E−07 | 7.37E−08 | 2.99E−08 | 7.18E−08 |
| | TGI | 2.76E−07 | 6.71E−06 | 3.35E−07 | 4.99E−07 | 1.99E−07 | 2.42E−07 |
| | LC50 | 8.08E−06 | 1.22E−05 | 8.79E−07 | 1.22E−05 | 6.51E−07 | 5.74E−07 |
| 204 | GI50 | 4.47E−08 | 1.40E−06 | 1.13E−07 | 1.60E−07 | 3.69E−08 | 8.88E−08 |
| | TGI | 1.71E−07 | 3.80E−06 | 2.28E−07 | 6.34E−06 | 1.72E−07 | 2.35E−07 |
| | LC50 | 3.92E−07 | 9.52E−06 | 4.63E−07 | 9.52E−06 | 4.52E−07 | 5.94E−07 |

| | | DU-145 | LN-caP | IGROV | IGROV-ET | SK-BR-3 | MEL-28 | A-549 | K-562 |
|---|---|---|---|---|---|---|---|---|---|
| 206 | GI50 | 2.18E−08 | 7.52E−08 | 5.27E−08 | 2.97E−08 | 7.01E−08 | 4.40E−08 | 5.58E−08 | 3.11E−08 |
| | TGI | 3.99E−08 | 4.75E−07 | 1.94E−07 | 1.90E−07 | 4.51E−07 | 1.69E−07 | 4.10E−07 | 1.11E−06 |
| | LC50 | 7.25E−08 | 3.33E−06 | 5.89E−07 | 5.89E−07 | 2.89E−06 | 1.04E−06 | 2.77E−06 | 4.23E−06 |
| 207 | GI50 | 2.30E−08 | 1.27E−07 | 7.63E−08 | 4.36E−08 | 2.02E−07 | 4.44E−08 | 9.14E−08 | 9.20E−08 |
| | TGI | 4.16E−08 | 9.44E−07 | 3.18E−07 | 2.86E−07 | 1.07E−06 | 2.45E−07 | 1.02E−06 | 3.06E−06 |
| | LC50 | 7.48E−08 | 4.10E−06 | 1.55E−06 | 2.38E−06 | 4.21E−06 | 4.60E−06 | 3.55E−06 | 9.26E−06 |

TABLE 1-continued

Activity data (Molar)

| | | | | | | | | | |
|---|---|---|---|---|---|---|---|---|---|
| 208 | GI50 | 8.78E−06 | 1.46E−06 | 8.78E−06 | 8.78E−06 | 5.01E−06 | 8.78E−06 | 8.78E−06 | |
| | TGI | 8.78E−06 | 2.91E−06 | 8.78E−06 | 8.78E−06 | 7.97E−06 | 8.78E−06 | 8.78E−06 | |
| | LC50 | 8.78E−06 | 5.83E−06 | 8.78E−06 | 8.78E−06 | 8.78E−06 | 8.78E−06 | 8.78E−06 | |
| 209 | GI50 | 4.29E−09 | 1.58E−08 | 3.37E−08 | 3.17E−08 | 4.78E−08 | 3.28E−08 | 4.28E−08 | |
| | TGI | 1.19E−08 | 5.60E−08 | 1.24E−07 | 7.01E−08 | 6.95E−08 | 8.39E−08 | 1.95E−07 | |
| | LC50 | 4.04E−08 | 2.33E−07 | 4.77E−07 | 3.45E−07 | 1.01E−07 | 4.80E−07 | 7.13E−07 | |
| 210 | GI50 | 1.81E−07 | | 3.17E−07 | 1.45E−07 | 3.97E−07 | | 4.77E−07 | 6.12E−07 |
| | TGI | 3.39E−07 | | 1.06E−06 | 3.66E−07 | 1.36E−06 | | 3.94E−06 | 2.13E−06 |
| | LC50 | 6.31E−07 | | 3.65E−06 | 9.20E−06 | 4.59E−06 | | 1.04E−05 | 6.17E−06 |
| 221 | GI50 | 4.31E−08 | 7.22E−08 | 8.19E−06 | 6.48E−06 | 1.53E−06 | 1.06E−07 | 8.02E−08 | 8.83E−08 |
| | TGI | 2.57E−07 | 5.02E−06 | 2.01E−05 | 2.01E−05 | 1.29E−05 | 2.01E−05 | 2.01E−05 | 2.01E−05 |
| | LC50 | 2.01E−05 | 2.01E−05 | 2.01E−05 | 2.01E−05 | 2.01E−05 | 2.01E−05 | 2.01E−05 | 2.01E−05 |
| 233 | GI50 | 7.83E−08 | 1.26E−07 | 4.99E−08 | 1.07E−07 | | 1.69E−07 | 3.12E−07 | 9.58E−08 |
| | TGI | 1.80E−07 | 5.57E−07 | 1.42E−07 | 7.21E−07 | | 4.75E−06 | 2.06E−06 | 1.09E−06 |
| | LC50 | 1.95E−05 | 3.72E−06 | 1.95E−05 | 1.95E−05 | | 1.95E−05 | 1.95E−05 | 8.61E−06 |
| 238 | GI50 | 4.58E−08 | 2.13E−06 | 7.99E−08 | 4.13E−08 | 1.53E−07 | 5.26E−08 | 4.58E−08 | 4.33E−08 |
| | TGI | 9.65E−08 | 1.65E−05 | 2.82E−07 | 1.44E−07 | 1.61E−06 | 3.51E−07 | 4.38E−07 | 2.47E−07 |
| | LC50 | 1.65E−05 | 1.65E−05 | 1.26E−06 | 1.65E−05 | 1.25E−05 | 1.65E−05 | 1.20E−06 | |
| 239 | GI50 | 5.83E−08 | | 2.42E−07 | 1.61E−07 | 2.06E−07 | 2.03E−07 | 1.64E−07 | 7.86E−08 |
| | TGI | 1.31E−07 | | 3.38E−06 | 4.05E−06 | 1.99E−06 | 2.60E−06 | 1.55E−05 | 2.16E−07 |
| | LC50 | 1.32E−06 | | 1.65E−05 | 1.65E−05 | 1.65E−05 | 1.65E−05 | 1.65E−05 | 5.29E−07 |
| 240 | GI50 | 6.06E−08 | 4.09E−06 | 1.36E−06 | 8.24E−08 | 5.93E−08 | 9.97E−08 | 1.26E−07 | 1.24E−07 |
| | TGI | 1.34E−07 | 1.65E−05 | 5.22E−07 | 3.66E−07 | 3.43E−07 | 3.81E−07 | 4.70E−07 | 4.50E−07 |
| | LC50 | 1.65E−05 | 1.65E−05 | 3.64E−06 | 1.29E−05 | 1.65E−05 | 1.44E−06 | 1.51E−06 | 2.09E−06 |

| | | PANC-1 | HT-29 | LOVO | LOVO-DOX | HELA | HELA-APL |
|---|---|---|---|---|---|---|---|
| 206 | GI50 | 1.37E−07 | 1.32E−06 | 1.67E−07 | 2.94E−07 | 5.05E−08 | 8.34E−08 |
| | TGI | 1.27E−06 | 1.05E−05 | 3.31E−07 | 1.01E−06 | 3.30E−07 | 5.23E−07 |
| | LC50 | 6.25E−06 | 1.05E−05 | 6.60E−07 | 6.37E−06 | 1.93E−06 | 2.82E−06 |
| 207 | GI50 | 1.27E−07 | 3.77E−06 | 1.89E−07 | 3.16E−07 | 4.22E−08 | 7.79E−08 |
| | TGI | 2.37E−06 | 9.26E−06 | 4.05E−07 | 2.85E−06 | 1.23E−06 | 1.50E−06 |
| | LC50 | 9.26E−06 | 9.26E−06 | 8.68E−07 | 9.26E−06 | 3.34E−06 | 3.71E−06 |
| 208 | GI50 | 5.92E−06 | 8.78E−06 | 8.78E−06 | 8.78E−06 | 2.08E−07 | 1.54E−07 |
| | TGI | 8.78E−06 | 8.78E−06 | 8.78E−06 | 8.78E−06 | 6.18E−07 | 3.85E−07 |
| | LC50 | 8.78E−06 | 8.78E−06 | 8.78E−06 | 8.78E−06 | 2.31E−06 | 1.14E−06 |
| 209 | GI50 | 6.74E−08 | 3.38E−06 | 1.19E−07 | 1.37E−07 | 6.62E−08 | 8.27E−08 |
| | TGI | 2.82E−07 | 9.99E−06 | 2.51E−07 | 4.88E−07 | 2.69E−07 | 2.21E−07 |
| | LC50 | 1.03E−06 | 1.05E−05 | 5.27E−07 | 2.60E−06 | 1.01E−06 | 5.17E−07 |
| 210 | GI50 | 3.98E−07 | 7.09E−06 | 2.05E−06 | 2.43E−06 | 6.11E−07 | 5.16E−07 |
| | TGI | 1.51E−06 | 1.04E−05 | 3.99E−06 | 6.04E−06 | 5.54E−06 | 3.08E−06 |
| | LC50 | 4.87E−06 | 1.04E−05 | 7.76E−06 | 1.04E−05 | 1.04E−05 | 1.04E−05 |
| 221 | GI50 | 7.86E−08 | 2.01E−05 | 2.41E−06 | 2.83E−06 | 5.64E−08 | 7.96E−08 |
| | TGI | 2.01E−05 | 2.01E−05 | 6.20E−06 | 1.42E−05 | 2.01E−05 | 2.01E−05 |
| | LC50 | 2.01E−05 | 2.01E−05 | 1.59E−05 | 2.01E−05 | 2.01E−05 | 2.01E−05 |
| 233 | GI50 | 3.41E−07 | 1.95E−05 | 5.45E−07 | 1.05E−06 | 1.91E−07 | 4.17E−07 |
| | TGI | 1.95E−05 | 1.95E−05 | 1.31E−06 | 1.54E−05 | 3.82E−06 | 3.15E−06 |
| | LC50 | 1.95E−05 | 1.95E−05 | 1.95E−05 | 1.95E−05 | 1.60E−05 | 1.43E−05 |
| 238 | GI50 | 2.54E−08 | 2.65E−06 | 5.70E−08 | 2.26E−06 | 5.22E−08 | 1.57E−07 |
| | TGI | 2.50E−07 | 1.06E−05 | 2.26E−07 | 8.98E−07 | 1.31E−07 | 5.16E−07 |
| | LC50 | 1.61E−06 | 1.65E−05 | 1.29E−06 | 1.65E−05 | 1.24E−06 | 1.76E−06 |
| 239 | GI50 | 2.32E−07 | 1.08E−05 | 6.92E−07 | 8.71E−07 | 2.34E−07 | 6.56E−07 |
| | TGI | 1.10E−05 | 1.65E−05 | 2.87E−06 | 1.65E−05 | 3.61E−06 | 4.18E−06 |
| | LC50 | 1.65E−05 | 1.65E−05 | 1.65E−05 | 1.65E−05 | 1.65E−05 | 1.65E−05 |
| 240 | GI50 | 7.05E−08 | 1.64E−06 | 1.70E−07 | 4.61E−07 | 5.75E−08 | 3.41E−07 |
| | TGI | 6.82E−07 | 1.59E−05 | 5.09E−07 | 1.15E−06 | 1.49E−07 | 1.40E−06 |
| | LC50 | 8.86E−06 | 1.65E−05 | 1.52E−06 | 1.65E−05 | 1.40E−06 | 7.61E−06 |

Example 3

Topoisomerase I Inhibition

The marine alkaloid lamellarin D (LAM-D, 3) has been recently characterized as a potent poison of human topoisomerase I endowed with remarkable cytotoxic activities against tumor cells. We report here the structure-activity relationship study in the LAM-D series.

Two groups of triester compounds incorporating various substituents on the three phenolic OH at positions 8, 14 and 20 of 6H-[1]benzopyrano[4',3':4,5]pyrrolo[2,1-α]isoquinolin-6-one pentacyclic planar chromophore typical of the parent alkaloid were tested as topoisomerase I inhibitors.

Compounds incorporating amino acid residues strongly promoted DNA cleavage by human topoisomerase I. LAM-D derivatives tri-substituted with leucine, valine, proline, phenylalanine or alanine residues, or a related amino side chain, stabilize topoisomerase I-DNA complexes. The DNA cleavage sites detected a T↓G or C↓G dinucleotides with these molecules were identical to that of LAM-D (3) but slightly different from those seen with camptothecin which stimulates topoisomerase I-mediated cleavage at T↓G only.

With prostate (DU-145 and LN-CaP), ovarian (IGROV and IGROV-ET resistant to ecteinascidin-743) and colon (LoVo and LoVo-Dox cells resistant to doxorubicin) cancer cells (but not with HT29 colon carcinoma cells), the most cytotoxic compounds correspond to the most potent topoisomerase I poisons. The observed correlation between cytotoxicity and topoisomerase I inhibition strongly suggests that topoisomerase I-mediated DNA cleavage assays can be used as a guide to the development of superior analogs in this series.

Two assays, based on DNA relaxation and DNA cleavage (Bailly, C. DNA relaxation and cleavage assays to study topoisomerase I inhibitors. *Methods Enzymol.* 2001, 340, 610-623) were used evaluate the effects of the lamellarin analogs on the catalytic activity of human topoisomerase I.

In the first assay, a supercoiled plasmid DNA was relaxed with topoisomerase I in the absence or presence of the test compounds, each tested at 1 μM. DNA relaxation products were then resolved by gel electrophoresis on agarose gels containing ethidium bromide to stain the DNA. The alkaloid camptothecin, used as a positive control, strongly promotes DNA cleavage by topoisomerase I. Similarly, the intensity of the band corresponding to nicked DNA is significantly amplified in the presence of LAM-D (3) indicating that this natural product also stabilizes DNA-topoisomerase I covalent complexes. This functional assay is useful to identify the topoisomerase I poisons among the various analogs synthesized. The analogous compounds with a 5-6 saturated bond (11, 22, 108, 109, 139) were inactive in this assay.

Different cationic groups, mostly amino acid residues, were incorporated at the three phenoxy positions of LAM-D. A marked inhibition of topoisomerase I was observed with the positively charged molecules 40 (Ala), 39 (Leu), 36 (Val), 33 (Pro) and 25 (Phe) but not with the corresponding NH-Boc derivatives or the non-planar C5-C6 analogues. The Phe derivative is significantly less potent than the other amino acid derivatives which are all more or less equally effective at inhibiting topoisomerase I. The stereospecificity was investigated with the Val derivatives for which we compared the activity of the (L) (36, 38, 135, 144) and (D) (17, 32, 34, 122) isomers but there was no difference between the two series. Compound 17 and 36 both stimulated DNA cleavage by the enzyme. No effect was observed with the Boc-protected analogs in the C5-C6 double stranded (38, 122) or C5-C6 single-stranded (32, 34, 135, 144) series. The amino compounds 24 and 169 were also found to inhibit topoisomerase I.

Concentration-dependent measurements were performed with each of the positive compounds identified and a few representative gels comparing the anti-topoisomerase I activity of LAM-D (3) with the three analogues Val(D) (17), Pro (33) and the amino compound 169 were done. This later compound is equally efficient to (3) in terms of stimulation of DNA cleavage by topoisomerase I. In all cases, the dose-response analysis confirmed that the cationic LAM-D analogues potently inhibit the enzyme.

It is clear that the introduction of an amino acid functionality on the phenolic OH groups at positions 8, 14 and 20 of LAM-D (3) is not detrimental to topoisomerase I inhibition. The extent of topoisomerase I-mediated DNA cleavage is fully maintained when a Leu, Val, Ala or Pro residue is incorporated on the LAM-D skeleton whereas a non charged group abolishes the anti-topoisomerase I activity. A phenylalanine residue is much less favorable than a proline or an alanine residue for example. The observations that the incorporation of a cationic group promoted topoisomerase I inhibition suggested that the enhanced capacity of the drugs to bind to DNA could be responsible for a better enzyme inhibition.

A second assay, based on the cleavage of a radiolabeled DNA substrate by topoisomerase I, was used to confirm that the cationic lamellarin derivatives do effectively function as topoisomerase I poisons. A 117-bp DNA restriction fragment uniquely end-labeled at the 3' end was subjected to cleavage by topoisomerase I in the presence of the different compounds and the resulting DNA cleavage products were resolved on sequencing-type polyacrylamide gels. The advantage of this assay is to detect the cleavage sites and to locate their positions with nucleotide resolution, providing thus information on the site selectivity of cleavage.

The reference drug CPT products three sites at nucleotide positions 26, 48 and 81 which all three correspond to T↓G sites. Cleavage at TG sites in the presence of CPT is believed to result from the interaction of topoisomerase I with the T residue combined with the stacking of the CPT molecule with the adjacent G residue. A fourth weak site can be detected at the top of the gels (T↓G107).

The sequence selectivity profiles are slightly different with the lamellarin analogs. LAM-D is less efficient than CPT for topoisomerase I-mediated DNA cleavage at sites T↓G48 and T↓G81 but it induces an additional cleavage site at C↓G73. This likely reflects a different mode of interaction with the topoisomerase I-DNA covalent complexes.

Cleavage profiles identical to that of 3 were obtained with the cationic derivatives such as 39 (Leu), 36 (Val), 33 (Pro) and 25 (Phe) but not with the corresponding NH-Boc derivatives or the non-planar C5-C6 analogue. The amino compounds 169 and 7 were also found to stimulate DNA cleavage by the enzyme and here also we found no difference between the (L) (36) and (D) (17) Val isomers. The results are thus entirely consistent with those obtained by the relaxation assay and therefore validate the conclusion that the cationic lamellarin derivatives potently inhibit topoisomerase I.

The invention claimed is:

1. A compound of the general formula III:

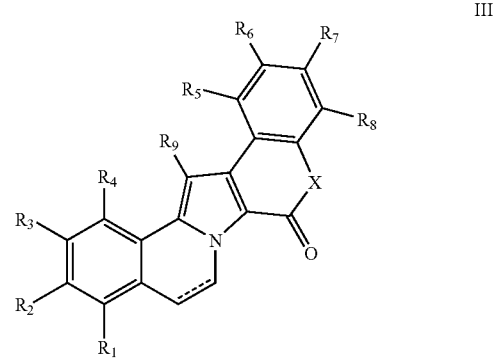

III wherein X is selected from the group consisting of NH, O and S;

wherein $R_1$, $R_2$, $R_3$, $R_4$, $R_5$, $R_6$, $R_7$, and $R_8$ are each independently selected from the group consisting of H, OH, OR', SH, SR', SOR', SO$_2$R', NHR', N(R')$_2$, N=R', NHCOR', N(COR')$_2$, NHSO$_2$R', NO$_2$, PO(R')$_2$, PO$_2$R', C(=O)H, C(=O)R', CO$_2$H, CO$_2$R', OPO(R')$_2$, OPO$_2$R', OC(=O)H, OC(=O)R', N=C(R')$_2$, substituted or unsubstituted $C_1$-$C_{12}$ alkyl, substituted or unsubstituted $C_1$-$C_{12}$ haloalkyl, substituted or unsubstituted $C_2$-$C_{12}$ alkenyl, substituted or unsubstituted $C_2$-$C_{12}$ alkynyl, substituted or unsubstituted aryl, substituted or unsubstituted aralkyl and substituted or unsubstituted heteroaromatic;

wherein $R_9$ is independently selected from the group consisting of H, OH, OR', SH, SR', SOR', SO$_2$R', NHR', N(R')$_2$, N=R', NHCOR', N(COR')$_2$, NHSO$_2$R', NO$_2$, PO(R')$_2$, PO$_2$R', C(=O)H, C(=O)R', CO$_2$H, CO$_2$R', OPO(R')$_2$, OPO$_2$R', OC(=O)H, OC(=O)R', N=C(R')$_2$, substituted or unsubstituted $C_1$-$C_{12}$ alkyl, substituted or unsubstituted $C_1$-$C_{12}$ haloalkyl, substituted or unsubstituted $C_2$-$C_{12}$ alkenyl, substituted or unsubstituted $C_2$-$C_{12}$ alkynyl, substituted or unsubstituted aralkyl, substituted or unsubstituted heteroaromatic, bromine, and iodine;

wherein each of the R' groups is independently selected from the group consisting of H, OH, $NO_2$, $NH_2$, SH, CN, halogen, C(=O)H, C(=O)$CH_3$, $CO_2H$, substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, substituted or unsubstituted $C_1$-$C_{18}$ alkoxyl, substituted or unsubstituted $C_1$-$C_{18}$ aminoalkyl, substituted or unsubstituted $C_1$-$C_{18}$ aminoacid or aminoacids chain, substituted or unsubstituted $C_1$-$C_{18}$ thioalkyl, substituted or unsubstituted $C_1$-$C_{18}$ alkylsulfinyl, substituted or unsubstituted $C_1$-$C_{18}$ alkylsulfonyl;

wherein the pairs of groups $R_1$ and $R_2$, $R_2$ and $R_3$, $R_3$ and $R_4$, $R_3$ and $R_9$, $R_4$ and $R_9$, $R_9$ and $R_5$, $R_9$ and $R_6$, or $R_6$ and $R_7$, $R_7$ and $R_8$ may be joined into a carbocyclic or heterocyclic ring system;

and the dotted line represents a single or double bond;

or a pharmaceutically acceptable salt or stereoisomer thereof.

2. A compound of the general formula IV:

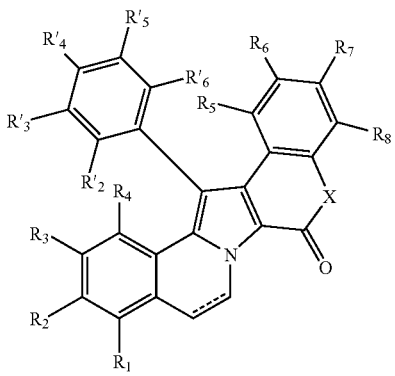

IV wherein X is selected from the group consisting of NH, O and S;

wherein $R_1$, $R_2$, $R_3$, $R_4$, $R_5$, $R_6$, $R_8$, $R'_2$, $R'_3$, $R'_4$, $R'_5$, and $R'_6$ are each independently selected from the group consisting of H, OH, OR', SH, SR', SOR', $SO_2R'$, NHR', N(R')$_2$, N=R', NHCOR', N(COR')$_2$, NHSO$_2$R', $NO_2$, PO(R')$_2$, PO$_2$R', C(=O)H, C(=O)R', $CO_2H$, $CO_2R'$, OPO(R')$_2$, OPO$_2$R', OC(=O)H, OC(=O)R', N=C(R')$_2$, substituted or unsubstituted $C_1$-$C_{12}$ alkyl, substituted or unsubstituted $C_1$-$C_{12}$ haloalkyl, substituted or unsubstituted $C_2$-$C_{12}$ alkenyl, substituted or unsubstituted $C_2$-$C_{12}$ alkynyl, substituted or unsubstituted aryl, substituted or unsubstituted aralkyl and substituted or unsubstituted heteroaromatic;

wherein $R_7$ is independently selected from the group consisting of OR', SH, SR', SOR', $SO_2R'$, NHR', N(R')$_2$, N=R', NHCOR', N(COR')$_2$, NHSO$_2$R', $NO_2$, PO(R')$_2$, PO$_2$R', C(=O)H, C(=O)R', $CO_2H$, $CO_2R'$, OPO(R')$_2$, OPO$_2$R', OC(=O)H, OC(=O)R', N=C(R')$_2$, substituted or unsubstituted $C_1$-$C_{12}$ alkyl, substituted or unsubstituted $C_1$-$C_{12}$ haloalkyl, substituted or unsubstituted $C_2$-$C_{12}$ alkenyl, substituted or unsubstituted $C_2$-$C_{12}$ alkynyl, substituted or unsubstituted aryl, substituted or unsubstituted aralkyl and substituted or unsubstituted heteroaromatic;

with the proviso tat $R_7$ is not Me, Et, Pr, COMe, OH, OMe, OAc, O$^i$Pr or OBn when X is O;

wherein each of the R' groups is independently selected from the group consisting of H, OH, $NO_2$, $NH_2$, SH, CN, halogen, C(=O)H, C(=O)$CH_3$, $CO_2H$, substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, substituted or unsubstituted $C_1$-$C_{18}$ alkoxyl, substituted or unsubstituted $C_1$-$C_{18}$ aminoalkyl, substituted or unsubstituted $C_1$-$C_{18}$ aminoacid or aminoacids chain, substituted or unsubstituted $C_1$-$C_{18}$ thioalkyl, substituted or unsubstituted $C_1$-$C_{18}$ alkylsulfinyl, substituted or unsubstituted $C_1$-$C_{18}$ alkylsulfonyl;

wherein the pairs of groups $R_1$ and $R_2$, $R_2$ and $R_3$, $R_3$ and $R_4$, or $R_7$ and $R_8$ may be joined into a carbocyclic or heterocyclic ring system;

and the dotted line represents a single or double bond;

or a pharmaceutically acceptable salt or stereoisomer thereof.

3. A compound according to claim 1 or 2 wherein X is O or NH.

4. A compound according to claim 1 or 2 wherein X is O.

5. A compound according to claim 1 or 2 wherein the dotted line is a double bond.

6. A compound according to claim 1 wherein each of $R_1$-$R_8$ is independently selected from H, OR', and OC(=O)R'.

7. A compound according to claim 1 or 2 wherein $R_3$ is selected from the group consisting of H, OH, and OR', with the proviso that when $R_3$ is OR', then R' is selected from a substituted or unsubstituted $C_1$-$C_{18}$ alkyl.

8. A compound according to claim 1 or 2 wherein $R_4$, $R_5$, $R_6$ and $R_8$ are each independently selected from the group consisting of H and OR', with the proviso that when $R_4$, $R_5$, $R_6$ or $R_8$ is OR', then R' is selected from a substituted or unsubstituted $C_1$-$C_{18}$ alkyl.

9. A compound according to claim 8 wherein $R_4$, $R_5$ and $R_8$ are H.

10. A compound according to claim 1 wherein $R_1$, $R_2$ and $R_7$ are each independently selected from the group consisting of H, OH, OR', OC(=O)R', $SO_2R'$, PO(R')$_2$, substituted or unsubstituted $C_1$-$C_{12}$ alkyl, $NO_2$, and $NH_2$, with the proviso that when $R_1$, $R_2$ or $R_7$ are OR', then R' is selected from a substituted or unsubstituted $C_1$-$C_{18}$ alkyl.

11. A compound according to claim 10 wherein $R_1$, $R_2$ and $R_7$ are OC(=O)R' wherein R' is a substituted or unsubstituted aminoacid or aminoacids chain.

12. A compound according to claim 2 wherein $R'_2$, $R'_3$ and $R'_6$ are each independently selected from the group consisting of H and OR', wherein R' is a substituted or unsubstituted $C_1$-$C_{18}$ alkyl.

13. A compound according to claim 2 wherein $R'_5$ is selected from the group consisting of H and OR', wherein R' is a substituted or unsubstituted $C_1$-$C_{18}$ alkyl.

14. A compound according to claim 2 wherein $R'_4$ is selected from the group consisting of H, OH, OR', OC(=O)R', $SO_2R'$, PO(R')$_2$, substituted or unsubstituted $C_1$-$C_{12}$ alkyl, $NO_2$, and $NH_2$, with the proviso that when $R'_4$ is OR', ten R' is selected from a substituted or unsubstituted $C_1$-$C_{18}$ alkyl.

15. A compound according to claim 14 wherein $R'_4$ is OR' and wherein R' is a substituted or unsubstituted aminoacid or aminoacids chain.

16. A compound according to claim 1 or 2 wherein at least one of $R_1$-$R_8$ and $R'_2$-$R'_6$ is not H, OH, $OCH_3$, and $SO_3Na$.

17. A pharmaceutical composition comprising a compound as defined in claim 1 or 2 or a pharmaceutically acceptable salt or stereoisomer thereof, and a pharmaceutically acceptable diluent or carrier.

18. A method of treating a tumor in a human which comprises administering to said human an effective amount of a compound as defined in claim 1 or 2 or a pharmaceutically acceptable salt or stereoisomer thereof.

19. A method of inhibiting topoisomerase I comprising administering to a human an amount effective for inhibiting topoisomerase I of a compound as defined in claim 1 or 2 or a pharmaceutically acceptable salt or stereoisomer thereof.

20. A compound of the general formula IV:

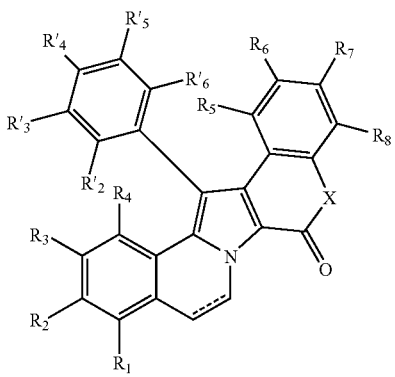

IV wherein X is selected from the group consisting of NH, O and S;

wherein $R_1$, $R_2$, $R_3$, $R_4$, $R_5$, $R_6$, $R_8$, $R'_2$, $R'_3$, $R'_4$, $R'_5$, and $R'_6$ are each independently selected from the group consisting of H, OH, OR', SH, SR', SOR', $SO_2R'$, NHR', $N(R')_2$, N=R', NHCOR', $N(COR')_2$, $NHSO_2R'$, $NO_2$, $PO(R')_2$, $PO_2R'$, C(=O)H, C(=O)R', $CO_2H$, $CO_2R'$, $OPO(R')_2$, $OPO_2R'$, OC(=O)H, OC(=O)R', N=C(R')$_2$, substituted or unsubstituted $C_1$-$C_{12}$ alkyl, substituted or unsubstituted $C_1$-$C_{12}$ haloalkyl, substituted or unsubstituted $C_2$-$C_{12}$ alkenyl, substituted or unsubstituted $C_2$-$C_{12}$ alkynyl, substituted or unsubstituted aryl, substituted or unsubstituted aralkyl and substituted or unsubstituted heteroaromatic;

wherein $R_7$ is independently selected from the group consisting of OR', SH, SR', SOR', $SO_2R'$, NHR', $N(R')_2$, N=R', NHCOR', $N(COR')_2$, $NHSO_2R'$, $NO_2$, $PO(R')_2$, $PO_2R'$, C(=O)H, $CO_2H$, $CO_2R'$, $OPO(R')_2$, $OPO_2R'$, OC(=O)H, OC(=O)R', N=C(R')$_2$, substituted or unsubstituted $C_1$-$C_{12}$ haloalkyl, substituted or unsubstituted $C_2$-$C_{12}$ alkenyl, substituted or unsubstituted $C_2$-$C_{12}$ alkynyl, substituted or unsubstituted aryl, substituted or unsubstituted aralkyl and substituted or unsubstituted heteroaromatic;

with the proviso that $R_7$ is not OH, OMe, OAc, $O^iPr$ or OBn when X is O;

wherein each of the R' groups is independently selected from the group consisting of H, OH, $NO_2$, $NH_2$, SH, CN, halogen, C(=O)H, C(=O)$CH_3$, $CO_2H$, substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, substituted or unsubstituted $C_1$-$C_{18}$ alkoxyl, substituted or unsubstituted $C_1$-$C_{18}$ aminoalkyl, substituted or unsubstituted $C_1$-$C_{18}$ aminoacid or aminoacids chain, substituted or unsubstituted $C_1$-$C_{18}$ thioalkyl, substituted or unsubstituted $C_1$-$C_{18}$ alkylsulfinyl, substituted or unsubstituted $C_1$-$C_{18}$ alkylsulfonyl;

wherein the pairs of groups $R_1$ and $R_2$, $R_2$ and $R_3$, $R_3$ and $R_4$, or $R_7$ and $R_8$ may be joined into a carbocyclic or heterocyclic ring system;

and the dotted line represents a single or double bond;

or a pharmaceutically acceptable salt or stereoisomer thereof.

21. A compound according to claim 7 wherein $R_3$ is methoxy.

22. A compound according to claim 13 wherein $R'_5$ is methoxy.

23. A compound according to claim 16 wherein at least two of $R_1$-$R_8$ and $R'_2$-$R'_6$ are not H, OH, $OCH_3$, or $SO_3Na$.

24. A compound according to claim 11 wherein R' is an aminoacid or aminoacids chain substituted with a cationic group.

25. A compound according to claim 15 wherein R' is an aminoacid or aminoacids chain substituted with a cationic group.

26. A compound according to claim 2 or 20 wherein each of $R_1$-$R_6$ and $R_8$ is independently selected from H, OR', and OC(=O)R' and wherein $R_7$ is selected from OR' and OC(=O)R'.

27. A compound according to claim 2 or 20 wherein $R_1$ and $R_2$ are each independently selected from the group consisting of H, OH, OR', OC(=O)R', $SO_2R'$, $PO(R')_2$, substituted or unsubstituted $C_1$-$C_{12}$ alkyl, $NO_2$, and $NH_2$, with the proviso that when $R_1$ or $R_2$ are OR', then R' is selected from a substituted or unsubstituted $C_1$-$C_{18}$ alkyl; and wherein $R_7$ is selected from the group consisting of OR', OC(=O)R', $SO_2R'$, $PO(R')_2$, substituted or unsubstituted $C_1$-$C_{12}$ alkyl, $NO_2$, and $NH_2$, with the proviso that when $R_7$ is OR', then R' is selected from a substituted or unsubstituted $C_1$-$C_{18}$ alkyl group.

28. A compound according to claim 12 wherein $R'_2$, $R'_3$, and $R'_6$ are H.

* * * * *

UNITED STATES PATENT AND TRADEMARK OFFICE
CERTIFICATE OF CORRECTION

PATENT NO. : 7,396,837 B2  Page 1 of 3
APPLICATION NO. : 10/524151
DATED : July 8, 2008
INVENTOR(S) : Bailly et al.

It is certified that error appears in the above-identified patent and that said Letters Patent is hereby corrected as shown below:

Column 5, line 47, the text "$R_9$ and $R_6$, or $R_6$ and $R_7$, $R_7$ and $R_5$" should read --$R_9$ and $R_6$, $R_6$ and $R_7$, or $R_7$ and $R_8$--

Columns 15 and 16, lines 28-67, the chemical scheme

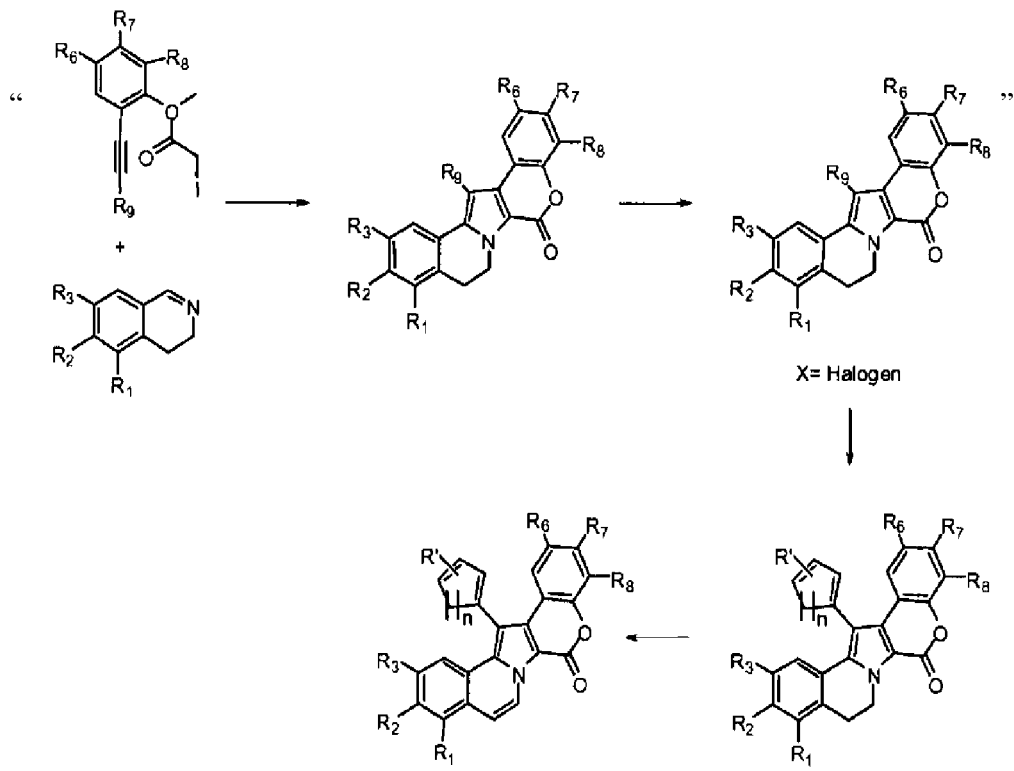

UNITED STATES PATENT AND TRADEMARK OFFICE
CERTIFICATE OF CORRECTION

PATENT NO.      : 7,396,837 B2  
APPLICATION NO. : 10/524151  
DATED           : July 8, 2008  
INVENTOR(S)     : Bailly et al.

Page 2 of 3

It is certified that error appears in the above-identified patent and that said Letters Patent is hereby corrected as shown below:

should read

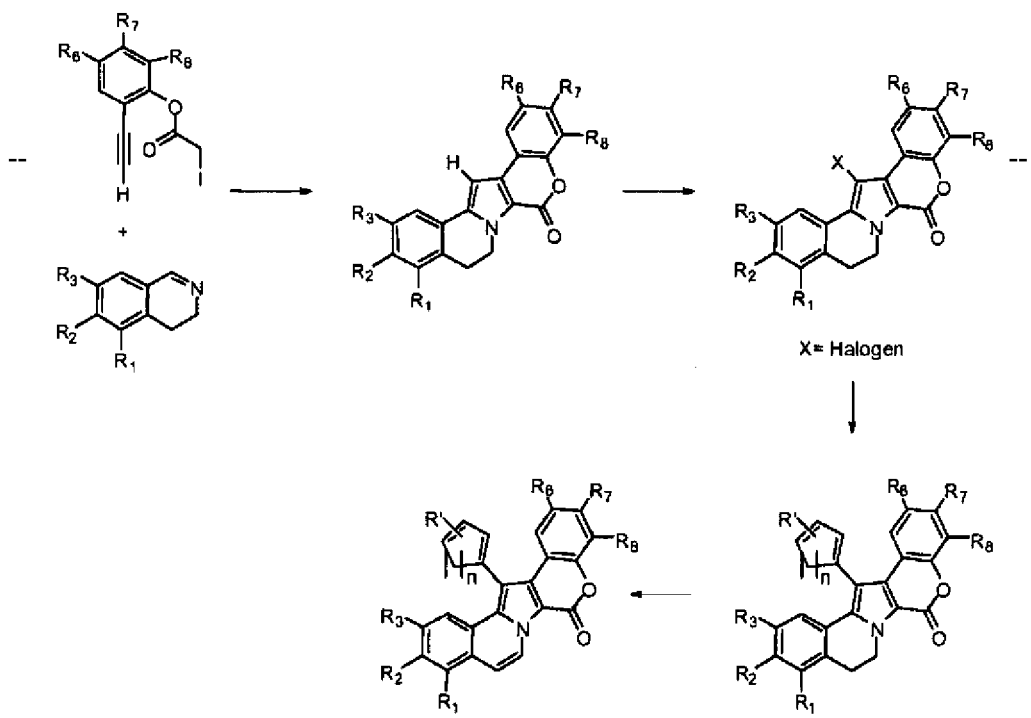

Claim 1, column 171, lines 20-21, the text "$R_9$ and $R_6$, or $R_6$ and $R_7$, $R_7$ and $R_8$" should read --$R_9$ and $R_6$, $R_6$ and $R_7$, or $R_7$ and $R_8$--

Claim 2, column 172, line 4, the text "with the proviso tat $R_7$ is not" should read --with the proviso that $R_7$ is not--

UNITED STATES PATENT AND TRADEMARK OFFICE
CERTIFICATE OF CORRECTION

PATENT NO.       : 7,396,837 B2
APPLICATION NO.  : 10/524151
DATED            : July 8, 2008
INVENTOR(S)      : Bailly et al.

It is certified that error appears in the above-identified patent and that said Letters Patent is hereby corrected as shown below:

Claim 14, column 172, line 61, the text "ten" should read --then--

Signed and Sealed this

Thirty-first Day of March, 2009

JOHN DOLL
*Acting Director of the United States Patent and Trademark Office*